(12) United States Patent
Damude et al.

(10) Patent No.: US 8,058,517 B2
(45) Date of Patent: *Nov. 15, 2011

(54) DELTA-8 DESATURASE AND ITS USE IN MAKING POLYUNSATURATED FATTY ACIDS

(75) Inventors: Howard Glenn Damude, Hockessin, DE (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 190 days.

This patent is subject to a terminal disclaimer.

(21) Appl. No.: 12/298,563

(22) PCT Filed: Apr. 26, 2007

(86) PCT No.: PCT/US2007/010257
§ 371 (c)(1),
(2), (4) Date: Oct. 27, 2008

(87) PCT Pub. No.: WO2007/127381
PCT Pub. Date: Nov. 8, 2007

(65) Prior Publication Data
US 2009/0313720 A1  Dec. 17, 2009

Related U.S. Application Data

(60) Provisional application No. 60/795,810, filed on Apr. 28, 2006, provisional application No. 60/837,789, filed on Aug. 15, 2006.

(51) Int. Cl.
*A01H 5/00* (2006.01)
*C12N 15/82* (2006.01)

(52) U.S. Cl. ........................................ 800/298; 435/419

(58) Field of Classification Search ........................ None
See application file for complete search history.

(56) References Cited

U.S. PATENT DOCUMENTS

| 5,968,809 | A | 10/1999 | Knutzon et al. |
|---|---|---|---|
| 5,972,664 | A | 10/1999 | Knutzon et al. |
| 6,051,754 | A | 4/2000 | Knutzon |
| 6,075,183 | A | 6/2000 | Knutzon et al. |
| 6,136,574 | A | 10/2000 | Knutzon et al. |
| 6,410,288 | B1 | 6/2002 | Knutzon et al. |
| 6,459,018 | B1 | 10/2002 | Knutzon |
| 6,825,017 | B1 | 11/2004 | Browse et al. |
| 2005/0047479 | A1 | 3/2005 | Underwood et al. |
| 2005/0047480 | A1 | 3/2005 | Carbonari |
| 2005/0273885 | A1 | 12/2005 | Singh et al. |
| 2006/0090221 | A1 | 4/2006 | Browse et al. |

FOREIGN PATENT DOCUMENTS

| WO | WO98/46763 | 10/1998 |
|---|---|---|
| WO | WO98/46764 | 10/1998 |
| WO | WO98/55625 | 12/1998 |
| WO | WO00/12720 | 3/2000 |
| WO | WO00/34439 | 6/2000 |
| WO | WO00/40705 | 7/2000 |
| WO | WO02/26946 | 4/2002 |
| WO | WO2004/057001 | 7/2004 |
| WO | WO2004/071178 | 8/2004 |
| WO | WO2004/071467 | 8/2004 |
| WO | WO2004/101753 | 11/2004 |
| WO | WO2004/101757 | 11/2004 |
| WO | WO2005/103253 | 11/2005 |
| WO | WO2006/012325 | 2/2006 |
| WO | WO2006/012326 | 2/2006 |

OTHER PUBLICATIONS

U.S. Appl. No. 60/583,041, filed Jun. 25, 2004, Howard Glenn Damude.
U.S. Appl. No. 11/166,003, filed Jun. 25, 2004, Howard Glenn Damude.
U.S. Appl. No. 60/739,989, filed Nov. 23, 2005, Howard Glenn Damude et al.
U.S. Appl. No. 10/985,109, filed Nov. 10, 2004, Howard Glenn Damude et al.
U.S. Appl. No. 10/985,254, filed Nov. 10, 2004, Narendra S. Yadav et al.
U.S. Appl. No. 11/265,761, filed Nov. 2, 2005, Howard Glenn Damude et al.
U.S. Appl. No. 11/264,784, filed Nov. 1, 2005, Howard Glenn Damude et al.
U.S. Appl. No. 11/264,737, filed Nov. 1, 2005, Howard Glenn Damude et al.
Spychalla et al., Identification of an Animal W-3 Fatty Acid Desaturase by Heterologous Expression in Arabidopis, Proc. Natl. Acad. Sci., 1997, vol. 94:1142-1147.
Wallis et al., The 8-Desaturase of Euglena Gracilis: An Alternate Pathway for Synthesis of 20-Carbon Polyunsaturated Fatty Acids, Arch. Biochem. and Biophys., 1999, vol. 365:307-316.
Qi et al., Production of Very Long Chain Polyunsaturated Omega-3 and Omega-6 Fatty Acids in Plants, Nat. Biotech., 2004, vol. 22:739-745.
Sayanova et al., The Alternative Pathway C20 8-Desaturase From the Non-Photosynthetic Organism Acanthamoeba Castellanii is an Atypical Cytochrome B-5 Fusion Desaturase, FEBS Lett., 2006, vol. 580:1946-1952.
National Center for Biotechnology Information General Identifier No. 83027409, Dec. 7, 2005, Y.B. Zhang et al., Identification and Characterization of a Novel 6-Fatty Acid Desaturase Gene From Rhizopus Stolonifer, ABB96724. National Center for Biotechnology Information General Identifier No. 83027408, Dec. 7, 2005, Y.B. Zhang et al., Identification and Characterization of a Novel 6-Fatty Acid Desaturase Gene From Rhizopus Stolonifer, DQ291156.
National Center for Biotechnology Information General Identifier No. 60499699, Nov. 1, 2005, H. Lu et al., Identification and Characterization of a Novel 6-Fatty Acid Desaturase Gene From Rhizopus Nigricans, AAX22052.
National Center for Biotechnology Information General Identifier No. 60499698, Nov. 1, 2005, H. Lu et al., Identification and Characterization of a Novel 6-Fatty Acid Desaturase Gene From Rhizopus Nigricans, AY795076.

(Continued)

*Primary Examiner* — Elizabeth McElwain

(57) ABSTRACT

Isolated nucleic acid fragments and recombinant constructs comprising such fragments encoding a delta-8 desaturase along with a method of making long-chain polyunsaturated fatty acids (PUFAs) using this delta-8 desaturase in plants and oleaginous yeast are disclosed.

6 Claims, 16 Drawing Sheets

OTHER PUBLICATIONS

National Center for Biotechnology Information General Identifier No. 34221934, Jul. 28, 2004, E. Sakuradani et al., Gene Cloning and Functional Analysis of a Second Delta 6-Fatty Acid Desaturase From an Arachidonic Acid-Producing Mortierella Fungus, BAC82361.

Sakuradani et al., Gene Cloning and Functional Analysis of a Second 6-Fatty Acid Desaturase From an Arachidonic Acid-Producing Mortierella Fungus, Biosci. Biotechnol. Biochem., 2003, vol. 67:704-711.

National Center for Biotechnology Information General Identifier No. 17226123, Mar. 9, 2006, B. Qi et al., Identification of a CDNA Encoding a Novel C18-Delta (9) Polyunsaturated Fatty Acid-Specific Elongating Activity From the Docosahexaenoic Acid (DHA)—Producing Microalga, Isochrysis Galbana, AAL37626.

National Center for Biotechnology Information General Identifier No. 17226122, Mar. 9, 2006, Qi et al., Identification of a CDNA Encoding a Novel C18-Delta (9) Polyunsaturated Fatty Acid-Specific Elongating Activity From the Docosahenaenoic Acid (DHA)—Producing Microalga, Isochrysis Galbana, AF390174.

Tonon et al., Identification of a Very Long Chain Polyunsaturated Fatty Acid DELTA4-desaturase from the Microalga Pavlova Lutheri. vol. 553(3), pp. 440-444, Oct. 23, 2003.

FIG. 8A

Fatty acid composition (wt.%)

| Event | 16:0 | 18:0 | 18:1 | LA | GLA | ALA | EDA | DGLA | ERA | ETA | C20 % delta-8 desat | EDA % delta-8 desat | ERA % delta-8 desat | Ratio (EDA/ERA) % desat |
|---|---|---|---|---|---|---|---|---|---|---|---|---|---|---|
| 1890-3-5-1 | 18.4 | 2.0 | 6.3 | 22.9 | 2.1 | 10.5 | 3.2 | 24.9 | 4.7 | 5.2 | 79.3 | 88.7 | 52.6 | 1.7 |
| -2 | 18.8 | 2.0 | 5.9 | 19.8 | 4.8 | 8.0 | 4.1 | 26.3 | 4.9 | 5.4 | 77.8 | 86.4 | 52.1 | 1.7 |
| -3 | 18.8 | 2.1 | 9.4 | 23.1 | 2.8 | 11.2 | 4.6 | 19.2 | 4.8 | 4.1 | 71.1 | 80.5 | 45.8 | 1.8 |
| -4 | 15.7 | 1.8 | 10.9 | 28.8 | 2.8 | 10.8 | 4.6 | 18.4 | 3.1 | 3.1 | 73.6 | 80.0 | 49.8 | 1.6 |
| -5 | 17.0 | 1.6 | 7.9 | 30.4 | 3.0 | 10.9 | 2.4 | 21.3 | 2.5 | 3.0 | 83.1 | 89.9 | 54.0 | 1.7 |
| -6 | 17.5 | 1.6 | 6.4 | 24.3 | 4.4 | 9.9 | 2.9 | 24.5 | 4.0 | 4.5 | 80.8 | 89.4 | 53.3 | 1.7 |
| -7 | 17.2 | 1.5 | 5.5 | 27.2 | 3.3 | 12.3 | 2.6 | 22.0 | 3.7 | 4.5 | 80.9 | 89.4 | 55.3 | 1.6 |
| -8 | 15.3 | 1.6 | 8.5 | 30.4 | 0.3 | 13.1 | 17.8 | 2.9 | 9.3 | 0.7 | 11.9 | 14.1 | 7.4 | 1.9 |
| -9 | 20.8 | 3.0 | 6.9 | 19.0 | 4.2 | 5.4 | 5.3 | 25.1 | 5.5 | 4.8 | 73.3 | 82.4 | 46.3 | 1.8 |
| -10 | 16.2 | 1.3 | 9.4 | 29.4 | 2.8 | 11.2 | 2.6 | 21.1 | 2.6 | 3.3 | 82.4 | 89.0 | 55.9 | 1.6 |
| -11 | 18.3 | 1.7 | 4.8 | 25.6 | 4.2 | 9.8 | 3.8 | 23.9 | 3.9 | 4.0 | 78.4 | 86.4 | 50.1 | 1.7 |
| -12 | 15.6 | 1.6 | 4.8 | 31.9 | 1.7 | 16.1 | 2.2 | 18.3 | 3.7 | 4.0 | 79.2 | 89.3 | 52.3 | 1.7 |
| Ave | 17.5 | 1.8 | 7.2 | 26.1 | 3.0 | 10.8 | 4.7 | 20.7 | 4.4 | 3.9 | 72.7 | 80.5 | 47.9 | 1.7 |
| 1890-4-2-1 | 16.6 | 1.8 | 13.7 | 30.0 | 1.1 | 9.8 | 5.0 | 17.5 | 3.1 | 1.5 | 70.2 | 77.8 | 33.5 | 2.3 |
| -2 | 18.3 | 1.5 | 10.9 | 31.5 | 1.0 | 16.1 | 3.9 | 13.3 | 2.5 | 0.9 | 68.8 | 77.2 | 27.2 | 2.8 |
| -3 | 16.5 | 1.6 | 7.6 | 28.9 | 1.5 | 16.6 | 4.5 | 13.4 | 7.0 | 2.5 | 58.2 | 75.0 | 26.7 | 2.8 |
| -4 | 13.6 | 1.5 | 9.2 | 31.7 | 0.6 | 20.7 | 8.9 | 6.5 | 6.6 | 0.7 | 31.7 | 42.1 | 10.1 | 4.2 |
| -5 | 15.7 | 2.1 | 10.8 | 31.5 | 1.3 | 19.7 | 3.4 | 10.3 | 3.3 | 1.9 | 64.4 | 75.3 | 35.7 | 2.1 |
| Ave | 16.1 | 1.7 | 10.4 | 30.7 | 1.1 | 16.6 | 5.1 | 12.2 | 4.5 | 1.5 | 58.7 | 69.5 | 26.6 | 2.9 |
| 1890-5-1-1 | 13.6 | 1.8 | 19.7 | 24.3 | 0.5 | 13.8 | 8.1 | 9.5 | 7.7 | 0.9 | 39.7 | 53.8 | 11.0 | 4.9 |
| -2 | 15.7 | 1.7 | 7.2 | 30.5 | 1.1 | 13.0 | 5.7 | 16.8 | 6.2 | 2.2 | 61.6 | 74.7 | 26.5 | 2.8 |
| -3 | 17.0 | 1.3 | 7.7 | 33.9 | 0.4 | 25.8 | 3.3 | 6.2 | 3.5 | 1.0 | 51.5 | 65.4 | 22.0 | 3.0 |
| -4 | 19.5 | 2.1 | 9.0 | 28.0 | 2.7 | 9.4 | 6.9 | 15.8 | 4.5 | 2.2 | 61.3 | 69.7 | 32.5 | 2.1 |
| -5 | 15.3 | 1.2 | 7.5 | 34.4 | 1.0 | 22.4 | 3.9 | 9.9 | 3.5 | 0.9 | 59.5 | 71.8 | 20.9 | 3.4 |
| Ave | 16.2 | 1.6 | 10.2 | 30.2 | 1.1 | 16.9 | 5.6 | 11.6 | 5.1 | 1.4 | 54.7 | 67.1 | 22.6 | 3.3 |

Fatty acid compositions listed in Table 8 are expressed as weight percent (wt. %).
16:0=palmitic acid, 18:0=stearic acid, 18:1=oleic acid, LA=linoleic acid, GLA=gamma-linoleic acid, ALA=alpha-linolenic acid, EDA=eicosadienoic acid, DGLA= dihomo-gamma-Linolenic, ERA=eicosatrienoic acid, ETA=eicosatetraenoic acid.

FIG. 8B

Fatty acid composition (wt. %)

| Event | 16:0 | 18:0 | 18:1 | LA | GLA | ALA | EDA | DGLA | ERA | ETA | C20 % delta-8 desat | EDA % delta-8 desat | ERA % delta-8 desat | Ratio (EDA/ERA) % desat |
|---|---|---|---|---|---|---|---|---|---|---|---|---|---|---|
| 1890-5-2-1 | 15.2 | 1.3 | 11.3 | 31.1 | 2.2 | 13.8 | 5.1 | 14.5 | 4.0 | 1.5 | 63.9 | 74.1 | 27.3 | 2.7 |
| -2 | 15.5 | 1.1 | 10.9 | 37.1 | 1.2 | 13.1 | 3.7 | 13.1 | 3.2 | 1.2 | 67.5 | 77.9 | 28.2 | 2.8 |
| -3 | 16.3 | 1.7 | 12.1 | 27.1 | 1.1 | 9.8 | 7.5 | 16.9 | 5.7 | 1.7 | 58.4 | 69.1 | 22.9 | 3.0 |
| -4 | 14.6 | 1.4 | 11.5 | 36.7 | 1.2 | 12.9 | 2.9 | 14.2 | 2.8 | 1.8 | 73.8 | 83.1 | 39.7 | 2.1 |
| -5 | 14.9 | 1.4 | 18.3 | 27.8 | 1.3 | 7.8 | 11.7 | 9.8 | 6.4 | 0.6 | 36.5 | 45.7 | 8.0 | 5.7 |
| Ave | 15.3 | 1.4 | 12.8 | 32.0 | 1.4 | 11.5 | 6.2 | 13.7 | 4.4 | 1.4 | 60.0 | 70.0 | 25.2 | 3.3 |
| 1890-5-4-1 | 15.6 | 1.1 | 9.7 | 35.9 | 1.3 | 14.8 | 3.9 | 12.6 | 4.1 | 1.0 | 63.1 | 76.5 | 20.4 | 3.7 |
| -2 | 14.4 | 1.5 | 12.1 | 28.1 | 1.6 | 12.1 | 7.0 | 15.6 | 5.9 | 1.8 | 57.4 | 68.9 | 23.5 | 2.9 |
| -3 | 14.2 | 1.0 | 11.6 | 32.9 | 1.1 | 10.8 | 7.5 | 15.0 | 4.7 | 1.2 | 57.0 | 66.7 | 20.2 | 3.3 |
| -4 | 15.0 | 1.1 | 13.3 | 37.2 | 1.0 | 17.7 | 2.8 | 9.1 | 2.2 | 0.7 | 66.5 | 78.7 | 25.4 | 3.0 |
| -5 | 16.2 | 1.2 | 8.6 | 31.4 | 2.3 | 9.8 | 6.7 | 19.3 | 3.5 | 0.9 | 66.5 | 74.2 | 21.3 | 3.5 |
| -6 | 14.6 | 1.7 | 10.5 | 28.0 | 1.4 | 14.1 | 7.8 | 15.1 | 5.7 | 1.2 | 54.9 | 66.1 | 17.7 | 3.7 |
| -7 | 14.2 | 1.7 | 14.5 | 31.6 | 1.0 | 11.4 | 7.3 | 13.5 | 3.9 | 0.9 | 56.3 | 65.0 | 19.2 | 3.4 |
| -8 | 14.7 | 1.2 | 10.8 | 34.9 | 1.0 | 15.4 | 4.1 | 13.6 | 3.2 | 1.2 | 67.0 | 76.9 | 26.7 | 2.9 |
| -9 | 15.8 | 1.1 | 8.0 | 25.5 | 1.7 | 8.6 | 9.2 | 22.6 | 5.7 | 1.7 | 62.0 | 71.0 | 22.9 | 3.1 |
| -10 | 16.5 | 1.4 | 9.3 | 32.9 | 1.9 | 10.7 | 6.2 | 16.3 | 3.5 | 1.2 | 64.4 | 72.4 | 26.4 | 2.7 |
| -11 | 14.4 | 1.0 | 9.1 | 35.2 | 1.9 | 14.7 | 5.5 | 14.3 | 3.0 | 0.8 | 64.1 | 72.2 | 22.0 | 3.3 |
| -12 | 15.0 | 1.5 | 16.1 | 24.7 | 1.2 | 8.4 | 8.5 | 17.0 | 6.3 | 1.3 | 55.3 | 66.8 | 17.1 | 3.9 |
| Ave | 15.0 | 1.3 | 11.1 | 31.5 | 1.4 | 12.4 | 6.4 | 15.3 | 4.3 | 1.2 | 61.2 | 71.1 | 21.9 | 3.3 |
| 1890-6-2-1 | 13.8 | 1.1 | 8.4 | 28.6 | 3.0 | 10.4 | 7.5 | 17.9 | 7.0 | 2.2 | 58.2 | 70.4 | 24.1 | 2.9 |
| -2 | 13.3 | 1.3 | 15.7 | 31.0 | 0.9 | 13.2 | 6.8 | 12.2 | 4.8 | 0.9 | 52.8 | 64.1 | 15.1 | 4.2 |
| -3 | 18.2 | 1.8 | 6.5 | 31.0 | 3.1 | 13.7 | 5.5 | 14.5 | 4.2 | 1.4 | 61.9 | 72.4 | 24.9 | 2.9 |
| -4 | 16.9 | 1.6 | 8.6 | 34.0 | 1.0 | 15.8 | 3.8 | 13.1 | 3.5 | 1.5 | 66.5 | 77.4 | 30.2 | 2.6 |
| -5 | 15.1 | 1.7 | 10.7 | 30.1 | 1.9 | 8.9 | 7.8 | 16.0 | 6.4 | 1.4 | 55.0 | 67.2 | 18.0 | 3.7 |
| Ave | 15.5 | 1.5 | 10.0 | 31.0 | 2.0 | 12.4 | 6.3 | 14.7 | 5.2 | 1.5 | 58.9 | 70.3 | 22.5 | 3.3 |

Fatty acid compositions listed in Table 8 are expressed as weight percent (wt. %).
16:0=palmitic acid, 18:0=stearic acid, 18:1=oleic acid, LA=linoleic acid, GLA=gamma-linoleic acid, ALA=alpha-linolenic acid, EDA=eicosadienoic acid, DGLA= dihomo-gamma-Linolenic, ERA=eicosatrienoic acid, ETA=eicosatetraenoic acid.

Fatty Acid Composition (wt.%)

| Event | Embryos Analyzed | 16:0 | 18:0 | 18:1 | LA | GLA | ALA | EDA | HGLA | ARA | ERA | JUN | ETA | EPA | DPA | Other | Total delta-8 %Desat |
|---|---|---|---|---|---|---|---|---|---|---|---|---|---|---|---|---|---|
| 4802-1-7 | 10 | 14.3 | 2.0 | 10.9 | 33.2 | 0.9 | 11.2 | 1.8 | 4.6 | 0.3 | 2.3 | 2.7 | 4.3 | 9.9 | 0.1 | 1.5 | 73.8 |
| 4802-5-1 | 10 | 14.1 | 3.2 | 12.4 | 3.8 | 0.0 | 33.7 | 0.6 | 1.1 | 0.6 | 5.2 | 2.2 | 10.9 | 9.3 | 0.1 | 2.8 | 73.7 |
| 4802-6-1 | 10 | 17.0 | 2.1 | 16.6 | 24.2 | 0.6 | 11.1 | 3.0 | 3.4 | 0.1 | 3.2 | 4.0 | 3.6 | 8.9 | 0.0 | 2.0 | 61.1 |
| 4801-8-1 | 10 | 18.1 | 3.0 | 17.0 | 4.7 | 0.0 | 31.7 | 0.1 | 0.8 | 0.0 | 5.3 | 4.3 | 5.5 | 7.5 | 0.0 | 1.9 | 58.3 |
| 4802-1-1 | 10 | 16.3 | 5.2 | 11.0 | 32.0 | 0.3 | 19.0 | 0.5 | 1.1 | 0.1 | 1.7 | 2.3 | 1.4 | 7.4 | 0.1 | 1.9 | 69.3 |
| 4801-2-11 | 9 | 16.5 | 3.1 | 15.1 | 30.0 | 0.7 | 9.6 | 3.2 | 5.2 | 0.3 | 2.8 | 2.3 | 2.4 | 7.2 | 0.2 | 1.5 | 64.8 |
| 4801-4-9 | 10 | 16.3 | 2.8 | 16.4 | 31.9 | 0.7 | 11.2 | 1.1 | 4.3 | 0.1 | 1.6 | 1.3 | 3.4 | 7.1 | 0.1 | 1.6 | 78.8 |
| 4802-3-14 | 7 | 13.9 | 2.5 | 14.6 | 36.2 | 0.8 | 13.6 | 0.9 | 3.6 | 1.7 | 0.7 | 1.2 | 1.2 | 6.7 | 0.2 | 2.1 | 82.5 |
| 4801-1-9 | 10 | 13.8 | 2.5 | 20.3 | 2.9 | 0.0 | 42.0 | 0.0 | 0.2 | 0.0 | 1.6 | 1.7 | 5.5 | 6.6 | 0.0 | 3.0 | 79.1 |
| 4801-4-2 | 10 | 16.3 | 2.6 | 22.1 | 5.3 | 0.1 | 28.6 | 0.7 | 1.2 | 0.0 | 5.9 | 3.6 | 4.8 | 6.6 | 0.1 | 2.2 | 55.4 |

DELTA-8 DESATURASE AND ITS USE IN MAKING POLYUNSATURATED FATTY ACIDS

This application claims the benefit of U.S. Provisional Application No. 60/795,810, filed Apr. 28, 2006, and U.S. Provisional Application No. 60/837,789, filed Aug. 15, 2006, the entire contents of which are herein incorporated by reference.

FIELD OF THE INVENTION

This invention pertains to a polynucleotide sequence encoding a delta-8 desaturase and the use of this desaturase in making long-chain polyunsaturated fatty acids (PUFAs).

BACKGROUND OF THE INVENTION

Fatty acids (lipids) are water-insoluble organic biomolecules that can be extracted from cells and tissues by nonpolar solvents such as chloroform, ether or benzene. Lipids have several important biological functions, serving as (1) structural components of membranes; (2) storage and transport forms of metabolic fuels; (3) a protective coating on the surface of many organisms; and, (4) cell-surface components concerned in cell recognition, species specificity and tissue immunity. More specifically, polyunsaturated fatty acids (PUFAs) are important components of the plasma membrane of the cell, where they may be found in such forms as phospholipids and also can be found in triglycerides. PUFAs also serve as precursors to other molecules of importance in human beings and animals, including the prostacyclins, leukotrienes and prostaglandins. There are two main families of PUFAs (i.e., the omega-3 fatty acids and the omega-6 fatty acids).

The human body is capable of producing most of the PUFAs which it requires to function. However, eicosapentaenoic acid (EPA; 20:5, delta-5,8,11,14,17) and docosahexaenoic acid (DHA; 22:6, delta-4,7,10,13,16,19) cannot be synthesized efficiently by the human body and thus must be supplied through the diet. Since the human body cannot produce adequate quantities of these PUFAs, they are called essential fatty acids. Because of their important roles in human health and nutrition, EPA and DHA are the subject of much interest as discussed herein.

DHA is a fatty acid of the omega-3 series according to the location of the last double bond in the methyl end. It is synthesized via alternating steps of desaturation and elongation (see FIG. 12). Production of DHA is important because of its beneficial effect on human health. For example, increased intake of DHA has been shown to be beneficial or have a positive effect in inflammatory disorders (e.g., rheumatoid arthritis), Type II diabetes, hypertension, atherosclerosis, depression, myocardial infarction, thrombosis, some cancers and for prevention of the onset of degenerative disorders such as Alzheimer's disease. Currently the major sources of DHA are oils from fish and algae.

EPA and arachidonic acid (AA or ARA; 20:4, delta-5,8,11, 14) are both delta-5 essential fatty acids. EPA belongs to the omega-3 series with five double bonds in the acyl chain, is found in marine food, and is abundant in oily fish from the North Atlantic. Beneficial or positive effects of increased intake of EPA have been shown in patients with coronary heart disease, high blood pressure, inflammatory disorders, lung and kidney diseases, Type II diabetes, obesity, ulcerative colitis, Crohn's disease, anorexia nervosa, burns, osteoarthritis, osteoporosis, attention deficit/hyperactivity disorder and early stages of colorectal cancer (see, for example, the review of McColl, J., *NutraCos.* 2(4):35-40 (2003)).

AA belongs to the omega-6 series with four double bonds. The lack of a double bond in the omega-3 position confers on AA different properties than those found in EPA. The eicosanoids produced from AA have strong inflammatory and platelet aggregating properties, whereas those derived from EPA have anti-inflammatory and anti-platelet aggregating properties. AA is recognized as the principal omega-6 fatty acid found in the human brain and an important component of breast milk and many infant formulas, based on its role in early neurological and visual development. AA can be obtained from some foods (such as meat, fish, and eggs), but the concentration is low.

Gamma-linolenic acid (GLA; 18:3, delta-6,9,12) is another essential fatty acid found in mammals. GLA is the metabolic intermediate for very long-chain omega-6 fatty acids and for various active molecules. In mammals, formation of long-chain PUFAs is rate-limited by delta-6 desaturation. Many physiological and pathological conditions such as aging, stress, diabetes, eczema, and some infections have been shown to depress the delta-6 desaturation step. In addition, GLA is readily catabolized from the oxidation and rapid cell division associated with certain disorders (e.g., cancer or inflammation).

As described above, research has shown that various omega fatty acids reduce the risk of heart disease, have a positive effect on children's development and on certain mental illnesses, autoimmune diseases and joint complaints. However, although there are many health benefits associated with a diet supplemented with these fatty acids, it is recognized that different PUFAs exert different physiological effects in the body (e.g., most notably, the opposing physiological effects of GLA and AA). Thus, production of oils using recombinant means is expected to have several advantages over production from natural sources. For example, recombinant organisms having preferred characteristics for oil production can be used, since the naturally occurring fatty acid profile of the host can be altered by the introduction of new biosynthetic pathways in the host and/or by the suppression of undesired pathways, thereby resulting in increased levels of production of desired PUFAs (or conjugated forms thereof) and decreased production of undesired PUFAs. Optionally, recombinant organisms can provide PUFAs in particular forms which may have specific uses; or, oil production can be manipulated such that the ratio of omega-3 to omega-6 fatty acids so produced is modified and/or a specific PUFA is produced without significant accumulation of other PUFA downstream or upstream products (e.g., production of oils comprising AA and lacking GLA).

The mechanism of PUFA synthesis frequently occurs via the delta-6 desaturation pathway. For example, long-chain PUFA synthesis in mammals proceeds predominantly by a delta-6 desaturation pathway, in which the first step is the delta-6 desaturation of linoleic acid (LA; 18:2, delta-9,12) and alpha-linolenic acid (ALA; 18:3, delta-9,12,15) to yield gamma-linolenic acid (GLA; 18:3, delta-6,9,12)) and stearidonic acid (STA; 18:4, delta-6,9,12,15), respectively. Further fatty acid elongation and desaturation steps give rise to arachidonic acid (AA or ARA) and eicosapentaenoic acid (EPA). Accordingly, genes encoding delta-6 desaturases, delta-6 elongase components (also identified as $C_{18/20}$ elongases) and delta-5 desaturases have been cloned from a variety of organisms including higher plants, algae, mosses, fungi, nematodes and humans. Humans can synthesize long-chain PUFAs from the essential fatty acids, LA and ALA; however biosynthesis of long-chain PUFAs is somewhat limited (they are regulated by dietary and hormonal changes), and LA and ALA must be obtained from the diet.

PCT Publication No. WO 02/26946 (published Apr. 4, 2002) describes isolated nucleic acid molecules encoding FAD4, FAD5, FAD5-2 and FAD6 fatty acid desaturase family members which are expressed in long-chain PUFA-producing organisms, e.g., *Thraustochytrium, Pythium irregulare, Schizichytrium* and *Crypthecodinium*. It is indicated that constructs containing the desaturase genes can be used in any expression system including plants, animals, and microorganisms for the production of cells capable of producing long-chain PUFAs.

PCT Publication No. WO 98/55625 (published Dec. 19, 1998) describes the production of PUFAs by expression of polyketide-like synthesis genes in plants.

PCT Publication No. WO 98/46764 (published Oct. 22, 1998) describes compositions and methods for preparing long-chain fatty acids in plants, plant parts and plant cells which utilize nucleic acid sequences and constructs encoding fatty acid desaturases, including delta-5 desaturases, delta-6 desaturases and delta-12 desaturases.

U.S. Pat. No. 6,075,183 (issued to Knutzon et al. on Jun. 13, 2000) describes methods and compositions for synthesis of long-chain PUFAs in plants.

U.S. Pat. No. 6,459,018 (issued to Knutzon et al. on Oct. 1, 2002) describes a method for producing STA in plant seed utilizing a construct comprising a DNA sequence encoding a delta-6 desaturase.

Spychalla et al. (*Proc. Natl. Acad. Sci. USA*, 94:1142-1147 (1997)) describes the isolation and characterization of a cDNA from *Caenorhabditis elegans* that, when expressed in *Arabidopsis*, encodes a fatty acid desaturase which can catalyze the introduction of an omega-3 double bond into a range of 18- and 20-carbon fatty acids.

An alternate pathway for the biosynthesis of AA and EPA operates in some organisms (i.e., the delta-9 elongase/delta-8 desaturase pathway). Here LA and ALA are first elongated to eicosadienoic acid (EDA; 20:2, delta-11,14) and eicosatrienoic acid (EtrA; 20:3, delta-11,14,17), respectively, by a delta-9 elongase. Subsequent delta-8 and delta-5 desaturation of these products yields AA and EPA. The delta-8 pathway is present inter alia, in euglenoid species where it is the dominant pathway for formation of 20-carbon PUFAs.

PCT Publication No. WO 2000/34439 (published Jun. 15, 2000) discloses amino acid and nucleic acid sequences for delta-5 and delta-8 desaturase enzymes. Based on the information presented in Applicants' Assignee's co-pending application having Provisional Application No. 60/583,041 filed Jun. 25, 2004 (U.S. application Ser. No. 11/166,003 filed Jun. 24, 2005 (PCT Publication No. WO 2006/012325 and WO 2006/012326; published Feb. 2, 2006)), it is apparent that the delta-8 desaturase nucleotide and amino acid sequences of PCT Publication No. WO 2000/34439 are not correct. However, the correct sequence is set forth in corresponding U.S. Pat. No. 6,825,017 (issued to Browse et al. on Nov. 30, 2004) that describes desaturases, in particular, delta-5 and delta-8 desaturases and their use in synthesizing PUFAs. Browse discloses the same delta-8 desaturase in U.S. Publication No. 2006090221 (published on Apr. 27, 2006).

Applicants' Assignee's co-pending application having U.S. application Ser. No. 11/166,003 filed Jun. 24, 2005 (PCT Publication No. WO 2006/012325 and WO 2006/012326; published Feb. 2, 2006) concerns a *Eulgena gracilis* delta-8 desaturase.

Wallis et al. (*Arch. Biochem. and Biophys.* 365(2):307-316 (May 1999)) describes the cloning of a gene that appears to encode a delta-8 desaturase in *Euglena gracilis*. This sequence appears to be the same sequence disclosed in PCT Publication No. WO 2000/34439.

Qi et al. (*Nat. Biotech.* 22(6):739-45 (2004)) describes the production of long-chain PUFAs using, among other things, a delta-8 desaturase from *Euglena gracilis*; however, the complete sequence of the delta-8 desaturase is not provided.

PCT Publication No. WO 2004/057001 (published Jul. 8, 2004) discloses amino acid and nucleic acid sequences for a delta-8 desaturase enzyme from *Euglena gracilis*.

PCT Publication No. WO 2005/103253 (published Apr. 22, 2005) discloses amino acid and nucleic acid sequences for a delta-8 desaturase enzyme from *Pavlova salina* (see also U.S. Publication No. 2005/0273885).

Sayanova et al. (*FEBS Lett.* 580:1946-1952 (2006)) describes the isolation of and characterization of a cDNA from the free living soil amoeba *Acanthamoeba castellanii* that, when expressed in *Arabidopsis*, encodes a $C_{20}$ delta-8 desaturase.

An expansive study of PUFAs from natural sources and from chemical synthesis are not sufficient for commercial needs. Therefore, it is of interest to find alternative means to allow production of commercial quantities of PUFAs. Biotechnology offers an attractive route for producing long-chain PUFAs in a safe, cost efficient manner in microorganisms and plants.

With respect to microorganisms, many algae, bacteria, molds and yeast can synthesize oils in the ordinary course of cellular metabolism. Thus, oil production involves cultivating the microorganism in a suitable culture medium to allow for oil synthesis, followed by separation of the microorganism from the fermentation medium and treatment for recovery of the intracellular oil. Attempts have been made to optimize production of fatty acids by fermentive means involving varying such parameters as microorganisms used, media and conditions that permit oil production. However, these efforts have proved largely unsuccessful in improving yield of oil or the ability to control the characteristics of the oil composition produced. One class of microorganisms that has not been previously examined as a production platform for PUFAs (prior to work by the Applicants' Assignee), however, are the oleaginous yeasts. These organisms can accumulate oil up to 80% of their dry cell weight. The technology for growing oleaginous yeast with high oil content is well developed (for example, see EP 0 005 277 B1; Ratledge, C., *Prog. Ind. Microbiol.* 16:119-206 (1982)), and may offer a cost advantage compared to commercial micro-algae fermentation for production of omega-3 or omega-6 PUFAs. Whole yeast cells may also represent a convenient way of encapsulating omega-3 or omega-6 PUFA-enriched oils for use in functional foods and animal feed supplements.

Applicants' Assignee's co-pending application having U.S. Provisional Application No. 60/739,989 filed Nov. 23, 2005, discloses a delta-9 elongase from *Eulgena gracils*.

WO 02/077213 (published Oct. 3, 2002) describes isolated nucleic acid molecules encoding a fatty acid elongase with specificity for linoleic acid or alpha-linolenic acid from *Isochrysis galbana* (i.e., delta-9 elongase).

U.S. Pat. No. 6,403,349 (issued Jun. 11, 2002) concerns the identification of nucleotide and amino acid sequences of an elongase gene derived from *Mortierella alpina*.

PCT Publication No. WO 2004/101757 and PCT Publication No. WO 2004/101753 (published Nov. 25, 2004) concern the production of PUFAs in oleaginous yeasts and are Applicants' Assignee's copending applications.

PCT Publication No. WO 2004/071467 (published Aug. 26, 2004) concerns the production of PUFAs in plants, while PCT Publication No. WO 2004/071178 (published Aug. 26, 2004) concerns annexin promoters and their use in expression of transgenes in plants; both are Applicants' Assignee's copending applications.

Applicants' Assignee's copending applications having U.S. application Ser. No. 10/985,109 and U.S. application Ser. No. 10/985,254 filed Nov. 10, 2004 (PCT Publication No. 2005/047479 and PCT Publication No. 2005/047480; published May 26, 2005) concerns delta-15 desaturase genes suitable for increasing levels of omega-3 fatty acids.

Applicants' Assignee's copending applications also include U.S. application Ser. No. 11/265,761 filed Nov. 2, 2005, U.S. application Ser. No. 11/264,784 filed Nov. 1, 2005, and U.S. application Ser. No. 11/264,737 filed Nov. 1, 2005 (methods of making EPA, ARA and DHA, respectively, in *Yarrowia lipolytica*), each claiming benefit of an earlier provisional filing date of Nov. 4, 2004.

SUMMARY OF THE INVENTION

The invention concerns an isolated polynucleotide comprising:
   (a) a nucleotide sequence encoding a polypeptide having delta-8 desaturase activity, wherein the polypeptide has at least 80% amino acid identity, based on the Clustal V method of alignment, when compared to an amino acid sequence as set forth in SEQ ID NO:16;
   (b) a nucleotide sequence encoding a polypeptide having delta-8 desaturase activity, wherein the nucleotide sequence has at least 80% sequence identity, based on the BLASTN method of alignment, when compared to a nucleotide sequence as set forth in SEQ ID NO:15; or
   (c) a complement of the nucleotide sequence of (a) or (b), wherein the complement and the nucleotide sequence consist of the same number of nucleotides and are 100% complementary.

In a second embodiment, the invention concerns codon optimization, specifically, an isolated nucleic acid molecule which encodes a delta-8 desaturase enzyme as set forth in SEQ ID NO:57 wherein at least 162 codons are codon-optimized for expression in *Yarrowia* sp.

In a third embodiment, the invention concerns a recombinant DNA construct comprising any of the polynucleotides of the invention operably linked to at least one regulatory sequence.

In a fourth embodiment, the invention concerns a cell comprising the recombinant DNA construct of the invention. Of interest are cells selected from the group consisting of plants and yeast.

In a fifth embodiment, the invention concerns a transformed *Yarrowia* sp. comprising the recombinant construct of the invention.

In a sixth embodiment, the invention concerns a method for transforming a cell, comprising transforming a cell with the recombinant construct of the invention and selecting those cells transformed with the recombinant construct of the invention.

In a seventh embodiment, the invention concerns a method for producing a transformed plant comprising transforming a plant cell with a polynucleotide of the invention and regenerating a plant from the transformed plant cell. A preferred plant is soybean.

In an eighth embodiment, the invention concerns a method for producing yeast comprising transforming a yeast cell with a polynucleotide of the invention and growing yeast from the transformed yeast cell and, in particular, oleaginous yeast.

In a ninth embodiment, the invention concerns a seed comprising the recombinant construct of the invention.

In a tenth embodiment, the invention concerns method for making long-chain polyunsaturated fatty acids in a cell comprising:
   (a) transforming a cell with the recombinant construct of the invention;
   (b) selecting those transformed cells that make long-chain polyunsaturated fatty acids.

In an eleventh embodiment, the invention concerns oil obtained from seed comprising the recombinant construct of the invention or yeast comprising the recombinant construct of the invention.

In a twelfth embodiment, the invention concerns a method for making long-chain polyunsaturated fatty acids in a plant cell comprising:
   (a) transforming a cell with the recombinant construct of the invention; and
   (b) selecting those transformed cells that make long-chain polyunsaturated fatty acids.

In a thirteenth embodiment, the invention concerns a method for producing at least one polyunsaturated fatty acid in a soybean cell comprising:
   (a) transforming a soybean cell with a first recombinant DNA construct comprising an isolated polynucleotide encoding at least one delta-8 desaturase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase;
   (b) regenerating a soybean plant from the transformed cell of step (a); and
   (c) selecting those seeds obtained from the plants of step (b) having an altered level of polyunsaturated fatty acids when compared to the level in seeds obtained from a nontransformed soybean plant.

In a fourteenth embodiment, the invention concerns an oilseed plant comprising:
   (a) a first recombinant DNA construct comprising an isolated polynucleotide encoding at least one delta-8 desaturase polypeptide, operably linked to at least one regulatory sequence; and
   (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase.

Also of interest are seeds obtained from such oilseed plants and oil obtained from these seeds.

In a fifteenth embodiment, the invention concerns food or feed which incorporates oil of the invention.

In a sixteenth embodiment, the invention concerns food or feed comprising an ingredient derived from the processing of the seeds of the invention.

In an seventeenth embodiment, the invention concerns an isolated polynucleotide comprising a nucleotide sequence encoding a polypeptide having delta-8 desaturase activity, wherein the nucleotide sequence has at least 90% sequence identity, based on the BLASTN method of alignment, when compared to a nucleotide sequence as set forth in SEQ ID NO:15.

In an eighteenth embodiment, the invention concerns method for making long-chain polyunsaturated fatty acids in a cell having a reduced level of by-product fatty acids, said method comprising:
(a) transforming a host cell with at least one recombinant DNA construct comprising an isolated polynucleotide encoding at least two delta-8 desaturases operably linked to at least one regulatory sequence; and
(b) selecting those transformed host cells obtained having a reduced level of by-product fatty acids, when compared to the level of such by-product fatty acids in a transformed host cell having at least one recombinant DNA construct comprising an isolated polynucleotide encoding one delta-8 desaturase operably linked to a regulatory sequence.

Biological Deposits

The following plasmids have been deposited with the American Type Culture Collection (ATCC), 10801 University Boulevard, Manassas, Va. 20110-2209, and bear the following designations, Accession Numbers and dates of deposit (Table 1).

TABLE 1

ATCC Deposits

| Plasmid | Accession Number | Date of Deposit |
|---|---|---|
| pKR72 | PTA-6019 | May 28, 2004 |
| pKR578 | PTA-6280 | Nov. 4, 2004 |
| pKR903 | PTA-7494 | Apr. 12, 2006 |

BRIEF DESCRIPTION OF THE DRAWINGS AND SEQUENCE LISTINGS

The invention can be more fully understood from the following detailed description and the accompanying drawings and Sequence Listing, which form a part of this application.

The sequence descriptions summarize the Sequences Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

FIGS. 8A and 8B show a table of the fatty acid profiles from somatic soybean embryos expressing the *Pavlova lutheri* delta-8 desaturase and *Isochrysis galbana* delta-9 elongase (see Example 12).

Figure 9:
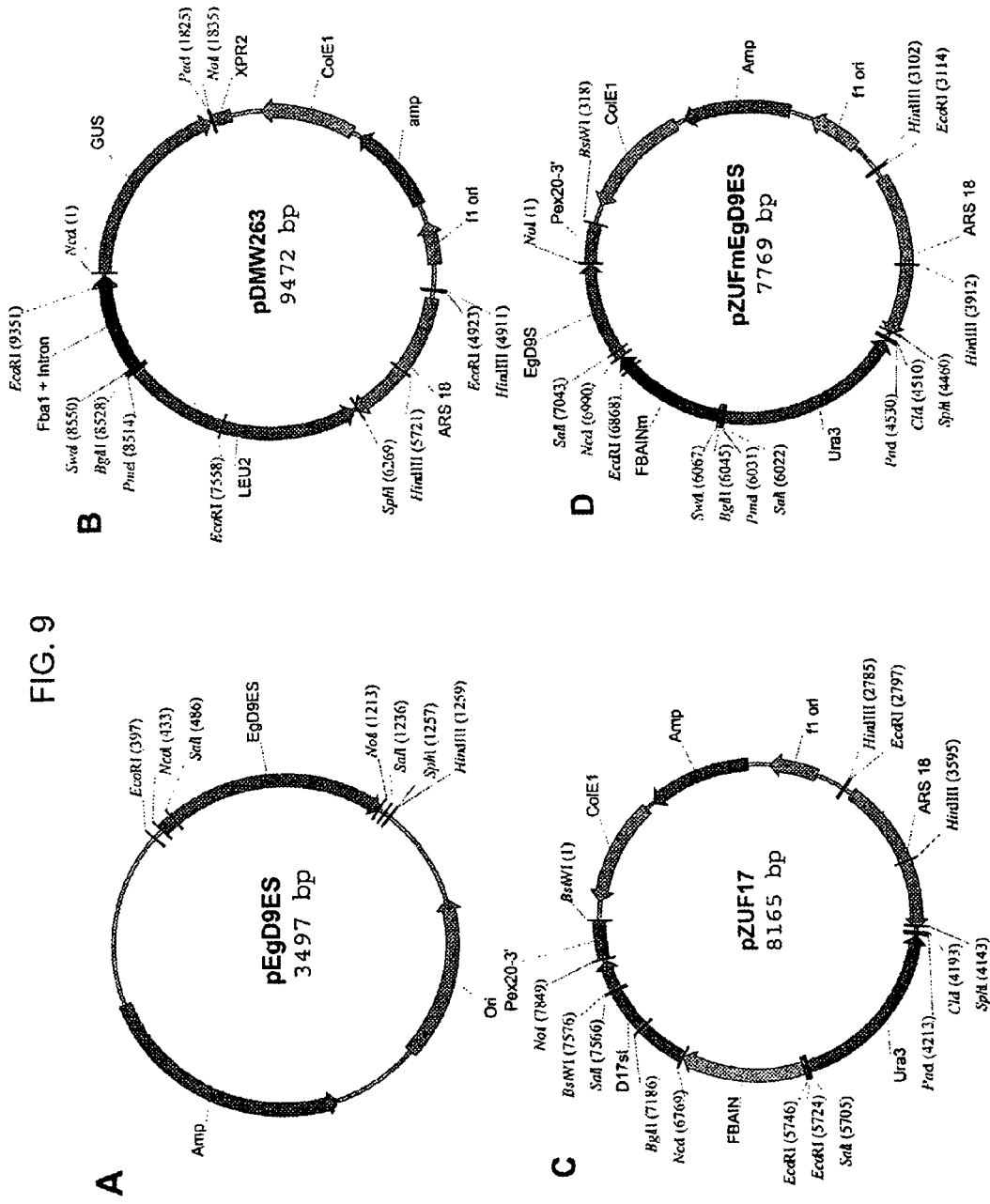

FIGS. 9-A, 9-B, 9-C and 9-D are maps of plasmids pEgD9ES, pDMW263, pZUF17 and pZUFmEgD9ES.

Figure 10:
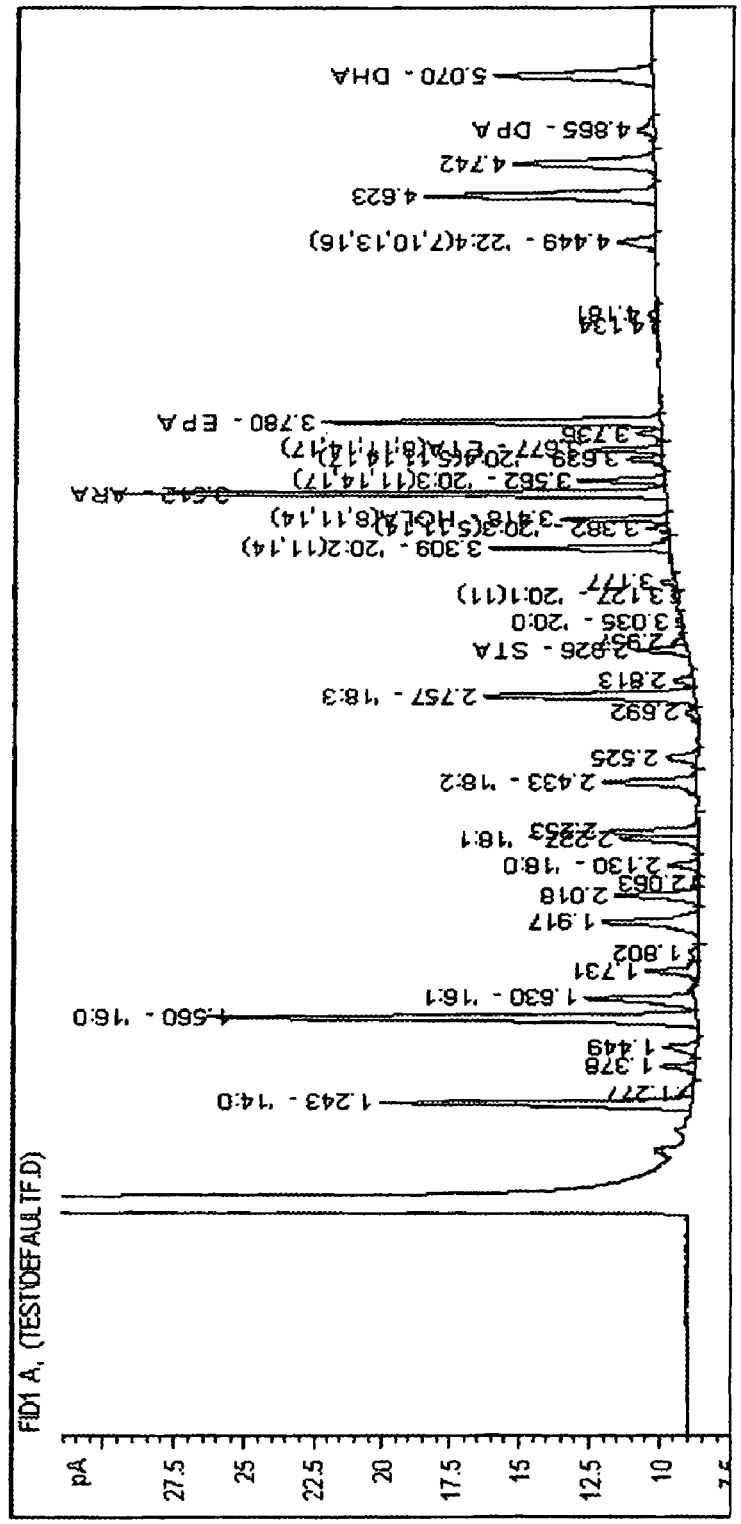

FIG. 10 shows a chromatogram of the lipid profile of an *Euglena gracilis* cell extract as described in the Examples.

Figure 11:
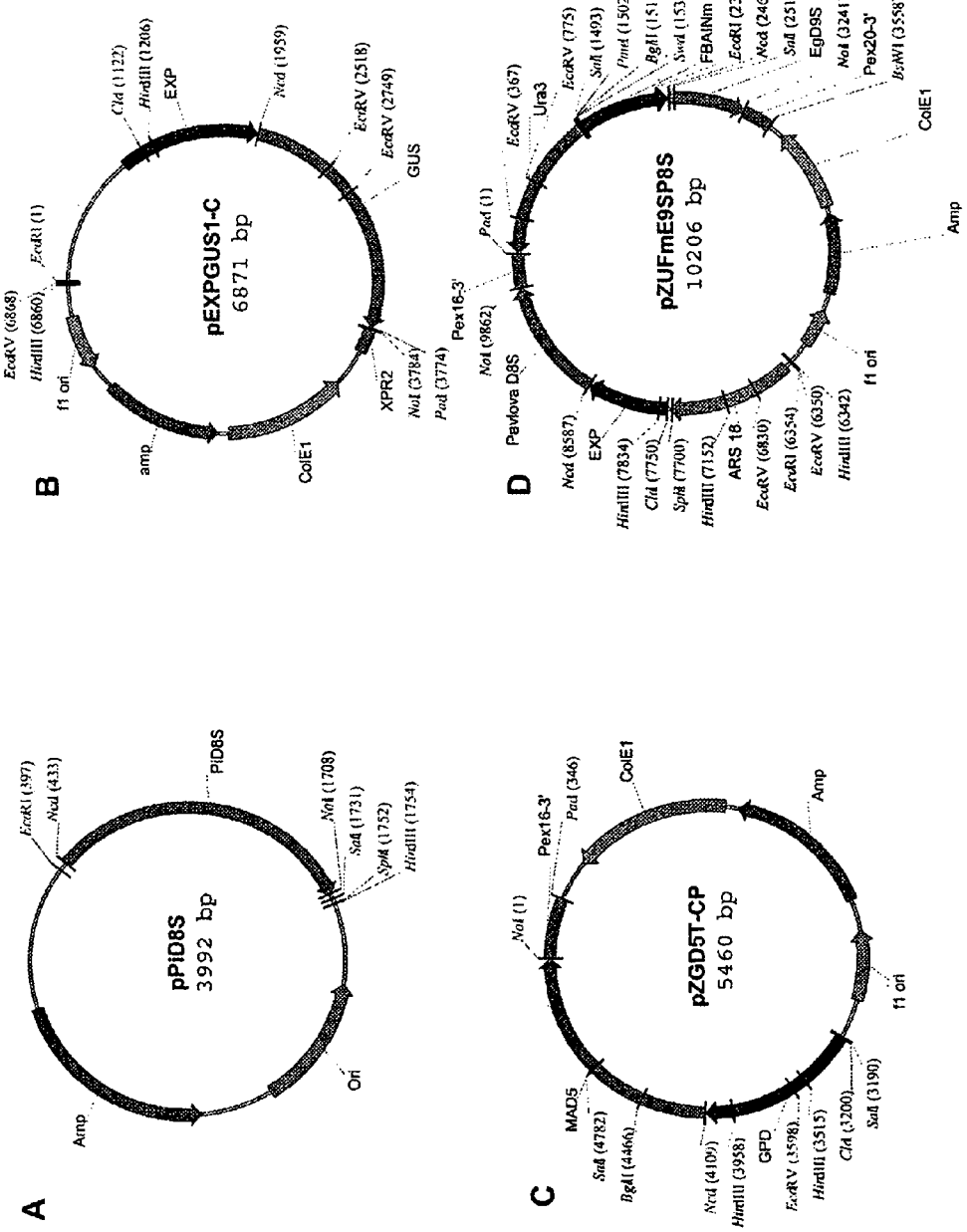

FIGS. 11-A, 11-B, 11-C and 11-D is a map of plasmids pPiD8S, pEXPGUS1-C and pZGD5T-CP and pZUFmE9SP8S.

Figure 12:
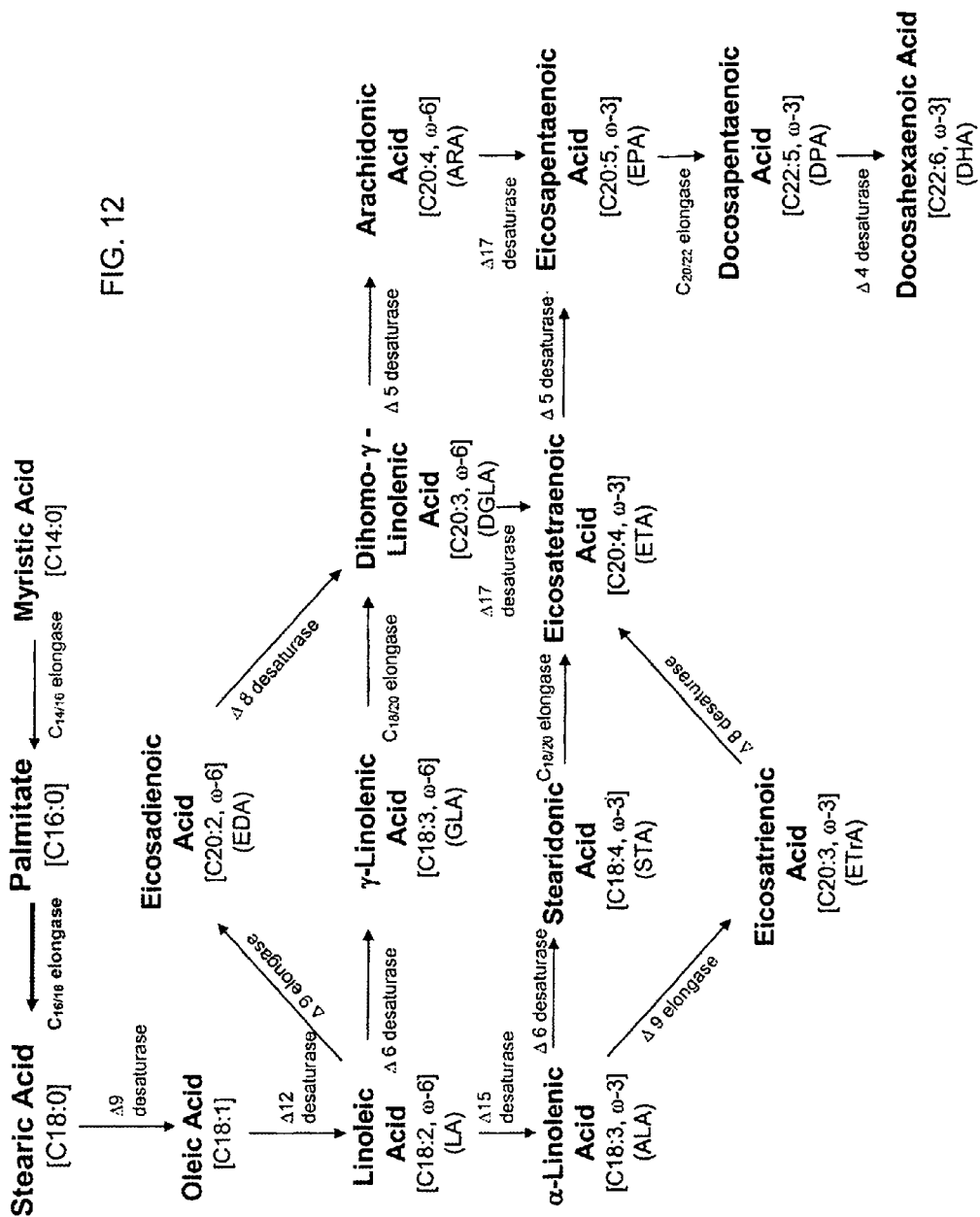

FIG. 12 is a representative omega-3 and omega-6 fatty acid pathway providing for the conversion of myristic acid through various intermediates to docosahexaenoic acid (DHA).

Figure 13A:
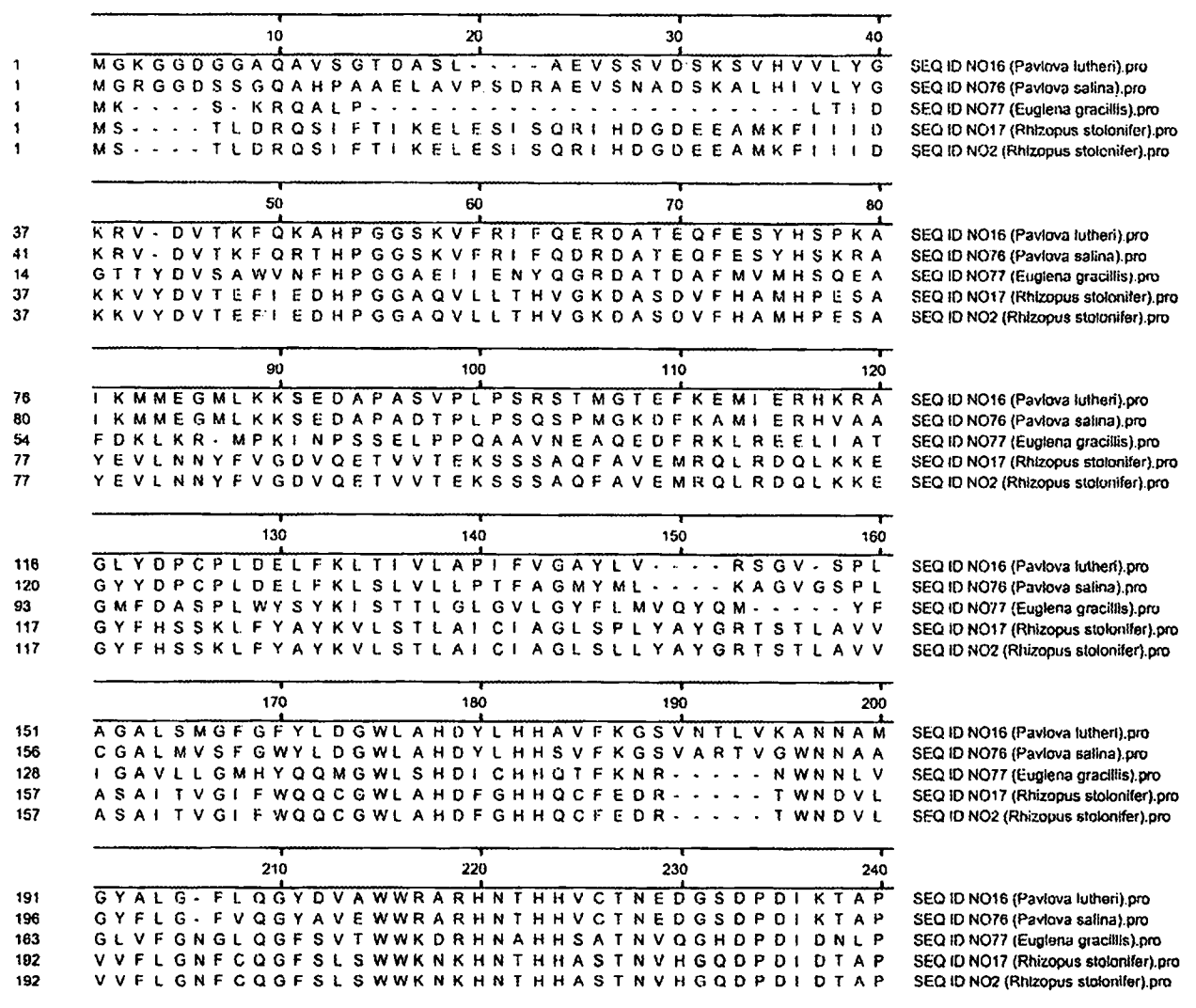
Figure 13B:
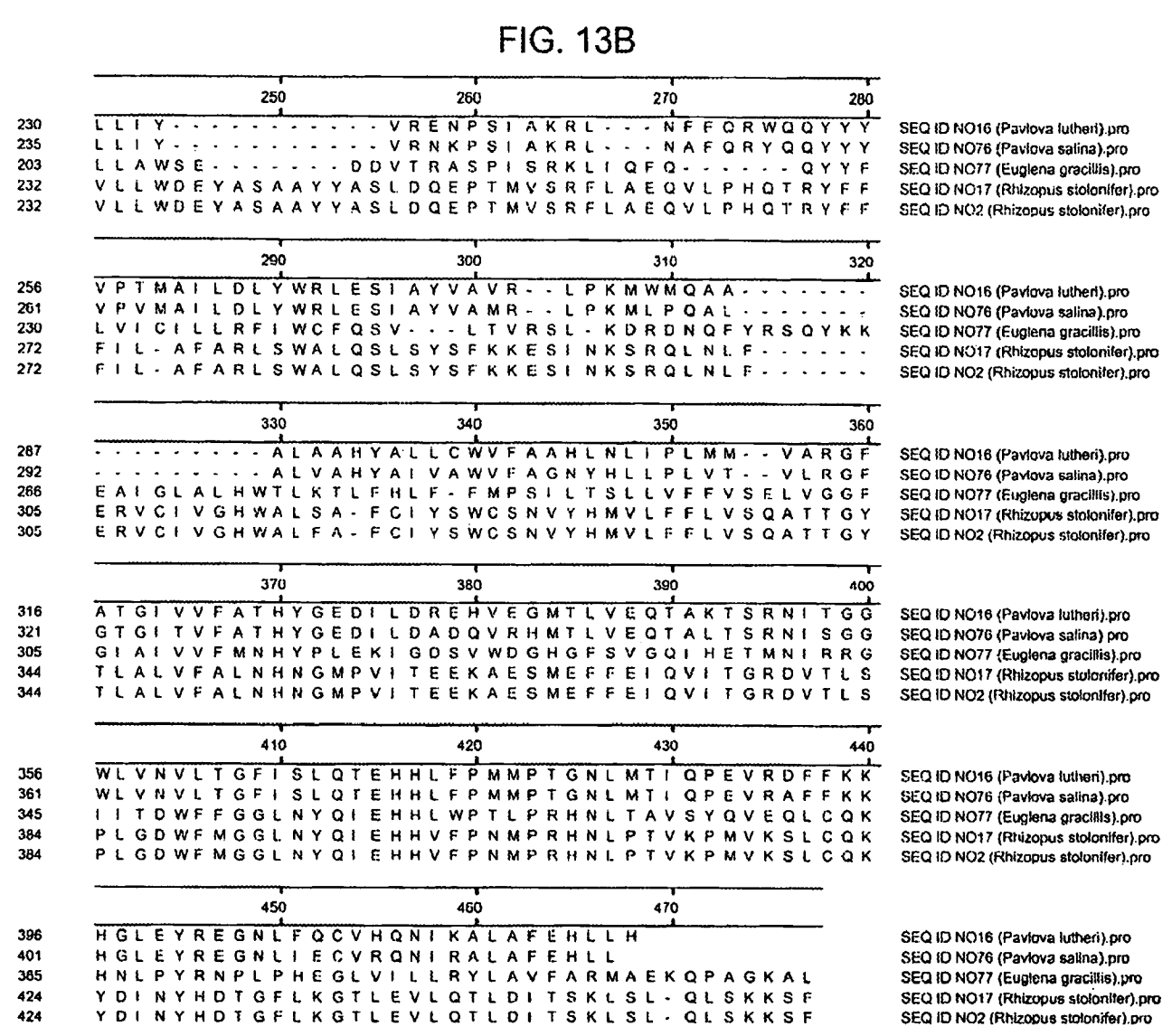

FIGS. 13A and 13B show a Clustal V alignment (with default parameters) of SEQ ID NO:16 (the amino acid sequence of the delta-8 desaturase of the instant invention), SEQ ID NO:76 (the amino acid sequence of *Pavlova salina* delta-8 desaturase sequence disclosed as SEQ ID NO:1 in PCT Publication No. WO 2005/103253; published Apr. 22, 2005), SEQ ID NO:77 (the amino acid sequence of *Euglena gracilis* delta-8 desaturase sequence disclosed as SEQ ID NO:2 in PCT Publication No. WO 2006/012325; published Feb. 2, 2006), SEQ ID NO:17 (the amino acid sequence for the *Rhizopus stolonifer* delta-6 fatty acid desaturase (NCBI Accession No. ABB96724 (GI 83027409), locus ABB96724, CDS DQ291156; Zhang et al., unpublished)) and SEQ ID NO:2 (the amino acid sequence for the *Rhizopus stolonifer* delta-6 fatty acid desaturase (NCBI Accession No. AAX22052 (GI 60499699), locus AAX22052, CDS AY795076; Lu et al., unpublished)).

Figure 7:
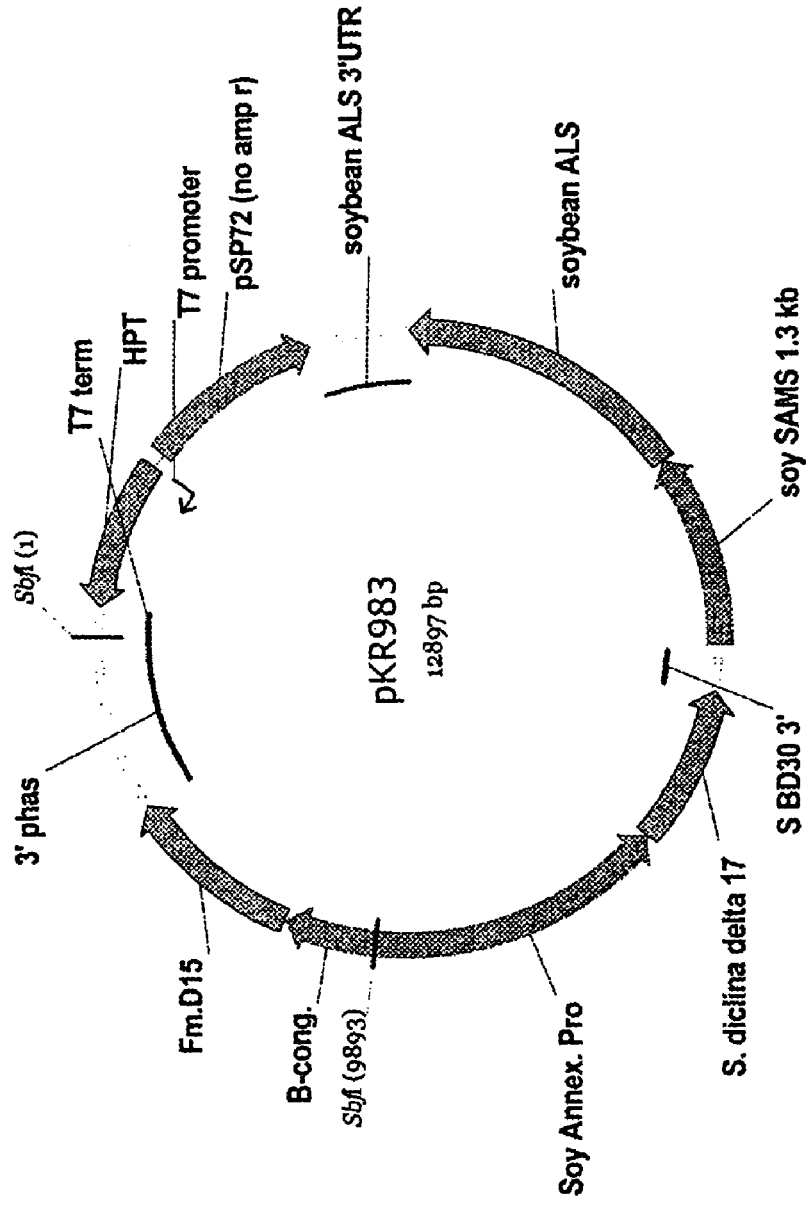
FIG. 7 is a map of plasmid pKR983 (soybean expression vector).

FIG. 14 shows the average fatty acid profile for the ten best EPA events of soybean embryogenic suspension culture (cv. Jack) transformed with the AscI fragments of pKR973 (SEQ ID NO:45, FIG. 5) and pKR983 (SEQ ID NO:56; FIG. 7) (see Example 22).

SEQ ID NO:1 is the sequence of the T7 primer.

SEQ ID NO:2 is the amino acid sequence for the *Rhizopus stolonifer* delta-6 fatty acid desaturase (NCBI Accession No. AAX22052 (GI 60499699), locus AAX22052, CDS AY795076; Lu et al., unpublished).

SEQ ID NO:3 is the sequence of a portion of the cDNA insert from clone eps1c.pk002.f22 (5' end of cDNA insert).

SEQ ID NO:4 is nucleotide sequence of the fully sequenced EST eps1c.pk002.f22:fis (full insert sequence—FIS).

SEQ ID NO:5 is the deduced amino acid sequence of SEQ ID NO:4 (clone eps1c.pk002.f22:fis).

SEQ ID NO:6 is the sequence of the SeqE primer.

SEQ ID NO:7 is the sequence of the SeqW primer.

SEQ ID NO:8 is the amino acid sequence of the *Mortierella alpina* delta-6 desaturase (NCBI Accession No. BAC82361 (GI 34221934), locus BAC82361, CDS AB070557; Sakuradani and Shimizu, *Biosci. Biotechnol. Biochem.* 67:704-711 (2003)).

SEQ ID NO:9 is the sequence of the AP1 universal primer.

SEQ ID NO:10 is the sequence of the GSP PvDES primer.

SEQ ID NO:11 is the sequence of the M13-28Rev primer.

SEQ ID NO:12 is the sequence of the PvDES seq primer.

SEQ ID NO:13 is the full 5' end sequence from genome walk of *Pavlova lutheri* delta-8 desaturase.

SEQ ID NO:14 is the nucleotide sequence of the *Pavlova lutheri* delta-8 desaturase of the instant invention.

SEQ ID NO:15 is the nucleotide sequence of the CDS of SEQ ID NO:14 (*Pavlova lutheri* delta-8 desaturase of the instant invention).

SEQ ID NO:16 is the deduced amino acid sequence of SEQ ID NO:15 (delta-8 desaturase of the instant invention).

SEQ ID NO:17 is the amino acid sequence for the *Rhizopus stolonifer* delta-6 fatty acid desaturase (NCBI Accession No.

ABB96724 (GI 83027409), locus ABB96724, CDS DQ291156; Zhang et al., unpublished).

SEQ ID NO:18 is the sequence of the PvDES5'Not-1 primer.

SEQ ID NO:19 is the sequence of the PvDES3'Not-1 primer.

SEQ ID NO:20 is the sequence of the GSP PvDES-2 primer.

SEQ ID NO:21 is the sequence of pY121.

SEQ ID NO:22 is the sequence of pKR123r.

SEQ ID NO:23 is the sequence of pKR900.

SEQ ID NO:24 is the sequence of pKR925.

SEQ ID NO:25 is the sequence of pKR902.

SEQ ID NO:26 is the sequence of pKR607.

SEQ ID NO:27 is the sequence of pKR903.

SEQ ID NO:28 is the sequence of the GPDsense primer.

SEQ ID NO:29 is the sequence of the GPDantisense primer.

SEQ ID NO:30 is the sequence of pY5-22GPD.

SEQ ID NO:31 is the sequence of pY118.

SEQ ID NO:32 is the nucleotide sequence of the CDS of *Euglena gracilis* delta-9 elongase.

SEQ ID NO:33 is the sequence of oEugEL1-1 primer.

SEQ ID NO:34 is the sequence of oEugEL1-2 primer.

SEQ ID NO:35 is the sequence of pKR906.

SEQ ID NO:36 is the sequence of pKR132.

SEQ ID NO:37 is the sequence of pKR953.

SEQ ID NO:38 is the sequence of pKR287.

SEQ ID NO:39 is the nucleotide sequence of the CDS of *Mortierella alpina* delta-5 desaturase, which is described in U.S. Pat. No. 6,075,183 and PCT Publication Nos. WO 2004/071467 and WO 2005/0479479.

SEQ ID NO:40 is the sequence of pKR277.

SEQ ID NO:41 is the sequence of pKR952.

SEQ ID NO:42 is the sequence of pKR457.

SEQ ID NO:43 is the sequence of the modified Kti/NotI/Kti3'Salb3' cassette.

SEQ ID NO:44 is the sequence of pKR970.

SEQ ID NO:45 is the sequence of pKR973.

SEQ ID NO:46 is the sequence of pKR72.

SEQ ID NO:47 is the sequence of pKR912.

SEQ ID NO:48 is the sequence of pKR886r.

SEQ ID NO:49 is the sequence of pKR271.

SEQ ID NO:50 is the sequence of pKR226.

SEQ ID NO:51 is the sequence of the oCon-1 primer.

SEQ ID NO:52 is the sequence of the oCon-2 primer.

SEQ ID NO:53 is the sequence of pKR179.

SEQ ID NO:54 is the sequence of pKR226.

SEQ ID NO:55 is the sequence of pKR582.

SEQ ID NO:56 is the sequence of pKR983.

SEQ ID NO:57 is the nucleotide sequence for the synthetic (codon-optimized) delta-8 desaturase derived from *Pavlova lutheri* codon-optimized for expression in *Yarrowia lipolytica*.

SEQ ID NO:58 is the sequence of pPiD8S.

SEQ ID NO:59 is the nucleotide sequence of the long-chain PUFA elongation enzyme from *Isochrysis galbana* (NCBI Accession No. AAL37626 (GI 17226123), locus AAL37626, CDS AF390174).

SEQ ID NO:60 is the 5' sequence of the cDNA insert from clone eeg1c.pk001.n5.f, while SEQ ID NO:61 is the 3' sequence of the cDNA insert from clone eeg1c.pk001.n5.f.

SEQ ID NO:61 is the 3' sequence of the cDNA insert from clone eeg1c.pk001.n5.f.

SEQ ID NO:62 is the sequence aligned from SEQ ID NO:60 and SEQ ID NO:61 (full cDNA sequence excluding polyA tail).

SEQ ID NO:63 is nucleotide sequence of the M13F universal primer.

SEQ ID NO:64 is the deduced amino acid sequence of SEQ ID NO:63 (delta-9 elongase—clone eeg1c.pk001.n5.f).

SEQ ID NO:65 amino acid sequence of the long-chain PUFA elongation enzyme from *Isochrysis galbana* (NCBI Accession No. AAL37626 (GI 17226123), locus AAL37626, CDS AF390174).

SEQ ID NO:66 is the nucleotide sequence of the synthetic (codon-optimized) delta-9 elongase derived from *Isochrysis galbana* codon-optimized for expression in *Yarrowia lipolytica*.

SEQ ID NO:67 is the sequence of pEgD9ES.

SEQ ID NO:68 is the sequence of pDMW263.

SEQ ID NO:69 is the sequence of pZUF17.

SEQ ID NO:70 is the sequence of pZUFmEgD9ES.

SEQ ID NO:71 is the sequence of pZUFmE9SP8S.

SEQ ID NO:72 is the sequence of pEXPGUS1-C.

SEQ ID NO:73 is the sequence of pZGD5T-CP.

SEQ ID NO:74 is the sequence of pYZDE2-S.

SEQ ID NO:75 is the sequence of pY5-22.

SEQ ID NO:76 is the amino acid sequence of *Pavlova salina* delta-8 desaturase sequence disclosed as SEQ ID NO:1 in PCT Publication No. WO 2005/103253 (published Apr. 22, 2005).

SEQ ID NO:77 is the amino acid sequence of *Eulgena gracilis* delta-8 desaturase sequence disclosed as SEQ ID NO:2 in Applicants' Assignee's co-pending application having application Ser. No. 11/166,003 filed Jun. 24, 2005 (PCT Publication No. WO 2006/012325; published Feb. 2, 2006).

SEQ ID NO:78 is the sequence of pY5-30.

DETAILED DESCRIPTION OF THE INVENTION

All patents, patent applications, and publications cited herein are incorporated by reference in their entirety.

In the context of this disclosure, a number of terms shall be utilized.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Fatty acids are described herein by a simple notation system of "X:Y", wherein the number before the colon indicates the number of carbon atoms in the fatty acid and the number after the colon is the number of double bonds that are present. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c, 12c), GLA (18:3, 6c, 9c, 12c) and ALA (18:3, 9c, 12c, 15c)). Unless otherwise specified 18:1, 18:2 and 18:3 refer to oleic, LA and linolenic fatty acids. If not specifically written as otherwise, double bonds are assumed to be of the cis configuration. For instance, the double bonds in 18:2 (9, 12) would be assumed to be in the cis configuration.

A representative pathway is illustrated in FIG. 12, providing for the conversion of myristic acid through various intermediates to DHA, which demonstrates how both omega-3 and omega-6 fatty acids may be produced from a common source.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the delta-9 elongase metabolic pathway (delta-15 desaturase, delta-9 elongase, delta-8 desaturase, delta-5 desaturase and delta-17 desaturase), EDA, ERA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the delta-9 elongase metabolic pathway (delta-15 desaturase, delta-9 elongase, delta-8 desaturase, delta-5 desaturase and delta-17 desaturase), sciadonic acid (SCI) and juniperonic acid (JUP) also can be produced by the action of a delta-5 desaturase on either EDA or ERA, respectively. They are considered to be "by-product fatty acids" since neither can be further converted to EPA by the action of other metabolic pathway enzymes.

A metabolic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of omega-3 and omega-6 fatty acids, the abbreviations that will be used throughout the remainder of the specification, and each compounds' chemical name.

TABLE 2

Nomenclature of Polyunsaturated Fatty Acids

| Common Name | Abbreviation | Chemical Name | Shorthand Notation |
| --- | --- | --- | --- |
| oleic | — | cis-9-octadecenoic | 18:1 |
| linoleic | LA | cis-9,12-octadecadienoic | 18:2 ω-6 |
| gamma-linolenic | GLA | cis-6,9,12-octadecatrienoic | 18:3 ω-6 |
| eicosadienoic | EDA | cis-11,14-eicosadienoic | 20:2 ω-6 |
| dihomo-gamma-linolenic | DGLA or HGLA | cis-8,11,14-eicosatrienoic | 20:3 ω-6 |
| sciadonic | SCI | cis-5,11,14-eicosatrienoic | 20:3b ω-6 |
| arachidonic | AA or ARA | cis-5,8,11,14-eicosatetraenoic | 20:4 ω-6 |
| alpha-linolenic | ALA | cis-9,12,15-octadecatrienoic | 18:3 ω-3 |
| stearidonic | STA | cis-6,9,12,15-octadecatetraenoic | 18:4 ω-3 |
| eicosatrienoic | ETrA or ERA | cis-11,14,17-eicosatrienoic | 20:3 ω-3 |

TABLE 2-continued

Nomenclature of Polyunsaturated Fatty Acids

| Common Name | Abbreviation | Chemical Name | Shorthand Notation |
| --- | --- | --- | --- |
| eicosa-tetraenoic | ETA | cis-8,11,14,17-eicosatetraenoic | 20:4 ω-3 |
| juniperonic | JUP | cis-5,11,14,17-eicosatrienoic | 20:4b ω-3 |
| eicosa-pentaenoic | EPA | cis-5,8,11,14,17-eicosapentaenoic | 20:5 ω-3 |
| docosa-pentaenoic | DPA | cis-7,10,13,16,19-docosapentaenoic | 22:5 ω-3 |
| docosa-hexaenoic | DHA | cis-4,7,10,13,6,19-docosahexaenoic | 22:6 ω-3 |

The term "essential fatty acid" refers to a particular PUFA that an organism must ingest in order to survive, being unable to synthesize the particular essential fatty acid de novo. For example, mammals can not synthesize the essential fatty acid LA. Other essential fatty acids include, but are not limited to, GLA, DGLA, AA, EPA and DHA.

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeasts and filamentous fungi. "Microbial oils" or "single cell oils" are those oils naturally produced by microorganisms during their lifespan. Such oils can contain long-chain PUFAs.

The term "PUFA biosynthetic pathway" refers to a metabolic process that converts oleic acid to LA, EDA, GLA, DGLA, AA, ALA, STA, ETrA, ETA, EPA, DPA and DHA. This process is well described in the literature (e.g., see PCT Publication No. WO 2005/003322). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzymes" refer to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/16}$ elongase, a $C_{16/18}$ elongase, a $C_{18/20}$ elongase and/or a $C_{20/22}$ elongase.

"Desaturase" is a polypeptide which can desaturate one or more fatty acids to produce a mono- or poly-unsaturated fatty acid or precursor which is of interest. Of particular interest herein are delta-8 desaturases that will desaturate a fatty acid between the eighth and ninth carbon atom numbered from the carboxyl-terminal end of the molecule and that can, for example, catalyze the conversion of EDA to DGLA and/or ETrA to ETA. Other useful fatty acid desaturases include, for example, (1) delta-5 desaturases that catalyze the conversion of DGLA to AA and/or ETA to EPA; (2) delta-6 desaturases that catalyze the conversion of LA to GLA and/or ALA to STA; (3) delta-4 desaturases that catalyze the conversion of DPA to DHA; (4) delta-12 desaturases that catalyze the conversion of oleic acid to LA; (5) delta-15 desaturases that catalyze the conversion of LA to ALA and/or GLA to STA; (6) delta-17 desaturases that catalyze the conversion of AA to EPA and/or DGLA to ETA; and (7) delta-9 desaturases that catalyze the conversion of palmitate to palmitoleic acid (16:1) and/or stearate to oleic acid (18:1).

The term "elongase system" refers to a suite of four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., *Plant Cell* 8:281-292 (1996)). In the first step, which has been found to be both substrate-specific and also rate-limiting, malonyl-CoA is condensed with a long-chain acyl-CoA to yield carbon dioxide ($CO_2$) and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA, LA to EDA, ALA to ERA and EPA to DPA.

For the purposes herein, an enzyme catalyzing the first condensation reaction (i.e., conversion of malonyl-CoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{14/16}$ elongase will utilize a $C_{14}$ substrate (e.g., myristic), a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). In like manner, and of particular interest herein, a "delta-9 elongase" is able to catalyze the conversion of LA and ALA to EDA and ETrA. It is important to note that some elongases have broad specificity and thus a single enzyme may be capable of catalyzing several elongase reactions (e.g., thereby acting as both a $C_{16/18}$ elongase and a $C_{18/20}$ elongase).

In preferred embodiments, it is desirable to empirically determine the specificity of a fatty acid elongase by transforming a suitable host with the gene for the fatty acid elongase and determining its effect on the fatty acid profile of the host. Fatty acid elongases from different species can display great variability in substrate specificity. For example, *Mortierella alpina* delta-6 elongase acts as a $C_{18/20}$ elongase (elongation of GLA to DGLA) in yeast, but can additionally act as a $C_{20/22}$ elongation of LA or ALA to EDA or ETrA, respectively, in soybean The term "delta-9 elongase/delta-8 desaturase pathway" refers to a elongase for the elongation of EPA to DPA or as a delta-9 elongase for the biosynthetic pathway for production of long-chain PUFAs. This pathway, at a minimum, comprises a delta-9 elongase and a delta-8 desaturase, thereby enabling biosynthesis of DGLA and/or ETA from LA and ALA, respectively.

The term "delta-9 elongase" refers to an enzyme that is capable of catalyzing at least one elongase reaction such as the elongation of linoleic (LA) or alpha-linolenic acid (ALA) to EDA or ETrA, respectively. It may act as a $C_{16/18}$ elongase, $C_{18/20}$ elongase and $C_{20/22}$ elongase and may have alternate, but not preferred, specificities for delta-5 and delta-6 fatty acids such as EPA and/or GLA, respectively.

The term "delta-8 desaturase" refers to an enzyme that is capable of catalyzing at least one desaturation reaction such as the desaturation of eicosadienoic acid (EDA) or eicosatrienoic acid (ETrA) to DGLA or ETA, respectively. It acts as a $C_{20}$ desaturase.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5%

SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

"Sequence identity" or "identity" in the context of nucleic acid or polypeptide sequences refers to the nucleic acid bases or amino acid residues in the two sequences that are the same when aligned for maximum correspondence over a specified comparison window.

Thus, "percentage of sequence identity" refers to the valued determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASARGENE bioinformatics computing suite (DNASTAR Inc., Madison, Wis.). Multiple alignment of the sequences are performed using the Clustal V method of alignment (Higgins, D. G. and Sharp, P. M. (1989) *Comput. Appl. Biosci.* 5:151-153; Higgins, D. G. et al. (1992) *Comput Appl. Biosci.* 8:189-191) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 55% to 100%. Indeed, any integer amino acid identity from 50% to 100% may be useful in describing the present invention. Also, of interest is any full-length or partial complement of this isolated nucleotide fragment.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described below.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "expression cassette" as used herein, refers to a discrete nucleic acid fragment into which a nucleic acid sequence or fragment can be moved.

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., *Plant J.* 16:651-659 (1998); Gura, *Nature* 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050, published Oct. 21, 1999; PCT Publication No. WO 02/00904, published Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083, published Aug. 20, 1998). Both of these co-suppressing phenomena have not been elucidated mechanistically, although genetic evidence has begun to unravel this complex situation (Elmayan et al., *Plant Cell* 10:1747-1757 (1998)).

The term "oleaginous" refers to those organisms that tend to store their energy source in the form of lipid (Weete, In: Fungal Lipid Biochemistry, $2^{nd}$ Ed., Plenum, 1980). Generally, the cellular oil content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)).

The term "oleaginous yeast" refers to those microorganisms classified as yeasts that make oil. It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The "Clustal V method of alignment" corresponds to the alignment method labeled Clustal V (described by Higgins and Sharp, *CABIOS.* 5:151-153 (1989)) and found in the MegAlign™ program of the LASERGENE bioinformatics computing suite (DNASTAR Inc., Madison, Wis.). The "default parameters" are the parameters preset by the manufacturer of the program. For multiple alignments, they correspond to GAP PENALTY=10 and GAP LENGTH PENALTY=10; and, for pairwise alignments, they are KTUPLE 1, GAP PENALTY=3, WINDOW=5 and DIAGONALS SAVED=5. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

"Progeny" comprises any subsequent generation of a plant.

The present invention concerns an isolated polynucleotide comprising:
  (a) a nucleotide sequence encoding a polypeptide having delta-8 desaturase activity, wherein the polypeptide has at least 80% amino acid identity, based on the Clustal V method of alignment, when compared to an amino acid sequence as set forth in SEQ ID NO:16;
  (b) a nucleotide sequence encoding a polypeptide having delta-8 desaturase activity, wherein the nucleotide sequence has at least 90% sequence identity, based on the BLASTN method of alignment, when compared to a nucleotide sequence as set forth in SEQ ID NO:15; or
  (c) a complement of the nucleotide sequence of (a) or (b), wherein the complement and the nucleotide sequence consist of the same number of nucleotides and are 100% complementary.

In still another aspect, this invention concerns an isolated polynucleotide comprising a nucleotide sequence encoding a polypeptide having delta-8 desaturase activity, wherein the nucleotide sequence has at least 80% sequence identity, based on the BLASTN method of alignment, when compared to a nucleotide sequence as set forth in SEQ ID NO:15.

It was found that a comparison of SEQ ID NO:15 and SEQ ID NO:57 using the BLASTN method of alignment with default parameters showed that these sequences had at least 86% sequence identity.

This delta-8 desaturase may be used alone or in combination with other desaturase and elongase components to produce various omega-6 and omega-3 PUFAs, including e.g., DGLA, ETA, AA, EPA, DPA and/or DHA (FIG. 12). One skilled in the art will recognize the appropriate combinations of the delta-8 desaturase of the invention herein in conjunction with a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/16}$ elongase, a $C_{16/18}$ elongase, a $C_{18/20}$ elongase and/or a $C_{20/22}$ elongase, based on the particular host cell (and its native PUFA profile and/or desaturase and/or elongase profile), the availability of substrate, and the desired end product(s).

At times, it may be desirable to minimize by-product fatty acids. The relative abundance of by-product fatty acids could be decreased by increasing total delta-8 desaturase activity. One approach to minimize by-product fatty acids would be to express more than one delta-8 desaturase (i.e., the same or different delta-8 desaturase). For instance, the presence of sciadonic acid (SCI) and/or juniperonic acid (JUP), commonly found in the seed lipids of gymnosperms (Wolff et al., *Lipids* 35(1):1-22 (2000)), such as those in the Pinaceae family (pine), might be considered by-product fatty acids of a delta-6 desaturase or delta-9-elongase pathway. Although these fatty acids are considered to have various health-enhancing properties themselves (Nakane et al., *Biol. Pharm. Bull.* 23: 758-761 (2000)), their presence as by-product fatty acids in an engineered PUFA pathway, such as in an oilseed crop, may not be desirable depending on the application.

In another embodiment, this invention concerns a recombinant construct comprising the polynucleotide of the invention operably linked to at least one regulatory sequence.

As was noted above, a promoter is a DNA sequence that directs cellular machinery of a plant to produce RNA from the contiguous coding sequence downstream (3') of the promoter.

The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, Kunitz trypsin inhibitor 3 promoter, annexin promoter, Gly1 promoter, beta subunit of beta conglycinin promoter, P34/Gly Bd m 30K promoter, albumin promoter, Leg A1 promoter and Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205 (1994); Li, Texas A&M University Ph.D. dissertation, pp. 107-128 (1997)); (3) the *Arabidopsis* ubiquitin extension protein promoters (Callis et al., *J Biol. Chem.* 265(21):12486-93 (1990)); (4) a tomato ubiquitin gene promoter (Rollfinke et al., *Gene.* 211 (2):267-76 (1998)); (5) a soybean heat shock protein promoter (Schoffl et al., *Mol Gen Genet.* 217(2-3): 246-53 (1989)); and, (6) a maize H3 histone gene promoter (Atanassova et al., *Plant Mol Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A Laboratory Manual;* $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*; John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or group of tissues that constitute a morphologically and functionally distinct part of a plant. The term "genome" refers to the following: (1) the entire complement of genetic material (genes and non-coding sequences) is present in each cell of an organism, or virus or organelle; (2) a complete set of chromosomes inherited as a (haploid) unit from one parent.

Thus, this invention also concerns a method for transforming a cell, comprising transforming a cell with the recombinant construct of the invention and selecting those cells transformed with the recombinant construct of Claim 5.

Also of interest is a method for producing a transformed plant comprising transforming a plant cell with the polynucleotide of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, F. *Microbiol. Sci.* 4:24-28 (1987)). Transformation of soybeans using direct delivery of DNA has been published using PEG fusion (PCT Publication No. WO 92/17598), electroporation (Chowrira, G. M. et al., *Mol. Biotechnol.* 3:17-23 (1995); Christou, P. et al., *Proc. Natl. Acad. Sci. U.S.A.* 84:3962-3966 (1987)), microinjection, or particle bombardment (McCabe, D. E. et. al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones. See, for example: Sambrook et al., Molecular Cloning: A Laboratory Manual, Cold Spring Harbor: N.Y. (1989); Maliga et al., Methods in Plant Molecular Biology, Cold Spring Harbor: N.Y. (1995); Birren et al., Genome Analysis: Detecting Genes, Vol. 1, Cold Spring Harbor: N.Y. (1998); Birren et al., Genome Analysis: Analyzing DNA, Vol. 2, Cold Spring Harbor: N.Y. (1998); Plant Molecular Biology: A Laboratory Manual, eds. Clark, Springer: NY (1997).

Examples of oilseed plants include, but are not limited to, soybean, *Brassica* species, sunflower, maize, cotton, flax and safflower.

Examples of polyunsaturated fatty acids having at least twenty carbon atoms and five or more carbon-carbon double bonds include, but are not limited to, omega-3 fatty acids such as EPA, DPA and DHA. Seeds obtained from such plants are also within the scope of this invention as well as oil obtained from such seeds.

In one embodiment this invention concerns an oilseed plant comprising: a) a first recombinant DNA construct comprising an isolated polynucleotide encoding a delta-8 desaturase polypeptide, operably linked to at least one regulatory sequence; and b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-12 desaturase, a delta-15 desaturase, a delta-17 desaturase, a delta-9 elongase, a $C_{14/16}$ elongase, a $C_{16/18}$ elongase, a $C_{18/20}$ elongase and a $C_{20/22}$ elongase.

Such desaturases are discussed, for example, in U.S. Pat. Nos. 6,075,183, 5,968,809, 6,136,574, 5,972,664, 6,051,754, 6,410,288 and PCT Publication Nos. WO 98/46763, WO 98/46764, WO 00/12720 and WO 00/40705.

The choice of combination of cassettes used depends in part on the PUFA profile and/or desaturase/elongase profile of the oilseed plant cells to be transformed and the long-chain PUFA which is to be expressed.

In another aspect, this invention concerns a method for making long-chain polyunsaturated fatty acids in a plant cell comprising:
(a) transforming a cell with the recombinant construct of the invention; and
(b) selecting those transformed cells that make long-chain polyunsaturated fatty acids.

In still another aspect, this invention concerns a method for producing at least one polyunsaturated fatty acid in a soybean cell comprising:
(a) transforming a soybean cell with a first recombinant DNA construct comprising an isolated polynucleotide encoding a delta-8 desaturase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-12 desaturase, a delta-15 desaturase, a delta-17 desaturase, a delta-9 elongase, a $C_{14/16}$ elongase, a $C_{16/18}$ elongase, a $C_{18/20}$ elongase and a $C_{20/22}$ elongase;
(b) regenerating a soybean plant from the transformed cell of step (a); and
(c) selecting those seeds obtained from the plants of step (b) having an altered level of polyunsaturated fatty acids when compared to the level in seeds obtained from a nontransformed soybean plant.

Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in Table 3.

TABLE 3

Generalized Steps for Soybean Oil and Byproduct Production

| Process Step | Process | Impurities Removed and/or By-Products Obtained |
|---|---|---|
| # 1 | soybean seed | |
| # 2 | oil extraction | meal |
| # 3 | degumming | lecithin |
| # 4 | alkali or physical refining | gums, free fatty acids, pigments |
| # 5 | water washing | soap |
| # 6 | bleaching | color, soap, metal |
| # 7 | (hydrogenation) | |
| # 8 | (winterization) | stearine |
| # 9 | deodorization | free fatty acids, tocopherols, sterols, volatiles |
| # 10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995).

Soybean oil is liquid at room temperature because it is relatively low in saturated fatty acids when compared with oils such as coconut, palm, palm kernel and cocoa butter. Many processed fats (including spreads, confectionary fats, hard butters, margarines, baking shortenings, etc.) require varying degrees of solidity at room temperature and can only be produced from soybean oil through alteration of its physical properties. This is most commonly achieved through catalytic hydrogenation.

Hydrogenation is a chemical reaction in which hydrogen is added to the unsaturated fatty acid double bonds with the aid of a catalyst such as nickel. High oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have also become controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

Compared to other vegetable oils, the oils of the invention are believed to function similarly to other oils in food applications from a physical standpoint. Partially hydrogenated oils, such as soybean oil, are widely used as ingredients for soft spreads, margarine and shortenings for baking and frying.

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases. For example, palmitate is converted to its unsaturated derivative (palmitoleic acid (16:1)) by the action of a delta-9 desaturase. Similarly, palmitate is elongated by a $C_{16/18}$ fatty acid elongase to form stearic acid (18:0), which can be converted to its unsaturated derivative by a delta-9 desaturase to thereby yield oleic acid (18:1).

Triacylglycerols (the primary storage unit for fatty acids) are formed by the esterification of two molecules of acyl-CoA to glycerol-3-phosphate to yield 1,2-diacylglycerol phosphate (commonly identified as phosphatidic acid). The phosphate is then removed, by phosphatidic acid phosphatase, to yield 1,2-diacylglycerol. Triacylglycerol is formed upon the addition of a third fatty acid by the action of a diacylglycerol-acyl transferase.

Many microorganisms, including algae, bacteria, molds and yeasts, can synthesize PUFAs and omega fatty acids in the ordinary course of cellular metabolism. Particularly well-studied are fungi including Schizochytrium aggregatm, species of the genus Thraustochytrium and Morteriella alpina. Additionally, many dinoflagellates (Dinophyceaae) naturally produce high concentrations of PUFAs. As such, a variety of genes involved in oil production have been identified through genetic means and the DNA sequences of some of these genes are publicly available. See, for example, AY131238, Y055118, AY055117, AF296076, AF007561, L11421, NM_031344, AF465283, AF465281, AF110510, AF465282, AF419296, AB052086, AJ250735, AF126799, AF126798 (delta-6 desaturases); AF199596, AF226273, AF320509, AB072976, AF489588, AJ510244, AF419297, AF07879, AF067654, AB022097 (delta-5 desaturases); AAG36933, AF110509, AB020033, AAL13300, AF417244, AF161219, AY332747, AAG36933, AF110509, X86736, AF240777, AB007640, AB075526, AP002063 (delta-12 desaturases); NP_441622, BAA18302, BAA02924, AAL36934 (delta-15 desaturases); AF338466, AF438199, E11368, E11367, D83185, U90417, AF085500, AY504633, NM_069854, AF230693 (delta-9 desaturases); AF390174 (delta-9 elongase); AF139720 and CQ831420 (delta-8 desaturase); and AX464731, NM_119617, NM_134255, NM_134383, NM_134382, NM_068396, NM_068392, NM_070713, NM_068746, NM_064685 (elongases).

Additionally, the patent literature provides many additional DNA sequences of genes (and/or details concerning several of the genes above and their methods of isolation) involved in PUFA production (e.g., PCT Publication No. WO 02/077213 (delta-9 elongases); PCT Publication No. WO 00/34439, WO 04/057001 and U.S. Pat. No. 6,825,017 (delta-8 desaturases); U.S. Pat. No. 5,968,809 (delta-6 desaturases); U.S. Pat. No. 5,972,664 and U.S. Pat. No. 6,075,183 (delta-5 desaturases); PCT Publication No. WO 94/11516, U.S. Pat. No. 5,443,974, PCT Publication No. WO 03/099216 and PCT Publication No. WO 05/047485 (delta-12 desaturases); PCT Publication No. WO 93/11245 (delta-15 desaturases); PCT Publication No. WO 91/13972 and U.S. Pat. No. 5,057,419 (delta-9 desaturases); U.S. Publication No. 2003/0196217 A1 (delta-17 desaturase); and PCT Publication No. WO 00/12720 and PCT Publication No. WO 2002/077213, U.S. Pat. No. 6,403,349, U.S. Pat. No. 6,677,145, and U.S. Publication No. 2004/0111763 ($C_{14/16}$, $C_{16/18}$ and $C_{18/20}$ elongases)). Each of these patents and applications are herein incorporated by reference in their entirety.

As will be obvious to one skilled in the art, the particular functionalities required to be introduced into a microbial host organism for production of a particular PUFA final product will depend on the host cell (and its native PUFA profile and/or desaturase/elongase profile), the availability of substrate and the desired end product(s). LA, GLA, EDA, DGLA, AA, ALA, STA, ETrA, ETA, EPA, DPA and DHA may all be produced in oleaginous yeasts, by introducing various combinations of the following PUFA enzyme functionalities: a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and/or a $C_{20/22}$ elongase. One skilled in the art will be able to identify various candidate genes encoding each of the above enzymes, according to publicly available literature (e.g., GenBank), the patent literature, and experimental analysis of microorganisms having the ability to produce PUFAs. The sequences may be derived from any source, e.g., isolated from a natural source (from bacteria, algae, fungi, plants, animals, etc.), produced via a semi-synthetic route or synthesized de novo. In some embodiments, manipulation of genes endogenous to the host is preferred; for other purposes, it is necessary to introduce heterologous genes.

Although the particular source of the desaturase and elongase genes introduced into the host is not critical to the invention, considerations for choosing a specific polypeptide having desaturase or elongase activity include (1) the substrate specificity of the polypeptide, (2) whether the polypeptide or a component thereof is a rate-limiting enzyme, (3) whether the desaturase or elongase is essential for synthesis of a desired PUFA, and/or (4) co-factors required by the polypeptide. The expressed polypeptide preferably has parameters compatible with the biochemical environment of its location in the host cell. For example, the polypeptide may have to compete for substrate with other enzymes in the host cell. Analyses of the KM and specific activity of the polypeptide are therefore considered in determining the suitability of a given polypeptide for modifying PUFA production in a given host cell. The polypeptide used in a particular host cell is one that can function under the biochemical conditions present in the intended host cell but otherwise can be any polypeptide having desaturase or elongase activity capable of modifying the desired PUFA.

In some cases, the host organism in which it is desirable to produce PUFAs will possess endogenous genes encoding some PUFA biosynthetic pathway enzymes. For example, oleaginous yeast can typically produce 18:2 fatty acids (and some have the additional capability of synthesizing 18:3 fatty acids); thus, oleaginous yeast typically possess native delta-12 desaturase activity and may also have delta-15 desaturases. In some embodiments, therefore, expression of the native desaturase enzyme is preferred over a heterologous (or "foreign") enzyme since (1) the native enzyme is optimized for interaction with other enzymes and proteins within the cell, and (2) heterologous genes are unlikely to share the same codon preference in the host organism. Additionally, advantages are incurred when the sequence of the native gene is known, as it permits facile disruption of the endogenous gene by targeted disruption.

In many instances, however, the appropriate desaturases and elongases are not present in the host organism of choice to enable production of the desired PUFA products. Thus, it is necessary to introduce heterologous genes. In one embodiment of the present invention, work was conducted toward the goal of the development of an oleaginous yeast that accumulates oils enriched in long-chain omega-3 and/or omega-6 fatty acids via expression of a delta-9 elongase/delta-8 desaturase pathway, to enable production of EDA, DGLA, ARA, ALA, ETrA, ETA, EPA, DPA and/or DHA.

In order to express genes encoding the delta-9 elongase/delta-8 desaturase pathway for the biosynthesis of long-chain PUFAs (e.g., AA and EPA) in these organisms, it was therefore necessary to (1) identify a suitable delta-9 elongase and delta-8 desaturase that functioned relatively efficiently in oleaginous yeast based on substrate-feeding trials, and, (2) subject the delta-9 elongase and delta-8 desaturase gene to codon-optimization techniques (infra) to further enhance the expression of the heterologous enzymes in the alternate oleaginous yeast host, to thereby enable maximal production of omega-3 and/or omega-6 fatty acids.

It will be obvious to one of skill in the art that heterologous genes will be expressed with variable efficiencies in an alternate host. Thus, omega-3 and/or omega-6 PUFA production may be optimized by selection of a particular desaturase or elongase whose level of expression in a heterologous host is preferred relative to the expression of an alternate desaturase or elongase in the host organism of interest. Furthermore, it may be desirable to modify the expression of particular PUFA biosynthetic pathway enzymes to achieve optimal conversion efficiency of each, according to the specific PUFA product composition of interest. A variety of genetic engineering techniques are available to optimize expression of a particular enzyme. Two such techniques include codon optimization and gene mutation, as described below. Genes produced by, for example, either of these two methods, having desaturase and/or elongase activity(s) would be useful in the invention herein for synthesis of omega-3 and/or omega-6 PUFAs.

As will be appreciated by one skilled in the art, it is frequently useful to modify a portion of the codons encoding a particular polypeptide that is to be expressed in a foreign host, such that the modified polypeptide uses codons that are preferred by the alternate host. Use of host-preferred codons can substantially enhance the expression of the foreign gene encoding the polypeptide.

In general, host-preferred codons can be determined within a particular host species of interest by examining codon usage in proteins (preferably those expressed in the largest amount) and determining which codons are used with highest frequency. Then, the coding sequence for a polypeptide of interest having desaturase or elongase activity can be synthesized in whole or in part using the codons preferred in the host species. All (or portions) of the DNA also can be synthesized to remove any destabilizing sequences or regions of secondary structure that would be present in the transcribed mRNA.

All (or portions) of the DNA also can be synthesized to alter the base composition to one more preferable in the desired host cell.

In the present invention, it is desirable to modify a portion of the codons encoding the polypeptide having delta-8 desaturase activity, to enhance the expression of the gene in a host organism including, but not limited to, a plant, plant parts and/or oleaginous yeast *Yarrowia lipolytica*. The nucleic acid sequence of the native gene (i.e., the *Pavlova lutheri* delta-8 desaturase defined herein as SEQ ID NOs:14, 15 and 16) is modified to employ host-preferred codons. This wildtype desaturase has 423 amino acids (SEQ ID NO:16); in the codon-optimized gene (SEQ ID NO:57), 166 bp of the 1272 bp coding region (13.1%) and 161 codons are codon-optimized (38.1%) and the translation initiation site is modified.

The skilled artisan will appreciate that modulation of the *Pavlova lutheri* delta-8 desaturase as well as numerous other heterologous delta-8 desaturases from variable sources can be codon-optimized to improve their expression in an oleaginous yeast host (e.g., see Example 18 herein, wherein a synthetic codon-optimized delta-8 desaturase derived from *Pavlova lutheri* was created for expression in *Yarrowia lipolytica*). The present invention comprises the complete sequence of the synthetic codon-optimized gene as reported in the accompanying Sequence Listing (SEQ ID NO:57), the complement of those complete sequences, and substantial portions of those sequences. Furthermore, the codon-optimization method described in PCT Publication No. WO 2004/101753 and described herein for optimization of the *Pavlova lutheri* delta-8 desaturase is equally applicable to other genes in the omega-3/omega-6 fatty acid biosynthetic pathway.

Methods for synthesizing sequences and bringing sequences together are well established in the literature. For example, in vitro mutagenesis and selection, site-directed mutagenesis, error prone PCR (Melnikov et al., *Nucleic Acids Research*, 27(4):1056-1062 (February 1999)), "gene shuffling" or other means can be employed to obtain mutations of naturally occurring desaturase or elongase genes (wherein such mutations may include deletions, insertions and point mutations, or combinations thereof). This would permit production of a polypeptide having desaturase or elongase activity, respectively, in vivo with more desirable physical and kinetic parameters for function in the host cell such as a longer half-life or a higher rate of production of a desired PUFA. Or, if desired, the regions of a polypeptide of interest (i.e., a desaturase or an elongase) important for enzymatic activity can be determined through routine mutagenesis, expression of the resulting mutant polypeptides and determination of their activities. An overview of these techniques are described in PCT Publication No. WO 2004/101757. All such mutant proteins and nucleotide sequences encoding them that are derived from the codon-optimized gene described herein are within the scope of the present invention.

Microbial production of omega-3 and/or omega-6 fatty acids has several advantages. For example, (1) many microbes are known with greatly simplified oil compositions compared with those of higher organisms, making purification of desired components easier, (2) microbial production is not subject to fluctuations caused by external variables, such as weather and food supply, (3) microbially produced oil is substantially free of contamination by environmental pollutants, (4) microbes can provide PUFAs in particular forms which may have specific uses, and (5) microbial oil production can be manipulated by controlling culture conditions, notably by providing particular substrates for microbially expressed enzymes, or by addition of compounds/genetic engineering to suppress undesired biochemical pathways.

In addition to these advantages, production of omega-3 and/or omega-6 fatty acids from recombinant microbes provides the ability to alter the naturally occurring microbial fatty acid profile by providing new biosynthetic pathways in the host or by suppressing undesired pathways, thereby increasing levels of desired PUFAs, or conjugated forms thereof, and decreasing levels of undesired PUFAs. For example, it is possible to modify the ratio of omega-3 to omega-6 fatty acids so produced, produce either omega-3 or omega-6 fatty acids exclusively while eliminating production of the alternate omega fatty acid, or engineer production of a specific PUFA without significant accumulation of other PUFA downstream or upstream products (e.g., enable biosynthesis of AA, EPA and/or DHA via the delta-9 elongase/delta-8 desaturase pathway, thereby avoiding synthesis of GLA and/or STA).

The genes and gene products described herein may be produced in heterologous microbial host cells, particularly in the cells of oleaginous yeasts (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the preferred desaturase and/or elongase sequences. These chimeric genes could then be introduced into appropriate microorganisms via transformation to provide high-level expression of the encoded enzymes.

Accordingly, it is expected that introduction of chimeric genes encoding a PUFA biosynthetic pathway, under the control of the appropriate promoters will result in increased production of omega-3 and/or omega-6 fatty acids. It is contemplated that it will be useful to express various combinations of these PUFA desaturase and elongase genes together in a host microorganism. It will be obvious to one skilled in the art that the particular genes included within a particular expression cassette(s) will depend on the host cell, its ability to synthesize PUFAs using native desaturases and elongases, the availability of substrate and the desired end product(s). For example, it may be desirable for an expression cassette to be constructed comprising genes encoding one or more of the following enzymatic activities: a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and/or a $C_{20/22}$ elongase. As such, the present invention encompasses a method of producing PUFAs comprising exposing a fatty acid substrate to the PUFA enzyme(s) described herein, such that the substrate is converted to the desired fatty acid product. Thus, each PUFA gene and corresponding enzyme product described herein (e.g., a wildtype, codon-optimized, synthetic and/or mutant enzyme having appropriate desaturase or elongase activity) can be used directly or indirectly for the production of PUFAs. Direct production of PUFAs occurs wherein the fatty acid substrate is converted directly into the desired fatty acid product without any intermediate steps or pathway intermediates. For example, production of AA would occur in a host cell which produces or which is provided DGLA, by adding or introducing into said cell an expression cassette that provides delta-5 desaturase activity. Similarly, expression of the delta-8 desaturase of the invention permits the direct synthesis of EDA and ETrA (when provided LA and ALA, respectively, as substrate). Thus, for example, the present invention may encompass a method of producing either EDA or ETrA, respectively, comprising:
 a) providing a host organism including, but not limited to, an oleaginous yeast comprising: (i) a gene encoding a delta-8 desaturase polypeptide as set forth in SEQ ID NO:16 or SEQ ID NO:57; and (ii) a source of desaturase substrate consisting of either EDA or ETrA, respectively; and,
 b) growing the yeast of step (a) in the presence of a suitable fermentable carbon source wherein the gene encoding a delta-8 desaturase polypeptide is expressed and EDA is converted to DGLA or ETrA is converted to ETA, respectively; and,
 c) optionally recovering the DGLA or ETA, respectively, of step (b).

In some preferred embodiments, the nucleotide sequence of a gene encoding a delta-8 desaturase polypeptide is set forth in SEQ ID NO:57 wherein at least 162 codons have been optimized for expression in Yarrowia.

In contrast, multiple genes encoding the PUFA biosynthetic pathway may be used in combination, such that a series of reactions occur to produce a desired PUFA. For example, expression cassette(s) encoding delta-9 elongase, delta-8 desaturase, delta-5 desaturase and delta-17 desaturase activity would enable a host cell that naturally produces LA, to instead produce ARA (such that LA is converted to EDA by delta-9 elongase; EDA may then be converted to DGLA by a delta-8 desaturase; DGLA is then converted to ARA by a delta-5 desaturase). In a related manner, expression of the delta-8 desaturase of the invention enables the direct/indirect production of ETA, EPA, DPA and/or DHA as down-stream PUFAs, if subsequent desaturase and elongation reactions are catalyzed. In a preferred embodiment, wherein the host cell is an oleaginous yeast, expression cassettes encoding each of the enzymes necessary for PUFA biosynthesis will need to be introduced into the organism, since naturally produced PUFAs in these organisms are limited to 18:2 fatty acids (i.e., LA), and less commonly, 18:3 fatty acids (i.e., ALA). Alternatively, substrate feeding may be required.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed host cell, although it is to be understood that such control regions need not be derived from the genes native to the specific species chosen as a production host.

Initiation control regions or promoters which are useful to drive expression of desaturase and/or elongase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest, alternatively, stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from (1) genes in the glycolytic pathway, such as alcohol dehydrogenase, glyceraldehyde-3-phosphate-dehydrogenase (PCT Publication No. WO 2005/003310), phosphoglycerate mutase (PCT Publication No. WO 2005/003310), fructose-bisphosphate aldolase (PCT Publication No. WO 2005/049805), phosphoglucose-isomerase, phosphoglycerate kinase, glycerol-3-phosphate O-acyltransferase (PCT Publication No. WO 2006/031937), etc.; or (2) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), ammonium transporter proteins (U.S. application Ser. No. 11/185,301), export proteins, etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, as demonstrated in the invention herein in Yarrowia lipolytica, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly Saccharomyces, Schizosaccharomyces, Candida, Yarrowia or Kluyveromyces. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: (1) the nature of the relevant transcriptional promoter and terminator sequences; (2) the number of copies of the cloned gene and whether the gene is plasmid-borne or integrated into the genome of the host cell; (3) the final cellular location of the synthesized foreign protein; (4) the efficiency of translation in the host organism and correct folding of the protein in the host organism; (5) the intrinsic stability of the mRNA and protein of the cloned gene within the host cell; and, (6) the codon usage within the cloned gene, such that its frequency approaches the frequency of preferred codon usage of the host cell. Each of these types of modifications are encompassed in the present invention, as means to further optimize expression of the PUFA biosynthetic pathway enzymes.

Once the DNA encoding a desaturase or elongase polypeptide suitable for expression in an oleaginous yeast has been obtained, it is placed in a plasmid vector capable of autonomous replication in a host cell; or, it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

A method of expressing genes in *Yarrowia lipolytica* is by integration of linear DNA into the genome of the host; and, integration into multiple locations within the genome can be particularly useful when high level expression of genes are desired. Toward this end, it is desirable to identify a sequence within the genome that is present in multiple copies.

Schmid-Berger et al. (*J. Bact.* 176(9):2477-2482 (1994)) discovered the first retrotransposon-like element Ylt1 in *Yarrowia lipolytica*. This retrotransposon is characterized by the presence of long terminal repeats (LTRs; each approximately 700 bp in length) called zeta regions. Ylt1 and solo zeta elements were present in a dispersed manner within the genome in at least 35 copies/genome and 50-60 copies/genome, respectively; both elements were determined to function as sites of homologous recombination. Further, work by Juretzek et al. (*Yeast* 18:97-113 (2001)) demonstrated that gene expression could be dramatically increased by targeting plasmids into the repetitive regions of the yeast genome (using linear DNA with LTR zeta regions at both ends), as compared to the expression obtained using low-copy plasmid transformants. Thus, zeta-directed integration can be ideal as a means to ensure multiple integration of plasmid DNA into *Yarrowia lipolytica*, thereby permitting high-level gene expression. Unfortunately, however, not all strains of *Yarrowia lipolytica* possess zeta regions (e.g., the strain identified as ATCC Accession No. 20362). When the strain lacks such regions, it is also possible to integrate plasmid DNA comprising expression cassettes into alternate loci to reach the desired copy number for the expression cassette. For example, preferred alternate loci include: the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the delta-12 desaturase gene locus, the Lip1 gene locus (GenBank Accession No. Z50020) and/or the Lip2 gene locus (GenBank Accession No. AJ012632).

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other constructs to maintain stable expression and prevent reassortment of elements among constructs. Judicious choice of regulatory regions, selection means and method of propagation of the introduced construct can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in PCT Publication No. WO 04/101757. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura-mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura-phenotype, wherein selection occurs based on 5-FOA resistance. Then, a cluster of multiple chimeric genes and a new Ura3 gene could be integrated into a different locus of the *Yarrowia* genome to thereby produce a new strain having a Ura+ phenotype. Subsequent integration would produce a new Ura3-strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the recombinantly expressed desaturases and/or elongases (and optionally other PUFA enzymes that are expressed within the host cell) may be produced by the host either naturally or transgenically, or they may be provided exogenously.

Methods for manipulating biochemical pathways are well known to those skilled in the art; and, it is expected that numerous manipulations will be possible to maximize omega-3 and/or omega-6 fatty acid biosynthesis in oleaginous yeasts, and particularly, in *Yarrowia lipolytica*. This may require metabolic engineering directly within the PUFA biosynthetic pathway or additional manipulation of pathways that contribute carbon to the PUFA biosynthetic pathway.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this.

To maximize production of omega-6 unsaturated fatty acids, it is well known to one skilled in the art that production is favored in a host microorganism that is substantially free of ALA. Thus, preferably, the host is selected or obtained by removing or inhibiting delta-15 or omega-3 type desaturase activity that permits conversion of LA to ALA. The endogenous desaturase activity can be reduced or eliminated by, for example, (1) providing a cassette for transcription of antisense sequences to the delta-15 desaturase transcription product, (2) disrupting the delta-15 desaturase gene through insertion, substitution and/or deletion of all or part of the target gene; or (3) using a host cell which naturally has [or has been mutated to have] low or no delta-15 desaturase activity. Inhibition of undesired desaturase pathways can also be accomplished through the use of specific desaturase inhibitors such as those described in U.S. Pat. No. 4,778,630.

Alternatively, it may be desirable to maximize production of omega-3 fatty acids (and minimize synthesis of omega-6 fatty acids). Thus, one could utilize a host microorganism wherein the delta-12 desaturase activity that permits conversion of oleic acid to LA is removed or inhibited, using any of the means described above (see also e.g., PCT Publication No. WO 2004/104167, herein incorporated entirely by reference). Subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

Beyond the immediate PUFA biosynthetic pathway, it is expected that manipulation of several other enzymatic pathways leading to the biosynthesis of precursor fatty acids may contribute to the overall net biosynthesis of specific PUFAs. Identification and manipulation of these related pathways will be useful in the future.

Additional copies of desaturase and elongase genes may be introduced into the host to increase the output of omega-3 and/or omega-6 fatty acid biosynthetic pathways. Expression of the desaturase or elongase genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of the desaturase or elongase genes, as demonstrated in the instant invention, is to increase the translational efficiency of the encoded mRNAs by replacement of codons in the native gene with those for optimal gene expression in the selected host microorganism.

Conversely, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA). For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al. *J. Bacteriol.* 171:4617-4622 (1989); Balbas et al. *Gene* 136:211-213 (1993); Gueldener et al. *Nucleic Acids Res.* 24:2519-2524 (1996); and Smith et al. *Methods Mol. Cell. Biol.* 5:270-277 (1996)).

Antisense technology is another method of down-regulating genes when the sequence of the target gene is known. To accomplish this, a nucleic acid segment from the desired gene is cloned and operably linked to a promoter such that the antisense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based (e.g., mutagenesis via UV radiation/chemical agents or use of transposable elements/transposons; see PCT Publication No. WO 2004/101757).

Within the context of the present invention, it may be useful to modulate the expression of the fatty acid biosynthetic pathway by any one of the methods described above. For example, the present invention provides methods whereby genes encoding key enzymes in the biosynthetic pathways are introduced into oleaginous yeasts for the production of omega-3 and/or omega-6 fatty acids. It will be particularly useful to express these genes in oleaginous yeasts that do not naturally possess omega-3 and/or omega-6 fatty acid biosynthetic pathways and coordinate the expression of these genes, to maximize production of preferred PUFA products using various means for metabolic engineering of the host organism.

Microbial host cells for production of omega fatty acids may include microbial hosts that grow on a variety of feedstocks, including simple or complex carbohydrates, fatty acids, organic acids, oils and alcohols, and/or hydrocarbons over a wide range of temperature and pH values.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Yarrowia lipolytica* strains designated as ATCC Accession Nos. 20362, 8862, 18944, 76982 and/or LGAM S(7)1 (Papanikolaou, S., and Aggelis, G., *Bioresour. Technol.* 82(1):43-9 (2002)).

The transformed microbial host cell is grown under conditions that optimize desaturase and elongase activities and produce the greatest and the most economical yield of the preferred PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., yeast nitrogen base (Difco Laboratories, Detroit, Mich.)).

Fermentation media in the present invention must contain a suitable carbon source. Suitable carbon sources are taught in WO 2004/101757. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as yeast nitrogen base (Difco Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. This approach is described in PCT Publication No. WO 2004/101757, as are various suitable fermentation process designs (i.e., batch, fed-batch and continuous) and considerations during growth.

The PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details.

The market place currently supports a large variety of food and feed products, incorporating omega-3 and/or omega-6 fatty acids (particularly ARA, EPA and DHA). It is contemplated that the plant oils of the invention and the yeast oils of the invention comprising long-chain PUFAs will function in food and feed products to impart the health benefits of current formulations. More specifically, oils of the invention containing omega-3 and/or omega-6 fatty acids will be suitable for use in a variety of food and feed products including, but not limited to food analogs, meat products, cereal products, baked foods, snack foods and dairy products.

Additionally the present oils may be used in formulations to impart health benefit in medical foods including medical nutritionals, dietary supplements, infant formula as well as pharmaceutical products. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

A "food analog" is a food-like product manufactured to resemble its food counterpart, whether meat, cheese, milk or the like, and is intended to have the appearance, taste, and texture of its counterpart. Thus, the term "food" as used herein also encompasses food analogs. Food analogs can be made use processes well known to those skilled in the art. U.S. Pat. Nos. 6,355,296 B1 and 6,187,367 B1 describe emulsified meat analogs and emulsified meat extenders. U.S. Pat. No. 5,206,050 B1 describes soy protein curd useful for cooked food analogs (also can be used as a process to form a curd useful to make food analogs). U.S. Pat. No. 4,284,656 to Hwa describes a soy protein curd useful for food analogs. U.S. Pat. No. 3,988,485 to Hibbert et al. describes a meat-like protein food formed from spun vegetable protein fibers. U.S. Pat. No. 3,950,564 to Puski et al. describes a process of making a soy based meat substitute and U.S. Pat. No. 3,925,566 to Reinhart et al. describes a simulated meat product. For example, soy protein that has been processed to impart a structure, chunk or fiber for use as a food ingredient is called "textured soy protein" (TSP). TSPs are frequently made to resemble meat, seafood, or poultry in structure and appearance when hydrated.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milks and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processed meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking (i.e., to dry or harden by subjecting to heat). Examples of a baked good product include, but are not limited to: bread, cakes, doughnuts, bars, pastas, bread crumbs, baked snacks, mini-biscuits, mini-crackers, mini-cookies, and mini-pretzels. As was mentioned above, oils of the invention can be used as an ingredient.

A snack food product comprises any of the above or below described food products.

A fried food product comprises any of the above or below described food products that has been fried.

The beverage can be in a liquid or in a dry powdered form.

For example, there can be mentioned non-carbonated drinks such as fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aqueous solution (e.g., see U.S. Pat. No. 4,670,285). Based on the worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ (Mead Johnson & Company) and Similac Advance™ (Ross Products Division, Abbott Laboratories)). Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yogurt or sour milk, cream, butter, condensed milk, dehydrated milk, coffee whitener, coffee creamer, ice cream, cheese, etc.

Additional food products into which the long-chain PUFA-containing oils of the invention could be included are, for example, chewing gums, confections and frostings, gelatins and puddings, hard and soft candies, jams and jellies, white granulated sugar, sugar substitutes, sweet sauces, toppings and syrups, and dry-blended powder mixes.

A health food product is any food product that imparts a health benefit and include functional foods, medical foods, medical nutritionals and dietary supplements. Additionally, the oils of the invention may be used in standard pharmaceutical compositions (e.g., the long-chain PUFA containing oils could readily be incorporated into the any of the above mentioned food products, to thereby produce a functional or medical food). For example, more concentrated formulations comprising ARA, EPA or DHA include capsules, powders, tablets, softgels, gelcaps, liquid concentrates and emulsions which can be used as a dietary supplement in humans or animals other than humans.

Animal feeds are generically defined herein as products intended for use as feed or for mixing in feed for animals other than humans. The long-chain PUFA containing oils of the invention can be used as an ingredient in various animal feeds.

More specifically, although not limited therein, it is expected that the oils of the invention can be used within pet food products, ruminant and poultry food products and aquacultural food products. Pet food products are those products intended to be fed to a pet (e.g., dog, cat, bird, reptile, rodent). These products can include the cereal and health food products above, as well as meat and meat byproducts, soy protein products, grass and hay products (e.g., alfalfa, timothy, oat or brome grass, vegetables). Ruminant and poultry food products are those wherein the product is intended to be fed to an animal (e.g., turkeys, chickens, cattle, swine). As with the pet foods above, these products can include cereal and health food products, soy protein products, meat and meat byproducts, and grass and hay products as listed above. Aquacultural food products (or "aquafeeds") are those products intended to be used in aquafarming which concerns the propagation, cultivation or farming of aquatic organisms and/or animals in fresh or marine waters.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The meaning of abbreviations is as follows: "sec" means second(s), "min" means minute(s), "h" means hour(s), "d" means day(s), "µl" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Transformation and Cultivation of *Yarrowia lipolytica*:

*Yarrowia lipolytica* strains with ATCC Accession Nos. 20362, 76982 and 90812 were purchased from the American Type Culture Collection (Rockville, Md.). *Yarrowia lipolytica* strains were typically grown at 28° C. on YPD agar (1% yeast extract, 2% bactopeptone, 2% glucose, 2% agar).

Transformation of *Yarrowia lipolytica* was performed according to the method of Chen, D. C. et al. (*Appl. Microbiol. Biotechnol.* 48(2):232-235 (1997)), unless otherwise noted. Briefly, *Yarrowia* was streaked onto a YPD plate and grown at 30° C. for approximately 18 h. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μL of resuspended cells, and maintained at 39° C. for 1 h with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (Difco Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (Difco Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*:

For fatty acid analysis, cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G. and Nishida, I., *Arch Biochem Biophys.* 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μL of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Example 1

*Pavlova lutheri* (CCMP459) cDNA Synthesis, Library Construction and Sequencing

A cDNA library of *Pavlova lutheri* (CCMP459) was synthesized as described in PCT Publication No. WO 2004/071467 ((published Aug. 26, 2004). Briefly, frozen pellets of Pav459 were obtained from Provasoli-Guillard National Center for Culture of Marine Phytoplankton (CCMP, West Boothbay Harbor, Me.). These pellets were crushed in liquid nitrogen and total RNA was extracted from Pav459 by using the Qiagen RNeasy® Maxi Kit (Qiagen, Valencia, Calif.), per manufacturers instructions. From this total RNA, mRNA was isolated using oligo dT cellulose resin, which was then used for the construction of a cDNA library using the pSport1 vector (Invitrogen, Carlsbad, Calif.). The cDNA thus produced was directionally cloned (5' SalI/3' NotI) into pSport1 vector. The Pav459 library contained approximately $6.1 \times 10^5$ clones per mL, each with an average insert size of approximately 1200 bp. The *Pavlova lutheri* library was named eps1c.

For sequencing, clones first were recovered from archived glycerol cultures grown/frozen in 384-well freezing media plates, and inoculated with an automatic QPix® colony picker (Genetix) in 96-well deep-well plates containing LB+100 mg/mL ampicillin. After growing 20 hours at 37° C., cells were pelleted by centrifugation and stored at −20° C. Plasmids then were isolated on an Eppendorf 5Prime robot, using a modified 96-well format alkaline lysis miniprep method (Eppendorf PerfectPrep®). Briefly, a filter and vacuum manifold was used to facilitate removal of cellular debris after acetate precipitation. Plasmid DNA was then bound on a second filter plate directly from the filtrate, washed, dried and eluted.

Plasmids were end-sequenced in 384-well plates, using vector-primed T7 primer (SEQ ID NO:1) and the ABI BigDye version 3 Prism sequencing kit. For the sequencing reaction, 100-200 ng of template and 6.4 pmoL of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers.

Example 2

Identification of Delta-8 Desaturase Enzyme Homologs from *Pavlova lutheri* cDNA Library eps1c cDNA clones encoding *Pavlova lutheri* delta-8 desaturase homologs (hereby called delta-8 desaturases) were identified by conducting BLAST (Basic Local Alignment Search Tool; Altschul et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States, *Nat. Genet.* 3:266-272 (1993)) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequence from clone eps1c.pk002.f22 revealed similarity of the protein encoded by the cDNA to the delta-6 desaturase from *Rhizopus stolonifer* (SEQ ID NO:2) (NCBI Accession No. AAX22052 (GI 60499699), locus AAX22052, CDS AY795076; Lu et al., unpublished). The sequence of a portion of the cDNA insert from clone eps1c.pk002.f22 is shown in SEQ ID NO:3 (5' end of cDNA insert). Subsequently, the full insert sequence (eps1c.pk002.f22:fis) was obtained and is shown in SEQ ID NO:4. Sequence for the deduced amino acid sequence (from nucleotide 1 of SEQ ID NO:4 to the first stop codon at nucleotide 864 of SEQ ID NO:4) is shown in SEQ ID NO:5. Full insert sequencing was carried out using a modified transposition protocol. Clones identified for FIS were recovered from archived glycerol stocks as single colonies, and plasmid DNA was isolated via alkaline lysis. Plasmid templates were transposed via the Template Generation System (TGS II) transposition kit (Finnzymes Oy, Espoo, Finland), following the manufacturer's protocol. The transposed DNA was transformed into EH10B electro-competent cells (Edge BioSystems, Gaithersburg, Md.) via electroporation. Multiple transformants were randomly selected from each transposition reaction, plasmid DNA was prepared, and templates were sequenced as above (ABI BigDye v3.1) outward from the transposition event site, utilizing unique primers SeqE (SEQ ID NO:6) and SeqW (SEQ ID NO:7).

Sequence data was collected (ABI Prism Collections software) and assembled using the Phrap sequence assembly program (P. Green, University of Washington, Seattle). Assemblies are viewed by the Consed sequence editor (D. Gordon, University of Washington, Seattle) for final editing.

The amino acid sequence set forth in SEQ ID NO:5 was evaluated by BLASTP, yielding a pLog value of 19.52 (E value of 3e-20) versus the delta-6 desaturase from *Mortierella alpina* (SEQ ID NO:8) (NCBI Accession No. BAC82361 (GI 34221934), locus BAC82361, CDS AB070557; Sakuradani and Shimizu, *Biosci. Biotechnol. Biochem.* 67:704-711 (2003)). Based on the results from the BLASTP comparison to the *Mortierella alpina* and other fatty acid desaturases, the *Pavlova lutheri* delta-8 desaturase was not full length and was lacking sequence at the 5' end.

Example 3

Cloning a Full-Length Delta-8 Desaturase from *Pavlova lutheri* Genomic DNA

Genomic DNA was isolated from *Pavlova lutheri* (CCMP459) using the Qiagen DNeasy® Plant Maxi Prep Kit according to the manufacturer's protocol. Using 1 maxi column per 1 gm of frozen cell pellet, a total of 122 µg of genomic DNA was isolated from 4 gm of *Pavlova lutheri* culture. The final concentration of genomic DNA was 22.8 ng/µL. GenomeWalker libraries were synthesized using the Universal GenomeWalker™ kit (BD Biosciences Clonetech, Palo Alto, Calif.) following the manufacturer's protocol (Prot #PT3042-1, version PRO3300). Briefly, four restriction digests were set up as per the protocol using 300 ng of genomic DNA per reaction. After phenol clean up, pellets were dissolved in 4 µL of water and adapters were ligated as per the protocol.

For the primary PCR, the Advantage®-GC Genomic PCR kit (BD Biosciences Clonetech) was used following the manufacturer's protocol (Prot #PT3090-1, version #PR1X433). For each restriction digest, 1 µL of library was combined with 22.8 µL of PCR grade water, 10 µL of 5×GC Genomic PCR Reaction Buffer, 2.2 µL of 25 mM $Mg(CH_3CO_2)_2$, 10 µL of GC-Melt (5 M), 1 µL of 50×dNTP mix (10 mM each), 1 µL of Advantage-GC Genomic Pol. Mix (50×), 1 µL of Universal GenomeWalker™ primer AP1 (10 µM, SEQ ID NO:9) and 1 µL of GSP PvDES (10 µM, SEQ ID NO:10). After denaturation at 95° C., the following reaction conditions were repeated 35 times: 94° C. for 30 sec, 68° C. for 6 min. After these reaction conditions, an additional extension at 68° C. was carried out for 6 min followed by cooling to 15° C. until removed.

The primary PCR reaction for each library was analyzed by agarose gel electrophoresis and DNA bands with molecular weights around 6 kb, 3.5 kb, 2.5 kb and 1.2 kb were observed. DNA bands for each library were purified using the Zymoclean™ Gel DNA Recovery Kit (Zymo Research, Orange, Calif.) following the manufacturer's protocol. The resulting DNA was cloned into the pGEM®-T Easy Vector (Promega) following the manufacturer's protocol and inserts were sequenced using the T7 (SEQ ID NO:1) and M13-28Rev (SEQ ID NO:11) primers as described above. Additional sequence was then obtained using a gene-specific sequencing primer PvDES seq (SEQ ID NO:12) that was derived from the newly acquired sequence data. The full 5' end sequence obtained by genome walking is shown in SEQ ID NO:13. The sequence of the overlapping regions of the genomic sequence (SEQ ID NO:13) and the fully sequenced EST eps1c.pk002.f22:fis (SEQ ID NO:4) were aligned using Sequencher™ (Version 4.2, Gene Codes Corporation, Ann Arbor, Mich.) using the Large Gap assembly algorithm. Interestingly, the comparison showed that the EST that was originally sequenced (SEQ ID NO:4) was lacking 459 bp when compared to the genomic sequence (SEQ ID NO:13). This missing sequence in the EST appeared to be a deletion rather than an intron as no clear intron splice sites were identified in the genomic DNA at the 5' end of the gene. The genomic sequence for the 5' end (SEQ ID NO:13) was combined with the 3' end of the EST sequence (SEQ ID NO:4) to give SEQ ID NO:14. Using EditSeq™ 6.1 sequence analysis software (DNASTAR Inc., Madison, Wis.), an ORF was identified (SEQ ID NO:15). The amino acid sequence coded for by SEQ ID NO:15 is shown in SEQ ID NO:16.

The amino acid sequence set forth in SEQ ID NO:16 was evaluated by BLASTP, yielding a pLog value of 35.10 (E value of 8e-36) versus the delta-6 desaturase from *Rhizopus stolonifer* (SEQ ID NO:17) (NCBI Accession No. ABB96724 (GI 83027409), locus ABB96724, CDS DQ291156; Zhang et al., unpublished). Furthermore, the *Pavlova lutheri* delta-8 desaturase is 78.0% identical to the *Pavlova saline* delta-8 desaturase sequence (SEQ ID NO:76) disclosed in PCT Publication No. WO 2005/103253 (published Apr. 22, 2005) using the Jotun Hein method. Sequence percent identity calculations performed by the Jotun Hein method (Hein, J. J., *Meth. Enz.* 183:626-645 (1990)) were done using the MegAlign™ v6.1 program of the LASARGENE bioinformatics computing suite (DNASTAR Inc., Madison, Wis.) with the default parameters for pairwise alignment (KTUPLE=2). The *Pavlova lutheri* delta-8 desaturase is 76.4% identical to the *Pavlova saline* delta-8 desaturase sequence using the Clustal V method. Sequence percent identity calculations performed by the Clustal V method (Higgins, D. G. and Sharp, P. M., *Comput. Appl. Biosci.* 5:151-153 (1989); Higgins et al., *Comput. Appl. Biosci.* 8:189-191 (1992)) were done using the MegAlign™ v6.1 program of the LASARGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10). BLAST scores and probabilities indicate that the instant nucleic acid fragment (SEQ ID NO:15) encodes an entire *Pavlova lutheri* delta-8 desaturase.

FIGS. 13A and 13B show a Clustal V alignment (with default parameters) of SEQ ID NO:16 (the amino acid sequence of the delta-8 desaturase of the instant invention), SEQ ID NO:76 (the amino acid sequence of *Pavlova saline* delta-8 desaturase sequence disclosed as SEQ ID NO:1 in PCT Publication No. WO 2005/103253; published Apr. 22, 2005), SEQ ID NO:77 (the amino acid sequence of *Euglena gracilis* delta-8 desaturase sequence disclosed as SEQ ID NO:2 in PCT Publication No. WO 2006/012325; published Feb. 2, 2006), SEQ ID NO:17 (the amino acid sequence for the *Rhizopus stolonifer* delta-6 fatty acid desaturase (NCBI Accession No. ABB96724 (GI 83027409), locus ABB96724, CDS DQ291156; Zhang et al., unpublished)) and SEQ ID NO:2 (the amino acid sequence for the *Rhizopus stolonifer* delta-6 fatty acid desaturase (NCBI Accession No. AAX22052 (GI 60499699), locus AAX22052, CDS AY795076; Lu et al., unpublished)). The results of the Clustal V alignment show that SEQ ID NO:16 is 76.4%, 22.6%, 22.2%, and 22.2% identical to SEQ ID NO:76, SEQ ID NO:77, SEQ ID NO:17 and SEQ ID NO:2, respectively.

Example 4

Cloning the *Pavlova lutheri* Delta-8 Desaturase from *Pavlova lutheri* cDNA

*Pavlova lutheri* (CCMP459) was obtained from CCMP and grown in 250 mL flasks containing 50 mL of F/2-Si medium (made using F/2 Family Medium Kit-KIT20F2 and Filtered Seqwater-SEA2 from CCMP) at 26° C. with shaking at 150 rpm. Cultures were transferred to new medium on a weekly basis using 1:4 (old culture:new medium) dilution.

Cultures from 28 flasks (1400 mL) were combined, cells were pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided. In this way, 2.6 mg of total RNA (2.6 mg/mL) was obtained from the pellet. The mRNA was isolated from 1.25 mg of total RNA using the mRNA Purification Kit (Amersham Biosciences, Piscataway, N.J.) following the manufacturer's protocol provided. In this way, 112 µg of mRNA was obtained.

cDNA was synthesized from 224 ng of mRNA using the SuperScript™ First-Strand Synthesis System for RT-PCR Kit (Invitrogen™ Life Technologies, Carlsbad, Calif.) with the provided oligo(dT) primer according to the manufacturer's protocol. After RNase H treatment as per the protocol, the *Pavlova lutheri* delta-8 desaturase was amplified from the resulting cDNA with oligonucleotide primers PvDES5'Not-1 (SEQ ID NO:18) and PvDES3'Not-1 (SEQ ID NO:19) using the conditions described below.

cDNA (2 µL) from the reaction described above was combined with 50 pmol of PvDES5'Not-1 (SEQ ID NO:18), 50 pmol of PvDES3'Not-1 (SEQ ID NO:19), 1 µL of PCR nucleotide mix (10 mM, Promega, Madison, Wis.), 5 µL of 10×PCR buffer (Invitrogen Corporation), 1.5 µL of $MgCl_2$ (50 mM, Invitrogen Corporation), 0.5 µL of Taq polymerase (Invitrogen Corporation) and water to 50 µL. The reaction conditions were 94° C. for 3 min followed by 35 cycles of 94° C. for 45 sec, 55° C. for 45 sec and 72° C. for 1 min. The PCR was finished at 72° C. for 7 min and then held at 4° C. The PCR reaction was analyzed by agarose gel electrophoresis on 5 µL and a DNA band with molecular weight around 1.3 kb was observed. The remaining 45 µL of product was separated by agarose gel electrophoresis and the DNA purified using the Zymoclean™ Gel DNA Recovery Kit (Zymo Research, Orange, Calif.) following the manufacturer's protocol. The resulting DNA was cloned into the PGEM®-T Easy Vector (Promega) following the manufacturer's protocol. Multiple clones were sequenced using the T7 (SEQ ID NO:1), M13-28Rev (SEQ ID NO:11) and PvDes-2 (SEQ ID NO:20) oligonucleotides. The sequence of the clones tested were identical to that of SEQ ID NO:15 and one of the correct clones (pLF113) was chosen for further expression studies.

Example 5

Cloning the *Pavlova lutheri* Delta-8 Desaturase into a Yeast Expression Vector

Figure 1:
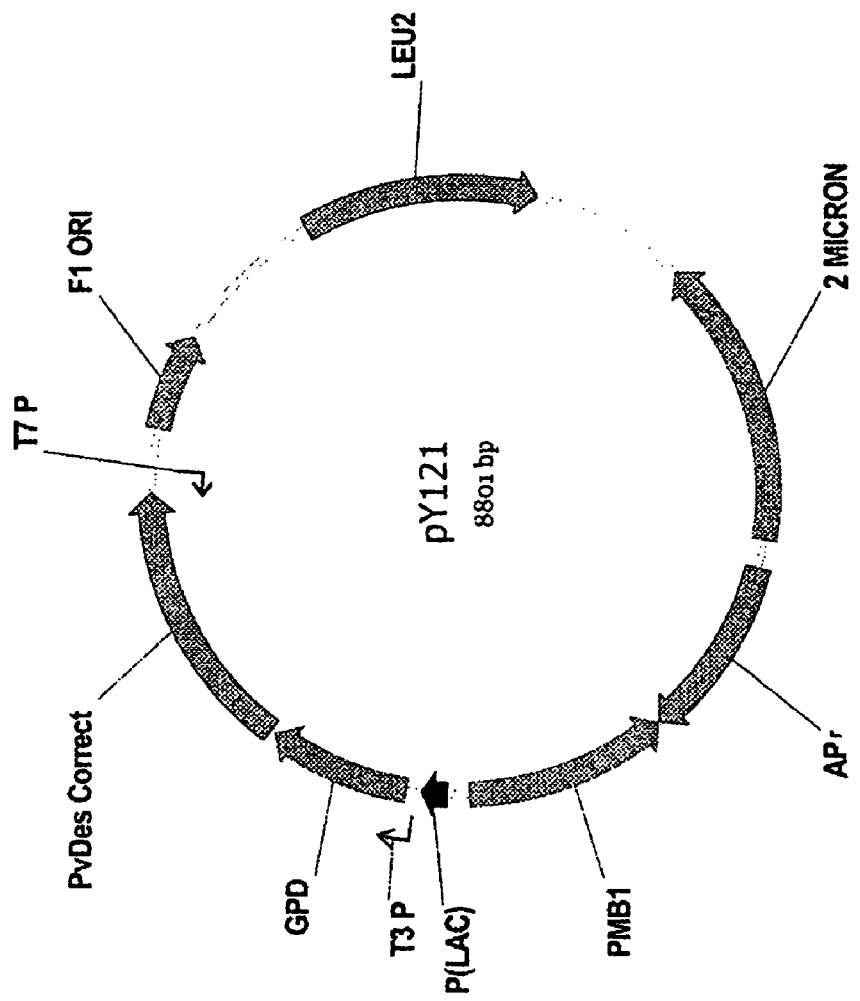
FIG. 1 is a map of plasmid pY121 (yeast expression vector).

The yeast episomal plasmid (YEp)-type vector pRS425 (Christianson et al., *Gene* 110:119-122 (1992)) contains sequences from the *Saccharomyces cerevisiae* 2µ endogenous plasmid, a LEU2 selectable marker and sequences based on the backbone of a multifunctional phagemid, pBluescript II SK(+). The *Saccharomyces cerevisiae* strong, constitutive glyceraldehyde-3-phosphate dehydrogenase (GPD) promoter was cloned between the Sac/I and SpeI sites of pRS425 in the same way as described by Jia et al. (*Physiol. Genom.* 3:83-92 (2000)) to produce pGPD-425. A NotI site was introduced into the BamHI site of pGPD-425, thus giving a NotI site flanked by BamHI sites, and this plasmid was called pY-75. The *Pavlova lutheri* delta-8 desaturase was released from pLF113 (from Example 4) by digestion with NotI and cloned into the NotI site of pY75 to produce pY121 (SEQ ID NO:21; FIG. 1).

Example 6

Cloning the *Pavlova lutheri* Delta-8 Desaturase into a Yarrowia Expression Vector The *Yarrowia* GPD promoter was amplified from plasmid pYZDE2-S (SEQ ID NO:74) using oligonucleotides GPD-sense (SEQ ID NO:28) and GPDantisense (SEQ ID NO:29). The "*Yarrowia* GPD" promoter within this chimeric gene refers to the 5' upstream untranslated region in front of the 'ATG' translation initiation codon of a protein encoded by the *Yarrowia lipolytica* glyceraldehyde-3-phosphate dehydrogenase (GPD) gene and that is necessary for expression (WO 2005/003310). The resulting DNA fragment was digested with SalI/NotI and cloned into the SalI/NotI fragment of pY5-22 (SEQ ID NO:75) thus replacing the TEF promoter and giving pY5-22GPD (SEQ ID NO: 30).

Figure 4:
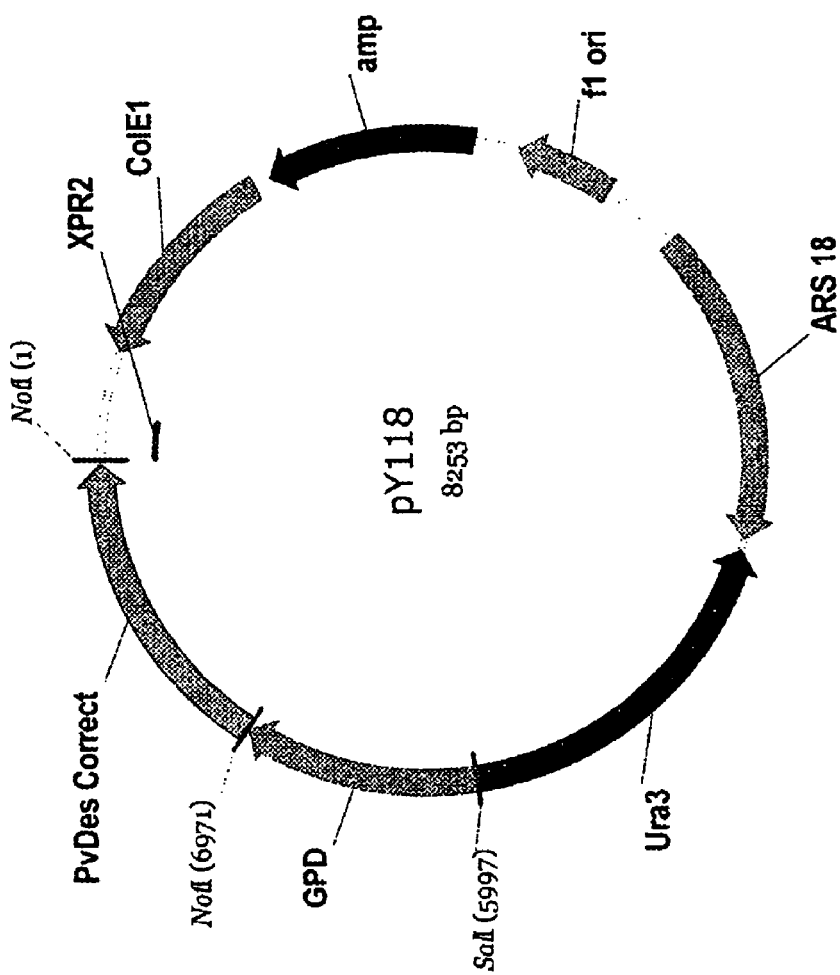
FIG. 4 is a map of plasmid pY118 (*Yarrowia* expression vector)

The *Pavlova lutheri* delta-8 desaturase was released from pLF113 (from Example 4) by digestion with NotI and cloned into the NotI site of pY5-22GPD to produce pY118 (SEQ ID NO:31; FIG. 4).

Example 7

Cloning the *Pavlova lutheri* Delta-8 Desaturase into a Soybean Expression Vector Vector pKR123r (SEQ ID NO:22), which was previously described in PCT Publication No. WO 2004/071467 (published Aug. 26, 2004; the contents of which are hereby incorporated by reference), contains a NotI site flanked by the Kunitz soybean Trypsin Inhibitor (KTi) promoter (Jofuku et al., *Plant Cell* 1:1079-1093 (1989)) and the KTi 3' termination region, the isolation of which is described in U.S. Pat. No. 6,372,965 (KTi/NotI/KTi3' cassette). The *Pavlova lutheri* delta-8 desaturase (SEQ ID NO:15) was released from pLF113 (from Example 4) by digestion with NotI and cloned into the NotI site of pKR123r to produce pKR900 (SEQ ID NO:23).

Plasmid pKR72 (ATCC Accession No. PTA-6019; SEQ ID NO:46, 7085 bp sequence), a derivative of pKS123 which was previously described in PCT Publication No. WO 2002/008269 (the contents of which are hereby incorporated by reference), contains the hygromycin B phosphotransferase gene (HPT) (Gritz, L. and Davies, J., *Gene* 25:179-188 (1983)), flanked by the T7 promoter and transcription terminator (T7prom/hpt/T7term cassette), and a bacterial origin of replication (ori) for selection and replication in bacteria (e.g., *E. coli*). In addition, pKR72 also contains the hygromycin B phosphotransferase gene, flanked by the 35S promoter (Odell et al., *Nature* 313:810-812 (1985)) and NOS 3' transcription terminator (Depicker et al., *J. Mol. Appl. Genet.* 1:561-570

(1982)) (35S/hpt/NOS3' cassette) for selection in plants such as soybean. pKR72 also contains a NotI restriction site, flanked by the promoter for the α' subunit of β-conglycinin (Beachy et al., *EMBO J.* 4:3047-3053 (1985)) and the 3' transcription termination region of the phaseolin gene (Doyle et al., *J. Biol. Chem.* 261:9228-9238 (1986)), thus allowing for strong tissue-specific expression in the seeds of soybean of genes cloned into the NotI site. The βcon/NotI/Phas3' cassette in plasmid pKR72 was removed by digestion with HindIII and the fragment containing the HPT gene was re-ligated to give pKR325 (SEQ ID NO:24), previously described in PCT Publication No. WO 2006/012325 (the contents of which are hereby incorporated by reference).

Figure 2:
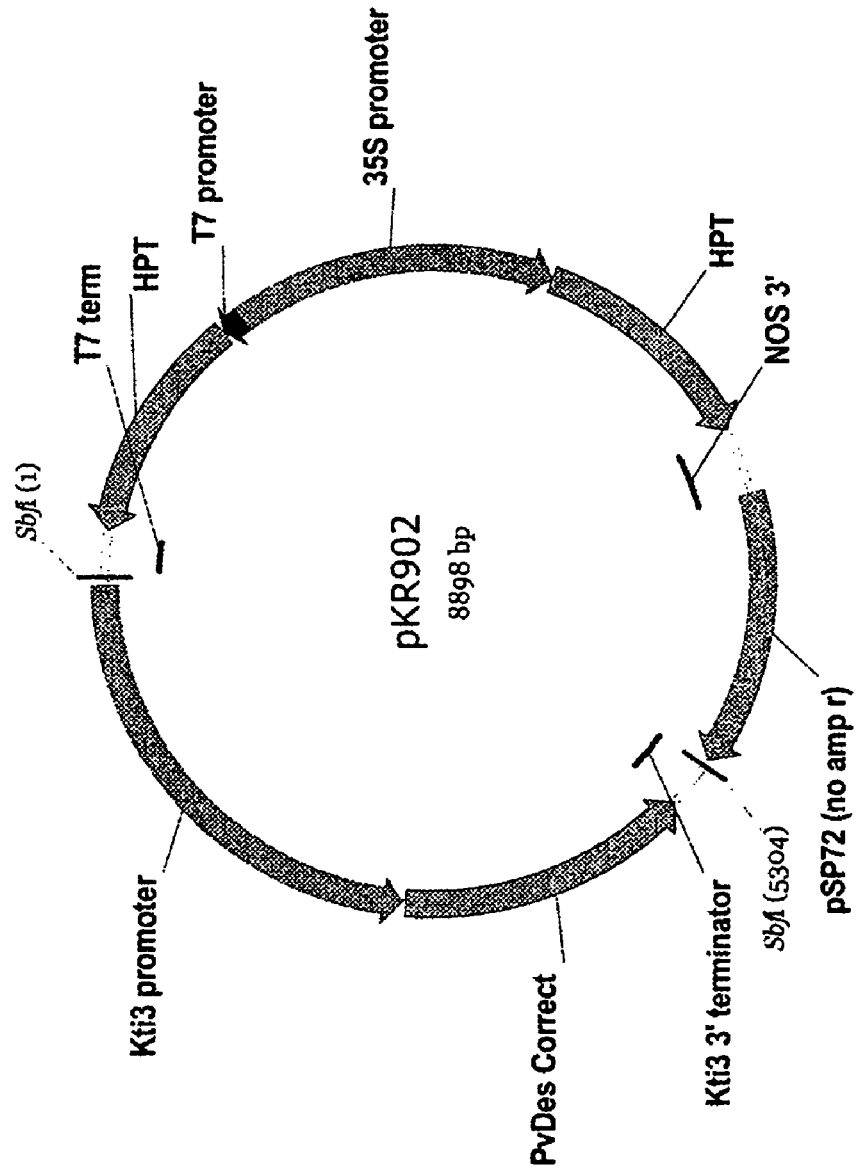
FIG. 2 is a map of plasmid pKR902 (soybean expression vector).

Plasmid pKR900 (SEQ ID NO:23) was then digested with SbfI and the fragment containing the *Pavlova lutheri* delta-8 desaturase was cloned into the SbfI site of pKR325 to produce pKR902 (SEQ ID NO:25). A schematic depiction of pK902 is shown in FIG. 2.

Example 8

Figure 3:
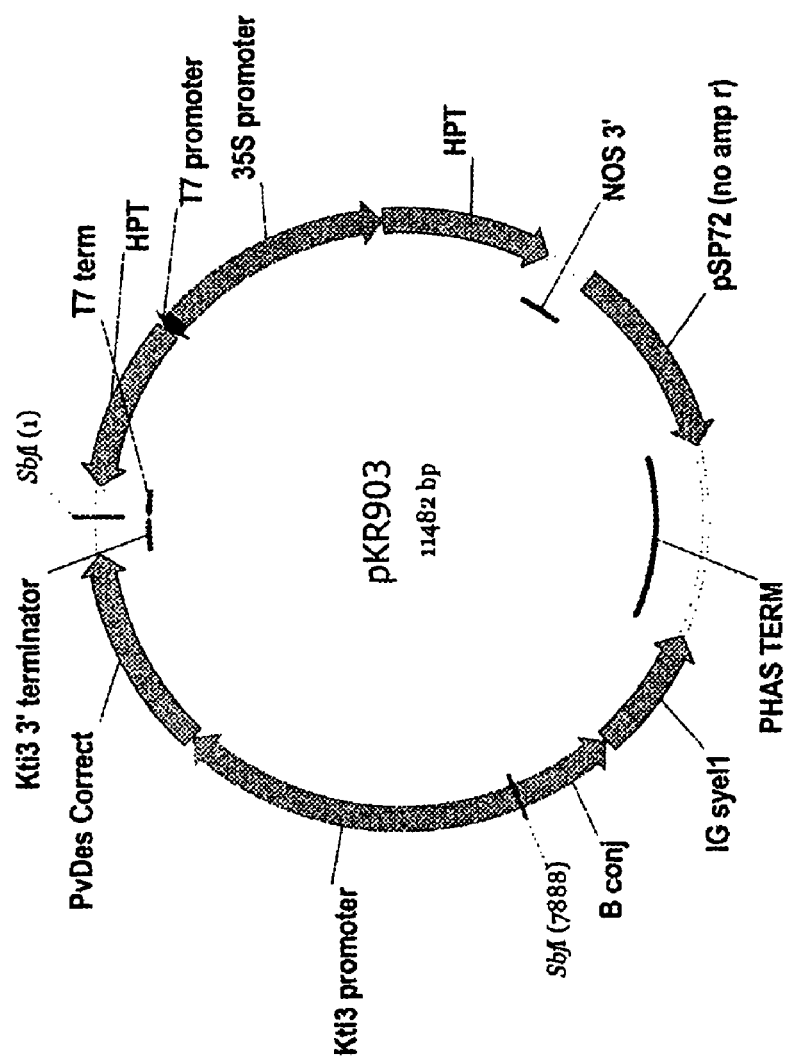
FIG. 3 is a map of plasmid pKR903 (soybean expression vector).

Cloning the *Pavlova lutheri* Delta-8 Desaturase into a Soybean Expression Vector and Co-Expression with the *Isochrysis galbana* Delta-9 Elongase Plasmid pKR900 (from Example 7; SEQ ID NO:23) was digested with SbfI and the fragment containing the *Pavlova lutheri* delta-8 desaturase was cloned into the SbfI site of pKR607 (SEQ ID NO:26), previously described in PCT Publication No. WO 2006/012325 (the contents of which are hereby incorporated by reference) to give pKR903 (SEQ ID NO:27). In this way, the *Pavlova lutheri* delta-8 desaturase is co-expressed with the *Isochrysis galbana* delta-9 elongase behind strong, seed-specific promoters. A schematic depiction of pK903 (ATCC Accession No. PTA-7494) is shown in FIG. 3.

Example 9

Functional Analysis of the *Pavlova lutheri* Delta-8 Desaturase in *Saccharomyces cerevisiae*

*Saccharomyces cerevisiae* expression plasmids pY121 and pY75 (from Example 5) were transformed into *Saccharomyces cerevisiae* INVSC1 (Invitrogen Corporation) using standard lithium acetate transformation procedures. Transformants were selected on DOBA media supplemented with CSM-leu (Qbiogene, Carlsbad, Calif.). Transformants were evaluated for delta-6, delta-8 and delta-5 desaturase activities in the following way. Transformants from each plate were inoculated into 2 mL of DOB medium supplemented with CSM-leu (Qbiogene) and 0.2% tergitol. Cells were grown for 1 day at 30° C. after which, 0.1 mL was transferred to 3 mL of the same medium supplemented with either linoleic acid [LA-18:2(9, 12)], α-linolenic acid [ALA-18:3(9, 12, 15)], dihomo-gamma-linolenic acid [DGLA-20:3(8, 11, 14)], eicosadienoic acid [EDA-20:2(11, 14)] or eicosatrienoic acid [ERA-20:3(11, 14, 17)] to 0.175 mM. These were incubated for 16 h at 30° C., 250 rpm and then pellets were obtained by centrifugation. Cells were washed once with water, pelleted by centrifugation and air dried. Pellets were transesterified (Roughan, G. and Nishida, I., *Arch. Biochem. Biophys.* 276 (1):38-46 (1990)) with 500 µL of 1% sodium methoxide for 30 min. at 50° C. after which 500 µL of 1M sodium chloride and 100 µL of heptane were added. After thorough mixing and centrifugation, fatty acid methyl esters (FAMEs) were analyzed by GC as described supra. In so doing, no desaturation activity for any of the substrates tested could be detected.

Example 10

Functional Analysis of the *Pavlova lutheri* Delta-8 Desaturase in *Yarrowia lipolytica*

A uracil ura3 auxotrophic strain of *Yarrowia lipolytica* (strain Y2224) was used for functional assays. To produce Y2224, *Yarrowia lipolytica* (ATCC Accession No. 20362) cells from a YPD plate were streaked onto a minimal medium plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto minimal medium plates containing 200 mg/mL 5-FOA and minimal medium plates lacking uracil and uridine to confirm uracil ura3 auxotrophy. One confirmed auxotroph was designated Y2224.

*Yarrowia lipolytica* strain Y2224 was grown at 28° C. on YPD agar (1% yeast extract, 2% bactopeptone, 2% glucose, 2% agar). For selection of transformants, minimal medium (0.17% yeast nitrogen base (DIFCO Laboratories, Detroit, Mich.) without ammonium sulfate or amino acids, 2% glucose, 0.1% proline, pH 6.1) was used. Supplements of adenine, leucine, lysine and/or uracil are added to a final concentration of 0.01%.

Transformation of *Yarrowia lipolytica*

Plasmid pY118, containing the *Pavlova lutheri* delta-8 desaturase, or pY5-22GPD, the vector control, were transformed into *Yarrowia lipolytica* strain Y2224 as described in the General Methods.

Briefly, *Yarrowia lipolytica* Strain #2224 was streaked onto a YPD plate and grown at 30° C. for approximately 18 h. Several large loopfuls of cells were scraped from the plate and resuspended in 1 mL of transformation buffer containing: 0.25 mL of 50% PEG, average MW 3350; 0.125 mL of 2 M Li acetate, pH 6.0; 0.125 mL of 2M DTT; and 50 µg sheared salmon sperm DNA. About 500 ng of pY118 or pY5-22GPD plasmid DNA were incubated in 100 µL of resuspended cells, and maintained at 39° C. for 1 h with vortex mixing at 15 min intervals. The cells were plated onto minimal media plates lacking uracil and maintained at 30° C. for 2 to 3 days Single colonies of transformant *Yarrowia lipolytica* containing pY118 or pY5-22GPD were grown in 3 mL minimal media lacking uracil supplemented with 0.2% tergitol at 30° C. for 1 day. After this, 0.1 mL was transferred to 3 mL of the same medium supplemented with either no fatty acid, α-linolenic acid [ALA-18:3(9, 12, 15)], dihomo-gamma-linolenic acid [DGLA-20:3(8, 11, 14)], eicosadienoic acid [EDA-20:2(11, 14)] or eicosatrienoic acid [ERA-20:3(11, 14, 17)] to 0.175 mM. These were incubated for 16 h at 30° C., 250 rpm and then pellets were obtained by centrifugation. Cells were washed once with water, pelleted by centrifugation and air dried. Pellets were transesterified as described supra. FAMEs from cells containing pY118 were analyzed by GC as for cells containing pY121 in Example 9. In so doing, no desaturation activity for any of the substrates tested could be detected.

Example 11

Transformation of Somatic Soybean Embryo Cultures

Culture Conditions:

Soybean embryogenic suspension cultures (cv. Jack) were maintained in 35 mL liquid medium SB196 (infra) on a rotary shaker, 150 rpm, 26° C. with cool white fluorescent lights on 16:8 hr day/night photoperiod at light intensity of 60-85 $\mu E/m2/s$. Cultures were subcultured every 7 days to two weeks by inoculating approximately 35 mg of tissue into 35 mL of fresh liquid SB196 (the preferred subculture interval is every 7 days).

Soybean embryogenic suspension cultures were transformed with the soybean expression plasmids by the method of particle gun bombardment (Klein et al., *Nature*, 327:70 (1987)) using a DuPont Biolistic PDS1000/HE instrument (helium retrofit) for all transformations.

Soybean Embryogenic Suspension Culture Initiation:

Soybean cultures were initiated twice each month with 5-7 days between each initiation. Pods with immature seeds from available soybean plants 45-55 days after planting were picked, removed from their shells and placed into a sterilized magenta box. The soybean seeds were sterilized by shaking them for 15 min in a 5% Clorox solution with 1 drop of ivory soap (i.e., 95 mL of autoclaved distilled water plus 5 mL Clorox and 1 drop of soap, mixed well). Seeds were rinsed using 2 1-liter bottles of sterile distilled water and those less than 4 mm were placed on individual microscope slides. The small end of the seed was cut and the cotyledons pressed out of the seed coat. Cotyledons were transferred to plates containing SB1 medium (25-30 cotyledons per plate). Plates were wrapped with fiber tape and stored for 8 weeks. After this time secondary embryos were cut and placed into SB196 liquid media for 7 days.

Preparation of DNA for Bombardment:

Either an intact plasmid or a DNA plasmid fragment containing the genes of interest and the selectable marker gene were used for bombardment. Fragments from soybean expression plasmids pKR902 and pKR903 were obtained by gel isolation of digested plasmids. In each case, 100 μg of plasmid DNA was used in 0.5 mL of the specific enzyme mix described below. Plasmids were digested with AscI (100 units) in NEBuffer 4 (20 mM Tris-acetate, 10 mM magnesium acetate, 50 mM potassium acetate, 1 mM dithiothreitol, pH 7.9), 100 μg/mL BSA, and 5 mM beta-mercaptoethanol at 37° C. for 1.5 hr. The resulting DNA fragments were separated by gel electrophoresis on 1% SeaPlaque GTG agarose (BioWhitaker Molecular Applications) and the DNA fragments containing gene cassettes were cut from the agarose gel. DNA was purified from the agarose using the GELase digesting enzyme following the manufacturer's protocol.

A 50 μL aliquot of sterile distilled water containing 3 mg of gold particles was added to 5 μL of a 1 μg/μL DNA solution (either intact plasmid or DNA fragment prepared as described above), 50 μL 2.5M $CaCl_2$ and 20 μL of 0.1 M spermidine. The mixture was shaken 3 min on level 3 of a vortex shaker and spun for 10 sec in a bench microfuge. After a wash with 400 μL of 100% ethanol, the pellet was suspended by sonication in 40 μL of 100% ethanol. Five μL of DNA suspension was dispensed to each flying disk of the Biolistic PDS1000/HE instrument disk. Each 5 μL aliquot contained approximately 0.375 mg gold particles per bombardment (i.e., per disk).

Tissue Preparation and Bombardment with DNA:

Approximately 150-200 mg of 7 day old embryonic suspension cultures were placed in an empty, sterile 60×15 mm petri dish and the dish was covered with plastic mesh. Tissue was bombarded 1 or 2 shots per plate with membrane rupture pressure set at 1100 PSI and the chamber was evacuated to a vacuum of 27-28 inches of mercury. Tissue was placed approximately 3.5 inches from the retaining/stopping screen.

Selection of Transformed Embryos:

Transformed embryos were selected using hygromycin as the selectable marker. Specifically, following bombardment, the tissue was placed into fresh SB196 media and cultured as described above. Six days post-bombardment, the SB196 is exchanged with fresh SB196 containing 30 mg/L hygromycin. The selection media was refreshed weekly. Four to six weeks post-selection, green, transformed tissue may was observed growing from untransformed, necrotic embryogenic clusters. Isolated, green tissue was removed and inoculated into multiwell plates to generate new, clonally propagated, transformed embryogenic suspension cultures.

Embryo Maturation:

Embryos were cultured for four-six weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 $\mu E/m^2s$. After this time embryo clusters were removed to a solid agar media, SB166, for 1-2 weeks. Clusters were then subcultured to medium SB103 for 3 weeks. During this period, individual embryos were removed from the clusters and screened for alterations in their fatty acid compositions as described supra.

Media Recipes:

| SB 196 - FN Lite Liquid Proliferation Medium (per liter) | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm | pH 5.8

| | FN Lite Stock Solutions | | |
|---|---|---|---|
| Stock Number | | 1000 mL | 500 mL |
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |

-continued

FN Lite Stock Solutions

| Stock Number | 1000 mL | 500 mL |
|---|---|---|
| $H_3BO_3$ | 0.62 g | 0.31 g |
| $Na_2MoO_4$—$2H_2O$ | 0.025 g | 0.0125 g |

*Add first, dissolve in dark bottle while stirring

SB1 Solid Medium (Per Liter)

1 package MS salts (Gibco/BRL—Cat. No. 11117-066)
1 mL B5 vitamins 1000× stock
31.5 g sucrose
2 mL 2,4-D (20 mg/L final concentration)
pH 5.7
8 g TC agar

SB 166 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
5 g activated charcoal
pH 5.7
2 g gelrite

SB 103 Solid Medium (Per Liter)

1 package MS salts (Gibco/BRL—Cat. No. 11117-066)
1 mL B5 vitamins 1000× stock
60 g maltose
750 mg MgCl2 hexahydrate
pH 5.7
2 g gelrite

SB 71-4 Solid Medium (Per Liter)

1 bottle Gamborg's B5 salts w/sucrose (Gibco/BRL—Cat. No. 21153-036)
pH 5.7
5 g TC agar

2,4-D Stock

Obtain premade from Phytotech Cat. No. D 295—concentration 1 mg/mL

B5 Vitamins Stock (Per 100 mL)

Store aliquots at −20° C.
10 g myo-inositol
100 mg nicotinic acid
100 mg pyridoxine HCl
1 g thiamine
If the solution does not dissolve quickly enough, apply a low level of heat via the hot stir plate.

Example 12

Functional Analysis of the *Pavlova lutheri* Delta-8 Desaturase in Somatic Soybean Embryos Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904, Example 3). Most importantly, the model system is also predictive of the fatty acid composition of seeds from plants derived from transgenic embryos.

Transgenic somatic soybean embryos containing pKR902 (Example 7) or pKR903 (Example 8) were analyzed in the following way. Fatty acid methyl esters were prepared from single, matured, somatic soy embryos by transesterification. Individual embryos were placed in a vial containing 50 µL of trimethylsulfonium hydroxide (TMSH) and 0.5 mL of hexane and incubated for 30 min at room temperature while shaking. Fatty acid methyl esters (5 µL injected from hexane layer) were separated and quantified using a Hewlett-Packard 6890 Gas Chromatograph fitted with an Omegawax 320 fused silica capillary column (Catalog #24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.). Routinely, 5-10 embryos per event were analyzed by GC, using the methodology described above.

Embryo fatty acid profiles for 20 events (5 embryos each) containing pKR902 (Example 7—*Pavlova lutheri* delta-8 desaturase only) were obtained. No delta-6 desaturase activity (i.e., conversion of LA to GLA or ALA to STA) could be detected in any of the events analyzed.

Embryo fatty acid profiles for 6 lines containing pKR903 (Example 8—*Pavlova lutheri* delta-8 desaturase and *Isochrysis galbana* delta-9 elongase) are shown in FIGS. 8A and 8B. Calculated overall % desaturation, % desaturation for n-3 and n-6 substrates and desaturation ratios are also shown in FIGS. 8A and 8B.

In summary of FIGS. 8A and 8B, the *Pavlova lutheri* delta-8 desaturase works well in soybean to convert both EDA and ERA to DGLA and ETA, respectively. The line with the highest average DGLA content (1890-3-5) had embryos with an average DGLA content of 20.7% and an average ETA content of 3.9%. The highest DGLA and ETA content for an individual embryo from this line was 26.3% and 5.4%, respectively. The highest average overall % desaturation (calculation described below) was 72.7% with the highest overall % desaturation for an individual embryo being 83.1%. When broken down into % desaturation for the n-6 and n-3 substrates, the highest average % desaturation was 80.5% and 47.9% for EDA and ERA, respectively. The highest % desaturation for an individual embryo was 89.9% and 55.9% for EDA and ERA, respectively. The *Pavlova lutheri* delta-8 desaturase has a preference for EDA over ERA with the average desaturation ratio ranging from 1.7 to 3.3. Interestingly, some GLA accumulates in embryos were the delta-8 desaturase is expressed well.

Furthermore, in summary of FIGS. 8A and 8B, the overall % desaturation (C20% delta-8 desaturation) was calculated by dividing the sum of the wt. % for DGLA and ETA by the sum of the wt. % for EDA, DGLA, ERA and ETA and multiplying by 100 to express as a %. The individual n-6 delta-8 desaturation (EDA % delta-8 desaturation) was calculated by dividing the sum of the wt. % for DGLA by the sum of the wt. % for EDA and DGLA and multiplying by 100 to express as a %. Similarly, the individual n-3 delta-8 desaturation (ERA % delta-8 desaturation) shown was calculated by dividing the sum of the wt. % for ETA by the sum of the wt. % for ERA and ETA and multiplying by 100 to express as a %. The ratio of delta-8 desaturation for n-6 versus n-3 substrates (ratio EDA/ERA % desaturation) was obtained by dividing the EDA % delta-8 desaturation by the ERA % delta-8 desaturation.

Example 13

Cloning the *Pavlova lutheri* Delta-8 Desaturase into a Soybean Expression Vector Containing the *Euglena gracilis* Delta-9 Elongase and *Mortierella alpina* Delta-5 Desaturase The *Euglena gracilis* delta-9 elongase (SEQ ID NO:32) was amplified with oligonucleotide primers oEugEL1-1 (SEQ ID NO:33) and oEugEL1-2 (SEQ ID NO:34) using the VentR® DNA Polymerase (Cat. No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906 (SEQ ID NO:35).

Plasmid pKR906 was digested with NotI and the fragment containing the *Euglena gracilis* delta-9 elongase was cloned into plasmid pKR132 (SEQ ID NO:36, which is described in PCT Publication No. WO 2004/071467) to give pKR953 (SEQ ID NO:37).

Vector pKR287 (SEQ ID NO:38; which is described in PCT Publication No. WO 2004/071467, published Aug. 26, 2004; the contents of which are hereby incorporated by reference), contains the *Mortierella alpina* delta-5 desaturase (SEQ ID NO:39), which is described in U.S. Pat. No. 6,075,183 and PCT Publication Nos. WO 2004/071467 and WO 2005/047479 (the contents of which are hereby incorporated by reference), flanked by the soybean glycinin Gy1 promoter and the pea leguminA2 3' termination region (Gy1/MaD5/legA2 cassette). Vector pKR287 was digested with SbfI/BsiWI and the fragment containing the Gy1/MaD5/legA2 cassette was cloned into the SbfI/BsiWI fragment of pKR277 (SEQ ID NO:40; which is described in PCT Publication No. WO 2004/071467, the contents of which are hereby incorporated by reference) to produce pK952 (SEQ ID NO:41).

Vector pKR457 (SEQ ID NO:42), which was previously described in PCT Publication No. WO 2005/047479 (the contents of which are hereby incorporated by reference), contains a NotI site flanked by the Kunitz soybean Trypsin Inhibitor (KTi) promoter (Jofuku et al., *Plant Cell* 1:1079-1093 (1989)) and the KTi 3' termination region, the isolation of which is described in U.S. Pat. No. 6,372,965, followed by the soy albumin transcription terminator, which was previously described in PCT Publication No. WO 2004/071467 (Kti/NotI/Kti3'Salb3' cassette). Through a number of subcloning steps, sequences containing Asp718 restriction sites were added to the 5' and 3' ends of the Kti/NotI/Kti3'Salb3' cassette to give SEQ ID NO:43. After cloning the NotI fragment of pLF113 (Example 4), containing the *Pavlova lutheri* delta-8 desaturase, into the modified Kti/NotI/Kti3'Salb3' cassette (SEQ ID NO:43), the DNA fragment was digested with Asp718 and cloned into the SbfI site of pKR952 (SEQ ID NO:41) to give pKR970 (SEQ ID NO:44).

Figure 5:
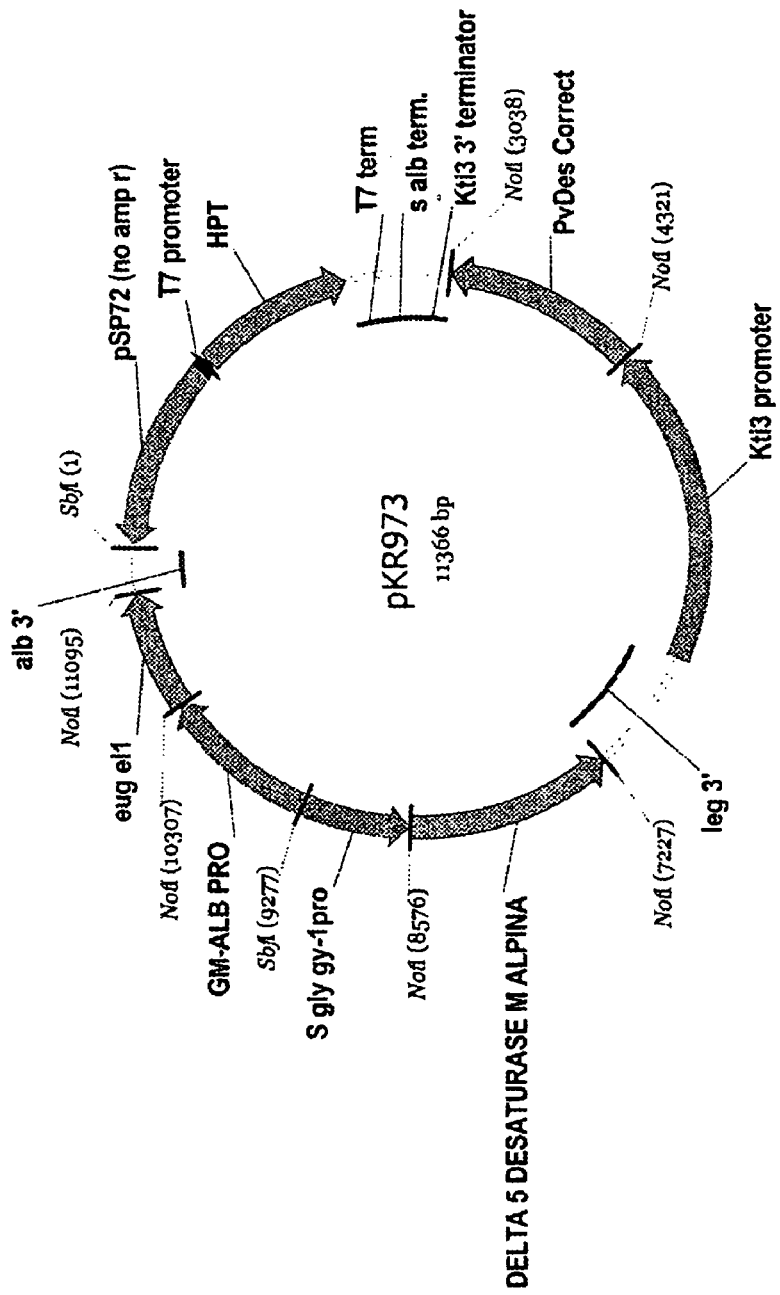
FIG. 5 is a map of plasmid pKR973 (soybean expression vector).

Plasmid pKR953 (SEQ ID NO:37) was digested with PstI and the fragment containing the *Euglena gracilis* delta-9 elongase was cloned into the SbfI site of pKR970 (SEQ ID NO:44) to give pKR973 (SEQ ID NO:45, FIG. 5).

In this way, the *Pavlova lutheri* delta-8 desaturase could be co-expressed with the *Mortierella alpina* delta-5 desaturase and the *Euglena gracilis* delta-9 elongase behind strong, seed-specific promoters.

Example 14

Figure 6:
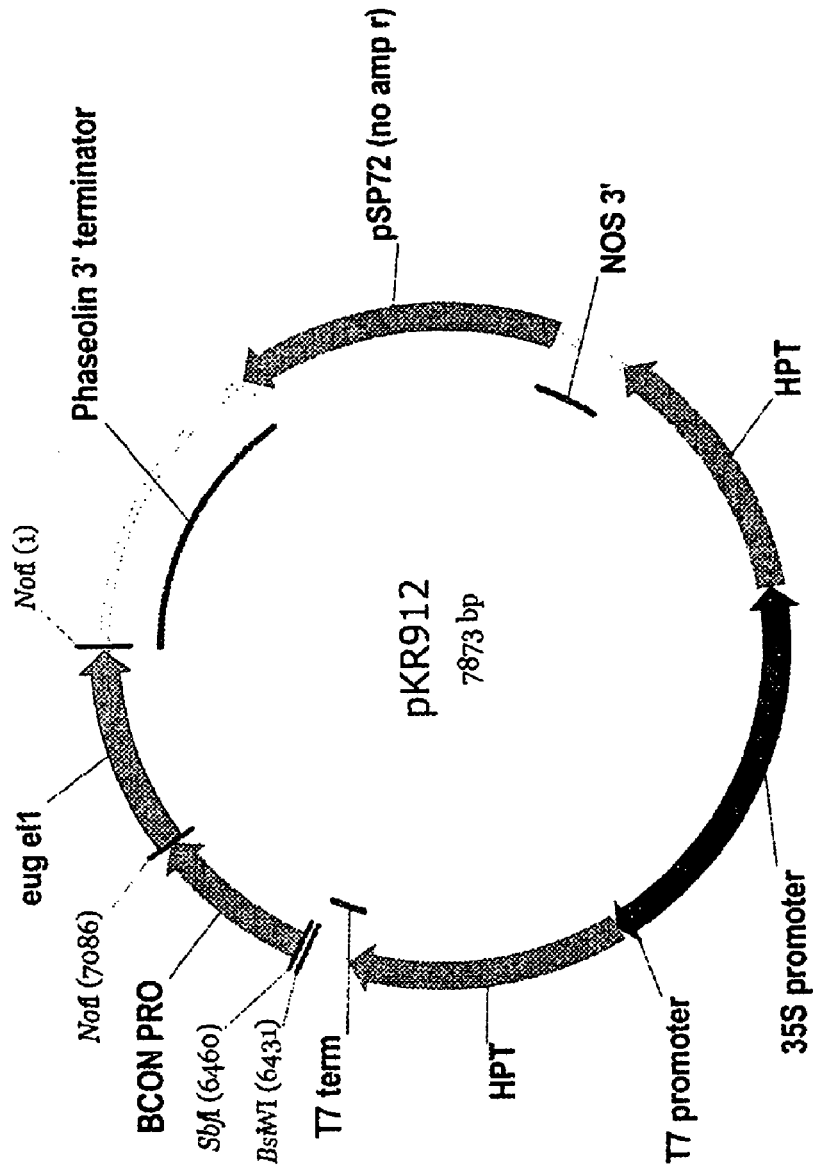
FIG. 6 is a map of plasmid pKR912 (soybean expression vector).

Cloning the *Euglena gracilis* Delta-9 Elongase into a Soybean Expression Vector The gene for the *Euglena gracilis* delta-9 elongase (SEQ ID NO:32) is released from pKR906 (SEQ ID NO:35) by digestion with NotI and cloned into the NotI site of pKR72 (SEQ ID NO:46 and has ATCC Accession No. PTA-6019) to produce pKR912 (SEQ ID NO:47). A schematic depiction of pKR912 is shown in FIG. 6.

Example 15

Construction of a Vector Containing the *Saprolegnia diclina* Delta-17 Desaturase and *Fusarium moniliforme* Delta-15 Desaturase Vector pKR886r (SEQ ID NO:48) was made by cloning the PstI fragment, containing the Ann/Sdd17/BD30 cassette from pKR271 (SEQ ID NO:49, which is described in PCT Publication No. WO 2004/071467) into the SbfI site of pKR226 (SEQ ID NO:50, which is described in PCT Publication No. WO 2004/071467).

The βcon/NotI/Phas3' cassette in plasmid pKR72 (SEQ ID NO:46 and has ATCC Accession No. PTA-6019) was amplified using oligonucleotide primers oCon-1 (SEQ ID NO:51) and oCon-2 (SEQ ID NO:52) using the VentR® DNA Polymerase (Cat. No. M0254S, New England Biolabs Inc., Beverly, Mass.) following the manufacturer's protocol. The resulting DNA fragment was digested with XbaI and cloned into the XbaI site of pUC19, to produce pKR179 (SEQ ID NO:53).

The *Fusarium moniliforme* delta-15 desaturase was released from plasmid pKR578 (SEQ ID NO:54, which is described in PCT Publication No. WO 2005/047479 and has ATCC Accession No. PTA-6280) by digestion with NotI and was cloned into the NotI site of plasmid pKR179 to give pKR582 (SEQ ID NO:55).

Vector pKR582 was digested with PstI and the fragment containing the *Fusarium moniliforme* delta-15 desaturase was cloned into the SbfI site of pKR886r (SEQ ID NO:48) to give pKR983 (SEQ ID NO:56). A schematic depiction of pKR983 is shown in FIG. 7.

Example 16

Co-Expressing Other Promoter/Gene/Terminator Cassette Combinations

In addition to the genes, promoters, terminators and gene cassettes described herein, one skilled in the art can appreciate that other promoter/gene/terminator cassette combinations can be synthesized in a way similar to, but not limited to, that described herein. For instance, PCT Publication Nos. WO 2004/071467 and WO 2004/071178 describe the isolation of a number of promoter and transcription terminator sequences for use in embryo-specific expression in soybean. Furthermore, PCT Publication Nos. WO 2004/071467, WO 2005/047479 and WO 2006/012325 describe the synthesis of multiple promoter/gene/terminator cassette combinations by ligating individual promoters, genes and transcription terminators together in unique combinations. Generally, a NotI site flanked by the suitable promoter (such as those listed in, but not limited to, Table 4) and a transcription terminator (such as those listed in, but not limited to, Table 5) is used to clone the desired gene. NotI sites can be added to a gene of interest such as those listed in, but not limited to, Table 6 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publication Nos. WO 2004/071467, WO 2005/047479 and WO 2006/012325 describe the further linking together of individual gene cassettes in unique combinations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 4

Seed-specific Promoters

| Promoter | Organism | Promoter Reference |
|---|---|---|
| β-conglycinin α'-subunit | soybean | Beachy et al., EMBO J. 4: 3047-3053 (1985) |
| kunitz trypsin inhibitor | soybean | Jofuku et al., Plant Cell 1: 1079-1093 (1989) |
| Annexin | soybean | WO 2004/071467 |
| glycinin Gy1 | soybean | WO 2004/071467 |
| albumin 2S | soybean | U.S. Pat. No. 6,177,613 |
| legumin A1 | pea | Rerie et al., Mol. Gen. Genet. 225: 148-157 (1991) |
| β-conglycinin β-subunit | soybean | WO 2004/071467 |
| BD30 (also called P34) | soybean | WO 2004/071467 |
| legumin A2 | pea | Rerie et al., Mol. Gen. Genet. 225: 148-157 (1991) |

TABLE 5

Transcription Terminators

| Transcription Terminator | Organism | Reference |
|---|---|---|
| phaseolin 3' | bean | WO 2004/071467 |
| kunitz trypsin inhibitor 3' | soybean | WO 2004/071467 |
| BD30 (also called P34) 3' | soybean | WO 2004/071467 |
| legumin A2 3' | pea | WO 2004/071467 |
| albumin 2S 3' | soybean | WO 2004/071467 |

TABLE 6

EPA Biosynthetic Pathway Genes

| Gene | Organism | Reference |
|---|---|---|
| delta-6 desaturase | Saprolegnia diclina | WO 2002/081668 |
| delta-6 desaturase | Mortierella alpina | U.S. Pat. No. 5,968,809 |
| elongase | Mortierella alpina | WO 2000/12720 |
|  |  | U.S. Pat. No. 6,403,349 |
| delta-5 desaturase | Mortierella alpina | U.S. Pat. No. 6,075,183 |
| delta-5 desaturase | Saprolegnia diclina | WO 2002/081668 |
| delta-15 desaturase | Fusarium moniliforme | WO 2005/047479 |
| delta-17 desaturase | Saprolegnia diclina | WO 2002/081668 |
| elongase | Thraustochytrium aureum | WO 2002/08401 U.S. Pat. No. 6,677,145 |
| elongase | Pavlova sp. | Pereira et al., Biochem. J. 384: 357-366 (2004) |
| delta-4 desaturase | Schizochytrium aggregatum | WO 2002/090493 |
| delta-9 elongase | Isochrysis galbana | WO 2002/077213 |
| delta-9 elongase | Euglena gracilis | U.S. Provisional Application No. 60/739,989 |
| delta-8 desaturase | Euglena gracilis | WO 2000/34439 U.S. Pat. No. 6,825,017 WO 2004/057001 WO 2006/012325 |
| delta-8 desaturase | Acanthamoeba castellanii | Sayanova et al., FEBS Lett. 580: 1946-1952 (2006) |
| delta-8 desaturase | Pavlova salina | WO 2005/103253 |
| delta-8 desaturase | Pavlova lutheri | instant application |

Example 17

Synthesis of a Codon-Optimized Delta-8 Desaturase Gene Derived from *Pavlova lutheri* in *Yarrowia lipolytica*

The codon usage of the delta-8 desaturase gene of *Pavlova lutheri* (SEQ ID NO:14; Example 4, supra) was optimized for expression in *Yarrowia lipolytica*, in a manner similar to that described in PCT Publication No. WO 2004/101753. Specifically, a codon-optimized delta-8 desaturase gene (designated "PiD8S"; SEQ ID NO:57) was designed based on the coding sequence of the delta-8 desaturase gene of the instant invention (SEQ ID NO:14), according to the *Yarrowia* codon usage pattern (PCT Publication No. WO 2004/101753), the consensus sequence around the 'ATG' translation initiation codon, and the general rules of RNA stability (Guhaniyogi, G. and Brewer, J., Gene 265(1-2):11-23 (2001)). In addition to modification of the translation initiation site, 161 bp of the 1272 bp coding region were modified (13.1%) and 161 codons were optimized (38.1%). None of the modifications in the codon-optimized gene changed the amino acid sequence of the encoded protein (SEQ ID NO:16). The designed PiD8S gene was synthesized by GenScript Corporation (Piscataway, N.J.) and cloned into pUC57 (GenBank Accession No. Y14837) to generate pPiD8S (SEQ ID NO:58; FIG. 11-A).

Example 18

Construction of Plasmid pZUFmEgD9ES, Comprising a Codon-Optimized Delta-9 Elongase Gene Derived from *Euglena gracilis*

The present Example describes the construction of plasmid pZUFmEgD9ES (SEQ ID NO:70), comprising a synthetic delta-9 elongase gene (derived from *Euglena gracilis*) that was codon-optimized for *Yarrowia lipolytica* (designated herein as "EgD9S" or "EgD9ES"). Plasmid pZUFmEgD9ES (SEQ ID NO: 70; FIG. 9-D) was constructed by three-way ligation using fragments from plasmids pEgD9ES, pDMW263 and pZUF17 (SEQ ID NO:67, SEQ ID NO:68 and SEQ ID NO:69, respectively; FIGS. 9-A, 9-B and 9-C, respectively). This plasmid was utilized to construct plasmid pZUFmE9SP8S (SEQ ID NO:71) comprising the synthetic codon-optimized PiD8S from Example 17 and EgD9S as described herein in Example 19, infra.

Euglena gracilis Growth Conditions, Lipid Profile and mRNA Isolation:

Euglena gracilis was obtained from Dr. Richard Triemer's lab at Michigan State University (East Lansing, Mich.). From 10 mL of actively growing culture, a 1 mL aliquot was transferred into 250 mL of Euglena gracilis (Eg) Medium in a 500 mL glass bottle. Eg medium was made by combining 1 g of sodium acetate, 1 g of beef extract (U126-01, Difco Laboratories, Detroit, Mich.), 2 g of Bacto® tryptone (0123-17-3, Difco Laboratories) and 2 g of Bacto® yeast extract (0127-17-9, Difco Laboratories) in 970 mL of water. After filter sterilizing, 30 mL of soil-water supernatant (15-3790, Carolina Biological Supply Company, Burlington, N.C.) was aseptically added to give the final Eg medium. Euglena gracilis cultures were grown at 23° C. with a 16 h light, 8 h dark cycle for 2 weeks with no agitation.

After 2 weeks, 10 mL of culture was removed for lipid analysis and centrifuged at 1,800×g for 5 min. The pellet was washed once with water and re-centrifuged. The resulting pellet was dried for 5 min under vacuum, resuspended in 100 µL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 µL injected from hexane layer) were separated and quantified using a Hewlett-Packard 6890 Gas Chromatograph fitted with an Omegawax 320 fused silica capillary column (Supelco Inc., Cat. No. 24152). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Nu-Chek Prep, Inc. Cat. No. U-99-A) and the resulting chromatogram is shown in FIG. 10.

The remaining 2 week culture (240 mL) was pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided (use 5 mL of reagent, dissolved RNA in 0.5 mL of water). In this way, 1 mg of total RNA (2 mg/mL) was obtained from the pellet. The mRNA was isolated from 1 mg of total RNA using the mRNA Purification Kit (Amersham Biosciences, Piscataway, N.J.) following the manufacturer's protocol provided. In this way, 85 µg of mRNA was obtained.

Euglena gracilis cDNA Synthesis, Library Construction and Sequencing:

A cDNA library was generated using the Cloneminer™ cDNA Library Construction Kit (Cat. No. 18249-029, Invitrogen Corporation, Carlsbad, Calif.) and following the manufacturer's protocol provided (Version B, 25-0608). Using the non-radiolabeling method, cDNA was synthesized from 3.2 µg of mRNA (described above) using the Biotin-attB2-Oligo (dT) primer. After synthesis of the first and second strand, the attB1 adapter was added, ligated and the cDNA was size fractionated using column chromatography. DNA from fractions 7 and 8 (size ranging from ~800-1500 bp) were concentrated, recombined into PDONR™222 and transformed into E. coli ElectroMAX™ DH10B™ T1 Phage-Resistant cells (Invitrogen Corporation). The Euglena gracilis library was named eeg1c.

For sequencing, clones first were recovered from archived glycerol cultures grown/frozen in 384-well freezing media plates, and replicated with a sterile 384 pin replicator (Genetix, Boston, Mass.) in 384-well microtiter plates containing LB+75 µg/mL Kanamycin (replicated plates). Plasmids then were isolated, using the Templiphi DNA sequencing template amplification kit method (Amersham Biosciences) following the manufacturer's protocol. Briefly, the Templiphi method uses bacteriophage φ29 DNA polymerase to amplify circular single-stranded or double-stranded DNA by isothermal rolling circle amplification (Dean et al., Genome Res. 11:1095-1099 (2001); Nelson et al., Biotechniques 32:S44-S47 (2002)). After growing 20 h at 37° C., cells from the replicated plate were added to 5 µL of dilution buffer and denatured at 95° C. for 3 min to partially lyse cells and release the denatured template. 5 µL of Templiphi premix then were added to each sample and the resulting reaction mixture was incubated at 30° C. for 16 h, then at 65° C. for 10 min to inactivate the φ29 DNA polymerase activity. DNA quantification with the PicoGreen® dsDNA Quantitation Reagent (Molecular Probes) was performed after diluting the amplified samples 1:3 in distilled water.

The amplified products then were denatured at 95° C. for 10 min and end-sequenced in 384-well plates, using the M13F universal primer (SEQ ID NO:63), and the ABI Big-Dye version 3.1 Prism Sequencing Kit. For the sequencing reaction, 100-200 ng of templates and 6.4 pmol of primers were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3730xl automated sequencers.

Identification of Long-Chain Polyunsaturated Fatty Acid Elongation Enzyme Homologs from Euglena gracilis cDNA Library eeg1c:

cDNA clones encoding long-chain polyunsaturated fatty acid elongation enzyme homologs (i.e., LC-PUFA ELO homologs or delta-9 elongases) were identified and analyzed by conducting BLAST searches for similarity to sequences contained in the BLAST "nr" database, as described supra (see Example 2).

The BLASTX search using the nucleotide sequences from clone eeg1c.pk001.n5.f revealed similarity of the protein encoded by the cDNA to the long-chain PUFA elongation enzyme from Isochrysis galbana (SEQ ID NO:59) (NCBI Accession No. AAL37626 (GI 17226123), locus AAL37626, CDS AF390174; Qi et al., FEBS Lett. 510(3):159-165 (2002)). The sequence of a portion of the cDNA insert from clone eeg1c.pk001.n5.f is shown in SEQ ID NO:60 (5' end of cDNA insert). Additional sequence was obtained from the 3' end of the cDNA insert of eeg1c.pk001.n5.1 as described above, but using the poly(A) tail-primed WobbleT oligonucleotides. Briefly, the WobbleT primer is an equimolar mix of 21 mer poly(T)A, poly(T)C and poly(T)G, used to sequence the 3' end of cDNA clones.

The 3' end sequence is shown in SEQ ID NO:61. Both the 5' and 3' sequences were aligned using Sequencher™ (Version 4.2, Gene Codes Corporation, Ann Arbor, Mich.) and the resulting sequence for the cDNA is shown in SEQ ID NO:62. Sequence for the coding sequence from the cDNA in eeg1c.pk001.n5.f and the corresponding deduced amino acid sequence is shown in SEQ ID NO:32 and SEQ ID NO:64, respectively.

The amino acid sequence set forth in SEQ ID NO:64 was evaluated by BLASTP, yielding a pLog value of 38.70 (E value of 2e-39) versus the *Isochrysis galbana* sequence (SEQ ID NO:65). The *Euglena gracilis* delta-9 elongase is 39.4% identical to the *Isochrysis galbana* delta-9 elongase sequence using the Jotun Hein method. Sequence percent identity calculations performed by the Jotun Hein method (Hein, J. J., *Meth. Enz.* 183:626-645 (1990)) were done using the MegAlign™ v6.1 program of the LASARGENE bioinformatics computing suite (DNASTAR Inc., Madison, Wis.) with the default parameters for pairwise alignment (KTUPLE=2). The *Euglena gracilis* delta-9 elongase is 31.8% identical to the *Isochrysis galbana* delta-9 elongase sequence using the Clustal V method. Sequence percent identity calculations performed by the Clustal V method (Higgins, D. G. and Sharp, P. M., *Comput. Appl. Biosci.* 5:151-153 (1989); Higgins et al., *Comput. Appl. Biosci.* 8:189-191 (1992)) were done using the MegAlign™ v6.1 program of the LASARGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10). BLAST scores and probabilities indicate that the instant nucleic acid fragment (SEQ ID NO:32) encode an entire *Euglena gracilis* delta-9 elongase.

Synthesis of the Codon-Optimized Delta-9 Elongase Gene:

The codon usage of the delta-9 elongase gene of *Euglena gracilis* (SEQ ID NOs:32 and 64) was optimized for expression in *Yarrowia lipolytica*, in a manner similar to that described supra (see Example 17) and WO 2004/101753. Specifically, a codon-optimized delta-9 elongase gene (designated "EgD9S"), SEQ ID NO:66) was designed, based on the coding sequence of the delta-9 elongase (clone eeg1c.pk001.n5.f), according to the *Yarrowia* codon usage pattern, the consensus sequence around the 'ATG' translation initiation codon, and the general rules of RNA stability (Guhaniyogi, G. and Brewer, J., supra)). In addition to the modification of the translation initiation site, 117 bp of the 777 bp coding region were modified (15.1%) and 106 codons were optimized (40.9%). None of the modifications in the codon-optimized gene changed the amino acid sequence of the encoded protein (SEQ ID NO:64). The designed EgD9S (also "EgD9ES") gene was synthesized by GenScript Corporation (Piscataway, N.J.) and was cloned into pUC57 (GenBank Accession No. Y14837) to generate pEgD9ES (SEQ ID NO:67; FIG. 9-A).

Construction of Plasmid pDMW263:

Plasmid pY5-30 (SEQ ID NO:78) (previously described in PCT Publication No. WO 2005/003310 (the contents of which are hereby incorporated by reference) is a shuttle plasmid that can replicate both in *E. coli* and *Yarrowia lipolytica*. Plasmid pY5-30 contains the following: a *Yarrowia* autonomous replication sequence (ARS18); a ColE1 plasmid origin of replication; an ampicillin-resistance gene (AmpR) for selection in *E. coli*; a *Yarrowia* LEU2 gene for selection in *Yarrowia*; and a chimeric TEF::GUS::XPR gene. Plasmid pDMW263 (SEQ ID NO:68; FIG. 9-B) was created from pY5-30, by replacing the TEF promoter with the *Yarrowia lipolytica* FBAINm promoter (PCT Publication No. WO 2005/049805) using techniques well known to one skilled in the art. Briefly, this promoter refers to a modified promoter which is located in the 5' upstream untranslated region in front of the 'ATG' translation initiation codon of the fructose-bis-phosphate aldolase enzyme (E.C. 4.1.2.13) encoded by the fba1 gene and that is necessary for expression, plus a portion of 5' coding region that has an intron, wherein FBAINm has a 52 bp deletion between the ATG translation initiation codon and the intron of the FBAIN promoter (thereby including only 22 amino acids of the N-terminus) and a new translation consensus motif after the intron. Table 7 summarizes the components of pDMW263.

TABLE 7

Components of Plasmid pDMW263

| RE Sites and Nucleotides Within SEQ ID NO: 68 | Description of Fragment and Chimeric Gene Components |
|---|---|
| 4992-4296 SalI/SacII (8505-2014) | ARS18 sequence (GenBank Accession No. A17608) FBAINm::GUS::XPR, comprising: FBAINm: *Yarrowia lipolytica* FBAINm promoter (WO 2005/049805) GUS: *E. coli* gene encoding β-glucuronidase (Jefferson, R. A., *Nature*. 14: 342: 837-838 (1989)) XPR: ~100 bp of the 3' region of the *Yarrowia* Xpr gene (GenBank Accession No. M17741) |
| 6303-8505 | *Yarrowia* Leu2 gene (GenBank Accession No. AF260230) |

Construction of Plasmid pZUF17:

Plasmid pZUF17 (SEQ ID NO:69; FIG. 9-C) possesses a similar backbone to that of pDMW236. However, the plasmid comprises a *Yarrowia* Ura3 gene for selection in *Yarrowia* and a chimeric FBAIN::D17S::Pex20 gene, instead of the LEU2 gene and chimeric FBAINm::GUS::XPR gene of pDMW263. Table 8 summarizes the components of pZUF17.

TABLE 8

Components of Plasmid pZUF17

| RE Sites and Nucleotides Within SEQ ID NO: 69 | Description of Fragment and Chimeric Gene Components |
|---|---|
| 2866-4170 CalI/PacI (5750-8165) | ARS18 sequence (GenBank Accession No. A17608) FBAIN::D17S::Pex20, comprising: FBAIN: *Yarrowia lipolytica* FBAIN promoter (WO 2005/049805) Δ17S: synthetic Δ17 desaturase gene derived from *Saprolegnia diclina* (US 2003/0196217 A1), codon-optimized for *Yarrowia lipolytica* (WO 2004/101757) Pex20: Pex20 terminator sequence of *Yarrowia* Pex20 gene (GenBank Accession No. AF054613) |
| 5703-4216 | *Yarrowia* Ura3 gene (GenBank Accession No. AJ306421) |

Final Construction of Plasmid pZUFmEgD9ES:

The NcoI/NotI fragment from plasmid pEgD9ES (SEQ ID NO:67; FIG. 9-A; comprising EgD9ES) and the SalI/NcoI fragment from pDMW263 (SEQ ID NO:68; FIG. 9-B; comprising the *Yarrowia lipolytica* FBAINm promoter) were used directionally to replace the SalI/NotI fragment of pZUF17 (SEQ ID NO:69; FIG. 9-C). This resulted in generation of pZUFmEgD9ES (SEQ ID NO:70; FIG. 9-D), comprising a chimeric FBAINm::EgD9ES::Pex20 gene.

Example 19

Construction of Plasmid pZUFmE9SP8S, Comprising the Codon-Optimized Delta-8 Desaturase Gene Derived from *Pavlova lutheri* and the Codon-Optimized Delta-9 Elongase Gene Derived from *Euglena gracilis*

The present Example describes the construction of plasmid pZUFmE9SP8S (SEQ ID NO:71), comprising the synthetic codon-optimized PiD8S from Example 17 and the synthetic codon-optimized EgD9ES from Example 18. Plasmid pZUFmE9SP8S (SEQ ID NO:71; FIG. 11-D) was constructed by four-way ligation using fragments from plasmids pPiD8S, pZUFmEgD9ES, pEXPGUS1-C and pZGD5T-CP (SEQ ID NO:58, SEQ ID NO:70, SEQ ID NO:72 and SEQ ID NO:73, respectively; FIGS. 11-A, 9-D, 11-B and 11-C, respectively). This plasmid was utilized to test functional co-expression of PiD8S and EgD9ES, as described in Example 20, infra.

Plasmid pEXPGUS1-C:

Plasmid pEXPGUS1-C (SEQ ID NO:72; FIG. 11-B) comprises a chimeric EXP1::GUS::XPR gene (nucleotides 953-3963 of SEQ ID NO:72). The "EXP1" promoter within this chimeric gene refers to the 5' upstream untranslated −1000 to −1 bp region in front of the 'ATG' translation initiation codon of a protein encoded by the *Yarrowia lipolytica* "YALI0C12034g" gene (GenBank Accession No. XM_501745) and that is necessary for expression. Based on significant homology of "YALI0C12034g" to the sp|Q12207 *Saccharomyces cerevisiae* non-classical export protein 2 (whose function is involved in a novel pathway of export of proteins that lack a cleavable signal sequence), this gene was designated as the exp1 gene, encoding a protein designated as EXP1 (U.S. application Ser. No. 11/265,761). "GUS" and "XPR" are defined as described above in Table 7.

Plasmid pZGD5T-CP:

Plasmid pZGD5T-CP (SEQ ID NO:73; FIG. 11-C) comprises a chimeric GPD::MAD5::Pex16 gene (nucleotides 3200-346 of SEQ ID NO:73). The "GPD" promoter within this chimeric gene refers to the 5' upstream untranslated region in front of the 'ATG' translation initiation codon of a protein encoded by the *Yarrowia lipolytica* glyceraldehyde-3-phosphate dehydrogenase (GPD) gene and that is necessary for expression (PCT Publication No. WO 2005/003310). The "MAD5" coding region of the chimeric gene corresponds to the *Mortierella alpina* Δ5 desaturase gene (GenBank Accession No. AF067654), while "Pex16" refers to the Pex16 terminator of the *Yarrowia* Pex16 gene (GenBank Accession No. U75433).

Final Construction of Plasmid pZUFmE9SP8S:

The NcoI/NotI fragment of plasmid pPiD8S (SEQ ID NO:58; FIG. 11-A; comprising the synthetic delta-8 desaturase gene of the present invention (i.e., PiD8S), the ClaI/NcoI fragment from pEXPGUS1-C (SEQ ID NO:72; FIG. 11-B; comprising the EXP1 promoter), and the NotI/PacI fragment from plasmid pZGD5T-CP (SEQ ID NO:73; FIG. 11-C; comprising the Pex16 terminator) were used directionally to replace the ClaI/PacI fragment of pZUFmEgD9ES (SEQ ID NO:70; FIG. 9-D) to generate pZUFmE9SP8S (SEQ ID NO:71; FIG. 11-D).

Example 20

Functional Expression of Plasmid pZUFmE9SP8S in *Yarrowia lipolytica*

The present Example describes expression of plasmid pZUFmE9SP8S, comprising the chimeric FBAINm::EgD9ES::Pex20 gene and the chimeric EXP::PiD8S::Pex16 gene. Expression of pZUFmE9SP8S in *Yarrowia lipolytica* led to the production of up to 2.8% EDA and 0.5% of DGLA.

Specifically, pZUFmE9SP8S (SEQ ID NO:71; FIG. 11-D) was transformed into *Yarrowia lipolytica* Y20362U (an autonomous Ura-mutant of ATCC Accession No. 20362, that was generated by selecting for FOA resistance) as described supra. The transformant cells were plated onto MM selection media plates and maintained at 30° C. for 2 to 3 days. Fifteen (15) transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 2.8% EDA (C20:2) and 0.3% of DGLA (C20:3) of total lipids produced in 13 of these 15 transformants, wherein the conversion efficiency of EDA to DGLA in these 13 strains was at an average rate of about 9.7%. Strain #7 produced 2.8% EDA and 0.5% of DGLA, with a conversion efficiency of about 15%. The term "conversion efficiency" refers to the efficiency by which a particular enzyme (e.g., the codon-optimized delta-8 desaturase identified herein as PiD8S) can convert substrate (i.e., EDA) to product (i.e., DGLA). The conversion efficiency was measured according to the following formula: ([product]/[substrate+product])*100, where 'product' includes the immediate product and all products in the pathway derived from it.

Example 21

Chlorsulfuron Selection (ALS) and Plant Regeneration

Chlorsulfuron (ALS) Selection:

Following bombardment, the tissue is divided between 2 flasks with fresh SB196 media and cultured as described in Example 11. Six to seven days post-bombardment, the SB196 is exchanged with fresh SB196 containing selection agent of 100 ng/mL chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants:

In order to obtain whole plants from embryogenic suspension cultures, the tissue must be regenerated. Embyros are matured as described in Example 11. After subculturing on medium SB103 for 3 weeks, individual embryos can be removed from the clusters and screened for alterations in their fatty acid compositions as described in Example 12. It should be noted that any detectable phenotype, resulting from the expression of the genes of interest, could be screened at this stage. This would include, but not be limited to, alterations in fatty acid profile, protein profile and content, carbohydrate content, growth rate, viability, or the ability to develop normally into a soybean plant.

Matured individual embryos are desiccated by placing them into an empty, small petri dish (35×10 mm) for approximately 4 to 7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then are planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for fatty acids as described in Example 12.

Media recipes can be found in Example 11 and chlorsulfuron stock is 1 mg/mL in 0.01 N ammonium hydroxide.

Example 22

Co-Expression of the *Euglena gracilis* Delta-9 Elongase with the *Pavlova lutheri* (CCMP459) Delta-8 Desaturase, the *Mortierella alpina* Delta-5 Desaturase, the *Saprolegnia diclina* Delta-17 Desaturase and the *Fusarium moniliforme* Delta-15 Desaturase in Soybean Embryos Transformed with Soybean Expression Vectors pKR973 and pKR983

Soybean embryogenic suspension culture (cv. Jack) was transformed with the AscI fragments of pKR973 (SEQ ID NO:45, FIG. 5) and pKR983 (SEQ ID NO:56; FIG. 7) (fragments containing the expression cassettes), as described for production in Example 11. Transformants were selected using chlorsulfuron as described in Example 21 and embryos were matured as described in Example 11. A subset of soybean embryos generated from each event (ten embryos per event) were harvested and analyzed for fatty acid composition as described in Example 12. Fatty acids were identified by comparison of retention times to those for authentic standards.

In this way, 243 events transformed with pKR973 and pKR983 were analyzed. From the 243 events analyzed, 117 were identified that produced EPA in at least one embryo out of ten analyzed at a relative abundance greater than 1.0% of the total fatty acids. Of these, 15 were identified that produced EPA in at least one embryo out of ten analyzed at a relative abundance greater than 10.0% of the total fatty acids. The average fatty acid profile for the ten best EPA events (average of seven to ten individual embryos) is shown in FIG. 14. Fatty acids are identified as 16:0 (palmitate), 18:0 (stearic acid), 18:1 (oleic acid), LA, GLA, ALA, EDA, DGLA, ARA, ERA, JUN, ETA, EPA and DPA; and, fatty acid compositions listed in FIG. 14 are expressed as a weight percent (wt. %) of total fatty acids. For FIG. 14, fatty acids listed as "others" include: 18:2 (5,9), STA, 20:0, 20:1(11), 20:2 (7, 11) or 20:2 (8, 11) and 20:3 (5, 11, 14). Each of these fatty acids is present at a relative abundance of less than 1% of the total fatty acids. The activity of the *Pavlova lutheri* (CCMP459) delta-8 desaturase is expressed as percent delta-8 desaturation (% Desat), calculated according to the following formula: ([product]/[substrate+product])*100.

More specifically, the combined percent delta-8 desaturation for EDA and ERA is shown as "Total delta-8% Desat", determined as: ([DGLA+ARA+ERA+ETA+EPA+DPA]/[EDA+DGLA+ARA+ERA+JUN+ETA+EPA+DPA])*100.

In summary of FIG. 14, the *Pavlova lutheri* (CCMP459) delta-8 desaturase functioned in soybean to convert both EDA and ERA to DGLA and ETA, respectively, and these were further converted to other LC-PUFAs. Line AFS 4802-3-14, the high EPA line with the highest average overall % delta-8 desaturation, had overall % delta-8 desaturation of 82.5%.

---

What is claimed is:

1. An oilseed plant comprising:
   (a) a first recombinant DNA construct comprising:
      (i) a nucleotide sequence encoding a polypeptide having delta-8 desaturase activity, wherein the polypeptide has at least 95% amino acid identity, based on the Clustal V method of alignment, when compared to an amino acid sequence as set forth in SEQ ID NO:16;
      (ii) a nucleotide sequence encoding a polypeptide having delta-8 desaturase activity, wherein the nucleotide sequence has at least 95% sequence identity, based on the BLASTN method of alignment, when compared to a nucleotide sequence as set forth in SEQ ID NO:15; or
      (iii) a complement of the nucleotide sequence of (a) or (b), wherein the complement and the nucleotide sequence consist of the same number of nucleotides and are 100% complementary,
   operably linked to at least one regulatory sequence; and
   (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase.

2. The oilseed plant of claim 1, wherein the oilseed plant is selected from the group consisting of soybean, *Brassica* species, sunflower, maize, cotton, flax and safflower.

3. The oilseed plant of claim 1 wherein the oilseed plant is selected from the group consisting of soybean, *Brassica* species, sunflower, maize, cotton, flax, and safflower and further wherein the polyunsaturated fatty acid is selected from the group consisting of arachidonic acid, eicosadienoic acid, eicosapentaenoic acid, eicosatetraenoic acid, eicosatrienoic acid, dihomo-gamma-linolenic acid, docosapentaenoic acid and docosahexaenoic acid.

4. A seed obtained from the oilseed plant of claim 1, wherein said comprises:
   (i) a nucleotide sequence encoding a polypeptide having delta-8 desaturase activity, wherein the polypeptide has at least 95% amino acid identity, based on the Clustal V method of alignment, when compared to an amino acid sequence as set forth in SEQ ID NO:16;
   (ii) a nucleotide sequence encoding a polypeptide having delta-8 desaturase activity, wherein the nucleotide sequence has at least 95% sequence identity, based on the BLASTN method of alignment, when compared to a nucleotide sequence as set forth in SEQ ID NO:15; or (iii) a complement of the nucleotide sequence of (a) or (b), wherein the complement and the nucleotide sequence consist of the same number of nucleotides and are 100% complementary.

5. Food or feed comprising the seed of claim 4.

6. Progeny of the plant of claim 1, wherein said progeny comprises:
  (i) a nucleotide sequence encoding a polypeptide having delta-8 desaturase activity, wherein the polypeptide has at least 95% amino acid identity, based on the Clustal V method of alignment, when compared to an amino acid sequence as set forth in SEQ ID NO:16;
  (ii) a nucleotide sequence encoding a polypeptide having delta-8 desaturase activity, wherein the nucleotide sequence has at least 95% sequence identity, based on the BLASTN method of alignment, when compared to a nucleotide sequence as set forth in SEQ ID NO:15; or
  (iii) a complement of the nucleotide sequence of (a) or (b), wherein the complement and the nucleotide sequence consist of the same number of nucleotides and are 100% complementary.

* * * * *

SEQUENCE LISTING

```
<160> NUMBER OF SEQ ID NOS: 78

<210> SEQ ID NO 1
<211> LENGTH: 19
<212> TYPE: DNA
<213> ORGANISM: Artificial Sequence
<220> FEATURE:
<223> OTHER INFORMATION: T7 primer

<400> SEQUENCE: 1
ggaaacagct atgaccatg                                               19

<210> SEQ ID NO 2
<211> LENGTH: 459
<212> TYPE: PRT
<213> ORGANISM: Rhizopus stolonifer

<400> SEQUENCE: 2

Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110
```

```
Leu Lys Lys Glu Gly Tyr Phe His Ser Ser Lys Leu Phe Tyr Ala Tyr
        115                 120                 125

Lys Val Leu Ser Thr Leu Ala Ile Cys Ile Ala Gly Leu Ser Leu Leu
130                 135                 140

Tyr Ala Tyr Gly Arg Thr Ser Thr Leu Ala Val Ala Ser Ala Ile
145                 150                 155                 160

Thr Val Gly Ile Phe Trp Gln Gln Cys Gly Trp Leu Ala His Asp Phe
                165                 170                 175

Gly His His Gln Cys Phe Glu Asp Arg Thr Trp Asn Asp Val Leu Val
            180                 185                 190

Val Phe Leu Gly Asn Phe Cys Gln Gly Phe Ser Leu Ser Trp Trp Lys
        195                 200                 205

Asn Lys His Asn Thr His His Ala Ser Thr Asn Val His Gly Gln Asp
    210                 215                 220

Pro Asp Ile Asp Thr Ala Pro Val Leu Leu Trp Asp Glu Tyr Ala Ser
225                 230                 235                 240

Ala Ala Tyr Tyr Ala Ser Leu Asp Gln Glu Pro Thr Met Val Ser Arg
                245                 250                 255

Phe Leu Ala Glu Gln Val Leu Pro His Gln Thr Arg Tyr Phe Phe
                260                 265                 270

Ile Leu Ala Phe Ala Arg Leu Ser Trp Ala Leu Gln Ser Leu Ser Tyr
            275                 280                 285

Ser Phe Lys Lys Glu Ser Ile Asn Lys Ser Arg Gln Leu Asn Leu Phe
        290                 295                 300

Glu Arg Val Cys Ile Val Gly His Trp Ala Leu Phe Ala Phe Cys Ile
305                 310                 315                 320

Tyr Ser Trp Cys Ser Asn Val Tyr His Met Val Leu Phe Phe Leu Val
                325                 330                 335

Ser Gln Ala Thr Thr Gly Tyr Thr Leu Ala Leu Val Phe Ala Leu Asn
            340                 345                 350

His Asn Gly Met Pro Val Ile Thr Glu Glu Lys Ala Glu Ser Met Glu
        355                 360                 365

Phe Phe Glu Ile Gln Val Ile Thr Gly Arg Asp Val Thr Leu Ser Pro
370                 375                 380

Leu Gly Asp Trp Phe Met Gly Gly Leu Asn Tyr Gln Ile Glu His His
385                 390                 395                 400

Val Phe Pro Asn Met Pro Arg His Asn Leu Pro Thr Val Lys Pro Met
                405                 410                 415

Val Lys Ser Leu Cys Gln Lys Tyr Asp Ile Asn Tyr His Asp Thr Gly
            420                 425                 430

Phe Leu Lys Gly Thr Leu Glu Val Leu Gln Thr Leu Asp Ile Thr Ser
        435                 440                 445

Lys Leu Ser Leu Gln Leu Ser Lys Lys Ser Phe
    450                 455

<210> SEQ ID NO 3
<211> LENGTH: 695
<212> TYPE: DNA
<213> ORGANISM: Pavlova lutheri

<400> SEQUENCE: 3
agggccaagg gtgccaacca ccttccacgt gagactacac accgtaggcc gatgggcaag      60
ggtggagacg gcggcgcgca ggcggtgagc gggaccgacg cgtctctcgc tgaggtgagc     120
tccgtcgata gcaagagcgt gcacgtcgtg ctctacggca agcgcgtgga tgtcacaaag     180
```

```
ttccagggct acgacgtggc ctggtggcgc gcgcgccata acacgcacca cgtgtgcacc      240
aacgaggatg gttcggaccc ggacatcaag acggcgcccc tgctcatcta cgtgcgagag      300
aacccgtcca ttgccaagcg gctcaacttc ttccagcgct ggcagcagta ctactatgtg      360
ccgaccatgg ccatcctcga cctctactgg cgcctggagt ccatcgcgta cgtggctgtg      420
cgcctgccta agatgtggat gcaggccgcc gctcttgccg ctcactacgc gctcctgtgc      480
tgggtcttcg cagcgcatct caacctcatc cctctcatga tggttgcacg cggcttcgcg      540
acgggcatcg ttgtctttgc aacccactat ggtgaggaca tcctcgaccg cgagcacgtc      600
gagggcatga cgctcgtcga gcagaccgcc aagacctccc gtaacatcac gggcggctgg      660
ctagtgaacg tgctcacggg cttcatctcc ctgca                                 695
```

```
<210> SEQ ID NO 4
<211> LENGTH: 1106
<212> TYPE: DNA
<213> ORGANISM: Pavlova lutheri

<400> SEQUENCE: 4
```

```
agggccaagg gtgccaacca ccttccacgt gagactacac accgtaggcc gatgggcaag       60
ggtggagacg gcggcgcgca ggcggtgagc gggaccgacg cgtctctcgc tgaggtgagc      120
tccgtcgata gcaagagcgt gcacgtcgtg ctctacggca agcgcgtgga tgtcacaaag      180
ttccagggct acgacgtggc ctggtggcgc gcgcgccata acacgcacca cgtgtgcacc      240
aacgaggatg gttcggaccc ggacatcaag acggcgcccc tgctcatcta cgtgcgagag      300
aacccgtcca ttgccaagcg gctcaacttc ttccagcgct ggcagcagta ctactatgtg      360
ccgaccatgg ccatcctcga cctctactgg cgcctggagt ccatcgcgta cgtggctgtg      420
cgcctgccta agatgtggat gcaggccgcc gctcttgccg ctcactacgc gctcctgtgc      480
tgggtcttcg cagcgcatct caacctcatc cctctcatga tggttgcacg cggcttcgcg      540
acgggcatcg ttgtctttgc aacccactat ggtgaggaca tcctcgaccg cgagcacgtc      600
gagggcatga cgctcgtcga gcagaccgcc aagacctccc gtaacatcac gggcggctgg      660
ctagtgaacg tgctcacggg cttcatctcc ctgcagaccg agcatcacct cttccccatg      720
atgcccaccg caacctaat  gactatccag cccgaggtac gcgacttctt caagaagcat      780
ggcctcgagt accgcgaggg caacctcttc cagtgcgtgc accagaacat caaggctctc      840
gccttcgagc acctcctcca ctgagcgtca ccactcaagc gtcctaagtg cacaggtact      900
gtcttctgac cgatggccgc gcggctccct cggctggcag tggggccaac gagtggcctc      960
gcgggatcgg gcacgatcgg gcctccatga aacttcagtg ttcagagaca agccgacaac     1020
ctccgcatcg tgagaaatct tttaaagcag tatgttccat cacgccgctt ttgcagtcaa     1080
taacattacc caaaaaaaaa aaaaaa                                          1106
```

```
<210> SEQ ID NO 5
<211> LENGTH: 287
<212> TYPE: PRT
<213> ORGANISM: Pavlova lutheri

<400> SEQUENCE: 5
```

```
Arg Ala Lys Gly Ala Asn His Leu Pro Arg Glu Thr Thr His Arg Arg
1               5                   10                  15

Pro Met Gly Lys Gly Gly Asp Gly Gly Ala Gln Ala Val Ser Gly Thr
            20                  25                  30

Asp Ala Ser Leu Ala Glu Val Ser Ser Val Asp Ser Lys Ser Val His
```

```
                35                  40                  45
Val Val Leu Tyr Gly Lys Arg Val Asp Val Thr Lys Phe Gln Gly Tyr
 50                  55                  60

Asp Val Ala Trp Trp Arg Ala Arg His Asn Thr His His Val Cys Thr
 65                  70                  75                  80

Asn Glu Asp Gly Ser Asp Pro Asp Ile Lys Thr Ala Pro Leu Leu Ile
                 85                  90                  95

Tyr Val Arg Glu Asn Pro Ser Ile Ala Lys Arg Leu Asn Phe Phe Gln
                100                 105                 110

Arg Trp Gln Gln Tyr Tyr Tyr Val Pro Thr Met Ala Ile Leu Asp Leu
                115                 120                 125

Tyr Trp Arg Leu Glu Ser Ile Ala Tyr Val Ala Val Arg Leu Pro Lys
130                 135                 140

Met Trp Met Gln Ala Ala Ala Leu Ala Ala His Tyr Ala Leu Leu Cys
145                 150                 155                 160

Trp Val Phe Ala Ala His Leu Asn Leu Ile Pro Leu Met Met Val Ala
                165                 170                 175

Arg Gly Phe Ala Thr Gly Ile Val Val Phe Ala Thr His Tyr Gly Glu
                180                 185                 190

Asp Ile Leu Asp Arg Glu His Val Glu Gly Met Thr Leu Val Glu Gln
                195                 200                 205

Thr Ala Lys Thr Ser Arg Asn Ile Thr Gly Gly Trp Leu Val Asn Val
210                 215                 220

Leu Thr Gly Phe Ile Ser Leu Gln Thr Glu His His Leu Phe Pro Met
225                 230                 235                 240

Met Pro Thr Gly Asn Leu Met Thr Ile Gln Pro Glu Val Arg Asp Phe
                245                 250                 255

Phe Lys Lys His Gly Leu Glu Tyr Arg Glu Gly Asn Leu Phe Gln Cys
                260                 265                 270

Val His Gln Asn Ile Lys Ala Leu Ala Phe Glu His Leu Leu His
                275                 280                 285

<210> SEQ ID NO 6
<211> LENGTH: 20
<212> TYPE: DNA
<213> ORGANISM: Artificial Sequence
<220> FEATURE:
<223> OTHER INFORMATION: primer SeqE

<400> SEQUENCE: 6
cgacacactc caatctttcc                                              20

<210> SEQ ID NO 7
<211> LENGTH: 20
<212> TYPE: DNA
<213> ORGANISM: Artificial Sequence
<220> FEATURE:
<223> OTHER INFORMATION: primer SeqW

<400> SEQUENCE: 7
ggtggctgga gttagacatc                                              20

<210> SEQ ID NO 8
<211> LENGTH: 457
<212> TYPE: PRT
<213> ORGANISM: Mortierella alpine

<400> SEQUENCE: 8

Met Ala Ala Ala Pro Ser Val Arg Thr Phe Thr Arg Ala Glu Ile Leu
```

```
1               5                   10                  15
Asn Ala Glu Ala Leu Asn Glu Gly Lys Lys Asp Ala Glu Ala Pro Phe
                20                  25                  30
Leu Met Ile Ile Asp Asn Lys Val Tyr Asp Val Arg Glu Phe Val Pro
                35                  40                  45
Asp His Pro Gly Gly Ser Val Ile Leu Thr His Val Gly Lys Asp Gly
 50                  55                  60
Thr Asp Val Phe Asp Thr Phe His Pro Glu Ala Ala Trp Glu Thr Leu
 65                  70                  75                  80
Ala Asn Phe Tyr Val Gly Asp Ile Asp Glu Ser Asp Arg Ala Ile Lys
                85                  90                  95
Asn Asp Asp Phe Ala Ala Glu Val Arg Lys Leu Arg Thr Leu Phe Gln
                100                 105                 110
Ser Leu Gly Tyr Tyr Asp Ser Ser Lys Ala Tyr Tyr Ala Phe Lys Val
                115                 120                 125
Ser Phe Asn Leu Cys Ile Trp Gly Leu Ser Thr Phe Ile Val Ala Lys
                130                 135                 140
Trp Gly Gln Thr Ser Thr Leu Ala Asn Val Leu Ser Ala Ala Leu Leu
145                 150                 155                 160
Gly Leu Phe Trp Gln Gln Cys Gly Trp Leu Ala His Asp Phe Leu His
                165                 170                 175
His Gln Val Phe Gln Asp Arg Phe Trp Gly Asp Leu Phe Gly Ala Phe
                180                 185                 190
Leu Gly Gly Val Cys Gln Gly Phe Ser Ser Ser Trp Trp Lys Asp Lys
                195                 200                 205
His Asn Thr His His Ala Ala Pro Asn Val His Gly Glu Asp Pro Asp
                210                 215                 220
Ile Asp Thr His Pro Leu Leu Thr Trp Ser Glu His Ala Leu Glu Met
225                 230                 235                 240
Phe Ser Asp Val Pro Asp Glu Glu Leu Thr Arg Met Trp Ser Arg Phe
                245                 250                 255
Met Val Leu Asn Gln Thr Trp Phe Tyr Phe Pro Ile Leu Ser Phe Ala
                260                 265                 270
Arg Leu Ser Trp Cys Leu Gln Ser Ile Met Phe Val Leu Pro Asn Gly
                275                 280                 285
Gln Ala His Lys Pro Ser Gly Ala Arg Val Pro Ile Ser Leu Val Glu
                290                 295                 300
Gln Leu Ser Leu Ala Met His Trp Thr Trp Tyr Leu Ala Thr Met Phe
305                 310                 315                 320
Leu Phe Ile Lys Asp Pro Val Asn Met Ile Val Tyr Phe Leu Val Ser
                325                 330                 335
Gln Ala Val Cys Gly Asn Leu Leu Ala Ile Val Phe Ser Leu Asn His
                340                 345                 350
Asn Gly Met Pro Val Ile Ser Lys Glu Glu Ala Val Asp Met Asp Phe
                355                 360                 365
Phe Thr Lys Gln Ile Ile Thr Gly Arg Asp Val His Pro Gly Leu Phe
370                 375                 380
Ala Asn Trp Phe Thr Gly Gly Leu Asn Tyr Gln Ile Glu His His Leu
385                 390                 395                 400
Phe Pro Ser Met Pro Arg His Asn Phe Ser Lys Ile Gln Pro Ala Val
                405                 410                 415
Glu Thr Leu Cys Lys Lys Tyr Gly Val Arg Tyr His Thr Thr Gly Met
                420                 425                 430
```

```
Ile Glu Gly Thr Ala Glu Val Phe Ser Arg Leu Asn Glu Val Ser Lys
    435                 440                 445

Ala Ala Ser Lys Met Gly Lys Ala Gln
    450                 455

<210> SEQ ID NO 9
<211> LENGTH: 22
<212> TYPE: DNA
<213> ORGANISM: Artificial Sequence
<220> FEATURE:
<223> OTHER INFORMATION: primer AP1

<400> SEQUENCE: 9
gtaatacgac tcactatagg gc                                              22

<210> SEQ ID NO 10
<211> LENGTH: 20
<212> TYPE: DNA
<213> ORGANISM: Artificial Sequence
<220> FEATURE:
<223> OTHER INFORMATION: primer GSP PvDES

<400> SEQUENCE: 10
ctgcgaagac ccagcacagg                                                 20

<210> SEQ ID NO 11
<211> LENGTH: 22
<212> TYPE: DNA
<213> ORGANISM: Artificial Sequence
<220> FEATURE:
<223> OTHER INFORMATION: primer M13-28Rev

<400> SEQUENCE: 11
gtaatacgac tcactatagg gc                                              22

<210> SEQ ID NO 12
<211> LENGTH: 21
<212> TYPE: DNA
<213> ORGANISM: Artificial Sequence
<220> FEATURE:
<223> OTHER INFORMATION: primer PavDes seq

<400> SEQUENCE: 12
ttgtggcgct caatcatctc c                                               21

<210> SEQ ID NO 13
<211> LENGTH: 1294
<212> TYPE: DNA
<213> ORGANISM: Pavlova lutheri

<400> SEQUENCE: 13
ctttgcgagc gcggcgcaga cgattgcggc ccgtagtgat cgcggtgcgc attgctgtgt     60
ttctagtttt gctgacgccc ggcccgataa tgacaccttc tcccgtttga aatactaata    120
agtaactata ttataatatt caaaggtggc gactatggat ctccttttct aaagttcagc    180
ggaattggga atcggagaaa tttcgagata tgtcataatc acgtgctcta tctcgaatga    240
accgcggccg gtgagcgatt actcgggaag ccaattccta ttaacgagtc agggggatc     300 tttgaggtga gtcggccacg cagagagagc aaggaatcat cctcatccgc cgttctcgag    360
aaagagccaa gggtgccaac caccttccac gtgagactac acaccgtagg ccgatgggca    420
agggtggaga cggcggcgcg caggcggcga gcgggaccga cgcatctctc gctgaggtga    480
gctccgtcga tagcaagagc gtgcgcgtcg tgctctacgg caagcgcgtg gatgtcacaa    540
```

| | |
|---|---|
| agttccagag ggcacacccg ggcgggagca aggtgttccg catcttccag gagcgcgacg | 600 |
| cgacggagca gttcgagtct taccactcgc ccaaggccat caagatgatg gagggcatgc | 660 |
| tcaagaagtc ggaggatgcg cccgcttccg tgcccctgcc ctcgcggtcc accatgggca | 720 |
| cggagttcaa ggagatgatt gagcgccaca gagggctgg tctctacgac ccttgcccgt | 780 |
| tggacgagct gttcaagctc accatcgtcc ttgcgcccat cttcgtgggc gcctatctcg | 840 |
| tgcggagcgg cgtctcgccc ctcgcgggcg cgctctccat gggctttggc ttctacctcg | 900 |
| acggctggct tgctcacrac tacctgcatc acgcagtctt caagggctcg gtcaacacgc | 960 |
| tcgtcaaggc gaacaacgcc atgggatacg ccctcggctt cctccagggc tacgacgtgg | 1020 |
| cctggtggcg cgcgcgccat aacacgcacc acgtgtgcac caacgaggat ggttcggacc | 1080 |
| cggacatcaa gacggcgccc ctgctcatct acgtgcgaga gaacccgtcc attgccaagc | 1140 |
| ggctcaactt cttccagcgc tggcagcagt actactatgt gccgaccatg gccatcctcg | 1200 |
| acctctactg gcgcctggag tccatcgcgt acgtggctgt gcgcctgcct aagatgtgga | 1260 |
| tgcaggccgc cgctcttgcc gctcactacg cgct | 1294 |

<210> SEQ ID NO 14
<211> LENGTH: 1927
<212> TYPE: DNA
<213> ORGANISM: Pavlova lutheri

<400> SEQUENCE: 14

| | |
|---|---|
| ctttgcgagc gcggcgcaga cgattgcggc ccgtagtgat cgcggtgcgc attgctgtgt | 60 |
| ttctagtttt gctgacgccc ggcccgataa tgacaccttc tcccgtttga atactaata | 120 |
| agtaactata ttataatatt caaaggtggc gactatggat ctccttttct aaagttcagc | 180 |
| ggaattggga atcggagaaa tttcgagata tgtcataatc acgtgctcta tctcgaatga | 240 |
| accgcggccg gtgagcgatt actcgggaag ccaattccta ttaacgagtc aggggggatc | 300 |
| tttgaggtga gtcggccacg cagagagagc aaggaatcat cctcatccgc cgttctcgag | 360 |
| aaagagccaa gggtgccaac caccttccac gtgagactac acaccgtagg ccgatgggca | 420 |
| agggtggaga cggcggcgcg caggcggtga gcggaccga cgcgtctctc gctgaggtga | 480 |
| gctccgtcga tagcaagagc gtgcacgtcg tgctctacgg caagcgcgtg gatgtcacaa | 540 |
| agttccagaa ggcacacccg ggcgggagca aggtgttccg catcttccag gagcgcgacg | 600 |
| cgacggagca gttcgagtct taccactcgc ccaaggccat caagatgatg gagggcatgc | 660 |
| tcaagaagtc ggaggatgcg cccgcttccg tgcccctgcc ctcgcggtcc accatgggca | 720 |
| cggagttcaa ggagatgatt gagcgccaca gagggctgg tctctacgac ccttgcccgt | 780 |
| tggacgagct gttcaagctc accatcgtcc ttgcgcccat cttcgtgggc gcctatctcg | 840 |
| tgcggagcgg cgtctcgccc ctcgcgggcg cgctctccat gggctttggc ttctacctcg | 900 |
| acggctggct tgctcacgac tacctgcatc acgcagtctt caagggctcg gtcaacacgc | 960 |
| tcgtcaaggc gaacaacgcc atgggatacg ccctcggctt cctccagggc tacgacgtgg | 1020 |
| cctggtggcg cgcgcgccat aacacgcacc acgtgtgcac caacgaggat ggttcggacc | 1080 |
| cggacatcaa gacggcgccc ctgctcatct acgtgcgaga gaacccgtcc attgccaagc | 1140 |
| ggctcaactt cttccagcgc tggcagcagt actactatgt gccgaccatg gccatcctcg | 1200 |
| acctctactg gcgcctggag tccatcgcgt acgtggctgt gcgcctgcct aagatgtgga | 1260 |
| tgcaggccgc cgctcttgcc gctcactacg cgctcctgtg ctgggtcttc gcagcgcatc | 1320 |
| tcaacctcat ccctctcatg atggttgcac gcggcttcgc gacgggcatc gttgtctttg | 1380 |

```
caacccacta tggtgaggac atcctcgacc gcgagcacgt cgagggcatg acgctcgtcg    1440
agcagaccgc caagacctcc cgtaacatca cgggcggctg gctagtgaac gtgctcacgg    1500
gcttcatctc cctgcagacc gagcatcacc tcttccccat gatgcccacc ggcaacctaa    1560
tgactatcca gcccgaggta cgcgacttct tcaagaagca tggcctcgag taccgcgagg    1620
gcaacctctt ccagtgcgtg caccagaaca tcaaggctct cgccttcgag cacctcctcc    1680
actgagcgtc accactcaag cgtcctaagt gcacaggtac tgtcttctga ccgatggccg    1740
cgcggctccc tcggctggca gtggggccaa cgagtggcct cgcgggatcg ggcacgatcg    1800
ggcctccatg aaacttcagt gttcagagac aagccgacaa cctccgcatc gtgagaaatc    1860
ttttaaagca gtatgttcca tcacgccgct tttgcagtca ataacattac ccaaaaaaaa    1920
aaaaaaa                                                              1927

<210> SEQ ID NO 15
<211> LENGTH: 1269
<212> TYPE: DNA
<213> ORGANISM: Pavlova lutheri

<400> SEQUENCE: 15
atgggcaagg gtggagacgg cggcgcgcag gcggtgagcg ggaccgacgc gtctctcgct      60
gaggtgagct ccgtcgatag caagagcgtg cacgtcgtgc tctacggcaa gcgcgtggat    120
gtcacaaagt tccagaaggc acacccgggc gggagcaagg tgttccgcat cttccaggag    180
cgcgacgcga cggagcagtt cgagtcttac cactcgccca aggccatcaa gatgatggag    240
ggcatgctca agaagtcgga ggatgcgccc gcttccgtgc ccctgccctc gcggtccacc    300
atgggcacgg agttcaagga gatgattgag cgccacaaga gggctggtct ctacgaccct    360
tgcccgttgg acgagctgtt caagctcacc atcgtccttg cgcccatctt cgtgggcgcc    420
tatctcgtgc ggagcggcgt ctcgcccctc gcgggcgcgc tctccatggg cttggcttc      480 tacctcgacg gctggcttgc tcacgactac ctgcatcacg cagtcttcaa gggctcggtc    540
aacacgctcg tcaaggcgaa caacgccatg ggatacgccc tcggcttcct ccagggctac    600
gacgtggcct ggtggcgcgc gcgccataac acgcaccacg tgtgcaccaa cgaggatggt    660
tcggacccgg acatcaagac ggcgcccctg ctcatctacg tgcgagagaa cccgtccatt    720
gccaagcggc tcaacttctt ccagcgctgg cagcagtact actatgtgcc gaccatggcc    780
atcctcgacc tctactggcg cctggagtcc atcgcgtacg tggctgtgcg cctgcctaag    840
atgtggatgc aggccgccgc tcttgccgct cactacgcgc tcctgtgctg ggtcttcgca    900
gcgcatctca acctcatccc tctcatgatg gttgcacgcg gcttcgcgac gggcatcgtt    960
gtctttgcaa cccactatgg tgaggacatc ctcgaccgcg agcacgtcga gggcatgacg   1020
ctcgtcgagc agaccgccaa gacctcccgt aacatcacgg gcggctggct agtgaacgtg   1080
ctcacgggct tcatctccct gcagaccgag catcacctct tccccatgat gcccaccggc   1140
aacctaatga ctatccagcc cgaggtacgc gacttcttca gaagcatgg cctcgagtac    1200 cgcgagggca acctcttcca gtgcgtgcac cagaacatca aggctctcgc cttcgagcac   1260
ctcctccac                                                           1269

<210> SEQ ID NO 16
<211> LENGTH: 423
<212> TYPE: PRT
<213> ORGANISM: Pavlova lutheri

<400> SEQUENCE: 16
```

```
Met Gly Lys Gly Gly Asp Gly Ala Gln Ala Val Ser Gly Thr Asp
1               5                   10                  15

Ala Ser Leu Ala Glu Val Ser Val Asp Ser Lys Ser Val His Val
            20                  25                  30

Val Leu Tyr Gly Lys Arg Val Asp Val Thr Lys Phe Gln Lys Ala His
            35                  40                  45

Pro Gly Gly Ser Lys Val Phe Arg Ile Phe Gln Glu Arg Asp Ala Thr
            50                  55                  60

Glu Gln Phe Glu Ser Tyr His Ser Pro Lys Ala Ile Lys Met Met Glu
65                      70                  75                  80

Gly Met Leu Lys Lys Ser Glu Asp Ala Pro Ala Ser Val Pro Leu Pro
                85                  90                  95

Ser Arg Ser Thr Met Gly Thr Glu Phe Lys Glu Met Ile Glu Arg His
                100                 105                 110

Lys Arg Ala Gly Leu Tyr Asp Pro Cys Pro Leu Asp Glu Leu Phe Lys
            115                 120                 125

Leu Thr Ile Val Leu Ala Pro Ile Phe Val Gly Ala Tyr Leu Val Arg
    130                 135                 140

Ser Gly Val Ser Pro Leu Ala Gly Ala Leu Ser Met Gly Phe Gly Phe
145                 150                 155                 160

Tyr Leu Asp Gly Trp Leu Ala His Asp Tyr Leu His His Ala Val Phe
                165                 170                 175

Lys Gly Ser Val Asn Thr Leu Val Lys Ala Asn Asn Ala Met Gly Tyr
            180                 185                 190

Ala Leu Gly Phe Leu Gln Gly Tyr Asp Val Ala Trp Trp Arg Ala Arg
        195                 200                 205

His Asn Thr His His Val Cys Thr Asn Glu Asp Gly Ser Asp Pro Asp
    210                 215                 220

Ile Lys Thr Ala Pro Leu Leu Ile Tyr Val Arg Glu Asn Pro Ser Ile
225                 230                 235                 240

Ala Lys Arg Leu Asn Phe Phe Gln Arg Trp Gln Tyr Tyr Tyr Tyr Val
            245                 250                 255

Pro Thr Met Ala Ile Leu Asp Leu Tyr Trp Arg Leu Glu Ser Ile Ala
        260                 265                 270

Tyr Val Ala Val Arg Leu Pro Lys Met Trp Met Gln Ala Ala Leu
    275                 280                 285

Ala Ala His Tyr Ala Leu Leu Cys Trp Val Phe Ala Ala His Leu Asn
    290                 295                 300

Leu Ile Pro Leu Met Met Val Ala Arg Gly Phe Ala Thr Gly Ile Val
305                 310                 315                 320

Val Phe Ala Thr His Tyr Gly Glu Asp Ile Leu Asp Arg Glu His Val
            325                 330                 335

Glu Gly Met Thr Leu Val Glu Gln Thr Ala Lys Thr Ser Arg Asn Ile
            340                 345                 350

Thr Gly Gly Trp Leu Val Asn Val Leu Thr Gly Phe Ile Ser Leu Gln
        355                 360                 365

Thr Glu His His Leu Phe Pro Met Met Pro Thr Gly Asn Leu Met Thr
    370                 375                 380

Ile Gln Pro Glu Val Arg Asp Phe Phe Lys Lys His Gly Leu Glu Tyr
385                 390                 395                 400

Arg Glu Gly Asn Leu Phe Gln Cys Val His Gln Asn Ile Lys Ala Leu
            405                 410                 415

Ala Phe Glu His Leu Leu His
            420
```

<210> SEQ ID NO 17
<211> LENGTH: 459
<212> TYPE: PRT
<213> ORGANISM: Rhizopus stolonifer

<400> SEQUENCE: 17

| | | | | | | | | | | | | | | |
|---|---|---|---|---|---|---|---|---|---|---|---|---|---|---|
| Met | Ser | Thr | Leu | Asp | Arg | Gln | Ser | Ile | Phe | Thr | Ile | Lys | Glu | Leu | Glu |
| 1 | | | | 5 | | | | | 10 | | | | | 15 | |
| Ser | Ile | Ser | Gln | Arg | Ile | His | Asp | Gly | Asp | Glu | Ala | Met | Lys | Phe | |
| | | | 20 | | | | | 25 | | | | | 30 | | |
| Ile | Ile | Ile | Asp | Lys | Lys | Val | Tyr | Asp | Val | Thr | Glu | Phe | Ile | Glu | Asp |
| | | 35 | | | | | 40 | | | | | 45 | | | |
| His | Pro | Gly | Gly | Ala | Gln | Val | Leu | Leu | Thr | His | Val | Gly | Lys | Asp | Ala |
| | 50 | | | | | 55 | | | | | 60 | | | | |
| Ser | Asp | Val | Phe | His | Ala | Met | His | Pro | Glu | Ser | Ala | Tyr | Glu | Val | Leu |
| 65 | | | | | 70 | | | | | 75 | | | | | 80 |
| Asn | Asn | Tyr | Phe | Val | Gly | Asp | Val | Gln | Glu | Thr | Val | Val | Thr | Glu | Lys |
| | | | | 85 | | | | | 90 | | | | | 95 | |
| Ser | Ser | Ser | Ala | Gln | Phe | Ala | Val | Glu | Met | Arg | Gln | Leu | Arg | Asp | Gln |
| | | | 100 | | | | | 105 | | | | | 110 | | |
| Leu | Lys | Lys | Glu | Gly | Tyr | Phe | His | Ser | Ser | Lys | Leu | Phe | Tyr | Ala | Tyr |
| | | 115 | | | | | 120 | | | | | 125 | | | |
| Lys | Val | Leu | Ser | Thr | Leu | Ala | Ile | Cys | Ile | Ala | Gly | Leu | Ser | Pro | Leu |
| | 130 | | | | | 135 | | | | | 140 | | | | |
| Tyr | Ala | Tyr | Gly | Arg | Thr | Ser | Thr | Leu | Ala | Val | Val | Ala | Ser | Ala | Ile |
| 145 | | | | | 150 | | | | | 155 | | | | | 160 |
| Thr | Val | Gly | Ile | Phe | Trp | Gln | Gln | Cys | Gly | Trp | Leu | Ala | His | Asp | Phe |
| | | | | 165 | | | | | 170 | | | | | 175 | |
| Gly | His | His | Gln | Cys | Phe | Glu | Asp | Arg | Thr | Trp | Asn | Asp | Val | Leu | Val |
| | | | 180 | | | | | 185 | | | | | 190 | | |
| Val | Phe | Leu | Gly | Asn | Phe | Cys | Gln | Gly | Phe | Ser | Leu | Ser | Trp | Trp | Lys |
| | | 195 | | | | | 200 | | | | | 205 | | | |
| Asn | Lys | His | Asn | Thr | His | Ala | Ser | Thr | Asn | Val | His | Gly | Gln | Asp | |
| | 210 | | | | | 215 | | | | | 220 | | | | |
| Pro | Asp | Ile | Asp | Thr | Ala | Pro | Val | Leu | Leu | Trp | Asp | Glu | Tyr | Ala | Ser |
| 225 | | | | | 230 | | | | | 235 | | | | | 240 |
| Ala | Ala | Tyr | Tyr | Ala | Ser | Leu | Asp | Gln | Glu | Pro | Thr | Met | Val | Ser | Arg |
| | | | | 245 | | | | | 250 | | | | | 255 | |
| Phe | Leu | Ala | Glu | Gln | Val | Leu | Pro | His | Gln | Thr | Arg | Tyr | Phe | Phe | Phe |
| | | | 260 | | | | | 265 | | | | | 270 | | |
| Ile | Leu | Ala | Phe | Ala | Arg | Leu | Ser | Trp | Ala | Leu | Gln | Ser | Leu | Ser | Tyr |
| | | 275 | | | | | 280 | | | | | 285 | | | |
| Ser | Phe | Lys | Lys | Glu | Ser | Ile | Asn | Lys | Ser | Arg | Gln | Leu | Asn | Leu | Phe |
| | 290 | | | | | 295 | | | | | 300 | | | | |
| Glu | Arg | Val | Cys | Ile | Val | Gly | His | Trp | Ala | Leu | Ser | Ala | Phe | Cys | Ile |
| 305 | | | | | 310 | | | | | 315 | | | | | 320 |
| Tyr | Ser | Trp | Cys | Ser | Asn | Val | Tyr | His | Met | Val | Leu | Phe | Phe | Leu | Val |
| | | | | 325 | | | | | 330 | | | | | 335 | |
| Ser | Gln | Ala | Thr | Thr | Gly | Tyr | Thr | Leu | Ala | Leu | Val | Phe | Ala | Leu | Asn |
| | | | 340 | | | | | 345 | | | | | 350 | | |
| His | Asn | Gly | Met | Pro | Val | Ile | Thr | Glu | Glu | Lys | Ala | Glu | Ser | Met | Glu |
| | | 355 | | | | | 360 | | | | | 365 | | | |
| Phe | Phe | Glu | Ile | Gln | Val | Ile | Thr | Gly | Arg | Asp | Val | Thr | Leu | Ser | Pro |
| | 370 | | | | | 375 | | | | | 380 | | | | |

Leu Gly Asp Trp Phe Met Gly Gly Leu Asn Tyr Gln Ile Glu His His
385                 390                 395                 400

Val Phe Pro Asn Met Pro Arg His Asn Leu Pro Thr Val Lys Pro Met
            405                 410                 415

Val Lys Ser Leu Cys Gln Lys Tyr Asp Ile Asn Tyr His Asp Thr Gly
            420                 425                 430

Phe Leu Lys Gly Thr Leu Glu Val Leu Gln Thr Leu Asp Ile Thr Ser
            435                 440                 445

Lys Leu Ser Leu Gln Leu Ser Lys Lys Ser Phe
        450                 455

<210> SEQ ID NO 18
<211> LENGTH: 30
<212> TYPE: DNA
<213> ORGANISM: Artificial Sequence
<220> FEATURE:
<223> OTHER INFORMATION: primer PvDES5primeNot-1

<400> SEQUENCE: 18
gcggccgcac catgggcaag ggtggagacg                                         30

<210> SEQ ID NO 19
<211> LENGTH: 27
<212> TYPE: DNA
<213> ORGANISM: Artificial Sequence
<220> FEATURE:
<223> OTHER INFORMATION: primer PvDES3primeNot-1

<400> SEQUENCE: 19
gcggccgctc agtggaggag gtgctcg                                            27

<210> SEQ ID NO 20
<211> LENGTH: 20
<212> TYPE: DNA
<213> ORGANISM: Artificial Sequence
<220> FEATURE:
<223> OTHER INFORMATION: primer GSP PvDES-2

<400> SEQUENCE: 20
gcatccacat cttaggcagg                                                    20

<210> SEQ ID NO 21
<211> LENGTH: 8801
<212> TYPE: DNA
<213> ORGANISM: Artificial Sequence
<220> FEATURE:
<223> OTHER INFORMATION: plasmid pY121

<400> SEQUENCE: 21
ggccgcaggg cggatccccc gggctgcagg aattcgatat caagcttatc gataccgtcg        60
acctcgaggg ggggcccggt acccaattcg ccctatagtg agtcgtatta cgcgcgctca       120
ctggccgtcg ttttacaacg tcgtgactgg gaaaaccctg gcgttaccca acttaatcgc       180
cttgcagcac atcccccttt cgccagctgg cgtaatagcg aagaggcccg caccgatcgc       240
ccttcccaac agttgcgcag cctgaatggc gaatggcgcg acgcgccctg tagcggcgca       300
ttaagcgcgg cgggtgtggt ggttacgcgc agcgtgaccg ctacacttgc cagcgcccta       360
gcgcccgctc ctttcgcttt cttcccttcc tttctcgcca cgttcgccgg ctttccccgt       420
caagctctaa atcgggggct ccctttaggg ttccgattta gtgctttacg gcacctcgac       480
cccaaaaaac ttgattaggg tgatggttca cgtagtgggc catcgccctg atagacggtt       540

```
tttcgccctt tgacgttgga gtccacgttc tttaatagtg gactcttgtt ccaaactgga      600
acaacactca accctatctc ggtctattct tttgatttat aagggatttt gccgatttcg      660
gcctattggt taaaaaatga gctgatttaa caaaaattta acgcgaattt taacaaaata      720
ttaacgttta caatttcctg atgcggtatt ttctccttac gcatctgtgc ggtatttcac      780
accgcatatc gacggtcgag gagaacttct agtatatcca catacctaat attattgcct      840
tattaaaaat ggaatcccaa caattacatc aaaatccaca ttctcttcaa aatcaattgt      900
cctgtacttc cttgttcatg tgtgttcaaa aacgttatat ttataggata attatactct      960
atttctcaac aagtaattgg ttgtttggcc gagcggtcta aggcgcctga ttcaagaaat     1020
atcttgaccg cagttaactg tgggaatact caggtatcgt aagatgcaag agttcgaatc     1080
tcttagcaac cattattttt ttcctcaaca taacgagaac acacaggggc gctatcgcac     1140
agaatcaaat tcgatgactg gaaatttttt gttaatttca gaggtcgcct gacgcatata     1200 ccttttcaa ctgaaaaatt gggagaaaaa ggaaaggtga gaggccggaa ccggcttttc      1260
atatagaata gagaagcgtt catgactaaa tgcttgcatc acaatacttg aagttgacaa     1320
tattatttaa ggacctattg ttttttccaa taggtggtta gcaatcgtct tactttctaa     1380
cttttcttac cttttacatt tcagcaatat atatatatat ttcaaggata taccattcta     1440
atgtctgccc ctatgtctgc ccctaagaag atcgtcgttt gccaggtga ccacgttggt      1500 caagaaatca cagccgaagc cattaaggtt cttaaagcta tttctgatgt tcgttccaat     1560
gtcaagttcg atttcgaaaa tcatttaatt ggtggtgctg ctatcgatgc tacaggtgtc     1620
ccacttccag atgaggcgct ggaagcctcc aagaaggttg atgccgtttt gttaggtgct     1680
gtggctggtc ctaaatgggg taccggtagt gttagacctg aacaaggttt actaaaaatc     1740
cgtaaagaac ttcaattgta cgccaactta agaccatgta actttgcatc cgactctctt     1800
ttagacttat ctccaatcaa gccacaattt gctaaaggta ctgacttcgt tgttgtcaga     1860
gaattagtgg gaggtattta ctttggtaag agaaggaag acgatggtga tggtgtcgct      1920
tgggatagtg aacaatacac cgttccagaa gtgcaaagaa tcacaagaat ggccgctttc     1980
atggccctac aacatgagcc accattgcct atttggtcct tggataaagc taatcttttg     2040
gcctcttcaa gattatggag aaaaactgtg gaggaaacca tcaagaacga attccctaca     2100
ttgaaggttc aacatcaatt gattgattct gccgccatga tcctagttaa gaacccaacc     2160
cacctaaatg gtattataat caccagcaac atgtttggtg atatcatctc cgatgaagcc     2220
tccgttatcc caggttcctt gggttttgttg ccatctgcgt ccttggcctc tttgccagac     2280
aagaacaccg catttggttt gtacgaacca tgccacggtt ctgctccaga tttgccaaag     2340
aataaggttg accctatcgc cactatcttg tctgctgcaa tgatgttgaa attgtcattg     2400
aacttgcctg aagaaggtaa ggccattgaa gatgcagtta aaaaggtttt ggatgcaggt     2460
atcagaactg tgattaggg tggttccaac agtaccaccg aagtcggtga tgctgtcgcc     2520
gaagaagtta agaaaatcct tgcttaaaaa gattctcttt ttttatgata tttgtacata     2580
aactttataa atgaaattca taatagaaac gacacgaaat tacaaaatgg aatatgttca     2640
tagggtagac gaaactatat acgcaatcta catacattta tcaagaagga gaaaaggag      2700 gatagtaaag gaatacaggt aagcaaattg atactaatgg ctcaacgtga taggaaaaa     2760 gaattgcact ttaacattaa tattgacaag gaggagggca ccacacaaaa agttaggtgt     2820
aacagaaaat catgaaacta cgattcctaa tttgatattg gaggattttc tctaaaaaaa     2880
aaaaaataca acaaataaaa aacactcaat gacctgacca tttgatggag tttaagtcaa     2940
```

```
taccttcttg aagcatttcc cataatggtg aaagttccct caagaatttt actctgtcag    3000
aaacggcctt acgacgtagt cgatatggtg cactctcagt acaatctgct ctgatgccgc    3060
atagttaagc cagccccgac acccgccaac acccgctgac gcgccctgac gggcttgtct    3120
gctcccggca tccgcttaca gacaagctgt gaccgtctcc gggagctgca tgtgtcagag    3180
gttttcaccg tcatcaccga aacgcgcgag acgaaagggc tcgtgatac gcctattttt    3240 ataggttaat gtcatgataa taatggtttc ttagtatgat ccaatatcaa aggaaatgat    3300
agcattgaag gatgagacta atccaattga ggagtggcag catatagaac agctaaaggg    3360
tagtgctgaa ggaagcatac gatacccgc atggaatggg ataatatcac aggaggtact    3420
agactacctt tcatcctaca taaatagacg catataagta cgcatttaag cataaacacg    3480
cactatgccg ttcttctcat gtatatatat atacaggcaa cacgcagata taggtgcgac    3540
gtgaacagtg agctgtatgt gcgcagctcg cgttgcattt tcggaagcgc tcgttttcgg    3600
aaacgctttg aagttcctat tccgaagttc ctattctcta gaaagtatag gaacttcaga    3660
gcgcttttga aaaccaaaag cgctctgaag acgcactttc aaaaaccaa aaacgcaccg    3720 gactgtaacg agctactaaa atattgcgaa taccgcttcc acaaacattg ctcaaaagta    3780
tctctttgct atatatctct gtgctatatc cctatataac ctacccatcc acctttcgct    3840
ccttgaactt gcatctaaac tcgacctcta cattttttat gtttatctct agtattactc    3900
tttagacaaa aaaattgtag taagaactat tcatagagtg aatcgaaaac aatacgaaaa    3960
tgtaaacatt tcctatacgt agtatataga gacaaaatag aagaaaccgt tcataatttt    4020
ctgaccaatg aagaatcatc aacgctatca ctttctgttc acaaagtatg cgcaatccac    4080
atcggtatag aatataatcg gggatgcctt tatcttgaaa aaatgcaccc gcagcttcgc    4140
tagtaatcag taaacgcggg aagtggagtc aggctttttt tatggaagag aaaatagaca    4200
ccaaagtagc cttcttctaa ccttaacgga cctacagtgc aaaaagttat caagagactg    4260
cattatagag cgcacaaagg agaaaaaaag taatctaaga tgctttgtta gaaaaatagc    4320
gctctcggga tgcatttttg tagaacaaaa agaagtata gattctttgt tggtaaaata    4380
gcgctctcgc gttgcatttc tgttctgtaa aaatgcagct cagattcttt gtttgaaaaa    4440
ttagcgctct cgcgttgcat ttttgtttta caaaaatgaa gcacagattc ttcgttggta    4500
aaatagcgct ttcgcgttgc atttctgttc tgtaaaaatg cagctcagat tctttgtttg    4560
aaaaattagc gctctcgcgt tgcattttg ttctacaaaa tgaagcacag atgcttcgtt    4620
caggtggcac ttttcgggga atgtgcgcg aacccctat tgtttatt ttctaaatac    4680 attcaaatat gtatccgctc atgagacaat aaccctgata aatgcttcaa taatattgaa    4740
aaaggaagag tatgagtatt caacatttcc gtgtcgccct tattcccttt tttgcggcat    4800
tttgccttcc tgtttttgct cacccagaaa cgctggtgaa agtaaaagat gctgaagatc    4860
agttgggtgc acgagtgggt tacatcgaac tggatctcaa cagcggtaag atccttgaga    4920
gttttcgccc cgaagaacgt tttccaatga tgagcacttt taaagttctg ctatgtggcg    4980
cggtattatc ccgtattgac gccgggcaag agcaactcgg tcgccgcata cactattctc    5040
agaatgactt ggttgagtac tcaccagtca cagaaaagca tcttacggat ggcatgacag    5100
taagagaatt atgcagtgct gccataacca tgagtgataa cactgcggcc aacttacttc    5160
tgacaacgat cggaggaccg aaggagctaa ccgcttttt gcacaacatg ggggatcatg    5220
taactcgcct tgatcgttgg gaaccggagc tgaatgaagc cataccaaac gacgagcgtg    5280
acaccacgat gcctgtagca atggcaacaa cgttgcgcaa actattaact ggcgaactac    5340
```

```
ttactctagc ttcccggcaa caattaatag actggatgga ggcggataaa gttgcaggac   5400
cacttctgcg ctcggccctt ccggctggct ggtttattgc tgataaatct ggagccggtg   5460
agcgtgggtc tcgcggtatc attgcagcac tggggccaga tggtaagccc tcccgtatcg   5520
tagttatcta cacgacgggg agtcaggcaa ctatggatga acgaaataga cagatcgctg   5580
agataggtgc ctcactgatt aagcattggt aactgtcaga ccaagtttac tcatatatac   5640
tttagattga tttaaaactt cattttaat ttaaaaggat ctaggtgaag atcctttttg   5700
ataatctcat gaccaaaatc ccttaacgtg agttttcgtt ccactgagcg tcagaccccg   5760
tagaaaagat caaaggatct tcttgagatc ctttttttct gcgcgtaatc tgctgcttgc   5820
aaacaaaaaa accaccgcta ccagcggtgg tttgtttgcc ggatcaagag ctaccaactc   5880
tttttccgaa ggtaactggc ttcagcagag cgcagatacc aaatactgtc cttctagtgt   5940
agccgtagtt aggccaccac ttcaagaact ctgtagcacc gcctacatac ctcgctctgc   6000
taatcctgtt accagtggct gctgccagtg gcgataagtc gtgtcttacc gggttggact   6060
caagacgata gttaccggat aaggcgcagc ggtcgggctg aacggggggt tcgtgcacac   6120
agcccagctt ggagcgaacg acctacaccg aactgagata cctacagcgt gagctatgag   6180
aaagcgccac gcttcccgaa gggagaaagg cggacaggta tccggtaagc ggcagggtcg   6240
gaacaggaga gcgcacgagg gagcttccag ggggaaacgc ctggtatctt tatagtcctg   6300
tcgggtttcg ccacctctga cttgagcgtc gatttttgtg atgctcgtca ggggggcgga   6360
gcctatggaa aaacgccagc aacgcggcct ttttacggtt cctggccttt tgctggcctt   6420
ttgctcacat gttctttcct gcgttatccc ctgattctgt ggataaccgt attaccgcct   6480
ttgagtgagc tgataccgct cgccgcagcc gaacgaccga gcgcagcgag tcagtgagcg   6540
aggaagcgga agagcgccca atacgcaaac cgcctctccc cgcgcgttgg ccgattcatt   6600
aatgcagctg gcacgacagg tttcccgact ggaaagcggg cagtgagcgc aacgcaatta   6660
atgtgagtta cctcactcat taggcacccc aggctttaca ctttatgctt ccggctccta   6720
tgttgtgtgg aattgtgagc ggataacaat ttcacacagg aaacagctat gaccatgatt   6780
acgccaagcg cgcaattaac cctcactaaa gggaacaaaa gctggagctc caccgcggga   6840
tttcgaaact aagttcttgg tgttttaaaa ctaaaaaaaa gactaactat aaaagtagaa   6900
tttaagaagt ttaagaaata gatttacaga attacaatca atacctaccg tctttatata   6960
cttattagtc aagtagggga ataatttcag ggaactggtt tcaacctttt ttttcagctt   7020
tttcaaaatc agagagagca gaaggtaata gaaggtgtaa gaaaatgaga tagatacatg   7080
cgtgggtcaa ttgccttgtg tcatcattta ctccaggcag gttgcatcac tccattgagg   7140
ttgtgcccgt ttttgcctg tttgtgcccc tgttctctgt agttgcgcta agagaatgga   7200
cctatgaact gatggttggt gaagaaaaca atattttggt gctgggattc ttttttttc   7260 tggatgccag cttaaaaagc gggctccatt atatttagtg gatgccagga ataaactgtt   7320
cacccagaca cctacgatgt tatatattct gtgtaacccg ccccctattt tgggcatgta   7380
cgggttacag cagaattaaa aggctaattt tttgactaaa taaagttagg aaaatcacta   7440
ctattaatta tttacgtatt ctttgaaatg gcagtattga taatgataaa ctcgaaatca   7500
ctagtggatc cgcccagcgg ccgcaccatg gcaagggtg gagacggcgg cgcgcaggcg   7560
gtgagcggga ccgacgcgtc tctcgctgag gtgagctccg tcgatagcaa gagcgtgcac   7620
gtcgtgctct acggcaagcg cgtggatgtc acaaagttcc agaaggcaca cccgggcggg   7680
agcaaggtgt tccgcatctt ccaggagcgc gacgcgacgg agcagttcga gtcttaccac   7740
```

```
tcgcccaagg ccatcaagat gatggagggc atgctcaaga agtcggagga tgcgcccgct      7800
tccgtgcccc tgccctcgcg gtccaccatg ggcacggagt tcaaggagat gattgagcgc      7860
cacaagaggg ctggtctcta cgacccttgc ccgttggacg agctgttcaa gctcaccatc      7920
gtccttgcgc ccatcttcgt gggcgcctat ctcgtgcgga gcggcgtctc gcccctcgcg      7980
ggcgcgctct ccatgggctt tggcttctac ctcgacggct ggcttgctca cgactacctg      8040
catcacgcag tcttcaaggg ctcggtcaac acgctcgtca aggcgaacaa cgccatggga      8100
tacgccctcg gcttcctcca gggctacgac gtggcctggt ggcgcgcgcg ccataacacg      8160
caccacgtgt gcaccaacga ggatggttcg gacccggaca tcaagacggc gcccctgctc      8220
atctacgtgc gagagaaccc gtccattgcc aagcggctca acttcttcca gcgctggcag      8280
cagtactact atgtgccgac catggccatc ctcgacctct actggcgcct ggagtccatc      8340
gcgtacgtgg ctgtgcgcct gcctaagatg tggatgcagg ccgccgctct tgccgctcac      8400
tacgcgctcc tgtgctgggt cttcgcagcg catctcaacc tcatccctct catgatggtt      8460
gcacgcggct tcgcgacggg catcgttgtc tttgcaaccc actatggtga ggacatcctc      8520
gaccgcgagc acgtcgaggg catgacgctc gtcgagcaga ccgccaagac ctcccgtaac      8580
atcacgggcg gctggctagt gaacgtgctc acgggcttca tctccctgca gaccgagcat      8640
cacctcttcc ccatgatgcc caccggcaac ctaatgacta tccagcccga ggtacgcgac      8700
ttcttcaaga agcatggcct cgagtaccgc gagggcaacc tcttccagtg cgtgcaccag      8760
aacatcaagg ctctcgcctt cgagcacctc ctccactgag c                         8801

<210> SEQ ID NO 22
<211> LENGTH: 4993
<212> TYPE: DNA
<213> ORGANISM: Artificial Sequence
<220> FEATURE:
<223> OTHER INFORMATION: plasmid pKR123r
<220> FEATURE:
<221> NAME/KEY: misc_feature
<222> LOCATION: (1126)..(1126)
<223> OTHER INFORMATION: n is a, c, g, or t

<400> SEQUENCE: 22
ctagacctgc aggatataat gagccgtaaa caaagatgat taagtagtaa ttaatacgta       60
ctagtaaaag tggcaaaaga taacgagaaa gaaccaattt ctttgcattc ggccttagcg      120
gaaggcatat ataagctttg attatttttat ttagtgtaat gatttcgtac aaccaaagca     180
tttatttagt actctcacac ttgtgtcgcg gccgcttggg gggctatgga agactttctt      240
agttagttgt gtgaataagc aatgttggga gaatcgggac tacttatagg ataggaataa      300
aacagaaaag tattaagtgc taatgaaata tttagactga taattaaaat cttcacgtat      360
gtccacttga tataaaaacg tcaggaataa aggaagtaca gtagaattta aaggtactct      420
ttttatatat acccgtgttc tcttttttggc tagctagttg cataaaaaat aatctatatt     480
tttatcatta ttttaaatat cttatgagat ggtaaatatt tatcataatt ttttttacta     540 ttattttatta tttgtgtgtg taatacatat agaagttaat tacaaatttt atttactttt     600
tcattatttt gatatgattc accattaatt tagtgttatt atttataata gttcatttta     660 atcttttgt atatattatg cgtgcagtac ttttttccta catataacta ctattacatt      720
ttatttatat aatatttta ttaatgaatt ttcgtgataa tatgtaatat tgttcattat      780
tatttcagat ttttttaaaaa tatttgtgtt attatttatg aaatatgtaa tttttttagt    840
atttgatttt atgatgataa agtgttctaa attcaaaaga agggggaaag cgtaaacatt     900
```

```
aaaaaacgtc atcaaacaaa aacaaaatct tgttaatamaa gataaaactg tttgttttga    960
tcactgttat ttcgtaatat aaaaacatta tttatatttta tattgttgac aaccaaattt   1020
gcctatcaaa tctaaccaat ataatgcatg cgtggcaggt aatgtactac catgaactta   1080
agtcatgaca taataaaccg tgaatctgac caatgcatgt acctanctaa attgtatttg   1140
tgacacgaag caaatgattc aattcacaat ggagatggga aacaaataat gaagaaccca   1200
gaactaagaa agcttttctg aaaaataaaa taaaggcaat gtcaaaagta tactgcatca   1260
tcagtccaga aagcacatga tattttttta tcagtatcaa tgcagctagt tttatttttac  1320 aatatcgata tagctagttt aaatatattg cagctagatt tataaatatt tgtgttatta   1380
tttatcattt gtgtaatcct gttttagta ttttagttta tatgatga taatgtattc    1440 caaatttaaa agaagggaaa taaatttaaa caagaaaaaa agtcatcaaa caaaaaacaa   1500
atgaaagggt ggaaagatgt taccatgtaa tgtgaatgtt acagtatttc ttttattata   1560
gagttaacaa attaactaat atgattttgt taataatgat aaaatatttt ttttattatt   1620
atttcataat ataaaaatag tttacttaat ataaaaaaa ttctatcgtt cacaacaaag   1680
ttggccacct aatttaacca tgcatgtacc catggaccat attaggtaac catcaaacct   1740
gatgaagaga taaagagatg aagacttaag tcataacaca aaaccataaa aaacaaaaat   1800
acaatcaacc gtcaatctga ccaatgcatg aaaaagctgc aatagtgagt ggcgacacaa   1860
agcacatgat tttcttacaa cggagataaa accaaaaaaa tatttcatga caacctaga    1920 acaaataaag cttttatata ataaatatat aaataaataa aggctatgga ataatatact   1980
tcaatatatt tggattaaat aaattgttgg cggggttgat atatttatac acacctaaag   2040
tcacttcaat ctcattttca cttaactttt atttttttt tcttttttatt tatcataaag    2100 agaatattga taatatactt tttaacatat ttttatgaca ttttttattg gtgaaaactt   2160
attaaaaatc ataaattttg taagttagat ttattaaag agttcctctt cttattttaa   2220 atttttttaat aaattttaa ataactaaaa tttgtgttaa aaatgttaaa aaatgtgtta    2280
ttaacccttc tcttcgagga cgtacgtcta gagtcgacct gcaggcatgc aagcttggcg   2340
taatcatggt catagctgtt tcctgtgtga aattgttatc cgctcacaat tccacacaac   2400
atacgagccg gaagcataaa gtgtaaagcc tggggtgcct aatgagtgag ctaactcaca   2460
ttaattgcgt tgcgctcact gcccgctttc cagtcgggaa acctgtcgtg ccagctgcat   2520
taatgaatcg gccaacgcgc ggggagaggc ggtttgcgta ttgggcgctc ttccgcttcc   2580
tcgctcactg actcgctgcg ctcggtcgtt cggctgcggc gagcggtatc agctcactca   2640
aaggcggtaa tacggttatc cacagaatca ggggataacg caggaaagaa catgtgagca   2700
aaaggccagc aaaaggccag gaaccgtaaa aaggccgcgt tgctggcgtt tttccatagg   2760
ctccgccccc ctgacgagca tcacaaaaat cgacgctcaa gtcagaggtg gcgaaacccg   2820
acaggactat aaagatacca ggcgtttccc cctggaagct ccctcgtgcg ctctcctgtt   2880
ccgaccctgc cgcttaccgg atacctgtcc gcctttctcc cttcgggaag cgtggcgctt   2940
tctcatagct cacgctgtag gtatctcagt tcggtgtagg tcgttcgctc caagctgggc   3000
tgtgtgcacg aaccccccgt tcagcccgac cgctgcgcct tatccggtaa ctatcgtctt   3060
gagtccaacc cggtaagaca cgacttatcg ccactggcag cagccactgg taacaggatt   3120
agcagagcga ggtatgtagg cggtgctaca gagttcttga agtggtggcc taactacggc   3180
tacactagaa ggacagtatt tggtatctgc gctctgctga agccagttac cttcggaaaa   3240
agagttggta gctcttgatc cggcaaacaa accaccgctg gtagcggtgg tttttttgtt   3300
```

```
tgcaagcagc agattacgcg cagaaaaaaa ggatctcaag aagatccttt gatcttttct    3360
acggggtctg acgctcagtg gaacgaaaac tcacgttaag ggattttggt catgagatta    3420 tcaaaagga tcttcaccta gatcctttta aattaaaaat gaagttttaa atcaatctaa     3480
agtatatatg agtaaacttg gtctgacagt taccaatgct taatcagtga ggcacctatc    3540
tcagcgatct gtctatttcg ttcatccata gttgcctgac tccccgtcgt gtagataact    3600
acgatacggg agggcttacc atctggcccc agtgctgcaa tgataccgcg agacccacgc    3660
tcaccggctc cagatttatc agcaataaac cagccagccg aagggccga gcgcagaagt     3720 ggtcctgcaa ctttatccgc ctccatccag tctattaatt gttgccggga agctagagta    3780
agtagttcgc cagttaatag tttgcgcaac gttgttgcca ttgctacagg catcgtggtg    3840
tcacgctcgt cgtttggtat ggcttcattc agctccggtt cccaacgatc aaggcgagtt    3900
acatgatccc ccatgttgtg caaaaaagcg gttagctcct tcggtcctcc gatcgttgtc    3960
agaagtaagt tggccgcagt gttatcactc atggttatgg cagcactgca taattctctt    4020
actgtcatgc catccgtaag atgcttttct gtgactggtg agtactcaac caagtcattc    4080
tgagaatagt gtatgcggcg accgagttgc tcttgcccgg cgtcaatacg ggataatacc    4140
gcgccacata gcagaacttt aaaagtgctc atcattggaa aacgttcttc ggggcgaaaa    4200
ctctcaagga tcttaccgct gttgagatcc agttcgatgt aacccactcg tgcacccaac    4260
tgatcttcag catcttttac tttcaccagc gtttctgggt gagcaaaaac aggaaggcaa    4320
aatgccgcaa aaaagggaat aagggcgaca cggaaatgtt gaatactcat actcttcctt    4380
tttcaatatt attgaagcat ttatcagggt tattgtctca tgagcggata catatttgaa    4440
tgtatttaga aaaataaaca aataggggtt ccgcgcacat ttccccgaaa agtgccacct    4500
gacgtctaag aaaccattat tatcatgaca ttaacctata aaaataggcg tatcacgagg    4560
ccctttcgtc tcgcgcgttt cggtgatgac ggtgaaaacc tctgacacat gcagctcccg    4620
gagacggtca cagcttgtct gtaagcggat gccgggagca gacaagcccg tcagggcgcg    4680
tcagcgggtg ttggcgggtg tcggggctgg cttaactatg cggcatcaga gcagattgta    4740
ctgagagtgc accatatgcg gtgtgaaata ccgcacagat gcgtaaggag aaaataccgc    4800
atcaggcgcc attcgccatt caggctgcgc aactgttggg aagggcgatc ggtgcgggcc    4860
tcttcgctat tacgccagct ggcgaaaggg ggatgtgctg caaggcgatt aagttgggta    4920
acgccagggt tttcccagtc acgacgttgt aaaacgacgg ccagtgaatt cgagctcggt    4980
acccggggat cct                                                       4993
```

<210> SEQ ID NO 23
<211> LENGTH: 6276
<212> TYPE: DNA
<213> ORGANISM: Artificial Sequence
<220> FEATURE:
<223> OTHER INFORMATION: plasmid pKR900
<220> FEATURE:
<221> NAME/KEY: misc_feature
<222> LOCATION: (4081)..(4081)
<223> OTHER INFORMATION: n is a, c, g, or t

<400> SEQUENCE: 23

```
ggccgcgaca caagtgtgag agtactaaat aaatgctttg gttgtacgaa atcattacac      60
taaataaaat aatcaaagct tatatatgcc ttccgctaag gccgaatgca agaaattgg      120 ttctttctcg ttatcttttg ccacttttac tagtacgtat taattactac ttaatcatct     180
ttgtttacgg ctcattatat cctgcaggtc tagaggatcc ccgggtaccg agctcgaatt    240
```

```
cactggccgt cgttttacaa cgtcgtgact gggaaaaccc tggcgttacc caacttaatc    300
gccttgcagc acatccccct ttcgccagct ggcgtaatag cgaagaggcc cgcaccgatc    360
gcccttccca acagttgcgc agcctgaatg gcgaatggcg cctgatgcgg tatttctcc     420 ttacgcatct gtgcggtatt tcacaccgca tatggtgcac tctcagtaca atctgctctg    480
atgccgcata gttaagccag ccccgacacc cgccaacacc cgctgacgcg ccctgacggg    540
cttgtctgct cccggcatcc gcttacagac aagctgtgac cgtctccggg agctgcatgt    600
gtcagaggtt ttcaccgtca tcaccgaaac gcgcgagacg aaagggcctc gtgatacgcc    660
tatttttata ggttaatgtc atgataataa tggtttctta cgtcaggt ggcacttttc      720 ggggaaatgt gcgcggaacc cctatttgtt tatttttcta aatacattca aatatgtatc    780
cgctcatgag acaataaccc tgataaatgc ttcaataata ttgaaaaagg aagagtatga    840
gtattcaaca tttccgtgtc gcccttattc cctttttgc ggcattttgc cttcctgttt     900
ttgctcaccc agaaacgctg gtgaaagtaa aagatgctga agatcagttg ggtgcacgag    960
tgggttacat cgaactggat ctcaacagcg gtaagatcct tgagagtttt cgccccgaag   1020
aacgttttcc aatgatgagc acttttaaag ttctgctatg tggcgcggta ttatcccgta   1080
ttgacgccgg gcaagagcaa ctcggtcgcc gcatacacta ttctcagaat gacttggttg   1140
agtactcacc agtcacagaa aagcatctta cggatggcat gacagtaaga gaattatgca   1200
gtgctgccat aaccatgagt gataacactg cggccaactt acttctgaca acgatcggag   1260
gaccgaagga gctaaccgct ttttgcaca acatggggga tcatgtaact cgccttgatc    1320
gttgggaacc ggagctgaat gaagccatac caaacgacga gcgtgacacc acgatgcctg   1380
tagcaatggc aacaacgttg cgcaaactat taactggcga actacttact ctagcttccc   1440
ggcaacaatt aatagactgg atggaggcgg ataaagttgc aggaccactt ctgcgctcgg   1500
cccttccggc tggctggttt attgctgata atctggagc cggtgagcgt gggtctcgcg    1560
gtatcattgc agcactgggg ccagatggta agccctcccg tatcgtagtt atctacacga   1620
cggggagtca ggcaactatg gatgaacgaa atagacagat cgctgagata ggtgcctcac   1680
tgattaagca ttggtaactg tcagaccaag tttactcata tatactttag attgatttaa   1740
aacttcattt ttaatttaaa aggatctagg tgaagatcct ttttgataat ctcatgacca   1800
aaatccctta acgtgagttt tcgttccact gagcgtcaga ccccgtagaa aagatcaaag   1860
gatcttcttg agatcctttt tttctgcgcg taatctgctg cttgcaaaca aaaaaaccac   1920
cgctaccagc ggtggtttgt ttgccggatc aagagctacc aactcttttt ccgaaggtaa   1980
ctggcttcag cagagcgcag ataccaaata ctgtccttct agtgtagccg tagttaggcc   2040
accacttcaa gaactctgta gcaccgccta catacctcgc tctgctaatc ctgttaccag   2100
tggctgctgc cagtggcgat aagtcgtgtc ttaccgggtt ggactcaaga cgatagttac   2160
cggataaggc gcagcggtcg ggctgaacgg ggggttcgtg cacacagccc agcttggagc   2220
gaacgaccta caccgaactg agatacctac agcgtgagct atgagaaagc gccacgcttc   2280
ccgaagggag aaaggcggac aggtatccgg taagcggcag ggtcggaaca ggagagcgca   2340
cgagggagct tccaggggga aacgcctggt atctttatag tcctgtcggg tttcgccacc   2400
tctgacttga gcgtcgattt ttgtgatgct cgtcaggggg gcggagccta tggaaaaacg   2460
ccagcaacgc ggccttttta cggttcctgg ccttttgctg gccttttgct cacatgttct   2520
ttcctgcgtt atcccctgat tctgtggata accgtattac cgcctttgag tgagctgata   2580
ccgctcgccg cagccgaacg accgagcgca gcgagtcagt gagcgaggaa gcggaagagc   2640
```

```
gcccaatacg caaaccgcct ctccccgcgc gttggccgat tcattaatgc agctggcacg    2700
acaggtttcc cgactggaaa gcgggcagtg agcgcaacgc aattaatgtg agttagctca    2760
ctcattaggc accccaggct ttacacttta tgcttccggc tcgtatgttg tgtggaattg    2820
tgagcggata caatttcac acaggaaaca gctatgacca tgattacgcc aagcttgcat    2880
gcctgcaggt cgactctaga cgtacgtcct cgaagagaag ggttaataac acatttttta    2940
acattttaa cacaaatttt agttatttaa aaatttatta aaaatttaa ataagaaga     3000
ggaactcttt aaataaatct aacttacaaa atttatgatt tttaataagt tttcaccaat    3060
aaaaaatgtc ataaaaatat gttaaaaagt atattatcaa tattctcttt atgataaata    3120
aaagaaaaa aaaaataaaa gttaagtgaa aatgagattg aagtgacttt aggtgtgtat    3180
aaatatatca accccgccaa caatttattt aatccaaata tattgaagta tattattcca    3240
tagcctttat ttatttatat atttattata taaaagcttt atttgttcta ggttgttcat    3300
gaaatatttt tttggtttta tctccgttgt aagaaaatca tgtgctttgt gtcgccactc    3360
actattgcag ctttttcatg cattggtcag attgacggtt gattgtattt ttgttttta    3420
tggttttgtg ttatgactta agtcttcatc tctttatctc ttcatcaggt ttgatggtta    3480
cctaatatgg tccatgggta catgcatggt taaattaggt ggccaacttt gttgtgaacg    3540
atagaatttt ttttatatta agtaaactat tttatatta tgaaataata ataaaaaaaa    3600
tattttatca ttattaacaa aatcatatta gttaatttgt taactctata ataaaagaaa    3660
tactgtaaca ttcacattac atggtaacat cttttccaccc tttcatttgt ttttgtttg    3720
atgactttt ttcttgttta aatttatttc ccttctttta aatttggaat acattatcat    3780
catatataaa ctaaaatact aaaaacagga ttacacaaat gataaataat aacacaaata    3840
tttataaatc tagctgcaat atatttaaac tagctatatc gatattgtaa aataaaacta    3900
gctgcattga tactgataaa aaaatatcat gtgctttctg gactgatgat gcagtatact    3960
tttgacattg cctttatttt attttcaga aaagctttct tagttctggg ttcttcatta    4020
tttgttccc atctccattg tgaattgaat catttgcttc gtgtcacaaa tacaatttag    4080
ntaggtacat gcattggtca gattcacggt ttattatgtc atgacttaag ttcatggtag    4140
tacattacct gccacgcatg cattatattg gttagatttg ataggcaaat ttggttgtca    4200
acaatataaa tataaataat gtttttatat tacgaaataa cagtgatcaa acaaacagt    4260
tttatcttta ttaacaagat tttgttttg tttgatgacg tttttttaatg tttacgcttt    4320
ccccttctt ttgaatttag aacactttat catcataaaa tcaaatacta aaaaattac     4380
atatttcata aataataaca caaatatttt taaaaaatct gaaataataa tgaacaatat    4440
tacatattat cacgaaaatt cattaataaa aatattat aaataaatg taatagtagt      4500
tatatgtagg aaaaaagtac tgcacgcata atatatacaa aaagattaaa atgaactatt    4560
ataaataata acactaaatt aatggtgaat catatcaaaa taatgaaaaa gtaaataaaa    4620
tttgtaatta acttctatat gtattacaca cacaaataat aaataatagt aaaaaaaatt    4680
atgataaata tttaccatct cataagatat ttaaaataat gataaaaata tagattattt    4740
tttatgcaac tagctagcca aaaagagaac acgggtatat ataaaaagag tacctttaaa    4800
ttctactgta cttcctttat tcctgacgtt tttatatcaa gtggacatac gtgaagattt    4860
taattatcag tctaaatatt tcattagcac ttaatacttt tctgttttat tcctatccta    4920
taagtagtcc cgattctccc aacattgctt attcacacaa ctaactaaga aagtcttcca    4980
tagccccca agcggccgca ccatgggcaa gggtggagac ggcggcgcgc aggcggtgag    5040
```

```
cgggaccgac gcgtctctcg ctgaggtgag ctccgtcgat agcaagagcg tgcacgtcgt      5100
gctctacggc aagcgcgtgg atgtcacaaa gttccagaag cacacccgg gcgggagcaa       5160 ggtgttccgc atcttccagg agcgcgacgc gacggagcag ttcgagtctt accactcgcc      5220
caaggccatc aagatgatgg agggcatgct caagaagtcg gaggatgcgc ccgcttccgt      5280 gccctgccc tcgcggtcca ccatgggcac ggagttcaag gagatgattg agcgccacaa       5340
gagggctggt ctctacgacc cttgcccgtt ggacgagctg ttcaagctca ccatcgtcct      5400
tgcgcccatc ttcgtgggcg cctatctcgt gcggagcggc gtctcgcccc tcgcgggcgc      5460
gctctccatg ggctttggct tctacctcga cggctggctt gctcacgact acctgcatca      5520
cgcagtcttc aagggctcgg tcaacacgct cgtcaaggcg aacaacgcca tgggatacgc      5580
cctcggcttc ctccagggct acgacgtggc ctggtggcgc gcgcgccata acacgcacca      5640
cgtgtgcacc aacgaggatg gttcggaccc ggacatcaag acggcgcccc tgctcatcta      5700
cgtgcgagag aacccgtcca ttgccaagcg gctcaacttc ttccagcgct ggcagcagta      5760
ctactatgtg ccgaccatgg ccatcctcga cctctactgg cgcctggagt ccatcgcgta      5820
cgtggctgtg cgcctgccta agatgtggat gcaggccgcc gctcttgccg ctcactacgc      5880
gctcctgtgc tgggtcttcg cagcgcatct caacctcatc cctctcatga tggttgcacg      5940
cggcttcgcg acgggcatcg ttgtctttgc aacccactat ggtgaggaca tcctcgaccg      6000
cgagcacgtc gagggcatga cgctcgtcga gcagaccgcc aagacctccc gtaacatcac      6060
gggcggctgg ctagtgaacg tgctcacggg cttcatctcc ctgcagaccg agcatcacct      6120
cttccccatg atgcccaccg gcaacctaat gactatccag cccgaggtac gcgacttctt      6180
caagaagcat ggcctcgagt accgcgaggg caacctcttc cagtgcgtgc accagaacat      6240
caaggctctc gccttcgagc acctcctcca ctgagc                                6276

<210> SEQ ID NO 24
<211> LENGTH: 5303
<212> TYPE: DNA
<213> ORGANISM: Artificial Sequence
<220> FEATURE:
<223> OTHER INFORMATION: primer pKR325

<400> SEQUENCE: 24
agcttggatc tcctgcagga tctggccggc cggatctcgt acggatccgt cgacggcgcg       60
cccgatcatc cggatatagt tcctcctttc agcaaaaaac ccctcaagac ccgtttagag      120
gccccaaggg gttatgctag ttattgctca gcggtggcag cagccaactc agcttccttt      180
cgggctttgt tagcagccgg atcgatccaa gctgtacctc actattcctt tgccctcgga      240
cgagtgctgg ggcgtcggtt tccactatcg gcgagtactt ctacacagcc atcggtccag      300
acggccgcgc ttctgcgggc gatttgtgta cgcccgacag tccggctcc ggatcggacg       360 attgcgtcgc atcgaccctg cgcccaagct gcatcatcga aattgccgtc aaccaagctc      420
tgatagagtt ggtcaagacc aatgcggagc atatacgccc ggagccgcgg cgatcctgca      480
agctccggat gcctccgctc gaagtagcgc gtctgctgct ccatacaagc caaccacggc      540
ctccagaaga agatgttggc gacctcgtat tgggaatccc cgaacatcgc ctcgctccag      600
tcaatgaccg ctgttatgcg gccattgtcc gtcaggacat tgttggagcc gaaatccgcg      660
tgcacgaggt gccggacttc ggggcagtcc tcggcccaaa gcatcagctc atcgagagcc      720
tgcgcgacgg acgcactgac ggtgtcgtcc atcacagttt gccagtgata cacatgggga      780
tcagcaatcg cgcatatgaa atcacgccat gtagtgtatt gaccgattcc ttgcggtccg      840
```

-continued

```
aatgggccga acccgctcgt ctggctaaga tcggccgcag cgatcgcatc catagcctcc    900
gcgaccggct gcagaacagc gggcagttcg gtttcaggca ggtcttgcaa cgtgacaccc    960
tgtgcacggc gggagatgca ataggtcagg ctctcgctga attccccaat gtcaagcact   1020
tccggaatcg ggagcgcggc cgatgcaaag tgccgataaa cataacgatc tttgtagaaa   1080
ccatcggcgc agctatttac ccgcaggaca tatccacgcc ctcctacatc gaagctgaaa   1140
gcacgagatt cttcgccctc cgagagctgc atcaggtcgg agacgctgtc gaacttttcg   1200
atcagaaact tctcgacaga cgtcgcggtg agttcaggct tttccatggg tatatctcct   1260
tcttaaagtt aaacaaaatt atttctagag ggaaaccgtt gtggtctccc tatagtgagt   1320
cgtattaatt tcgcgggatc gagatcgatc caattccaat cccacaaaaa tctgagctta   1380
acagcacagt tgctcctctc agagcagaat cgggtattca cacectcat atcaactact   1440
acgttgtgta taacggtcca catgccggta tatacgatga ctggggttgt acaaaggcgg   1500
caacaaacgg cgttcccgga gttgcacaca agaaatttgc cactattaca gaggcaagag   1560
cagcagctga cgcgtacaca acaagtcagc aaacagacag gttgaacttc atccccaaag   1620
gagaagctca actcaagccc aagagctttg ctaaggccct aacaagccca ccaaagcaaa   1680
aagcccactg gctcacgcta ggaaccaaaa ggcccagcag tgatccagcc ccaaaagaga   1740
tctcctttgc cccggagatt acaatggacg atttcctcta tctttacgat ctaggaagga   1800
agttcgaagg tgaaggtgac gacactatgt tcaccactga taatgagaag gttagcctct   1860
tcaatttcag aaagaatgct gacccacaga tggttagaga ggcctacgca gcaggtctca   1920
tcaagacgat ctacccgagt aacaatctcc aggagatcaa ataccttccc aagaaggtta   1980
aagatgcagt caaagattc aggactaatt gcatcaagaa cacagagaaa gacatatttc   2040
tcaagatcag aagtactatt ccagtatgga cgattcaagg cttgcttcat aaaccaaggc   2100
aagtaataga gattggagtc tctaaaaagg tagttcctac tgaatctaag gccatgcatg   2160
gagtctaaga ttcaaatcga ggatctaaca gaactcgccg tgaagactgg cgaacagttc   2220
atacagagtc ttttacgact caatgacaag aagaaaatct tcgtcaacat ggtggagcac   2280
gacactctgg tctactccaa aaatgtcaaa gatacagtct cagaagacca aagggctatt   2340
gagacttttc aacaaggat aatttcggga aacctcctcg gattccattg cccagctatc   2400
tgtcacttca tcgaaaggac agtagaaaag gaaggtggct cctacaaatg ccatcattgc   2460
gataaaggaa aggctatcat tcaagatgcc tctgccgaca gtggtcccaa agatggaccc   2520
ccacccacga ggagcatcgt ggaaaaagaa gacgttccaa ccacgtcttc aaagcaagtg   2580
gattgatgtg acatctccac tgacgtaagg gatgacgcac aatcccacta tccttcgcaa   2640
gacccttcct ctatataagg aagttcattt catttggaga ggacacgctc gagctcattt   2700
ctctattact tcagccataa caaaagaact cttttctctt cttattaaac catgaaaaag   2760
cctgaactca ccgcgacgtc tgtcgagaag tttctgatcg aaaagttcga cagcgtctcc   2820
gacctgatgc agctctcgga gggcgaagaa tctcgtgctt tcagcttcga tgtaggaggg   2880
cgtggatatg tcctgcgggt aaatagctgc gccgatggtt tctacaaaga tcgttatgtt   2940
tatcggcact ttgcatcggc cgcgctcccg attccggaag tgcttgacat ggggaattc   3000
agcgagagcc tgacctattg catctcccgc cgtgcacagg tgtcacgtt gcaagacctg   3060
cctgaaaccg aactgcccgc tgttctgcag ccggtcgcgg aggccatgga tgcgatcgct   3120
gcggccgatc ttagccagac gagcgggttc ggcccattcg gaccgcaagg aatcggtcaa   3180
tacactacat ggcgtgattt catatgcgcg attgctgatc cccatgtgta tcactggcaa   3240
```

```
actgtgatgg acgacaccgt cagtgcgtcc gtcgcgcagg ctctcgatga gctgatgctt    3300
tgggccgagg actgccccga agtccggcac ctcgtgcacg cggatttcgg ctccaacaat    3360
gtcctgacgg acaatggccg cataacagcg gtcattgact ggagcgaggc gatgttcggg    3420
gattcccaat acgaggtcgc caacatcttc ttctggaggc cgtggttggc ttgtatggag    3480
cagcagacgc gctacttcga gcggaggcat ccggagcttg caggatcgcc gcggctccgg    3540
gcgtatatgc tccgcattgg tcttgaccaa ctctatcaga gcttggttga cggcaatttc    3600
gatgatgcag cttgggcgca gggtcgatgc gacgcaatcg tccgatccgg agccgggact    3660
gtcgggcgta cacaaatcgc ccgcagaagc gcggccgtct ggaccgatgg ctgtgtagaa    3720
gtactcgccg atagtggaaa ccgacgcccc agcactcgtc cgagggcaaa ggaatagtga    3780
ggtacctaaa gaaggagtgc gtcgaagcag atcgttcaaa catttggcaa taaagtttct    3840
taagattgaa tcctgttgcc ggtcttgcga tgattatcat ataatttctg ttgaattacg    3900
ttaagcatgt aataattaac atgtaatgca tgacgttatt tatgagatgg gtttttatga    3960
ttagagtccc gcaattatac atttaatacg cgatagaaaa caaaatatag cgcgcaaact    4020
aggataaatt atcgcgcgcg gtgtcatcta tgttactaga tcgatgtcga atcgatcaac    4080
ctgcattaat gaatcggcca acgcgcgggg agaggcggtt tgcgtattgg gcgctcttcc    4140
gcttcctcgc tcactgactc gctgcgctcg gtcgttcggc tgcggcgagc ggtatcagct    4200
cactcaaagg cggtaatacg gttatccaca gaatcagggg ataacgcagg aaagaacatg    4260
tgagcaaaag gccagcaaaa ggccaggaac cgtaaaaagg ccgcgttgct ggcgtttttc    4320
cataggctcc gcccccctga cgagcatcac aaaaatcgac gctcaagtca gaggtggcga    4380
aacccgacag gactataaag ataccaggcg tttccccctg gaagctccct cgtgcgctct    4440
cctgttccga ccctgccgct taccggatac ctgtccgcct ttctcccttc gggaagcgtg    4500
gcgctttctc aatgctcacg ctgtaggtat ctcagttcgg tgtaggtcgt tcgctccaag    4560
ctgggctgtg tgcacgaacc ccccgttcag cccgaccgct gcgccttatc cggtaactat    4620
cgtcttgagt ccaacccggt aagacacgac ttatcgccac tggcagcagc cactggtaac    4680
aggattagca gagcgaggta tgtaggcggt gctacagagt tcttgaagtg gtggcctaac    4740
tacggctaca ctagaaggac agtatttggt atctgcgctc tgctgaagcc agttaccttc    4800
ggaaaaagag ttggtagctc ttgatccggc aaacaaacca ccgctggtag cggtggtttt    4860
tttgtttgca agcagcagat tacgcgcaga aaaaaggat ctcaagaaga tcctttgatc    4920
ttttctacgg ggtctgacgc tcagtggaac gaaaactcac gttaagggat tttggtcatg    4980
acattaacct ataaaaatag gcgtatcacg aggccctttc gtctcgcgcg tttcggtgat    5040
gacggtgaaa acctctgaca catgcagctc ccggagacgg tcacagcttg tctgtaagcg    5100
gatgccggga gcagacaagc ccgtcagggc gcgtcagcgg gtgttggcgg gtgtcggggc    5160
tggcttaact atgcggcatc agagcagatt gtactgagag tgcaccatat ggacatattg    5220
tcgttagaac gcggctacaa ttaatacata accttatgta tcatacacat acgatttagg    5280
tgacactata gaacggcgcg cca                                           5303
```

<210> SEQ ID NO 25
<211> LENGTH: 8898
<212> TYPE: DNA
<213> ORGANISM: Artificial Sequence
<220> FEATURE:
<223> OTHER INFORMATION: plasmid pKR902
<220> FEATURE:
<221> NAME/KEY: misc_feature
<222> LOCATION: (7701)..(7701)

<223> OTHER INFORMATION: n is a, c, g, or t

<400> SEQUENCE: 25

```
ggatctggcc ggccggatct cgtacggatc cgtcgacggc gcgcccgatc atccggatat    60
agttcctcct ttcagcaaaa aaccccctcaa gacccgttta gaggcccaa ggggttatgc   120
tagttattgc tcagcggtgg cagcagccaa ctcagcttcc tttcgggctt tgttagcagc   180
cggatcgatc caagctgtac ctcactattc ctttgccctc ggacgagtgc tggggcgtcg   240
gtttccacta tcggcgagta cttctacaca gccatcggtc cagacggccg cgcttctgcg   300
ggcgatttgt gtacgcccga cagtcccggc tccggatcgg acgattgcgt cgcatcgacc   360
ctgcgcccaa gctgcatcat cgaaattgcc gtcaaccaag ctctgataga gttggtcaag   420
accaatgcgg agcatatacg cccggagccg cggcgatcct gcaagctccg gatgcctccg   480
ctcgaagtag cgcgtctgct gctccataca agccaaccac ggcctccaga agaagatgtt   540
ggcgacctcg tattgggaat ccccgaacat cgcctcgctc cagtcaatga ccgctgttat   600
gcggccattg tccgtcagga cattgttgga gccgaaatcc gcgtgcacga ggtgccggac   660
ttcggggcag cctcggccc aaagcatcag ctcatcgaga gcctgcgcga cggacgcact   720
gacggtgtcg tccatcacag tttgccagtg atacacatgg ggatcagcaa tcgcgcatat   780
gaaatcacgc catgtagtgt attgaccgat tccttgcggt ccgaatgggc cgaacccgct   840
cgtctggcta agatcggccg cagcgatcgc atccatagcc tccgcgaccg gctgcagaac   900
agcgggcagt tcggtttcag gcaggtcttg caacgtgaca ccctgtgcac ggcgggagat   960
gcaataggtc aggctctcgc tgaattcccc aatgtcaagc acttccggaa tcgggagcgc  1020
ggccgatgca aagtgccgat aaacataacg atctttgtag aaaccatcgg cgcagctatt  1080
tacccgcagg acatatccac gccctcctac atcgaagctg aaagcacgag attcttcgcc  1140
ctccgagagc tgcatcaggt cggagacgct gtcgaacttt tcgatcagaa acttctcgac  1200
agacgtcgcg gtgagttcag gcttttccat gggtatatct ccttcttaaa gttaaacaaa  1260
attatttcta gagggaaacc gttgtggtct ccctatagtg agtcgtatta atttcgcggg  1320
atcgagatcg atccaattcc aatcccacaa aaatctgagc ttaacagcac agttgctcct  1380
ctcagagcag aatcgggtat tcaacaccct catatcaact actacgttgt gtataacggt  1440
ccacatgccg gtatatacga tgactggggt tgtacaaagg cggcaacaaa cggcgttccc  1500
ggagttgcac acaagaaatt tgccactatt acagaggcaa gagcagcagc tgacgcgtac  1560
acaacaagtc agcaaacaga caggttgaac ttcatcccca aggagaagc tcaactcaag  1620
cccaagagct ttgctaaggc cctaacaagc ccaccaaagc aaaaagccca ctggctcacg  1680
ctaggaacca aaaggcccag cagtgatcca gccccaaaag agatctcctt tgccccggag  1740
attacaatgg acgatttcct ctatctttac gatctaggaa ggaagttcga aggtgaaggt  1800
gacgacacta tgttcaccac tgataatgag aaggttagcc tcttcaattt cagaaagaat  1860
gctgacccac agatggttag agaggcctac gcagcaggtc tcatcaagac gatctacccg  1920
agtaacaatc tccaggagat caaataccct cccaagaagg ttaaagatgc agtcaaaaga  1980
ttcaggacta attgcatcaa gaacacagag aaagacatat ttctcaagat cagaagtact  2040
attccagtat ggacgattca aggcttgctt cataaaccaa gcaagtaat agagattgga  2100
gtctctaaaa aggtagttcc tactgaatct aaggccatgc atggagtcta agattcaaat  2160
cgaggatcta acgaactcg ccgtgaagac tggcgaacag ttcatacaga gtctttacg  2220
actcaatgac aagaagaaaa tcttcgtcaa catggtggag cacgacactc tggtctactc  2280
```

```
caaaaatgtc aaagatacag tctcagaaga ccaaagggct attgagactt ttcaacaaag    2340
gataatttcg ggaaacctcc tcggattcca ttgcccagct atctgtcact tcatcgaaag    2400
gacagtagaa aaggaaggtg gctcctacaa atgccatcat tgcgataaag gaaaggctat    2460
cattcaagat gcctctgccg acagtggtcc caaagatgga cccccaccca cgaggagcat    2520
cgtggaaaaa gaagacgttc caaccacgtc ttcaaagcaa gtggattgat gtgacatctc    2580
cactgacgta agggatgacg cacaatccca ctatccttcg caagacccct cctctatata    2640
aggaagttca tttcatttgg agaggacacg ctcgagctca tttctctatt acttcagcca    2700
taacaaaaga actcttttct cttcttatta aaccatgaaa aagcctgaac tcaccgcgac    2760
gtctgtcgag aagtttctga tcgaaaagtt cgacagcgtc tccgacctga tgcagctctc    2820
ggagggcgaa gaatctcgtg ctttcagctt cgatgtagga gggcgtggat atgtcctgcg    2880
ggtaaatagc tgcgccgatg gtttctacaa agatcgttat gtttatcggc actttgcatc    2940
ggccgcgctc ccgattccgg aagtgcttga cattggggaa ttcagcgaga gcctgaccta    3000
ttgcatctcc cgccgtgcac agggtgtcac gttgcaagac ctgcctgaaa ccgaactgcc    3060
cgctgttctg cagccggtcg cggaggccat ggatgcgatc gctgcggccg atcttagcca    3120
gacgagcggg ttcggcccat tcggaccgca aggaatcggt caatacacta catggcgtga    3180
tttcatatgc gcgattgctg atccccatgt gtatcactgg caaactgtga tggacgacac    3240
cgtcagtgcg tccgtcgcgc aggctctcga tgagctgatg ctttgggccg aggactgccc    3300
cgaagtccgg cacctcgtgc acgcggattt cggctccaac aatgtcctga cggacaatgg    3360
ccgcataaca gcggtcattg actggagcga ggcgatgttc ggggattccc aatacgaggt    3420
cgccaacatc ttcttctgga ggccgtggtt ggcttgtatg gagcagcaga cgcgctactt    3480
cgagcggagg catccggagc ttgcaggatc gccgcggctc cgggcgtata tgctccgcat    3540
tggtcttgac caactctatc agagcttggt tgacggcaat ttcgatgatg cagcttgggc    3600
gcagggtcga tgcgacgcaa tcgtccgatc cggagccggg actgtcgggc gtacacaaat    3660
cgcccgcaga agcgcggccg tctggaccga tggctgtgta aagtactcg ccgatagtgg    3720 aaaccgacgc cccagcactc gtccgagggc aaaggaatag tgaggtacct aaagaaggag    3780
tgcgtcgaag cagatcgttc aaacatttgg caataaagtt tcttaagatt gaatcctgtt    3840
gccggtcttg cgatgattat catataattt ctgttgaatt acgttaagca tgtaataatt    3900
aacatgtaat gcatgacgtt atttatgaga tgggtttta tgattagagt cccgcaatta    3960
tacatttaat acgcgataga aaacaaaata tagcgcgcaa actaggataa attatcgcgc    4020
gcggtgtcat ctatgttact agatcgatgt cgaatcgatc aacctgcatt aatgaatcgg    4080
ccaacgcgcg gggagaggcg gtttgcgtat tgggcgctct tccgcttcct cgctcactga    4140
ctcgctgcgc tcggtcgttc ggctgcggcg agcggtatca gctcactcaa aggcggtaat    4200
acggttatcc acagaatcag gggataacgc aggaaagaac atgtgagcaa aaggccagca    4260
aaaggccagg aaccgtaaaa aggccgcgtt gctggcgttt ttccataggc tccgcccccc    4320
tgacgagcat cacaaaaatc gacgctcaag tcagaggtgg cgaaacccga caggactata    4380
aagataccag gcgtttcccc ctggaagctc cctcgtgcgc tctcctgttc cgaccctgcc    4440
gcttaccgga tacctgtccg cctttctccc ttcgggaagc gtggcgcttt ctcaatgctc    4500
acgctgtagg tatctcagtt cggtgtaggt cgttcgctcc aagctgggct gtgtgcacga    4560
accccccgtt cagcccgacc gctgcgcctt atccggtaac tatcgtcttg agtccaaccc    4620
ggtaagacac gacttatcgc cactggcagc agccactggt aacaggatta gcagagcgag    4680
```

```
gtatgtaggc ggtgctacag agttcttgaa gtggtggcct aactacggct acactagaag    4740
gacagtattt ggtatctgcg ctctgctgaa gccagttacc ttcggaaaaa gagttggtag    4800 ctccttgatcc ggcaaacaaa ccaccgctgg tagcggtggt ttttttgttt gcaagcagca   4860
gattacgcgc agaaaaaaag gatctcaaga agatcctttg atcttttcta cggggtctga    4920
cgctcagtgg aacgaaaact cacgttaagg gattttggtc atgacattaa cctataaaaa    4980
taggcgtatc acgaggccct ttcgtctcgc gcgtttcggt gatgacggtg aaaacctctg    5040
acacatgcag ctcccggaga cggtcacagc ttgtctgtaa gcggatgccg ggagcagaca    5100
agcccgtcag ggcgcgtcag cgggtgttgg cgggtgtcgg gctggctta actatgcggc     5160 atcagagcag attgtactga gagtgcacca tatggacata ttgtcgttag aacgcggcta    5220
caattaatac ataaccttat gtatcataca catacgattt aggtgacact atagaacggc    5280
gcgccaagct tggatctcct gcaggatata atgagccgta acaaagatg attaagtagt    5340 aattaatacg tactagtaaa agtggcaaaa gataacgaga aagaaccaat ttctttgcat    5400
tcggccttag cggaaggcat atataagctt tgattatttt atttagtgta atgatttcgt    5460
acaaccaaag catttattta gtactctcac acttgtgtcg cggccgctca gtggaggagg    5520
tgctcgaagg cgagagcctt gatgttctgg tgcacgcact ggaagaggtt gccctcgcgg    5580
tactcgaggc catgcttctt gaagaagtcg cgtacctcgg gctggatagt cattaggttg    5640
ccggtgggca tcatggggaa gaggtgatgc tcggtctgca gggagatgaa gcccgtgagc    5700
acgttcacta gccagccgcc cgtgatgtta cgggaggtct tggcggtctg ctcgacgagc    5760
gtcatgccct cgacgtgctc gcggtcgagg atgtcctcac catagtgggt tgcaaagaca    5820
acgatgcccg tcgcgaagcc gcgtgcaacc atcatgagag ggatgaggtt gagatgcgct    5880
gcgaagaccc agcacaggag cgcgtagtga gcggcaagag cggcggcctg catccacatc    5940
ttaggcaggc gcacagccac gtacgcgatg gactccaggc gccagtagag gtcgaggatg    6000
gccatggtcg gcacatagta gtactgctgc cagcgctgga agaagttgag ccgcttggca    6060
atggacgggt tctctcgcac gtagatgagc aggggcgccg tcttgatgtc cgggtccgaa    6120
ccatcctcgt tggtgcacac gtggtgcgtg ttatggcgcg cgcgccacca ggccacgtcg    6180
tagccctgga ggaagccgag ggcgtatccc atggcgttgt tcgccttgac gagcgtgttg    6240
accgagccct tgaagactgc gtgatgcagg tagtcgtgag caagccagcc gtcgaggtag    6300
aagccaaagc ccatggagag cgcgcccgcg aggggcgaga cgccgctccg cacgagatag    6360
gcgcccacga agatgggcgc aaggacgatg gtgagcttga acagtcgtc caacgggcaa    6420 gggtcgtaga gaccagccct cttgtggcgc tcaatcatct ccttgaactc cgtgcccatg    6480
gtggaccgcg agggcagggg cacggaagcg ggcgcatcct ccgacttctt gagcatgccc    6540
tccatcatct tgatggcctt gggcgagtgg taagactcga actgctccgt cgcgtcgcgc    6600
tcctggaaga tgcggaacac cttgctcccg cccgggtgtg ccttctggaa ctttgtgaca    6660
tccacgcgct tgccgtagag cacgacgtgc acgctcttgc tatcgacgga gctcacctca    6720
gcgagagacg cgtcggtccc gctcaccgcc tgcgcgccgc cgtctccacc cttgcccatg    6780
gtgcggccgc ttgggggggct atggaagact ttcttagtta gttgtgtgaa taagcaatgt    6840
tgggagaatc gggactactt ataggatagg aataaaacag aaaagtatta agtgctaatg    6900
aaatatttag actgataatt aaaatcttca cgtatgtcca cttgatataa aaacgtcagg    6960
aataaaggaa gtacagtaga atttaaaggt actcttttta tatatacccg tgttctcttt    7020
ttggctagct agttgcataa aaaataatct atattttat cattatttta aatatcttat    7080
```

-continued

```
gagatggtaa atatttatca taattttttt tactattatt tattatttgt gtgtgtaata    7140
catatagaag ttaattacaa atttttattta cttttcatt attttgatat gattcaccat    7200
taatttagtg ttattattta taatagttca ttttaatctt tttgtatata ttatgcgtgc    7260 agtactttt tcctacatat aactactatt acatttttatt tatataatat ttttattaat    7320
gaattttcgt gataatatgt aatattgttc attattattt cagatttttt aaaaatattt    7380
gtgttattat ttatgaaata tgtaattttt ttagtatttg attttatgat gataaagtgt    7440
tctaaattca aagaaggggg gaaagcgtaa acattaaaaa acgtcatcaa acaaaaacaa    7500
aatcttgtta ataagataaa aactgtttgt tttgatcact gttatttcgt aatataaaaa    7560
cattatttat atttatattg ttgacaacca aatttgccta tcaaatctaa ccaatataat    7620
gcatgcgtgg caggtaatgt actaccatga acttaagtca tgacataata aaccgtgaat    7680
ctgaccaatg catgtaccta nctaaattgt atttgtgaca cgaagcaaat gattcaattc    7740
acaatggaga tgggaaacaa ataatgaaga acccagaact aagaaagctt ttctgaaaaa    7800
taaaataaag gcaatgtcaa aagtatactg catcatcagt ccagaaagca catgatattt    7860
ttttatcagt atcaatgcag ctagttttat tttacaatat cgatatagct agtttaaata    7920
tattgcagct agatttataa atatttgtgt tattatttat catttgtgta atcctgtttt    7980
tagtatttta gtttatatat gatgataatg tattccaaat ttaaagaag ggaaataaat    8040 ttaaacaaga aaaaaagtca tcaaacaaaa aacaaatgaa agggtggaaa gatgttacca    8100
tgtaatgtga atgttacagt atttctttta ttatagagtt aacaaattaa ctaatatgat    8160
tttgttaata atgataaaat attttttta ttattatttc ataatataaa aatagtttac    8220
ttaatataaa aaaattcta tcgttcacaa caaagttggc cacctaattt aaccatgcat    8280
gtacccatgg accatattag gtaaccatca aacctgatga agagataaag agatgaagac    8340
ttaagtcata acacaaaacc ataaaaaaca aaaatacaat caaccgtcaa tctgaccaat    8400
gcatgaaaaa gctgcaatag tgagtggcga cacaaagcac atgattttct tacaacggag    8460
ataaaaccaa aaaatatttt catgaacaac ctagaacaaa taaagctttt atataataaa    8520
tatataaata aataaaggct atggaataat atacttcaat atatttggat taaataaatt    8580
gttggcgggg ttgatatatt tatacacacc taaagtcact tcaatctcat tttcacttaa    8640
cttttatttt ttttttcttt ttatttatca taaagagaat attgataata acttttttaa    8700
catattttta tgacatttt tattggtgaa aacttattaa aaatcataaa ttttgtaagt    8760
tagatttatt taaagagttc ctcttcttat tttaaatttt ttaataaatt tttaaataac    8820
taaaatttgt gttaaaaatg ttaaaaaatg tgttattaac ccttctcttc gaggacgtac    8880
gtctagagtc gacctgca                                                  8898
```

<210> SEQ ID NO 26
<211> LENGTH: 7887
<212> TYPE: DNA
<213> ORGANISM: Artificial Sequence
<220> FEATURE:
<223> OTHER INFORMATION: plasmid pKR607

<400> SEQUENCE: 26

```
ggccgcagta tatcttaaat tctttaatac ggtgtactag gatattgaac tggttcttga    60
tgatgaaaac ctgggccgag attgcagcta tttatagtca taggtcttgt taacatgcat   120
ggacatttgg ccacggggtg gcatgcagtt tgacgggtgt tgaaataaac aaaaatgagg   180
tggcggaaga gaatacgagt ttgaggttgg gttagaaaca acaaatgtga gggctcatga   240
```

-continued

```
tgggttgagt tggtgaatgt tttgggctgc tcgattgaca cctttgtgag tacgtgttgt      300
tgtgcatggc ttttggggtc cagttttttt ttcttgacgc ggcgatcctg atcagctagt      360
ggataagtga tgtccactgt gtgtgattgc gttttttgttt gaattttatg aacttagaca     420
ttgctatgca aaggatactc tcattgtgtt ttgtcttctt ttgttccttg cttttttctt      480
atgatccaag agactagtca gtgttgtggc attcgagact accaagatta attatgatgg      540
gggaaggata agtaactgat tagtacggac tgttaccaaa ttaattaata agcggcaaat      600
gaagggcatg gatcaaaagc ttggatctcc tgcaggatct ggccggccgg atctcgtacg      660
gatccgtcga cggcgcgccc gatcatccgg atatagttcc tcctttcagc aaaaaacccc      720
tcaagacccg tttagaggcc ccaaggggtt atgctagtta ttgctcagcg gtggcagcag      780
ccaactcagc ttcctttcgg gctttgttag cagccggatc gatccaagct gtacctcact      840
attcctttgc cctcggacga gtgctggggc gtcggtttcc actatcggcg agtacttcta      900
cacagccatc ggtccagacg gccgcgcttc tgcgggcgat ttgtgtacgc ccgacagtcc      960
cggctccgga tcggacgatt gcgtcgcatc gaccctgcgc ccaagctgca tcatcgaaat     1020
tgccgtcaac caagctctga tagagttggt caagaccaat gcggagcata tacgcccgga     1080
gccgcggcga tcctgcaagc tccggatgcc tccgctcgaa gtagcgcgtc tgctgctcca     1140
tacaagccaa ccacggcctc cagaagaaga tgttggcgac ctcgtattgg gaatccccga     1200
acatcgcctc gctccagtca atgaccgctg ttatgcggcc attgtccgtc aggacattgt     1260
tggagccgaa atccgcgtgc acgaggtgcc ggacttcggg gcagtcctcg gcccaaagca     1320
tcagctcatc gagagcctgc gcgacggacg cactgacggt gtcgtccatc acagtttgcc     1380
agtgatacac atggggatca gcaatcgcgc atatgaaatc acgccatgta gtgtattgac     1440
cgattccttg cggtccgaat gggccgaacc cgctcgtctg gctaagatcg gccgcagcga     1500
tcgcatccat agcctccgcg accggctgca gaacagcggg cagttcggtt tcaggcaggt     1560
cttgcaacgt gacaccctgt gcacggcggg agatgcaata ggtcaggctc tcgctgaatt     1620
ccccaatgtc aagcacttcc ggaatcggga gcgcggccga tgcaaagtgc cgataaacat     1680
aacgatcttt gtagaaacca tcggcgcagc tatttacccg caggacatat ccacgccctc     1740
ctacatcgaa gctgaaagca cgagattctt cgccctccga gagctgcatc aggtcggaga     1800
cgctgtcgaa cttttcgatc agaaacttct cgacagacgt cgcggtgagt tcaggctttt     1860
ccatgggtat atctccttct taaagttaaa caaaattatt tctagaggga accgttgtg      1920 gtctccctat agtgagtcgt attaatttcg cgggatcgag atcgatccaa ttccaatccc     1980
acaaaaatct gagcttaaca gcacagttgc tcctctcaga gcagaatcgg gtattcaaca     2040
ccctcatatc aactactacg ttgtgtataa cggtccacat gccggtatat acgatgactg     2100
gggttgtaca aaggcggcaa caaacggcgt tcccggagtt gcacacaaga aatttgccac     2160
tattacagag gcaagagcag cagctgacgc gtacacaaca agtcagcaaa cagacaggtt     2220
gaacttcatc cccaaggag aagctcaact caagcccaag agctttgcta aggccctaac      2280
aagcccacca aagcaaaaag cccactggct cacgctagga accaaaaggc ccagcagtga     2340
tccagcccca aaagagatct cctttgcccc ggagattaca atggacgatt tcctctatct     2400
ttacgatcta ggaaggaagt tcgaaggtga aggtgacgac actatgttca ccactgataa     2460
tgagaaggtt agcctcttca atttcagaaa gaatgctgac ccacagatgg ttagagaggc     2520
ctacgcagca ggtctcatca agacgatcta cccgagtaac aatctccagg atcaaata      2580 ccttcccaag aaggttaaag atgcagtcaa aagattcagg actaattgca tcaagaacac     2640
```

-continued

```
agagaaagac atatttctca agatcagaag tactattcca gtatggacga ttcaaggctt    2700
gcttcataaa ccaaggcaag taatagagat tggagtctct aaaaaggtag ttcctactga    2760
atctaaggcc atgcatggag tctaagattc aaatcgagga tctaacagaa ctcgccgtga    2820
agactggcga acagttcata cagagtcttt tacgactcaa tgacaagaag aaaatcttcg    2880
tcaacatggt ggagcacgac actctggtct actccaaaaa tgtcaaagat acagtctcag    2940
aagaccaaag ggctattgag acttttcaac aaaggatata ttcgggaaac ctcctcggat    3000
tccattgccc agctatctgt cacttcatcg aaaggacagt agaaaaggaa ggtggctcct    3060
acaaatgcca tcattgcgat aaaggaaagg ctatcattca agatgcctct gccgacagtg    3120
gtcccaaaga tggaccccca cccacgagga gcatcgtgga aaaagaagac gttccaacca    3180
cgtcttcaaa gcaagtggat tgatgtgaca tctccactga cgtaagggat gacgcacaat    3240
cccactatcc ttcgcaagac ccttcctcta tataaggaag ttcatttcat ttggagagga    3300
cacgctcgag ctcatttctc tattacttca gccataacaa agaactctt ttctcttctt    3360
attaaaccat gaaaaagcct gaactcaccg cgacgtctgt cgagaagttt ctgatcgaaa    3420
agttcgacag cgtctccgac ctgatgcagc tctcggaggg cgaagaatct cgtgctttca    3480
gcttcgatgt aggagggcgt ggatatgtcc tgcgggtaaa tagctgcgcc gatggtttct    3540
acaaagatcg ttatgtttat cggcactttg catcggccgc gctcccgatt ccggaagtgc    3600
ttgacattgg ggaattcagc gagagcctga cctattgcat ctcccgccgt gcacagggtg    3660
tcacgttgca agacctgcct gaaaccgaac tgcccgctgt tctgcagccg gtcgcggagg    3720
ccatggatgc gatcgctgcg gccgatctta gccagacgag cgggttcggc ccattcggac    3780
cgcaaggaat cggtcaatac actacatggc gtgatttcat atgcgcgatt gctgatcccc    3840
atgtgtatca ctggcaaact gtgatggacg acaccgtcag tgcgtccgtc gcgcaggctc    3900
tcgatgagct gatgctttgg gccgaggact gccccgaagt ccggcacctc gtgcacgcgg    3960
atttcggctc caacaatgtc ctgacggaca atggccgcat aacagcggtc attgactgga    4020
gcgaggcgat gttcggggat tcccaatacg aggtcgccaa catcttcttc tggaggccgt    4080
ggttggcttg tatggagcag cagacgcgct acttcgagcg gaggcatccg gagcttgcag    4140
gatcgccgcg gctccgggcg tatatgctcc gcattggtct tgaccaactc tatcagagct    4200
tggttgacgg caatttcgat gatgcagctt gggcgcaggg tcgatgcgac gcaatcgtcc    4260
gatccggagc cgggactgtc gggcgtacac aaatcgcccg cagaagcgcg gccgtctgga    4320
ccgatggctg tgtagaagta ctcgccgata gtggaaaccg acgccccagc actcgtccga    4380
gggcaaagga atagtgaggt acctaaagaa ggagtgcgtc gaagcagatc gttcaaacat    4440
ttggcaataa agtttcttaa gattgaatcc tgttgccggt cttgcgatga ttatcatata    4500
atttctgttg aattacgtta agcatgtaat aattaacatg taatgcatga cgttatttat    4560
gagatgggtt tttatgatta gagtcccgca attatacatt taatacgcga tagaaaacaa    4620
aatatagcgc gcaaactagg ataaattatc gcgcgcggtg tcatctatgt tactagatcg    4680
atgtcgaatc gatcaacctg cattaatgaa tcggccaacg cgcggggaga ggcggtttgc    4740
gtattgggcg ctcttccgct tcctcgctca ctgactcgct gcgctcggtc gttcggctgc    4800
ggcgagcggt atcagctcac tcaaaggcgg taatacggtt atccacagaa tcaggggata    4860
acgcaggaaa gaacatgtga gcaaaaggcc agcaaaaggc caggaaccgt aaaaaggccg    4920
cgttgctggc gtttttccat aggctccgcc cccctgacga gcatcacaaa aatcgacgct    4980
caagtcagag gtggcgaaac ccgacaggac tataaagata ccaggcgttt ccccctggaa    5040
```

```
gctccctcgt gcgctctcct gttccgaccc tgccgcttac cggataccty tccgcctttc    5100
tcccttcggg aagcgtggcg cttctcaat gctcacgctg taggtatctc agttcggtgt     5160
aggtcgttcg ctccaagctg ggctgtgtgc acgaaccccc cgttcagccc gaccgctgcg    5220
ccttatccgg taactatcgt cttgagtcca acccggtaag acacgactta tcgccactgg    5280
cagcagccac tggtaacagg attagcagag cgaggtatgt aggcggtgct acagagttct    5340
tgaagtggtg gcctaactac ggctacacta aaggacagt atttggtatc tgcgctctgc     5400
tgaagccagt taccttcgga aaaagagttg gtagctcttg atccggcaaa caaccaccg     5460
ctggtagcgg tggtttttttt gtttgcaagc agcagattac gcgcagaaaa aaggatctc    5520
aagaagatcc tttgatcttt tctacgggt ctgacgctca gtggaacgaa aactcacgtt     5580
aagggatttt ggtcatgaca ttaacctata aaaataggcg tatcacgagg ccctttcgtc    5640
tcgcgcgttt cggtgatgac ggtgaaaacc tctgacacat gcagctcccg gagacggtca    5700
cagcttgtct gtaagcggat gccgggagca gacaagcccg tcaggcgcg tcagcggtg     5760
ttggcgggtg tcgggctgg cttaactatg cggcatcaga gcagattgta ctgagagtgc    5820
accatatgga catattgtcg ttagaacgcg gctacaatta atacataacc ttatgtatca    5880
tacacatacg atttaggtga cactatagaa cggcgcgcca agcttgttga aacatccctg    5940
aagtgtctca ttttatttta tttattcttt gctgataaaa aaataaaata aagaagcta     6000
agcacacggt caaccattgc tctactgcta aaagggttat gtgtagtgtt ttactgcata    6060
aattatgcag caaacaagac aactcaaatt aaaaaatttc ctttgcttgt ttttttgttg    6120
tctctgactt gactttcttg tggaagttgg ttgtataagg attgggacac cattgtcctt    6180
cttaatttaa ttttattctt tgctgataaa aaaaaaaatt tcatatagtg ttaaataata    6240
atttgttaaa taaccaaaaa gtcaaatatg tttactctcg tttaaataat tgagattcgt    6300
ccagcaaggc taaacgattg tatagattta tgacaatatt tactttttta tagataaatg    6360
ttatattata ataaatttat atacatatat tatatgttat ttattattat tttaaatcct    6420
tcaatatttt atcaaaccaa ctcataattt ttttttttatc tgtaagaagc aataaaatta    6480
aatagaccca ctttaaggat gatccaacct ttatacagag taagagagtt caaatagtac    6540
cctttcatat acatatcaac taaaatatta gaaatatcat ggatcaaacc ttataaagac    6600
attaaataag tggataagta taatatataa atgggtagta tataatatat aaatggatac    6660
aaacttctct ctttataatt gttatgtctc cttaacatcc taatataata cataagtggg    6720
taatatataa tatataaatg gagacaaact tcttccatta taattgttat gtcttcttaa    6780
cacttatgtc tcgttcacaa tgctaaggtt agaattgttt agaaagtctt atagtacaca    6840
tttgttttttg tactatttga agcattccat aagccgtcac gattcagatg atttataata    6900
ataagaggaa atttatcata gaacaataag gtgcatagat agagtgttaa tatatcataa    6960
catcctttgt ttattcatag aagaagtgag atggagctca gttattatac tgttacatgg    7020
tcggatacaa tattccatgc tctccatgag ctcttacacc tacatgcatt ttagttcata    7080
cttgcggccg ctaaagctgc ttaccagcct tagcggattt cttggtggcc aggttgtcct    7140
ggtaaaagaa gtgacagaac aggagaaaga cagatccgac gtaggcgtag ttgaaagccc    7200
aggagaacag cttgcccttg tcagagttga agcagggaac gttgatgtag tcccagacca    7260
ggagaaagcc accgacgaac tggcaaatct gcatggcagt gatcagaggc ttggccttga    7320
acttgtagcc agcggcagtc agtccatagt aggtgtacat gatggtgtga atgaacgagt    7380
taaagaacat gaagatccac acaccctcgt tgtgcagtcg aatgccgagg tagacgtccc    7440
```

```
agggagctcc aaagtgatgg aaggcctgca gaaaggacac tcgcttgccc ttgaggacca    7500
gccaagcggt gtcgaggtac tccacgtact tagaatagta gaaggccttg gcagtccagg    7560
tgaacagctt ggagtcccag acaggagagg gacactgaaa gagaggctgg ggagtatcac    7620
cggtctgtct tcgcagccag gctccagtac cgtagtccca gccgagagcg gtggcagtca    7680
cgtagaagga cagggcagag aagagagcca ggaggacgtt gtaccagatc atggaggttc    7740
ggtaggctcc tttcttctcg tccacgagac cagagtttcg caggagaggc ttcaggagca    7800
ggtaggagaa ggtgccaatg aggatttcgg gatcggtgac ggcagcccag attcgctcgc    7860
cagcgtcgtt ggccagagcc atggtgc                                        7887

<210> SEQ ID NO 27
<211> LENGTH: 11482
<212> TYPE: DNA
<213> ORGANISM: Artificial Sequence
<220> FEATURE:
<223> OTHER INFORMATION: plasmid pKR903
<220> FEATURE:
<221> NAME/KEY: misc_feature
<222> LOCATION: (9081)..(9081)
<223> OTHER INFORMATION: n is a, c, g, or t

<400> SEQUENCE: 27
ggatctggcc ggccggatct cgtacggatc cgtcgacggc gcgcccgatc atccggatat      60
agttcctcct ttcagcaaaa aaccccctcaa gacccgttta gaggccccaa ggggttatgc    120
tagttattgc tcagcggtgg cagcagccaa ctcagcttcc tttcgggctt tgttagcagc    180
cggatcgatc caagctgtac ctcactattc ctttgccctc ggacgagtgc tggggcgtcg    240
gtttccacta tcggcgagta cttctacaca gccatcggtc cagacggccg cgcttctgcg    300
ggcgatttgt gtacgcccga cagtcccggc tccggatcgg acgattgcgt cgcatcgacc    360
ctgcgcccaa gctgcatcat cgaaattgcc gtcaaccaag ctctgataga gttggtcaag    420
accaatgcgg agcatatacg cccggagccg cggcgatcct gcaagctccg gatgcctccg    480
ctcgaagtag cgcgtctgct gctccataca agccaaccac ggcctccaga agaagatgtt    540
ggcgacctcg tattgggaat ccccgaacat cgcctcgctc cagtcaatga ccgctgttat    600
gcggccattg tccgtcagga cattgttgga gccgaaatcc gcgtgcacga ggtgccggac    660
ttcggggcag tcctcggccc aaagcatcag ctcatcgaga gcctgcgcga cggacgcact    720
gacggtgtcg tccatcacag tttgccagtg atacacatgg ggatcagcaa tcgcgcatat    780
gaaatcacgc catgtagtgt attgaccgat tccttgcggt ccgaatgggc cgaacccgct    840
cgtctggcta agatcggccg cagcgatcgc atccatagcc tccgcgaccg gctgcagaac    900
agcgggcagt tcggtttcag gcaggtcttg caacgtgaca ccctgtgcac ggcgggagat    960
gcaataggtc aggctctcgc tgaattcccc aatgtcaagc acttccggaa tcgggagcgc   1020
ggccgatgca aagtgccgat aaacataacg atctttgtag aaaccatcgg cgcagctatt   1080
tacccgcagg acatatccac gccctcctac atcgaagctg aaagcacgag attcttcgcc   1140
ctccgagagc tgcatcaggt cggagacgct gtcgaacttt tcgatcagaa acttctcgac   1200
agacgtcgcg gtgagttcag gctttttcat gggtatatct ccttcttaaa gttaaacaaa   1260
attatttcta gagggaaacc gttgtggtct ccctatagtg agtcgtatta atttcgcggg   1320
atcgagatcg atccaattcc aatcccacaa aaatctgagc ttaacagcac agttgctcct   1380
ctcagagcag aatcgggtat tcaacaccct catatcaact actacgttgt gtataacggt   1440
ccacatgccg gtatatacga tgactggggt tgtacaaagg cggcaacaaa cggcgttccc   1500
```

-continued

```
ggagttgcac acaagaaatt tgccactatt acagaggcaa gagcagcagc tgacgcgtac    1560
acaacaagtc agcaaacaga caggttgaac ttcatcccca aaggagaagc tcaactcaag    1620
cccaagagct tgctaaggc cctaacaagc ccaccaaagc aaaaagccca ctggctcacg     1680
ctaggaacca aaaggcccag cagtgatcca gccccaaaag agatctcctt tgccccggag    1740
attacaatgg acgatttcct ctatctttac gatctaggaa ggaagttcga aggtgaaggt    1800
gacgacacta tgttcaccac tgataatgag aaggttagcc tcttcaattt cagaaagaat    1860
gctgacccac agatggttag agaggcctac gcagcaggtc tcatcaagac gatctacccg    1920
agtaacaatc tccaggagat caaataccct cccaagaagg ttaaagatgc agtcaaaaga    1980
ttcaggacta attgcatcaa gaacacagag aaagacatat ttctcaagat cagaagtact    2040
attccagtat ggacgattca aggcttgctt cataaaccaa ggcaagtaat agagattgga    2100
gtctctaaaa aggtagttcc tactgaatct aaggccatgc atggagtcta agattcaaat    2160
cgaggatcta acagaactcg ccgtgaagac tggcgaacag ttcatacaga gtcttttacg    2220
actcaatgac aagaagaaaa tcttcgtcaa catggtggag cacgacactc tggtctactc    2280
caaaaatgtc aaagatacag tctcagaaga ccaagggct attgagactt ttcaacaaag     2340
gataatttcg ggaaacctcc tcggattcca ttgcccagct atctgtcact tcatcgaaag    2400
gacagtagaa aaggaaggtg gctcctacaa atgccatcat tgcgataaag gaaaggctat    2460
cattcaagat gcctctgccg acagtggtcc caaagatgga cccccaccca cgaggagcat    2520
cgtggaaaaa gaagacgttc caaccacgtc ttcaaagcaa gtggattgat gtgacatctc    2580
cactgacgta agggatgacg cacaatccca ctatccttcg caagaccctt cctctatata    2640
aggaagttca tttcatttgg agaggacacg ctcgagctca tttctctatt acttcagcca    2700
taacaaaaga actcttttct cttcttatta aaccatgaaa aagcctgaac tcaccgcgac    2760
gtctgtcgag aagtttctga tcgaaaagtt cgacagcgtc tccgacctga tgcagctctc    2820
ggagggcgaa gaatctcgtg cttttcagctt cgatgtagga gggcgtggat atgtcctgcg    2880
ggtaaatagc tgcgccgatg gtttctacaa agatcgttat gtttatcggc actttgcatc    2940
ggccgcgctc ccgattccgg aagtgcttga cattgggaa ttcagcgaga gcctgaccta     3000
ttgcatctcc cgccgtgcac agggtgtcac gttgcaagac ctgcctgaaa ccgaactgcc    3060
cgctgttctg cagccggtcg cggaggccat ggatgcgatc gctgcggccg atcttagcca    3120
gacgagcggg ttcggcccat tcggaccgca aggaatcggt caatacacta catggcgtga    3180
tttcatatgc gcgattgctg atccccatgt gtatcactgg caaactgtga tggacgacac    3240
cgtcagtgcg tccgtcgcgc aggctctcga tgagctgatg ctttgggccg aggactgccc    3300
cgaagtccgg cacctcgtgc acgcggattt cggctccaac aatgtcctga cggacaatgg    3360
ccgcataaca gcggtcattg actggagcga ggcgatgttc ggggattccc aatacgaggt    3420
cgccaacatc ttcttctgga ggccgtggtt ggcttgtatg gagcagcaga cgcgctactt    3480
cgagcggagg catccggagc ttgcaggatc gccgcggctc cggcgtata tgctccgcat     3540 tggtcttgac caactctatc agagcttggt tgacggcaat ttcgatgatg cagcttgggc    3600
gcagggtcga tgcgacgcaa tcgtccgatc cggagccggg actgtcgggc gtacacaaat    3660
cgcccgcaga agcgcggccg tctggaccga tggctgtgta gaagtactcg ccgatagtgg    3720
aaaccgacgc cccagcactc gtccgagggc aaaggaatag tgaggtacct aaagaaggag    3780
tgcgtcgaag cagatcgttc aaacatttgg caataaagtt tcttaagatt gaatcctgtt    3840
gccggtcttg cgatgattat catataattt ctgttgaatt acgttaagca tgtaataatt    3900
```

```
aacatgtaat gcatgacgtt atttatgaga tgggttttta tgattagagt cccgcaatta    3960
tacatttaat acgcgataga aaacaaaata tagcgcgcaa actaggataa attatcgcgc    4020
gcggtgtcat ctatgttact agatcgatgt cgaatcgatc aacctgcatt aatgaatcgg    4080
ccaacgcgcg gggagaggcg gtttgcgtat tgggcgctct tccgcttcct cgctcactga    4140
ctcgctgcgc tcggtcgttc ggctgcggcg agcggtatca gctcactcaa aggcggtaat    4200
acggttatcc acagaatcag gggataacgc aggaaagaac atgtgagcaa aaggccagca    4260
aaaggccagg aaccgtaaaa aggccgcgtt gctggcgttt ttccataggc tccgcccccc    4320
tgacgagcat cacaaaaatc gacgctcaag tcagaggtgg cgaaacccga caggactata    4380
aagataccag gcgtttcccc ctggaagctc cctcgtgcgc tctcctgttc cgaccctgcc    4440
gcttaccgga tacctgtccg cctttctccc ttcgggaagc gtggcgcttt ctcaatgctc    4500
acgctgtagg tatctcagtt cggtgtaggt cgttcgctcc aagctgggct gtgtgcacga    4560
accccccgtt cagcccgacc gctgcgcctt atccggtaac tatcgtcttg agtccaaccc    4620
ggtaagacac gacttatcgc cactggcagc agccactggt aacaggatta gcagagcgag    4680
gtatgtaggc ggtgctacag agttcttgaa gtggtggcct aactacggct acactagaag    4740
gacagtattt ggtatctgcg ctctgctgaa gccagttacc ttcggaaaaa gagttggtag    4800
ctcttgatcc ggcaaacaaa ccaccgctgg tagcggtggt ttttttgttt gcaagcagca    4860
gattacgcgc agaaaaaaag gatctcaaga agatcctttg atcttttcta cggggtctga    4920
cgctcagtgg aacgaaaact cacgttaagg gattttggtc atgacattaa cctataaaaa    4980
taggcgtatc acgaggccct ttcgtctcgc gcgtttcggt gatgacggtg aaaacctctg    5040
acacatgcag ctcccggaga cggtcacagc ttgtctgtaa gcggatgccg ggagcagaca    5100
agcccgtcag ggcgcgtcag cgggtgttgg cgggtgtcgg gctggctta actatgcggc    5160 atcagagcag attgtactga gagtgcacca tatggacata ttgtcgttag aacgcggcta    5220
caattaatac ataaccttat gtatcataca catacgattt aggtgacact atagaacggc    5280
gcgccaagct tgttgaaaca tccctgaagt gtctcatttt attttattta ttctttgctg    5340
ataaaaaaat aaaataaaag aagctaagca cacggtcaac cattgctcta ctgctaaaag    5400
ggttatgtgt agtgttttac tgcataaatt atgcagcaaa caagacaact caaattaaaa    5460
aatttccttt gcttgttttt tgttgtctc tgacttgact tcttgtgga agttggttgt    5520 ataaggattg ggacaccatt gtccttctta atttaatttt attctttgct gataaaaaaa    5580
aaaatttcat atagtgttaa ataataattt gttaaataac caaaaagtca aatatgttta    5640
ctctcgttta aataattgag attcgtccag caaggctaaa cgattgtata gatttatgac    5700
aatatttact ttttttataga taaatgttat attataataa atttatatac atatattata    5760
tgttatttat tattatttta aatccttcaa tattttatca aaccaactca taatttttt    5820 tttatctgta agaagcaata aaattaaata gacccacttt aaggatgatc caaccttat    5880 acagagtaag agagttcaaa tagtaccctt tcatatacat atcaactaaa atattagaaa    5940
tatcatggat caaaccttat aaagacatta ataagtgga taagtataat atataaatgg    6000
gtagtatata atatataaat ggatacaaac ttctctcttt ataattgtta tgtctcctta    6060
acatcctaat ataatacata agtgggtaat atataatata taaatggaga caaacttctt    6120
ccattataat tgttatgtct tcttaacact tatgtctcgt tcacaatgct aaggttagaa    6180
ttgtttagaa agtcttatag tacacatttg tttttgtact atttgaagca ttccataagc    6240
cgtcacgatt cagatgattt ataataataa gaggaaattt atcatagaac aataaggtgc    6300
```

```
atagatagag tgttaatata tcataacatc ctttgtttat tcatagaaga agtgagatgg   6360
agctcagtta ttatactgtt acatggtcgg atacaatatt ccatgctctc catgagctct   6420
tacacctaca tgcattttag ttcatacttg cggccgctaa agctgcttac cagccttagc   6480
ggatttcttg gtggccaggt tgtcctggta aagaagtga cagaacagga gaaagacaga   6540
tccgacgtag gcgtagttga aagcccagga gaacagcttg cccttgtcag agttgaagca   6600
gggaacgttg atgtagtccc agaccaggag aaagccaccg acgaactggc aaatctgcat   6660
ggcagtgatc agaggcttgg ccttgaactt gtagccagcg gcagtcagtc catagtaggt   6720
gtacatgatg gtgtgaatga acgagttaaa gaacatgaag atccacacac cctcgttgtg   6780
cagtcgaatg ccgaggtaga cgtcccaggg agctccaaag tgatggaagg cctgcagaaa   6840
ggacactcgc ttgcccttga ggaccagcca agcggtgtcg aggtactcca cgtacttaga   6900
atagtagaag gccttggcag tccaggtgaa cagcttggag tcccagacag gagagggaca   6960
ctgaaagaga ggctggggag tatcaccggt ctgtcttcgc agccaggctc cagtaccgta   7020
gtcccagccg agagcggtgg cagtcacgta gaaggacagg gcagagaaga gagccaggag   7080
gacgttgtac cagatcatgg aggttcggta ggctcctttc ttctcgtcca cgagaccaga   7140
gtttcgcagg agaggcttca ggagcaggta ggagaaggtg ccaatgagga tttcgggatc   7200
ggtgacggca gcccagattc gctcgccagc gtcgttggcc agagccatgg tgcggccgca   7260
gtatatctta aattctttaa tacggtgtac taggatattg aactggttct tgatgatgaa   7320
aacctgggcc gagattgcag ctatttatag tcataggtct tgttaacatg catggacatt   7380
tggccacggg gtggcatgca gtttgacggg tgttgaaata aacaaaaatg aggtggcgga   7440
agagaatacg agtttgaggt tgggttagaa caacaaatg tgagggctca tgatgggttg   7500
agttggtgaa tgttttgggc tgctcgattg acacctttgt gagtacgtgt tgttgtgcat   7560
ggcttttggg gtccagtttt tttttcttga cgcggcgatc ctgatcagct agtggataag   7620
tgatgtccac tgtgtgtgat tgcgttttg tttgaatttt atgaacttag acattgctat   7680
gcaaaggata ctctcattgt gttttgtctt cttttgttcc ttggcttttt cttatgatcc   7740
aagagactag tcagtgttgt ggcattcgag actaccaaga ttaattatga tgggggaagg   7800
ataagtaact gattagtacg gactgttacc aaattaatta ataagcggca aatgaagggc   7860
atggatcaaa agcttggatc tcctgcaggt cgactctaga cgtacgtcct cgaagagaag   7920
ggttaataac acatttttta acattttaa cacaatttt agttatttaa aaatttatta   7980
aaaaatttaa aataagaaga ggaactcttt aaataaatct aacttacaaa atttatgatt   8040
tttaataagt tttcaccaat aaaaaatgtc ataaaaatat gttaaaaagt atattatcaa   8100
tattctcttt atgataaata aaagaaaaa aaaataaaa gttaagtgaa aatgagattg   8160
aagtgacttt aggtgtgtat aaatatatca accccgccaa caatttattt aatccaaata   8220
tattgaagta tattattcca tagcctttat ttatttatat atttattata taaaagctttt  8280 atttgttcta ggttgttcat gaaatatttt tttggttta tctccgttgt aagaaaatca   8340
tgtgctttgt gtcgccactc actattgcag cttttttcatg cattggtcag attgacggtt   8400
gattgtattt ttgttttta tggttttgtg ttatgactta agtcttcatc tctttatctc   8460
ttcatcaggt ttgatggtta cctaatatgg tccatgggta catgcatggt taaattaggt   8520
ggccaacttt gttgtgaacg atagaatttt ttttatatta agtaaactat ttttatatta   8580
tgaaataata ataaaaaaaa tatttttatca ttattaacaa aatcatatta gttaatttgt   8640
taactctata ataaaagaaa tactgtaaca ttcacattac atggtaacat ctttccaccc   8700
```

```
tttcatttgt tttttgtttg atgacttttt ttcttgttta aatttatttc ccttcttttα    8760
aatttggaat acattatcat catatataaa ctaaaatact aaaaacagga ttacacaaat    8820
gataaataat aacacaaata tttataaatc tagctgcaat atatttaaac tagctatatc    8880
gatattgtaa aataaaacta gctgcattga tactgataaa aaaatatcat gtgctttctg    8940
gactgatgat gcagtatact tttgacattg cctttatttt attttcaga aaagctttct     9000
tagttctggg ttcttcatta tttgtttccc atctccattg tgaattgaat catttgcttc    9060
gtgtcacaaa tacaatttag ntaggtacat gcattggtca gattcacggt ttattatgtc    9120
atgacttaag ttcatggtag tacattacct gccacgcatg cattatattg gttagatttg    9180
ataggcaaat ttggttgtca acaatataaa tataaataat gttttatat tacgaaataa     9240
cagtgatcaa aacaaacagt tttatcttta ttaacaagat tttgttttg tttgatgacg     9300
tttttaatg tttacgcttt ccccttctt ttgaatttag aacactttat catcataaaa      9360
tcaaatacta aaaaattac atatttcata aataataaca caaatatttt taaaaatct      9420
gaaataataa tgaacaatat tacatattat cacgaaaatt cattaataaa aatattatat    9480
aaataaaatg taatagtagt tatatgtagg aaaaagtac tgcacgcata atatatacaa     9540
aaagattaaa atgaactatt ataaataata acactaaatt aatggtgaat catatcaaaa    9600
taatgaaaaa gtaaataaaa tttgtaatta acttctatat gtattacaca cacaaataat    9660
aaataatagt aaaaaaatt atgataaata tttaccatct cataagatat ttaaaataat     9720
gataaaata tagattattt tttatgcaac tagctagcca aaaagagaac acgggtatat     9780
ataaaaagag taccttttaaa ttctactgta cttccttat tcctgacgtt tttatatcaa    9840
gtggacatac gtgaagattt taattatcag tctaaatatt tcattagcac ttaatacttt   9900
tctgttttat tcctatccta taagtagtcc cgattctccc aacattgctt attcacacaa   9960
ctaactaaga aagtcttcca tagcccccca agcggccgca ccatgggcaa gggtggagac  10020
ggcggcgcgc aggcggtgag cgggaccgac gcgtctctcg ctgaggtgag ctccgtcgat  10080
agcaagagcg tgcacgtcgt gctctacggc aagcgcgtgg atgtcacaaa gttccagaag  10140
gcacacccgg gcgggagcaa ggtgttccgc atcttccagg agcgcgacgc gacggagcag  10200
ttcgagtctt accactcgcc caaggccatc aagatgatgg agggcatgct caagaagtcg  10260
gaggatgcgc ccgcttccgt gcccctgccc tcgcggtcca ccatgggcac ggagttcaag  10320
gagatgattg agcgccacaa gagggctggt ctctacgacc cttgcccgtt ggacgagctg  10380
ttcaagctca ccatcgtcct tgcgcccatc ttcgtgggcg cctatctcgt gcggagcggc  10440
gtctcgcccc tcgcgggcgc gctctccatg ggctttggct tctacctcga cggctggctt  10500
gctcacgact acctgcatca cgcagtcttc aagggctcgg tcaacacgct cgtcaaggcg  10560
aacaacgcca tgggatacgc cctcggcttc ctccagggct acgacgtggc ctggtggcgc  10620
gcgcgccata acacgcacca cgtgtgcacc aacgaggatg gttcggaccc ggacatcaag  10680
acggcgcccc tgctcatcta cgtgcgagag aacccgtcca ttgccaagcg gctcaacttc  10740
ttccagcgct ggcagcagta ctactatgtg ccgaccatgg ccatcctcga cctctactgg  10800
cgcctggagt ccatcgcgta cgtggctgtg cgcctgccta agatgtggat gcaggccgcc  10860
gctcttgccg ctcactacgc gctcctgtgc tgggtcttcg cagcgcatct caacctcatc  10920
cctctcatga tggttgcacg cggcttcgcg acgggcatcg ttgtctttgc aacccactat  10980
ggtgaggaca tcctcgaccg cgagcacgtc gagggcatga cgctcgtcga gcagaccgcc  11040
aagacctccc gtaacatcac gggcggctgg ctagtgaacg tgctcacggg cttcatctcc  11100
```

```
ctgcagaccg agcatcacct cttccccatg atgcccaccg gcaacctaat gactatccag    11160
cccgaggtac gcgacttctt caagaagcat ggcctcgagt accgcgaggg caacctcttc    11220
cagtgcgtgc accagaacat caaggctctc gccttcgagc acctcctcca ctgagcggcc    11280
gcgacacaag tgtgagagta ctaaataaat gctttggttg tacgaaatca ttacactaaa    11340
taaaataatc aaagcttata tatgccttcc gctaaggccg aatgcaaaga aattggttct    11400
ttctcgttat cttttgccac ttttactagt acgtattaat tactacttaa tcatctttgt    11460
ttacggctca ttatatcctg ca                                             11482

<210> SEQ ID NO 28
<211> LENGTH: 18
<212> TYPE: DNA
<213> ORGANISM: Artificial Sequence
<220> FEATURE:
<223> OTHER INFORMATION: GPDsense primer

<400> SEQUENCE: 28
atacgagatc gtcaaggg                                                  18

<210> SEQ ID NO 29
<211> LENGTH: 26
<212> TYPE: DNA
<213> ORGANISM: Artificial Sequence
<220> FEATURE:
<223> OTHER INFORMATION: GPDantisense primer

<400> SEQUENCE: 29
gcggccgcgg attgatgtgt gtttaa                                         26

<210> SEQ ID NO 30
<211> LENGTH: 6970
<212> TYPE: DNA
<213> ORGANISM: Artificial Sequence
<220> FEATURE:
<223> OTHER INFORMATION: plasmid pY5-22GPD

<400> SEQUENCE: 30
tcgacgcagt aggatgtcct gcacgggtct ttttgtgggg tgtggagaaa ggggtgcttg    60
gagatggaag ccggtagaac cgggctgctt gtgcttggag atggaagccg gtagaaccgg    120
gctgcttggg gggatttggg gccgctgggc tccaaagagg ggtaggcatt tcgttggggt    180
tacgtaattg cggcatttgg gtcctgcgcg catgtcccat tggtcagaat tagtccggat    240
aggagactta tcagccaatc acagcgccgg atccacctgt aggttgggtt gggtgggagc    300 accctccac agagtagagt caaacagcag cagcaacatg atagttgggg gtgtgcgtgt    360
taaaggaaaa aaagaagct tgggttatat tcccgctcta tttagaggtt gcgggataga    420
cgccgacgga gggcaatggc gccatggaac cttgcggata tcgatacgcc gcggcggact    480
gcgtccgaac cagctccagc agcgtttttt ccggcgcatt gagccgactg cgaccccgcc    540
aacgtgtctt ggcccacgca ctcatgtcat gttggtgttg ggaggccact tttaagtag    600 cacaaggcac ctagctcgca gcaaggtgtc cgaaccaaag aagcggctgc agtggtgcaa    660
acggggcgga acggcgggaa aaagccacg ggggcacgaa ttgaggcacg ccctcgaatt    720
tgagacgagt cacggcccca ttcgcccgcg caatggctcg ccaacgcccg gtcttttgca    780
ccacatcagg ttaccccaag ccaaaccttt gtgttaaaaa gcttaacata ttataccgaa    840
cgtaggtttg gcgggcttg ctccgtctgt ccaaggcaac atttatataa gggtctgcat    900
cgccggctca attgaatctt ttttcttctt ctcttctcta tattcattct tgaattaaac    960
```

-continued

| | |
|---|---|
| acacatcaat ccgcggccgc caccgcggcc cgagattccg gcctcttcgg ccgccaagcg | 1020 |
| acccgggtgg acgtctagag gtacctagca attaacagat agtttgccgg tgataattct | 1080 |
| cttaacctcc cacactcctt tgacataacg atttatgtaa cgaaactgaa atttgaccag | 1140 |
| atattgtgtc cgcggtggag ctccagcttt tgttcccttt agtgagggtt aatttcgagc | 1200 |
| ttggcgtaat catggtcata gctgtttcct gtgtgaaatt gttatccgct cacaattcca | 1260 |
| cacaacgtac gagccggaag cataaagtgt aaagcctggg gtgcctaatg agtgagctaa | 1320 |
| ctcacattaa ttgcgttgcg ctcactgccc gctttccagt cgggaaacct gtcgtgccag | 1380 |
| ctgcattaat gaatcggcca acgcgcgggg agaggcggtt tgcgtattgg gcgctcttcc | 1440 |
| gcttcctcgc tcactgactc gctgcgctcg gtcgttcggc tgcggcgagc ggtatcagct | 1500 |
| cactcaaagg cggtaatacg gttatccaca gaatcagggg ataacgcagg aaagaacatg | 1560 |
| tgagcaaaag gccagcaaaa ggccaggaac cgtaaaaagg ccgcgttgct ggcgtttttc | 1620 |
| cataggctcc gccccctga cgagcatcac aaaaatcgac gctcaagtca gaggtggcga | 1680 |
| aacccgacag gactataaag ataccaggcg tttccccctg gaagctccct cgtgcgctct | 1740 |
| cctgttccga ccctgccgct taccggatac ctgtccgcct ttctcccttc gggaagcgtg | 1800 |
| gcgctttctc atagctcacg ctgtaggtat ctcagttcgg tgtaggtcgt tcgctccaag | 1860 |
| ctgggctgtg tgcacgaacc ccccgttcag cccgaccgct gcgccttatc cggtaactat | 1920 |
| cgtcttgagt ccaacccggt aagacacgac ttatcgccac tggcagcagc cactggtaac | 1980 |
| aggattagca gagcgaggta tgtaggcggt gctacagagt tcttgaagtg gtggcctaac | 2040 |
| tacggctaca ctagaaggac agtatttggt atctgcgctc tgctgaagcc agttaccttc | 2100 |
| ggaaaaagag ttggtagctc ttgatccggc aaacaaacca ccgctggtag cggtggtttt | 2160 |
| tttgtttgca agcagcagat tacgcgcaga aaaaaaggat ctcaagaaga tcctttgatc | 2220 |
| ttttctacgg ggtctgacgc tcagtggaac gaaaactcac gttaagggat tttggtcatg | 2280 |
| agattatcaa aaaggatctt cacctagatc cttttaaatt aaaaatgaag ttttaaatca | 2340 |
| atctaaagta tatatgagta aacttggtct gacagttacc aatgcttaat cagtgaggca | 2400 |
| cctatctcag cgatctgtct atttcgttca tccatagttg cctgactccc cgtcgtgtag | 2460 |
| ataactacga tacgggaggg cttaccatct ggccccagtg ctgcaatgat accgcgagac | 2520 |
| ccacgctcac cggctccaga tttatcagca ataaaccagc cagccggaag ggccgagcgc | 2580 |
| agaagtggtc ctgcaacttt atccgcctcc atccagtcta ttaattgttg ccgggaagct | 2640 |
| agagtaagta gttcgccagt taatagtttg cgcaacgttg ttgccattgc tacaggcatc | 2700 |
| gtggtgtcac gctcgtcgtt tggtatggct tcattcagct ccggttccca acgatcaagg | 2760 |
| cgagttacat gatcccccat gttgtgcaaa aaagcggtta gctccttcgg tcctccgatc | 2820 |
| gttgtcagaa gtaagttggc cgcagtgtta tcactcatgg ttatggcagc actgcataat | 2880 |
| tctcttactg tcatgccatc cgtaagatgc ttttctgtga ctggtgagta ctcaaccaag | 2940 |
| tcattctgag aatagtgtat gcggcgaccg agttgctctt gcccggcgtc aatacgggat | 3000 |
| aataccgcgc cacatagcag aactttaaaa gtgctcatca ttggaaaacg ttcttcgggg | 3060 |
| cgaaaactct caaggatctt accgctgttg agatccagtt cgatgtaacc cactcgtgca | 3120 |
| cccaactgat cttcagcatc ttttactttc accagcgttt ctgggtgagc aaaaacagga | 3180 |
| aggcaaaatg ccgcaaaaaa gggaataagg gcgacacgga aatgttgaat actcatactc | 3240 |
| ttcctttttc aatattattg aagcatttat cagggttatt gtctcatgag cggatacata | 3300 |
| tttgaatgta tttagaaaaa taaacaaata ggggttccgc gcacatttcc ccgaaaagtg | 3360 |

```
ccacctgacg cgccctgtag cggcgcatta agcgcggcgg gtgtggtggt tacgcgcagc    3420
gtgaccgcta cacttgccag cgccctagcg cccgctcctt tcgctttctt cccttccttt    3480
ctcgccacgt tcgccggctt tccccgtcaa gctctaaatc gggggctccc tttagggttc    3540
cgatttagtg ctttacggca cctcgacccc aaaaaacttg attagggtga tggttcacgt    3600
agtgggccat cgccctgata gacggttttt cgcccttttga cgttggagtc cacgttcttt    3660
aatagtggac tcttgttcca aactggaaca acactcaacc ctatctcggt ctattctttt    3720
gatttataag ggattttgcc gatttcggcc tattggttaa aaaatgagct gatttaacaa    3780
aaatttaacg cgaattttaa caaaatatta acgcttacaa tttccattcg ccattcaggc    3840
tgcgcaactg ttgggaaggg cgatcggtgc gggcctcttc gctattacgc cagctggcga    3900
aagggggatg tgctgcaagg cgattaagtt gggtaacgcc agggttttcc cagtcacgac    3960
gttgtaaaac gacggccagt gaattgtaat acgactcact atagggcgaa ttgggtaccg    4020
ggccccccct cgaggtcgat ggtgtcgata agcttgatat cgaattcatg tcacacaaac    4080
cgatcttcgc ctcaaggaaa cctaattcta catccgagag actgccgaga tccagtctac    4140
actgattaat tttcgggcca ataatttaaa aaaatcgtgt tatataatat tatatgtatt    4200
atatatatac atcatgatga tactgacagt catgtcccat tgctaaatag acagactcca    4260
tctgccgcct ccaactgatg ttctcaatat ttaaggggtc atctcgcatt gtttaataat    4320
aaacagactc catctaccgc ctccaaatga tgttctcaaa atatattgta tgaacttatt    4380
tttattactt agtattatta gacaacttac ttgctttatg aaaaacacttt cctatttagg    4440
aaacaattta taatggcagt tcgttcattt aacaatttat gtagaataaa tgttataaat    4500
gcgtatggga atcttaaat atggatagca taaatgatat ctgcattgcc taattcgaaa    4560
tcaacagcaa cgaaaaaaat cccttgtaca acataaaatag tcatcgagaa atatcaacta    4620
tcaaagaaca gctattcaca cgttactatt gagattatta ttggacgaga atcacacact    4680
caactgtctt tctctcttct agaaatacag gtacaagtat gtactattct cattgttcat    4740
acttctagtc atttcatccc acatattcct tggatttctc tccaatgaat gacattctat    4800
cttgcaaatt caacaattat aataagatat accaaagtag cggtatagtg gcaatcaaaa    4860
agcttctctg gtgtgcttct cgtatttatt tttattctaa tgatccatta aaggtatata    4920
tttatttctt gttatataat cctttgttt attacatggg ctggatacat aaaggtatttt    4980
tgatttaatt ttttgcttaa attcaatccc ccctcgttca gtgtcaactg taatggtagg    5040
aaattaccat acttttgaag aagcaaaaaa aatgaaagaa aaaaaaaatc gtatttccag    5100
gttagacgtt ccgcagaatc tagaatgcgg tatgcggtac attgttcttc gaacgtaaaa    5160
gttgcgctcc ctgagatatt gtacattttt gcttttacaa gtacaagtac atcgtacaac    5220
tatgtactac tgttgatgca tccacaacag tttgtttttgt ttttttttgt ttttttttt    5280
tctaatgatt cattaccgct atgtatacct acttgtactt gtagtaagcc gggttattgg    5340
cgttcaatta atcatagact tatgaatctg cacggtgtgc gctgcgagtt acttttagct    5400
tatgcatgct acttgggtgt aatattggga tctgttcgga aatcaacgga tgctcaaccg    5460
atttcgacag taattaatta agtcatacac aagtcagctt tcttcgagcc tcatataagt    5520
ataagtagtt caacgtatta gcactgtacc cagcatctcc gtatcgagaa acacaacaac    5580
atgccccatt ggacagatca tgcggataca caggttgtgc agtatcatac atactcgatc    5640
agacaggtcg tctgaccatc atacaagctg aacaagcgct ccatacttgc acgctctcta    5700
tatacacagt taaattacat atccatagtc taacctctaa cagttaatct tctggtaagc    5760
```

| | |
|---|---|
| ctcccagcca gccttctggt atcgcttggc ctcctcaata ggatctcggt tctggccgta | 5820 |
| cagacctcgg ccgacaatta tgatatccgt tccggtagac atgacatcct caacagttcg | 5880 |
| gtactgctgt ccgagagcgt ctcccttgtc gtcaagaccc accccggggg tcagaataag | 5940 |
| ccagtcctca gagtcgccct taggtcggtt ctgggcaatg aagccaacca caaactcggg | 6000 |
| gtcggatcgg gcaagctcaa tggtctgctt ggagtactcg ccagtggcca gagagccctt | 6060 |
| gcaagacagc tcggccagca tgagcagacc tctggccagc ttctcgttgg gagagggac | 6120 |
| taggaactcc ttgtactggg agttctcgta gtcagagacg tcctccttct tctgttcaga | 6180 |
| gacagttcc tcggcaccag ctcgcaggcc agcaatgatt ccggttccgg gtacaccgtg | 6240 |
| ggcgttggtg atatcggacc actcggcgat tcggtgacac cggtactggt gcttgacagt | 6300 |
| gttgccaata tctgcgaact ttctgtcctc gaacaggaag aaaccgtgct taagagcaag | 6360 |
| ttccttgagg gggagcacag tgccggcgta ggtgaagtcg tcaatgatgt cgatatgggt | 6420 |
| tttgatcatg cacacataag gtccgacctt atcggcaagc tcaatgagct ccttggtggt | 6480 |
| ggtaacatcc agagaagcac acaggttggt tttcttggct gccacgagct tgagcactcg | 6540 |
| agcggcaaag gcggacttgt ggacgttagc tcgagcttcg taggagggca ttttggtggt | 6600 |
| gaagaggaga ctgaaataaa tttagtctgc agaacttttt atcggaaccct tatctggggc | 6660 |
| agtgaagtat atgttatggt aatagttacg agttagttga acttatagat agactggact | 6720 |
| atacggctat cggtccaaat tagaaagaac gtcaatggct ctctgggcgt cgccttttgcc | 6780 |
| gacaaaaatg tgatcatgat gaaagccagc aatgacgttg cagctgatat tgttgtcggc | 6840 |
| caaccgcgcc gaaaacgcag ctgtcagacc cacagcctcc aacgaagaat gtatcgtcaa | 6900 |
| agtgatccaa gcacactcat agttggagtc gtactccaaa ggcggcaatg acgagtcaga | 6960 |
| cagatactcg | 6970 |

<210> SEQ ID NO 31
<211> LENGTH: 8253
<212> TYPE: DNA
<213> ORGANISM: Artificial Sequence
<220> FEATURE:
<223> OTHER INFORMATION: plasmid pY118

<400> SEQUENCE: 31

| | |
|---|---|
| ggccgccacc gcggcccgag attccggcct cttcggccgc caagcgaccc gggtggacgt | 60 |
| ctagaggtac ctagcaatta acagatagtt tgccggtgat aattctctta acctcccaca | 120 |
| ctcctttgac ataacgattt atgtaacgaa actgaaattt gaccagatat tgtgtccgcg | 180 |
| gtggagctcc agcttttgtt ccctttagtg agggttaatt tcgagcttgg cgtaatcatg | 240 |
| gtcatagctg ttcctgtgt gaaattgtta tccgctcaca attccacaca acgtacgagc | 300 |
| cggaagcata aagtgtaaag cctggggtgc ctaatgagtg agctaactca cattaattgc | 360 |
| gttgcgctca ctgcccgctt tccagtcggg aaacctgtcg tgccagctgc attaatgaat | 420 |
| cggccaacgc gcgggagag gcggttgcg tattgggcgc tcttccgctt cctcgctcac | 480 |
| tgactcgctg cgctcggtcg ttcggctgcg gcgagcggta tcagctcact caaaggcggt | 540 |
| aatacggtta ccacagaat caggggataa cgcaggaaag aacatgtgag caaaaggcca | 600 |
| gcaaaaggcc aggaaccgta aaaaggccgc gttgctggcg ttttccata ggctccgccc | 660 |
| ccctgacgag catcacaaaa atcgacgctc aagtcagagg tggcgaaacc cgacaggact | 720 |
| ataaagatac caggcgtttc cccctggaag ctccctcgtg cgctctcctg ttccgacccct | 780 |
| gccgcttacc ggatacctgt ccgcctttct cccttcggga agcgtggcgc tttctcatag | 840 |

```
ctcacgctgt aggtatctca gttcggtgta ggtcgttcgc tccaagctgg gctgtgtgca    900
cgaaccccc gttcagcccg accgctgcgc cttatccggt aactatcgtc ttgagtccaa    960
cccggtaaga cacgacttat cgccactggc agcagccact ggtaacagga ttagcagagc   1020
gaggtatgta ggcggtgcta cagagttctt gaagtggtgg cctaactacg ctacactag   1080
aaggacagta tttggtatct gcgctctgct gaagccagtt accttcggaa aaagagttgg   1140
tagctcttga tccggcaaac aaaccaccgc tggtagcggt ggttttttg tttgcaagca    1200
gcagattacg cgcagaaaaa aaggatctca agaagatcct ttgatctttt ctacggggtc   1260
tgacgctcag tggaacgaaa actcacgtta agggattttg gtcatgagat tatcaaaaag   1320
gatcttcacc tagatccttt taaattaaaa atgaagtttt aaatcaatct aaagtatata   1380
tgagtaaact tggtctgaca gttaccaatg cttaatcagt gaggcaccta tctcagcgat   1440
ctgtctattt cgttcatcca tagttgcctg actccccgtc gtgtagataa ctacgatacg   1500
ggagggctta ccatctggcc ccagtgctgc aatgataccg cgagacccac gctcaccggc   1560
tccagattta tcagcaataa accagccagc cggaagggcc gagcgcagaa gtggtcctgc   1620
aactttatcc gcctccatcc agtctattaa ttgttgccgg gaagctagag taagtagttc   1680
gccagttaat agtttgcgca acgttgttgc cattgctaca ggcatcgtgg tgtcacgctc   1740
gtcgtttggt atggcttcat tcagctccgg ttcccaacga tcaaggcgag ttacatgatc   1800
ccccatgttg tgcaaaaaag cggttagctc cttcggtcct ccgatcgttg tcagaagtaa   1860
gttggccgca gtgttatcac tcatggttat ggcagcactg cataattctc ttactgtcat   1920
gccatccgta agatgctttt ctgtgactgg tgagtactca accaagtcat tctgagaata   1980
gtgtatgcgg cgaccgagtt gctcttgccc ggcgtcaata cgggataata ccgcgccaca   2040
tagcagaact ttaaaagtgc tcatcattgg aaaacgttct cggggcgaa aactctcaag   2100
gatcttaccg ctgttgagat ccagttcgat gtaaccccact cgtgcaccca actgatcttc   2160
agcatctttt actttcacca gcgtttctgg gtgagcaaaa acaggaaggc aaaatgccgc   2220
aaaaaaggga ataagggcga cacgaaaatg ttgaatactc atactcttcc ttttcaata   2280
ttattgaagc atttatcagg gttattgtct catgagcgga tacatatttg aatgtattta   2340
gaaaaataaa caaatagggg ttccgcgcac atttccccga aaagtgccac ctgacgcgcc   2400
ctgtagcggc gcattaagcg cggcgggtgt ggtggttacg cgcagcgtga ccgctacact   2460
tgccagcgcc ctagcgcccg ctcctttcgc tttcttccct tcctttctcg ccacgttcgc   2520
cggctttccc cgtcaagctc taaatcgggg gctccctta gggttccgat ttagtgcttt   2580
acggcacctc gaccccaaaa aacttgatta gggtgatggt tcacgtagtg gccatcgcc   2640
ctgatagacg ttttttcgcc ctttgacgtt ggagtccacg ttctttaata gtggactctt   2700
gttccaaact ggaacaacac tcaaccctat ctcggtctat tcttttgatt tataagggat   2760
tttgccgatt tcggcctatt ggttaaaaaa tgagctgatt taacaaaaat ttaacgcgaa   2820
ttttaacaaa atattaacgc ttacaatttc cattcgccat tcaggctgcg caactgttgg   2880
gaagggcgat cggtgcgggc ctcttcgcta ttacgccagc tggcgaaagg gggatgtgct   2940
gcaaggcgat taagttgggt aacgccaggg ttttcccagt cacgacgttg taaaacgacg   3000
gccagtgaat tgtaatacga ctcactatag ggcgaattgg gtaccgggcc ccccctcgag   3060
gtcgatggtg tcgataagct tgatatcgaa ttcatgtcac acaaaccgat cttcgcctca   3120
aggaaaccta attctacatc cgagagactg ccgagatcca gtctcactg attaattttc   3180
gggccaataa tttaaaaaaa tcgtgttata taatattata tgtattatat atatacatca   3240
```

```
tgatgatact gacagtcatg tcccattgct aaatagacag actccatctg ccgcctccaa    3300
ctgatgttct caatatttaa ggggtcatct cgcattgttt aataataaac agactccatc    3360
taccgcctcc aaatgatgtt ctcaaaatat attgtatgaa cttatttttta ttacttagta    3420 ttattagaca acttacttgc tttatgaaaa acacttccta tttaggaaac aatttataat    3480
ggcagttcgt tcatttaaca atttatgtag aataaatgtt ataaatgcgt atgggaaatc    3540
ttaaatatgg atagcataaa tgatatctgc attgcctaat tcgaaatcaa cagcaacgaa    3600
aaaaatccct tgtacaacat aaatagtcat cgagaaatat caactatcaa agaacagcta    3660
ttcacacgtt actattgaga ttattattgg acgagaatca cacactcaac tgtctttctc    3720
tcttctagaa atacaggtac aagtatgtac tattctcatt gttcatactt ctagtcattt    3780
catcccacat attccttgga tttctctcca atgaatgaca ttctatcttg caaattcaac    3840
aattataata agatatacca aagtagcggt atagtggcaa tcaaaaagct tctctggtgt    3900
gcttctcgta tttattttta ttctaatgat ccattaaagg tatatattta tttcttgtta    3960
tataatcctt ttgtttatta catgggctgg atacataaag gtattttgat ttaattttttt   4020 gcttaaattc aatccccccct cgttcagtgt caactgtaat ggtaggaaat taccatactt   4080
ttgaagaagc aaaaaaaatg aaagaaaaaa aaaatcgtat ttccaggtta gacgttccgc    4140
agaatctaga atgcggtatg cggtacattg ttcttcgaac gtaaaagttg cgctccctga    4200
gatattgtac atttttgctt ttacaagtac aagtacatcg tacaactatg tactactgtt    4260
gatgcatcca caacagtttg ttttgttttt ttttgttttt ttttttttcta atgattcatt    4320 accgctatgt atacctactt gtacttgtag taagccgggt tattggcgtt caattaatca    4380
tagacttatg aatctgcacg gtgtgcgctg cgagttactt ttagcttatg catgctactt    4440
gggtgtaata ttgggatctg ttcggaaatc aacggatgct caaccgatttt cgacagtaat    4500 taattaagtc atacacaagt cagctttctt cgagcctcat ataagtataa gtagttcaac    4560
gtattagcac tgtacccagc atctccgtat cgagaaacac aacaacatgc cccattggac    4620
agatcatgcg gatacacagg ttgtgcagta tcatacatac tcgatcagac aggtcgtctg    4680
accatcatac aagctgaaca agcgctccat acttgcacgc tctctatata cacagttaaa    4740
ttacatatcc atagtctaac ctctaacagt taatcttctg gtaagcctcc cagccagcct    4800
tctggtatcg cttggcctcc tcaataggat ctcggttctg gccgtacaga cctcggccga    4860
caattatgat atccgttccg gtagacatga catcctcaac agttcggtac tgctgtccga    4920
gagcgtctcc cttgtcgtca agacccaccc cgggggtcag aataagccag tcctcagagt    4980
cgcccttagg tcggttctgg gcaatgaagc caaccacaaa ctcggggtcg gatcgggcaa    5040
gctcaatggt ctgcttggag tactcgccag tggccagaga gcccttgcaa gacagctcgg    5100
ccagcatgag cagacctctg gccagcttct cgttgggaga ggggactagg aactccttgt    5160
actgggagtt ctcgtagtca gagcgtcct ccttcttctg ttcagagaca gtttcctcgg    5220
caccagctcg caggccagca atgattccgg ttccgggtac accgtgggcg ttggtgatat    5280
cggaccactc ggcgattcgg tgacaccggt actggtgctt gacagtgttg ccaatatctg    5340
cgaactttct gtcctcgaac aggaagaaac cgtgcttaag agcaagttcc ttgaggggga    5400
gcacagtgcc ggcgtaggtg aagtcgtcaa tgatgtcgat atgggttttg atcatgcaca    5460
cataaggtcc gaccttatcg gcaagctcaa tgagctcctt ggtggtggta acatccagag    5520
aagcacacag gttggttttc ttggctgcca cgagcttgag cactcgagcg gcaaaggcgg    5580
acttgtggac gttagctcga gcttcgtagg agggcatttt ggtggtgaag aggagactga    5640
```

```
aataaattta gtctgcagaa ctttttatcg gaaccttatc tggggcagtg aagtatatgt    5700
tatggtaata gttacgagtt agttgaactt atagatagac tggactatac ggctatcggt    5760
ccaaattaga aagaacgtca atggctctct gggcgtcgcc tttgccgaca aaaatgtgat    5820
catgatgaaa gccagcaatg acgttgcagc tgatattgtt gtcggccaac cgcgccgaaa    5880
acgcagctgt cagacccaca gcctccaacg aagaatgtat cgtcaaagtg atccaagcac    5940
actcatagtt ggagtcgtac tccaaaggcg gcaatgacga gtcagacaga tactcgtcga    6000
cgcagtagga tgtcctgcac gggtctttt gtggggtgtg gagaaagggg tgcttggaga    6060
tggaagccgg tagaaccggg ctgcttgtgc ttggagatgg aagccggtag aaccgggctg    6120
cttgggggga tttggggccg ctgggctcca aagagggta ggcatttcgt tggggttacg    6180
taattgcggc atttgggtcc tgcgcgcatg tcccattggt cagaattagt ccggatagga    6240
gacttatcag ccaatcacag cgccggatcc acctgtaggt tgggttgggt gggagcaccc    6300
ctccacagag tagagtcaaa cagcagcagc aacatgatag ttgggggtgt gcgtgttaaa    6360
ggaaaaaaaa gaagcttggg ttatattccc gctctattta gaggttgcgg gatagacgcc    6420
gacggagggc aatggcgcca tggaaccttg cggatatcga tacgccgcgg cggactgcgt    6480
ccgaaccagc tccagcagcg ttttttccgg gccattgagc cgactgcgac cccgccaacg    6540
tgtcttggcc cacgcactca tgtcatgttg gtgttgggag gccacttttt aagtagcaca    6600
aggcacctag ctcgcagcaa ggtgtccgaa ccaaagaagc ggctgcagtg gtgcaaacgg    6660
ggcggaaacg gcgggaaaaa gccacggggg cacgaattga ggcacgccct cgaatttgag    6720
acgagtcacg gccccattcg cccgcgcaat ggctcgccaa cgcccggtct tttgcaccac    6780
atcaggttac cccaagccaa acctttgtgt taaaaagctt aacatattat accgaacgta    6840
ggtttgggcg ggcttgctcc gtctgtccaa ggcaacattt atataagggt ctgcatcgcc    6900
ggctcaattg aatcttttt cttcttctct tctctatatt cattcttgaa ttaaacacac    6960
atcaatccgc ggccgcacca tgggcaaggg tggagacggc ggcgcgcagg cggtgagcgg    7020
gaccgacgcg tctctcgctg aggtgagctc cgtcgatagc aagagcgtgc acgtcgtgct    7080
ctacggcaag cgcgtggatg tcacaaagtt ccagaaggca cacccgggcg ggagcaaggt    7140
gttccgcatc ttccaggagc gcgacgcgac ggagcagttc gagtcttacc actcgcccaa    7200
ggccatcaag atgatggagg gcatgctcaa gaagtcggag gatgcgcccg cttccgtgcc    7260
cctgccctcg cggtccacca tgggcacgga gttcaaggag atgattgagc gccacaagag    7320
ggctggtctc tacgacccct tgcccgttgga cgagctgttc aagctcacca tcgtccttgc    7380
gcccatcttc gtgggcgcct atctcgtgcg gagcggcgtc tcgcccctcg cgggcgcgct    7440
ctccatgggc tttggcttct acctcgacgg ctggcttgct cacgactacc tgcatcacgc    7500
agtcttcaag ggctcggtca acacgctcgt caaggcgaac aacgccatgg gatacgccct    7560
cggcttcctc cagggctacg acgtggcctg gtggcgcgcg cgcccataaca cgcaccacgt    7620
gtgcaccaac gaggatggtt cggacccgga catcaagacg gcgcccctgc tcatctacgt    7680
gcgagagaac ccgtccattg ccaagcggct caacttcttc cagcgctggc agcagtacta    7740
ctatgtgccg accatggcca tcctcgacct ctactggcgc ctggagtcca tcgcgtacgt    7800
ggctgtgcgc ctgcctaaga gtggatgca ggccgccgct cttgccgctc actacgcgct    7860
cctgtgctgg gtcttcgcag cgcatctcaa cctcatccct ctcatgatgg ttgcacgcgg    7920
cttcgcgacg gcatcgttg tctttgcaac ccactatggt gaggacatcc tcgaccgcga    7980
gcacgtcgag ggcatgacgc tcgtcgagca gaccgccaag acctcccgta acatcacggg    8040
```

```
cggctggcta gtgaacgtgc tcacgggctt catctccctg cagaccgagc atcacctctt      8100
ccccatgatg cccaccggca acctaatgac tatccagccc gaggtacgcg acttcttcaa      8160
gaagcatggc ctcgagtacc gcgagggcaa cctcttccag tgcgtgcacc agaacatcaa      8220
ggctctcgcc ttcgagcacc tcctccactg agc                                  8253

<210> SEQ ID NO 32
<211> LENGTH: 777
<212> TYPE: DNA
<213> ORGANISM: Euglena gracilis

<400> SEQUENCE: 32
atggaggtgg tgaatgaaat agtctcaatt gggcaggaag ttttacccaa agttgattat        60
gcccaactct ggagtgatgc cagtcactgt gaggtgcttt acttgtccat cgcatttgtc       120
atcttgaagt tcactcttgg cccccttggt ccaaaaggtc agtctcgtat gaagtttgtt       180
ttcaccaatt acaaccttct catgtccatt tattcgttgg gatcattcct ctcaatggca       240
tatgccatgt acaccatcgg tgttatgtct gacaactgcg agaaggcttt tgacaacaac       300
gtcttcagga tcaccacgca gttgttctat ttgagcaagt tcctggagta tattgactcc       360
ttctatttgc cactgatggg caagcctctg acctggttgc aattcttcca tcatttgggg       420
gcaccgatgg atatgtggct gttctataat taccgaaatg aagctgtttg gattttgtg        480 ctgttgaatg gtttcatcca ctggatcatg tacggttatt attggaccag attgatcaag       540
ctgaagttcc ccatgccaaa atccctgatt acatcaatgc agatcattca attcaatgtt       600
ggtttctaca ttgtctggaa gtacaggaac attccctgtt atcgccaaga tgggatgagg       660
atgtttggct ggttcttcaa ttacttttat gttggcacag tcttgtgttt gttcttgaat       720
ttctatgtgc aaacgtatat cgtcaggaag cacaagggag ccaaaaagat tcagtga         777

<210> SEQ ID NO 33
<211> LENGTH: 30
<212> TYPE: DNA
<213> ORGANISM: Artificial Sequence
<220> FEATURE:
<223> OTHER INFORMATION: sense oligonucleotide EugEL1-1 primer

<400> SEQUENCE: 33
agcggccgca ccatggaggt ggtgaatgaa                                          30

<210> SEQ ID NO 34
<211> LENGTH: 30
<212> TYPE: DNA
<213> ORGANISM: Artificial Sequence
<220> FEATURE:
<223> OTHER INFORMATION: sense oligonucleotide EugEL1-2 primer

<400> SEQUENCE: 34
tgcggccgct cactgaatct ttttggctcc                                          30

<210> SEQ ID NO 35
<211> LENGTH: 4311
<212> TYPE: DNA
<213> ORGANISM: Artificial Sequence
<220> FEATURE:
<223> OTHER INFORMATION: plasmid pKR906

<400> SEQUENCE: 35
agcggccgca ccatggaggt ggtgaatgaa atagtctcaa ttgggcagga agttttaccc        60
aaagttgatt atgcccaact ctggagtgat gccagtcact gtgaggtgct ttacttgtcc      120
```

-continued

| | |
|---|---|
| atcgcatttg tcatcttgaa gttcactctt ggccccttg gtccaaaagg tcagtctcgt | 180 |
| atgaagtttg ttttcaccaa ttacaacctt ctcatgtcca tttattcgtt gggatcattc | 240 |
| ctctcaatgg catatgccat gtacaccatc ggtgttatgt ctgacaactg cgagaaggct | 300 |
| tttgacaaca acgtcttcag gatcaccacg cagttgttct atttgagcaa gttcctggag | 360 |
| tatattgact ccttctattt gccactgatg ggcaagcctc tgacctggtt gcaattcttc | 420 |
| catcatttgg gggcaccgat ggatatgtgg ctgttctata attaccgaaa tgaagctgtt | 480 |
| tggattttg tgctgttgaa tggtttcatc cactggatca tgtacggtta ttattggacc | 540 |
| agattgatca agctgaagtt ccccatgcca aaatccctga ttacatcaat gcagatcatt | 600 |
| caattcaatg ttggtttcta cattgtctgg aagtacagga acattccctg ttatcgccaa | 660 |
| gatgggatga ggatgtttgg ctggttcttc aattactttt atgttggcac agtcttgtgt | 720 |
| ttgttcttga atttctatgt gcaaacgtat atcgtcagga agcacaaggg agccaaaaag | 780 |
| attcagtgag cggccgcacc tgaattccag cacactggcg gccgttacta gtggatccga | 840 |
| gctcggtacc aagcttgatg catagcttga gtattctaac gcgtcaccta aatagcttgg | 900 |
| cgtaatcatg gtcatagctg tttcctgtgt gaaattgtta tccgctcaca attccacaca | 960 |
| acatacgagc cggaagcata agtgtaaag cctggggtgc ctaatgagtg agctaactca | 1020 |
| cattaattgc gttgcgctca ctgcccgctt tccagtcggg aaacctgtcg tgccagctgc | 1080 |
| attaatgaat cggccaacgc gcggggagag cggtttgcg tattgggcgc tcttccgctt | 1140 |
| cctcgctcac tgactcgctg cgctcggtcg ttcggctgcg cgagcggta tcagctcact | 1200 |
| caaaggcggt aatacggtta ccacagaat caggggataa cgcaggaaag aacatgtgag | 1260 |
| caaaaggcca gcaaaagccc aggaaccgta aaaaggccgc gttgctggcg ttttccata | 1320 |
| ggctccgccc ccctgacgag catcacaaaa atcgacgctc aagtcagagg tggcgaaacc | 1380 |
| cgacaggact ataaagatac caggcgtttc cccctggaag ctccctcgtg cgctctcctg | 1440 |
| ttccgaccct gccgcttacc ggatacctgt ccgcctttct cccttcggga agcgtggcgc | 1500 |
| tttctcatag ctcacgctgt aggtatctca gttcggtgta ggtcgttcgc tccaagctgg | 1560 |
| gctgtgtgca cgaaccccc gttcagcccg accgctgcgc cttatccggt aactatcgtc | 1620 |
| ttgagtccaa cccggtaaga cacgacttat cgccactggc agcagccact ggtaacagga | 1680 |
| ttagcagagc gaggtatgta ggcggtgcta cagagttctt gaagtggtgg cctaactacg | 1740 |
| gctacactag aaggacagta tttggtatct gcgctctgct gaagccagtt accttcggaa | 1800 |
| aaagagttgg tagctcttga tccggcaaac aaaccaccgc tggtagcggt ggttttttg | 1860 |
| tttgcaagca gcagattacg cgcagaaaaa aaggatctca agaagatcct ttgatctttt | 1920 |
| ctacggggtc tgacgctcag tggaacgaaa actcacgtta agggattttg gtcatgagat | 1980 |
| tatcaaaaag gatcttcacc tagatccttt taaattaaaa atgaagtttt agcacgtgtc | 2040 |
| agtcctgctc ctcggccacg aagtgcacg agttgccggc cggtcgcgc agggcgaact | 2100 |
| cccgccccca cggctgctcg ccgatctcgg tcatggccgg cccggaggcg tcccggaagt | 2160 |
| tcgtggacac gacctccgac cactcggcgt acagctcgtc caggccgcgc acccacaccc | 2220 |
| aggccagggt gttgtccggc accacctggt cctggaccgc gctgatgaac agggtcacgt | 2280 |
| cgtcccggac cacaccggcg aagtcgtcct ccacgaagtc ccgggagaac ccgagccggt | 2340 |
| cggtccagaa ctcgaccgct ccggcgacgt cgcgcgcggt gagcaccgga acggcactgg | 2400 |
| tcaacttggc catggtggcc ctcctcacgt gctattattg aagcatttat cagggttatt | 2460 |
| gtctcatgag cggatacata tttgaatgta tttagaaaaa taaacaaata ggggttccgc | 2520 |

| | |
|---|---:|
| gcacatttcc ccgaaaagtg ccacctgtat gcggtgtgaa ataccgcaca gatgcgtaag | 2580 |
| gagaaaatac cgcatcagga aattgtaagc gttaataatt cagaagaact cgtcaagaag | 2640 |
| gcgatagaag gcgatgcgct gcgaatcggg agcggcgata ccgtaaagca cgaggaagcg | 2700 |
| gtcagcccat tcgccgccaa gctcttcagc aatatcacgg gtagccaacg ctatgtcctg | 2760 |
| atagcggtcc gccacaccca gccggccaca gtcgatgaat ccagaaaagc ggccattttc | 2820 |
| caccatgata ttcggcaagc aggcatcgcc atgggtcacg acgagatcct cgccgtcggg | 2880 |
| catgctcgcc ttgagcctgg cgaacagttc ggctggcgcg agcccctgat gctcttcgtc | 2940 |
| cagatcatcc tgatcgacaa gaccggcttc catccgagta cgtgctcgct cgatgcgatg | 3000 |
| tttcgcttgg tggtcgaatg ggcaggtagc cggatcaagc gtatgcagcc gccgcattgc | 3060 |
| atcagccatg atggatactt tctcggcagg agcaaggtga gatgacagga gatcctgccc | 3120 |
| cggcacttcg cccaatagca gccagtccct tcccgcttca gtgacaacgt cgagcacagc | 3180 |
| tgcgcaagga acgcccgtcg tggccagcca cgatagccgc gctgcctcgt cttgcagttc | 3240 |
| attcagggca ccggacaggt cggtcttgac aaaaagaacc gggcgcccct gcgctgacag | 3300 |
| ccggaacacg gcggcatcag agcagccgat tgtctgttgt gcccagtcat agccgaatag | 3360 |
| cctctccacc caagcggccg gagaacctgc gtgcaatcca tcttgttcaa tcatgcgaaa | 3420 |
| cgatcctcat cctgtctctt gatcagagct tgatccctg cgccatcaga tccttggcgg | 3480 |
| cgagaaagcc atccagttta ctttgcaggg cttcccaacc ttaccagagg gcgccccagc | 3540 |
| tggcaattcc ggttcgcttg ctgtccataa aaccgcccag tctagctatc gccatgtaag | 3600 |
| cccactgcaa gctacctgct ttctctttgc gcttgcgttt tcccttgtcc agatagccca | 3660 |
| gtagctgaca ttcatccggg gtcagcaccg tttctgcgga ctggctttct acgtgaaaag | 3720 |
| gatctaggtg aagatccttt ttgataatct catgcctgac atttatattc cccagaacat | 3780 |
| caggttaatg gcgttttga tgtcattttc gcggtggctg agatcagcca cttcttcccc | 3840 |
| gataacggag accggcacac tggccatatc ggtggtcatc atgcgccagc tttcatcccc | 3900 |
| gatatgcacc accgggtaaa gttcacggga gactttatct gacagcagac gtgcactggc | 3960 |
| caggggggatc accatccgtc gccccggcgt gtcaataata tcactctgta catccacaaa | 4020 |
| cagacgataa cggctctctc ttttataggt gtaaaccttta aactgccgta cgtataggct | 4080 |
| gcgcaactgt tgggaagggc gatcggtgcg ggcctcttcg ctattacgcc agctggcgaa | 4140 |
| aggggggatgt gctgcaaggc gattaagttg ggtaacgcca gggttttccc agtcacgacg | 4200 |
| ttgtaaaacg acggccagtg aattgtaata cgactcacta tagggcgaat tgggccctct | 4260 |
| agatgcatgc tcgagcggcc gccagtgtga tggatatctg cagaattcag g | 4311 |

<210> SEQ ID NO 36
<211> LENGTH: 3983
<212> TYPE: DNA
<213> ORGANISM: Artificial Sequence
<220> FEATURE:
<223> OTHER INFORMATION: plasmid pKR132

<400> SEQUENCE: 36

| | |
|---|---:|
| ctagagtcga cctgcaggca tgcaagcttg gcgtaatcat ggtcatagct gtttcctgtg | 60 |
| tgaaattgtt atccgctcac aattccacac aacatacgag ccggaagcat aaagtgtaaa | 120 |
| gcctggggtg cctaatgagt gagctaactc acattaattg cgttgcgctc actgcccgct | 180 |
| ttccagtcgg gaaacctgtc gtgccagctg cattaatgaa tcggccaacg cgcggggaga | 240 |
| ggcggtttgc gtattgggcg ctcttccgct tcctcgctca ctgactcgct gcgctcggtc | 300 |

```
gttcggctgc ggcgagcggt atcagctcac tcaaaggcgg taatacggtt atccacagaa    360 tcagggata  acgcaggaaa gaacatgtga gcaaaaggcc agcaaaaggc caggaaccgt    420
aaaaaggccg cgttgctggc gttttttccat aggctccgcc cccctgacga gcatcacaaa    480
aatcgacgct caagtcagag gtggcgaaac ccgacaggac tataaagata ccaggcgttt    540
ccccctggaa gctccctcgt gcgctctcct gttccgaccc tgccgcttac cggatacctg    600
tccgcctttc tcccttcggg aagcgtggcg ctttctcata gctcacgctg taggtatctc    660
agttcggtgt aggtcgttcg ctccaagctg ggctgtgtgc acgaaccccc cgttcagccc    720
gaccgctgcg ccttatccgg taactatcgt cttgagtcca acccggtaag acacgactta    780
tcgccactgg cagcagccac tggtaacagg attagcagag cgaggtatgt aggcggtgct    840
acagagttct tgaagtggtg gcctaactac ggctacacta aaggacagt atttggtatc    900 tgcgctctgc tgaagccagt taccttcgga aaaagagttg gtagctcttg atccggcaaa    960
caaaccaccg ctggtagcgg tggttttttt gtttgcaagc agcagattac gcgcagaaaa    1020
aaaggatctc aagaagatcc tttgatcttt tctacggggt ctgacgctca gtggaacgaa    1080
aactcacgtt aagggatttt ggtcatgaga ttatcaaaaa ggatcttcac ctagatcctt    1140
ttaaattaaa aatgaagttt taaatcaatc taaagtatat atgagtaaac ttggtctgac    1200
agttaccaat gcttaatcag tgaggcacct atctcagcga tctgtctatt tcgttcatcc    1260
atagttgcct gactccccgt cgtgtagata actacgatac gggagggctt accatctggc    1320
cccagtgctg caatgatacc gcgagaccca cgctcaccgg ctccagattt atcagcaata    1380
aaccagccag ccggaagggc cgagcgcaga agtggtcctg caactttatc cgcctccatc    1440
cagtctatta attgttgccg ggaagctaga gtaagtagtt cgccagttaa tagtttgcgc    1500
aacgttgttg ccattgctac aggcatcgtg gtgtcacgct cgtcgtttgg tatggcttca    1560
ttcagctccg gttcccaacg atcaaggcga gttacatgat cccccatgtt gtgcaaaaaa    1620
gcggttagct ccttcggtcc tccgatcgtt gtcagaagta agttggccgc agtgttatca    1680
ctcatggtta tggcagcact gcataattct cttactgtca tgccatccgt aagatgcttt    1740
tctgtgactg gtgagtactc aaccaagtca ttctgagaat agtgtatgcg gcgaccgagt    1800
tgctcttgcc cggcgtcaat acgggataat accgcgccac atagcagaac tttaaaagtg    1860
ctcatcattg gaaaacgttc ttcggggcga aaactctcaa ggatcttacc gctgttgaga    1920
tccagttcga tgtaacccac tcgtgcaccc aactgatctt cagcatcttt tactttcacc    1980
agcgtttctg ggtgagcaaa aacaggaagg caaaatgccg caaaaaaggg aataagggcg    2040
acacggaaat gttgaatact catactcttc cttttcaat attattgaag catttatcag    2100
ggttattgtc tcatgagcgg atacatattt gaatgtattt agaaaaataa acaaataggg    2160
gttccgcgca catttccccg aaaagtgcca cctgacgtct aagaaaccat tattatcatg    2220
acattaacct ataaaaatag gcgtatcacg aggccctttc gtctcgcgcg tttcggtgat    2280
gacggtgaaa acctctgaca catgcagctc ccggagacgg tcacagcttg tctgtaagcg    2340
gatgccggga gcagacaagc ccgtcagggc gcgtcagcgg gtgttggcgg gtgtcggggc    2400
tggcttaact atgcggcatc agagcagatt gtactgagag tgcaccatat gcggtgtgaa    2460
ataccgcaca gatgcgtaag gagaaaatac cgcatcaggc gccattcgcc attcaggctg    2520
cgcaactgtt gggaagggcg atcggtgcgg gcctcttcgc tattacgcca gctggcgaaa    2580
gggggatgtg ctgcaaggcg attaagttgg gtaacgccag ggttttccca gtcacgacgt    2640
tgtaaaacga cggccagtga attcgagctc ggtacccggg gatcctctag acctgcaggc    2700
```

| | |
|---|---:|
| caactgcgtt tggggctcca gattaaacga cgccgtttcg ttcctttcgc ttcacggctt | 2760 |
| aacgatgtcg tttctgtctg tgcccaaaaa ataaaggcat tgttatttg caccagatat | 2820 |
| ttactaagtg caccctagtt tgacaagtag gcgataatta caaatagatg cggtgcaaat | 2880 |
| aataaattt gaaggaaata attacaaaag aacagaactt atatttactt tattttaaaa | 2940 |
| aactaaaatg aaagaacaaa aaaagtaaaa aatacaaaaa atgtgcttta accactttca | 3000 |
| ttatttgtta cagaaagtat gattctactc aaattgatct gttgtatctg gtgctgcctt | 3060 |
| gtcacactgg cgatttcaat cccctaaaga tatggtgcaa actgcgaagt gatcaatatc | 3120 |
| tgctcggtta atttagatta attaataata ttcaacgtga tgtaccaaaa aaagacaatt | 3180 |
| ttttgctcca ttgacaaatt aaacctcatc aaggtaattt ccaaacctat aagcaaaaaa | 3240 |
| atttcacatt aattggcccg caatcctatt agtcttatta tactagagta ggaaaaaaaa | 3300 |
| caattacaca acttgtctta ttattctcta tgctaatgaa tatttttccc ttttgttaga | 3360 |
| aatcagtgtt tcctaattta ttgagtatta attccactca ccgcatatat ttaccgttga | 3420 |
| ataagaaaat tttacacata attcttttta agataaataa tttttttata ctagatctta | 3480 |
| tatgattacg tgaagccaag tgggttatac taatgatata taatgtttga tagtaatcag | 3540 |
| tttataaacc aaatgcatgg aaatgttacg tggaagcacg taaattaaca agcattgaag | 3600 |
| caaatgcagc caccgcacca aaaccacccc acttcacttc cacgtaccat attccatgca | 3660 |
| actacaacac cctaaaactt caataaatgc ccccaccttc acttcacttc acccatcaat | 3720 |
| agcaagcggc cgcgaagtta aaagcaatgt tgtcacttgt cgtactaaca catgatgtga | 3780 |
| tagtttatgc tagctagcta aacataagc tgtctctgag tgtgttgtat attaataaag | 3840 |
| atcatcactg gtgaatggtg atcgtgtacg taccctactt agtaggcaat ggaagcactt | 3900 |
| agagtgtgct ttgtgcatgg ccttgcctct gttttgagac ttttgtaatg ttttcgagtt | 3960 |
| taaatctttg cctttgcgta cgt | 3983 |

<210> SEQ ID NO 37
<211> LENGTH: 4771
<212> TYPE: DNA
<213> ORGANISM: Artificial Sequence
<220> FEATURE:
<223> OTHER INFORMATION: plasmid pKR953

<400> SEQUENCE: 37

| | |
|---|---:|
| ggccgcgaag ttaaaagcaa tgttgtcact tgtcgtacta acacatgatg tgatagttta | 60 |
| tgctagctag ctataacata agctgtctct gagtgtgttg tatattaata aagatcatca | 120 |
| ctggtgaatg gtgatcgtgt acgtacccta cttagtaggc aatggaagca cttagagtgt | 180 |
| gcttgtgca tggccttgcc tctgttttga cttttgta atgttttcga gtttaaatct | 240 |
| ttgcctttgc gtacgtctag agtcgacctg caggcatgca agcttggcgt aatcatggtc | 300 |
| atagctgttt cctgtgtgaa attgttatcc gctcacaatt ccacacaaca tacgagccgg | 360 |
| aagcataaag tgtaaagcct ggggtgccta atgagtgagc taactcacat taattgcgtt | 420 |
| gcgctcactg cccgctttcc agtcgggaaa cctgtcgtgc cagctgcatt aatgaatcgg | 480 |
| ccaacgcgcg gggagaggcg gtttgcgtat tgggcgctct tccgcttcct cgctcactga | 540 |
| ctcgctgcgc tcggtcgttc ggctgcggcg agcggtatca gctcactcaa aggcggtaat | 600 |
| acggttatcc acagaatcag gggataacgc aggaaagaac atgtgagcaa aaggccagca | 660 |
| aaaggccagg aaccgtaaaa aggccgcgtt gctggcgttt ttccataggc tccgcccccc | 720 |
| tgacgagcat cacaaaaatc gacgctcaag tcagaggtgg cgaaacccga caggactata | 780 |

```
aagataccag gcgtttcccc ctggaagctc cctcgtgcgc tctcctgttc cgaccctgcc    840
gcttaccgga tacctgtccg cctttctccc ttcgggaagc gtggcgcttt ctcatagctc    900
acgctgtagg tatctcagtt cggtgtaggt cgttcgctcc aagctgggct gtgtgcacga    960
accccccgtt cagcccgacc gctgcgcctt atccggtaac tatcgtcttg agtccaaccc   1020
ggtaagacac gacttatcgc cactggcagc agccactggt aacaggatta gcagagcgag   1080
gtatgtaggc ggtgctacag agttcttgaa gtggtggcct aactacggct acactagaag   1140
gacagtattt ggtatctgcg ctctgctgaa gccagttacc ttcggaaaaa gagttggtag   1200
ctcttgatcc ggcaaacaaa ccaccgctgg tagcggtggt ttttttgttt gcaagcagca   1260
gattacgcgc agaaaaaaag gatctcaaga agatcctttg atcttttcta cggggtctga   1320
cgctcagtgg aacgaaaact cacgttaagg gattttggtc atgagattat caaaaaggat   1380
cttcacctag atccttttaa attaaaaatg aagttttaaa tcaatctaaa gtatatatga   1440
gtaaacttgg tctgacagtt accaatgctt aatcagtgag gcacctatct cagcgatctg   1500
tctatttcgt tcatccatag ttgcctgact ccccgtcgtg tagataacta cgatacggga   1560
gggcttacca tctggcccca gtgctgcaat gataccgcga cccacgctca ccggctcc    1620 agatttatca gcaataaacc agccagccgg aagggccgag cgcagaagtg gtcctgcaac   1680
tttatccgcc tccatccagt ctattaattg ttgccgggaa gctagagtaa gtagttcgcc   1740
agttaatagt ttgcgcaacg ttgttgccat tgctacaggc atcgtggtgt cacgctcgtc   1800
gtttggtatg gcttcattca gctccggttc ccaacgatca aggcgagtta catgatcccc   1860
catgttgtgc aaaaaagcgg ttagctcctt cggtcctccg atcgttgtca gaagtaagtt   1920
ggccgcagtg ttatcactca tggttatggc agcactgcat aattctctta ctgtcatgcc   1980
atccgtaaga tgcttttctg tgactggtga gtactcaacc aagtcattct gagaatagtg   2040
tatgcggcga ccgagttgct cttgcccggc gtcaatacgg gataataccg cgccacatag   2100
cagaacttta aaagtgctca tcattggaaa acgttcttcg gggcgaaaac tctcaaggat   2160
cttaccgctg ttgagatcca gttcgatgta acccactcgt gcacccaact gatcttcagc   2220
atcttttact ttcaccagcg tttctgggtg agcaaaaaca ggaaggcaaa atgccgcaaa   2280
aaagggaata agggcgacac ggaaatgttg aatactcata ctcttccttt ttcaatatta   2340
ttgaagcatt tatcagggtt attgtctcat gagcggatac atatttgaat gtatttagaa   2400
aaataaacaa atagggggttc gcgcacatt tccccgaaaa gtgccacctg acgtctaaga   2460
aaccattatt atcatgacat taacctataa aaataggcgt atcacgaggc ctttcgtct    2520 cgcgcgtttc ggtgatgacg gtgaaaacct ctgacacatg cagctcccgg agacggtcac   2580
agcttgtctg taagcggatg ccgggagcag acaagcccgt cagggcgcgt cagcgggtgt   2640
tggcgggtgt cggggctggc ttaactatgc ggcatcagag cagattgtac tgagagtgca   2700
ccatatgcgg tgtgaaatac cgcacagatg cgtaaggaga aaataccgca tcaggcgcca   2760
ttcgccattc aggctgcgca actgttggga agggcgatcg gtgcgggcct cttcgctatt   2820
acgccagctg gcgaaagggg gatgtgctgc aaggcgatta agttgggtaa cgccaggtt    2880 ttcccagtca cgacgttgta aaacgacggc cagtgaattc gagctcggta cccggggatc   2940
ctctagacct gcaggccaac tgcgtttggg gctccagatt aaacgacgcc gtttcgttcc   3000
tttcgcttca cggcttaacg atgtcgtttc tgtctgtgcc caaaaaataa aggcatttgt   3060
tatttgcacc agatatttac taagtgcacc ctagtttgac aagtaggcga taattacaaa   3120
tagatgcggt gcaaataata aatttgaagg gaaataatta caaagaaca gaacttatat    3180
```

-continued

| | |
|---|---|
| ttactttatt ttaaaaaact aaaatgaaag aacaaaaaaa gtaaaaaata caaaaaatgt | 3240 |
| gctttaacca ctttcattat ttgttacaga aagtatgatt ctactcaaat tgatctgttg | 3300 |
| tatctggtgc tgccttgtca cactggcgat ttcaatcccc taaagatatg gtgcaaactg | 3360 |
| cgaagtgatc aatatctgct cggttaattt agattaatta ataatattca acgtgatgta | 3420 |
| ccaaaaaaag acaattttt gctccattga caaattaaac ctcatcaagg taatttccaa | 3480 |
| acctataagc aaaaaaattt cacattaatt ggcccgcaat cctattagtc ttattatact | 3540 |
| agagtaggaa aaaaaacaat tacacaactt gtcttattat tctctatgct aatgaatatt | 3600 |
| tttccctttt gttagaaatc agtgtttcct aatttattga gtattaattc cactcaccgc | 3660 |
| atatatttac cgttgaataa gaaaattta cacataattc tttttaagat aaataatttt | 3720 |
| tttatactag atcttatatg attacgtgaa gccaagtggg ttatactaat gatatataat | 3780 |
| gtttgatagt aatcagttta taaaccaaat gcatggaaat gttacgtgga agcacgtaaa | 3840 |
| ttaacaagca ttgaagcaaa tgcagccacc gcaccaaaac caccccactt cacttccacg | 3900 |
| taccatattc catgcaacta caacacccta aaacttcaat aaatgccccc accttcactt | 3960 |
| cacttcacccc atcaatagca agcggccgca ccatggaggg ggtgaatgaa atagtctcaa | 4020 |
| ttgggcagga agttttaccc aaagttgatt atgcccaact ctggagtgat gccagtcact | 4080 |
| gtgaggtgct ttacttgtcc atcgcatttg tcatcttgaa gttcactctt ggccccttg | 4140 |
| gtccaaaagg tcagtctcgt atgaagtttg ttttcaccaa ttacaacctt ctcatgtcca | 4200 |
| tttattcgtt gggatcattc ctctcaatgg catatgccat gtacaccatc ggtgttatgt | 4260 |
| ctgacaactg cgagaaggct tttgacaaca acgtcttcag gatcaccacg cagttgttct | 4320 |
| atttgagcaa gttcctggag tatattgact ccttctattt gccactgatg ggcaagcctc | 4380 |
| tgacctggtt gcaattcttc catcatttgg gggcaccgat ggatatgtgg ctgttctata | 4440 |
| attaccgaaa tgaagctgtt tggatttttg tgctgttgaa tggtttcatc cactggatca | 4500 |
| tgtacggtta ttattggacc agattgatca agctgaagtt ccccatgcca aaatccctga | 4560 |
| ttacatcaat gcagatcatt caattcaatg ttggtttcta cattgtctgg aagtacagga | 4620 |
| acattccctg ttatcgccaa gatgggatga ggatgtttgg ctggttcttc aattactttt | 4680 |
| atgttggcac agtcttgtgt ttgttcttga atttctatgt gcaaacgtat atcgtcagga | 4740 |
| agcacaaggg agccaaaaag attcagtgag c | 4771 |

<210> SEQ ID NO 38
<211> LENGTH: 5492
<212> TYPE: DNA
<213> ORGANISM: Artificial Sequence
<220> FEATURE:
<223> OTHER INFORMATION: plasmid pKR287

<400> SEQUENCE: 38

| | |
|---|---|
| ggccgcattt cgcaccaaat caatgaaagt aataatgaaa agtctgaata agaatactta | 60 |
| ggcttagatg cctttgttac ttgtgtaaaa taacttgagt catgtacctt tggcggaaac | 120 |
| agaataaata aaaggtgaaa ttccaatgct ctatgtataa gttagtaata cttaatgtgt | 180 |
| tctacggttg tttcaatatc atcaaactct aattgaaact ttagaaccac aaatctcaat | 240 |
| cttttcttaa tgaaatgaaa atcttaatt gtaccatgtt tatgttaaac accttacaat | 300 |
| tggttggaga ggaggaccaa ccgatgggac aacattggga gaaagagatt caatggagat | 360 |
| ttggatagga gaacaacatt cttttttcact tcaatacaag atgagtgcaa cactaaggat | 420 |
| atgtatgaga ctttcagaag ctacgacaac atagatgagt gaggtggtga ttcctagcaa | 480 |

```
gaaagacatt agaggaagcc aaaatcgaac aaggaagaca tcaagggcaa gagacaggac    540
catccatctc aggaaaagga gctttgggat agtccgagaa gttgtacaag aaattttttg    600
gagggtgagt gatgcattgc tggtgacttt aactcaatca aaattgagaa agaaagaaaa    660 gggaggggc tcacatgtga atagaaggga acgggagaa ttttacagtt ttgatctaat     720
gggcatccca gctagtggta acatattcac catgtttaac cttcacgtac gtctagagga    780
tccccgggta ccgagctcga attcactggc cgtcgtttta caacgtcgtg actgggaaaa    840
ccctggcgtt acccaactta atcgccttgc agcacatccc cctttcgcca gctggcgtaa    900
tagcgaagag gcccgcaccg atcgcccttc ccaacagttg cgcagcctga atggcgaatg    960
gcgcctgatg cggtattttc tccttacgca tctgtgcggt atttcacacc gcatatggtg    1020
cactctcagt acaatctgct ctgatgccgc atagttaagc cagccccgac acccgccaac    1080
acccgctgac gcgccctgac gggcttgtct gctcccggca tccgcttaca gacaagctgt    1140
gaccgtctcc gggagctgca tgtgtcagag gttttcaccg tcatcaccga aacgcgcgag    1200
acgaaagggc ctcgtgatac gcctattttt ataggttaat gtcatgataa taatggtttc    1260
ttagacgtca ggtggcactt ttcggggaaa tgtgcgcgga acccctattt gtttattttt    1320
ctaaatacat tcaaatatgt atccgctcat gagacaataa ccctgataaa tgcttcaata    1380
atattgaaaa aggaagagta tgagtattca acatttccgt gtcgccctta ttccctttt     1440 tgcggcattt tgccttcctg ttttgctca cccagaaacg ctggtgaaag taaaagatgc     1500
tgaagatcag ttgggtgcac gagtgggtta catcgaactg gatctcaaca gcggtaagat    1560
ccttgagagt tttcgccccg aagaacgttt tccaatgatg agcactttta agttctgct    1620 atgtggcgcg gtattatccc gtattgacgc cgggcaagag caactcggtc gccgcataca    1680
ctattctcag aatgacttgg ttgagtactc accagtcaca gaaaagcatc ttacggatgg    1740
catgacagta agagaattat gcagtgctgc cataaccatg agtgataaca ctgcggccaa    1800
cttacttctg acaacgatcg gaggaccgaa ggagctaacc gcttttttgc acaacatggg    1860
ggatcatgta actcgccttg atcgttggga accggagctg aatgaagcca taccaaacga    1920
cgagcgtgac accacgatgc ctgtagcaat ggcaacaacg ttgcgcaaac tattaactgg    1980
cgaactactt actctagctt cccggcaaca attaatagac tggatggagg cggataaagt    2040
tgcaggacca cttctgcgct cggcccttcc ggctggctgg tttattgctg ataaatctgg    2100
agccggtgag cgtgggtctc gcggtatcat tgcagcactg gggccagatg gtaagccctc    2160
ccgtatcgta gttatctaca cgacggggag tcaggcaact atggatgaac gaaatagaca    2220
gatcgctgag ataggtgcct cactgattaa gcattggtaa ctgtcagacc aagtttactc    2280
atatatactt tagattgatt taaaacttca ttttaatt aaaaggatct aggtgaagat     2340 ccttttgat aatctcatga ccaaaatccc ttaacgtgag ttttcgttcc actgagcgtc     2400
agaccccgta gaaaagatca aaggatcttc ttgagatcct ttttttctgc gcgtaatctg    2460
ctgcttgcaa acaaaaaaac caccgctacc agcggtggtt tgtttgccgg atcaagagct    2520
accaactctt tttccgaagg taactggctt cagcagagcg cagataccaa atactgtcct    2580
tctagtgtag ccgtagttag gccaccactt caagaactct gtagcaccgc ctacatacct    2640
cgctctgcta atcctgttac cagtggctgc tgccagtggc gataagtcgt gtcttaccgg    2700
gttggactca agacgatagt taccggataa ggcgcagcgg tcgggctgaa cggggggttc    2760
gtgcacacag cccagcttgg agcgaacgac ctacaccgaa ctgagatacc tacagcgtga    2820
gctatgagaa agcgccacgc ttcccgaagg gagaaaggcg gacaggtatc cggtaagcgg    2880
```

| | |
|---|---|
| cagggtcgga acaggagagc gcacgaggga gcttccaggg ggaaacgcct ggtatcttta | 2940 |
| tagtcctgtc gggtttcgcc acctctgact tgagcgtcga tttttgtgat gctcgtcagg | 3000 |
| ggggcggagc ctatggaaaa acgccagcaa cgcggccttt ttacggttcc tggccttttg | 3060 |
| ctggcctttt gctcacatgt tctttcctgc gttatcccct gattctgtgg ataaccgtat | 3120 |
| taccgccttt gagtgagctg ataccgctcg ccgcagccga acgaccgagc gcagcgagtc | 3180 |
| agtgagcgag gaagcggaag agcgcccaat acgcaaaccg cctctccccg cgcgttggcc | 3240 |
| gattcattaa tgcagctggc acgacaggtt tcccgactgg aaagcgggca gtgagcgcaa | 3300 |
| cgcaattaat gtgagttagc tcactcatta ggcaccccag gctttacact ttatgcttcc | 3360 |
| ggctcgtatg ttgtgtggaa ttgtgagcgg ataacaattt cacacaggaa acagctatga | 3420 |
| ccatgattac gccaagcttg catgcctgca ggctagccta agtacgtact caaaatgcca | 3480 |
| acaaataaaa aaaagttgc tttaataatg ccaaaacaaa ttaataaaac acttacaaca | 3540 |
| ccggatttt tttaattaaa atgtgccatt taggataaat agttaatatt tttaataatt | 3600 |
| atttaaaaag ccgtatctac taaaatgatt tttatttggt tgaaatatt aatatgttta | 3660 |
| aatcaacaca atctatcaaa attaaactaa aaaaaaata agtgtacgtg gttaacatta | 3720 |
| gtacagtaat ataagaggaa aatgagaaat taagaaattg aaagcgagtc taatttttaa | 3780 |
| attatgaacc tgcatatata aaaggaaaga aagaatccag gaagaaaaga aatgaaacca | 3840 |
| tgcatggtcc cctcgtcatc acgagtttct gccatttgca atagaaacac tgaaacacct | 3900 |
| ttctctttgt cacttaattg agatgccgaa gccacctcac accatgaact tcatgaggtg | 3960 |
| tagcacccaa ggcttccata gccatgcata ctgaagaatg tctcaagctc agcaccctac | 4020 |
| ttctgtgacg tgtccctcat tcaccttcct ctcttcccta taaataacca cgcctcaggt | 4080 |
| tctccgcttc acaactcaaa cattctctcc attggtcctt aaacactcat cagtcatcac | 4140 |
| cgcggccgca tgggaacgga ccaaggaaaa accttcacct gggaagagct ggcggcccat | 4200 |
| aacaccaagg acgacctact cttggccatc cgcggcaggg tgtacgatgt cacaaagttc | 4260 |
| ttgagccgcc atcctggtgg agtggacact ctcctgctcg gagctggccg agatgttact | 4320 |
| ccggtctttg agatgtatca cgcgtttggg gctgcagatg ccattatgaa gaagtactat | 4380 |
| gtcggtacac tggtctcgaa tgagctgccc atcttcccgg agccaacggt gttccacaaa | 4440 |
| accatcaaga cgagagtcga gggctacttt acggatcgga acattgatcc caagaataga | 4500 |
| ccagagatct ggggacgata cgctcttatc tttggatcct tgatcgcttc ctactacgcg | 4560 |
| cagctctttg tgccttttcgt tgtcgaacgc acatggcttc aggtggtgtt tgcaatcatc | 4620 |
| atgggatttg cgtgcgcaca agtcggactc aaccctcttc atgatgcgtc tcacttttca | 4680 |
| gtgacccaca accccactgt ctggaagatt ctggagcca cgcacgactt tttcaacgga | 4740 |
| gcatcgtacc tggtgtggat gtaccaacat atgctcggcc atcacccta caccaacatt | 4800 |
| gctggagcag atcccgacgt gtcgacgtct gagcccgatg ttcgtcgtat caagcccaac | 4860 |
| caaaagtggt ttgtcaacca catcaaccag cacatgtttg ttccttttcct gtacggactg | 4920 |
| ctggcgttca aggtgcgcat tcaggacatc aacattttgt actttgtcaa gaccaatgac | 4980 |
| gctattcgtg tcaatcccat ctcgacatgg cacactgtga tgttctgggg cggcaaggct | 5040 |
| ttctttgtct ggtatcgcct gattgttccc ctgcagtatc tgcccctggg caaggtgctg | 5100 |
| ctcttgttca cggtcgcgga catggtgtcg tcttactggc tggcgctgac cttccaggcg | 5160 |
| aaccacgttg ttgaggaagt tcagtggccg ttgcctgacg agaacgggat catccaaaag | 5220 |
| gactgggcag ctatgcaggt cgagactacg caggattacg cacacgattc gcacctctgg | 5280 |

| | |
|---|---:|
| accagcatca ctggcagctt gaactaccag gctgtgcacc atctgttccc caacgtgtcg | 5340 |
| cagcaccatt atcccgatat tctggccatc atcaagaaca cctgcagcga gtacaaggtt | 5400 |
| ccataccttg tcaaggatac gttttggcaa gcatttgctt cacatttgga gcacttgcgt | 5460 |
| gttcttggac tccgtcccaa ggaagagtag gc | 5492 |

<210> SEQ ID NO 39
<211> LENGTH: 1338
<212> TYPE: DNA
<213> ORGANISM: Mortierella alpine

<400> SEQUENCE: 39

| | |
|---|---:|
| atgggaacgg accaaggaaa aaccttcacc tgggaagagc tggcggccca taacaccaag | 60 |
| gacgacctac tcttggccat ccgcggcagg gtgtacgatg tcacaaagtt cttgagccgc | 120 |
| catcctggtg gagtggacac tctcctgctc ggagctggcc gagatgttac tccggtcttt | 180 |
| gagatgtatc acgcgtttgg ggctgcagat gccattatga agaagtacta tgtcggtaca | 240 |
| ctggtctcga atgagctgcc catcttcccg gagccaacgg tgttccacaa aaccatcaag | 300 |
| acgagagtcg agggctactt tacgatcgg aacattgatc ccaagaatag accagagatc | 360 |
| tggggacgat acgctcttat ctttggatcc ttgatcgctt cctactacgc gcagctcttt | 420 |
| gtgcctttcg ttgtcgaacg cacatggctt caggtggtgt ttgcaatcat catgggattt | 480 |
| gcgtgcgcac aagtcggact caaccctctt catgatgcgt ctcactttc agtgacccac | 540 |
| aaccccactg tctggaagat tctgggagcc acgcacgact ttttcaacgg agcatcgtac | 600 |
| ctggtgtgga tgtaccaaca tatgctcggc catcacccct acaccaacat tgctggagca | 660 |
| gatcccgacg tgtcgacgtc tgagcccgat gttcgtcgta tcaagcccaa ccaaaagtgg | 720 |
| tttgtcaacc acatcaacca gcacatgttt gttcctttcc tgtacggact gctggcgttc | 780 |
| aaggtgcgca ttcaggacat caacattttg tactttgtca agaccaatga cgctattcgt | 840 |
| gtcaatccca tctcgacatg gcacactgtg atgttctggg gcggcaaggc tttctttgtc | 900 |
| tggtatcgcc tgattgttcc cctgcagtat ctgcccctgg gcaaggtgct gctcttgttc | 960 |
| acggtcgcgg acatggtgtc gtcttactgg ctggcgctga ccttccaggc gaaccacgtt | 1020 |
| gttgaggaag ttcagtggcc gttgcctgac gagaacggga tcatccaaaa ggactgggca | 1080 |
| gctatgcagg tcgagactac gcaggattac gcacacgatt cgcacctctg gaccagcatc | 1140 |
| actggcagct tgaactacca ggctgtgcac catctgttcc ccaacgtgtc gcagcaccat | 1200 |
| tatcccgata ttctggccat catcaagaac acctgcagcg agtacaaggt tccatacctt | 1260 |
| gtcaaggata cgttttggca agcatttgct tcacatttgg agcacttgcg tgttcttgga | 1320 |
| ctccgtccca aggaagag | 1338 |

<210> SEQ ID NO 40
<211> LENGTH: 2577
<212> TYPE: DNA
<213> ORGANISM: Artificial Sequence
<220> FEATURE:
<223> OTHER INFORMATION: plasmid pKR277

<400> SEQUENCE: 40

| | |
|---|---:|
| agcttggatc tcctgcagga tctggccggc cggatctcgt acggatccgt cgacggcgcg | 60 |
| cccgatcatc cggatatagt tcctcctttc agcaaaaaac ccctcaagac ccgtttagag | 120 |
| gccccaaggg gttatgctag ttattgctca gcggtggcag cagccaactc agcttccttt | 180 |
| cgggctttgt tagcagccgg atcgatccaa gctgtacctc actattcctt tgccctcgga | 240 |

```
cgagtgctgg ggcgtcggtt tccactatcg gcgagtactt ctacacagcc atcggtccag    300
acggccgcgc ttctgcgggc gatttgtgta cgcccgacag tcccggctcc ggatcggacg    360
attgcgtcgc atcgaccctg cgcccaagct gcatcatcga aattgccgtc aaccaagctc    420
tgatagagtt ggtcaagacc aatgcggagc atatacgccc ggagccgcgg cgatcctgca    480
agctccggat gcctccgctc gaagtagcgc gtctgctgct ccatacaagc caaccacggc    540
ctccagaaga agatgttggc gacctcgtat tgggaatccc cgaacatcgc ctcgctccag    600
tcaatgaccg ctgttatgcg gccattgtcc gtcaggacat tgttggagcc gaaatccgcg    660
tgcacgaggt gccggacttc ggggcagtcc tcggcccaaa gcatcagctc atcgagagcc    720
tgcgcgacgg acgcactgac ggtgtcgtcc atcacagttt gccagtgata cacatgggga    780
tcagcaatcg cgcatatgaa atcacgccat gtagtgtatt gaccgattcc ttgcggtccg    840
aatgggccga acccgctcgt ctggctaaga tcggccgcag cgatcgcatc catagcctcc    900
gcgaccggct gcagaacagc gggcagttcg gtttcaggca ggtcttgcaa cgtgacaccc    960
tgtgcacggc gggagatgca ataggtcagg ctctcgctga attccccaat gtcaagcact   1020
tccggaatcg ggagcgcggc cgatgcaaag tgccgataaa cataacgatc tttgtagaaa   1080
ccatcggcgc agctatttac ccgcaggaca tatccacgcc ctcctacatc gaagctgaaa   1140
gcacgagatt cttcgccctc cgagagctgc atcaggtcgg agacgctgtc gaactttcg    1200 atcagaaact tctcgacaga cgtcgcggtg agttcaggct tttccatggg tatatctcct   1260
tcttaaagtt aaacaaaatt atttctagag ggaaaccgtt gtggtctccc tatagtgagt   1320
cgtattaatt tcgcgggatc gagatctgat caacctgcat taatgaatcg gccaacgcgc   1380
ggggagaggc ggtttgcgta ttgggcgctc ttccgcttcc tcgctcactg actcgctgcg   1440
ctcggtcgtt cggctgcggc gagcggtatc agctcactca aaggcggtaa tacggttatc   1500
cacagaatca ggggataacg caggaaagaa catgtgagca aaaggccagc aaaaggccag   1560
gaaccgtaaa aaggccgcgt tgctggcgtt tttccatagg ctccgccccc ctgacgagca   1620
tcacaaaaat cgacgctcaa gtcagaggtg gcgaaacccg acaggactat aaagatacca   1680
ggcgtttccc cctggaagct ccctcgtgcg ctctcctgtt ccgaccctgc cgcttaccgg   1740
atacctgtcc gcctttctcc cttcgggaag cgtggcgctt tctcaatgct cacgctgtag   1800
gtatctcagt tcggtgtagg tcgttcgctc caagctgggc tgtgtgcacg aaccccccgt   1860
tcagcccgac cgctgcgcct tatccggtaa ctatcgtctt gagtccaacc cggtaagaca   1920
cgacttatcg ccactggcag cagccactgg taacaggatt agcagagcga ggtatgtagg   1980
cggtgctaca gagttcttga agtggtggcc taactacggc tacactagaa ggacagtatt   2040
tggtatctgc gctctgctga agccagttac cttcggaaaa agagttggta gctcttgatc   2100
cggcaaacaa accaccgctg gtagcggtgg tttttttgtt tgcaagcagc agattacgcg   2160
cagaaaaaaa ggatctcaag aagatccttt gatcttttct acggggtctg acgctcagtg   2220
gaacgaaaac tcacgttaag ggattttggt catgacatta acctataaaa ataggcgtat   2280
cacgaggccc tttcgtctcg cgcgtttcgg tgatgacggt gaaaacctct gacacatgca   2340
gctcccggag acggtcacag cttgtctgta agcggatgcc gggagcagac aagcccgtca   2400
gggcgcgtca gcgggtgttg gcgggtgtcg ggctggctt aactatgcgg catcagagca   2460
gattgtactg agagtgcacc atatggacat attgtcgtta aacgcggct acaattaata   2520 cataaccttta tgtatcatac acatacgatt taggtgacac tatagaacgg cgcgcca    2577
```

<210> SEQ ID NO 41

<211> LENGTH: 5364
<212> TYPE: DNA
<213> ORGANISM: Artificial Sequence
<220> FEATURE:
<223> OTHER INFORMATION: plasmid pKR952

<400> SEQUENCE: 41

```
ggctagccta agtacgtact caaaatgcca acaaataaaa aaaagttgc tttaataatg      60
ccaaaacaaa ttaataaaac acttacaaca ccggattttt tttaattaaa atgtgccatt    120
taggataaat agttaatatt tttaataatt atttaaaaag ccgtatctac taaaatgatt    180
tttatttggt tgaaaatatt aatatgttta aatcaacaca atctatcaaa attaaactaa    240
aaaaaaaata agtgtacgtg gttaacatta gtacagtaat ataagaggaa aatgagaaat    300
taagaaattg aaagcgagtc taattttttaa attatgaacc tgcatatata aaaggaaaga    360
aagaatccag gaagaaaaga aatgaaacca tgcatggtcc cctcgtcatc acgagtttct    420
gccatttgca atagaaacac tgaaacacct ttctctttgt cacttaattg agatgccgaa    480
gccacctcac accatgaact tcatgaggtg tagcacccaa ggcttccata gccatgcata    540
ctgaagaatg tctcaagctc agcaccctac ttctgtgacg tgtccctcat tcacttcct    600
ctcttcccta taataacca cgcctcaggt tctccgcttc acaactcaaa cattctctcc    660
attggtcctt aaacactcat cagtcatcac cgcggccgca tgggaacgga ccaaggaaaa    720
accttcacct gggaagagct ggcggcccat aacaccaagg acgacctact cttggccatc    780
cgcggcaggg tgtacgatgt cacaaagttc ttgagccgcc atcctggtgg agtggacact    840
ctcctgctcg gagctggccg agatgttact ccggtctttg agatgtatca cgcgtttggg    900
gctgcagatg ccattatgaa gaagtactat gtcggtacac tggtctcgaa tgagctgccc    960
atcttcccgg agccaacggt gttccacaaa accatcaaga cgagagtcga gggctacttt   1020
acggatcgga acattgatcc caagaataga ccagagatct ggggacgata cgctcttatc   1080
tttggatcct tgatcgcttc ctactacgcg cagctctttg tgccttttcgt tgtcgaacgc   1140
acatggcttc aggtggtgtt tgcaatcatc atgggatttg cgtgcgcaca agtcggactc   1200
aaccctcttc atgatgcgtc tcactttttca gtgacccaca accccactgt ctggaagatt   1260
ctgggagcca cgcacgactt tttcaacgga gcatcgtacc tggtgtggat gtaccaacat   1320
atgctcggcc atcaccccta caccaacatt gctggagcag atcccgacgt gtcgacgtct   1380
gagcccgatg ttcgtcgtat caagcccaac caaaagtggt tgtcaaccaa catcaaccag   1440
cacatgtttg ttccttttcct gtacggactg ctggcgttca aggtgcgcat tcaggacatc   1500
aacatttttgt actttgtcaa gaccaatgac gctattcgtg tcaatcccat ctcgacatgg   1560
cacactgtga tgttctgggg cggcaaggct ttctttgtct ggtatcgcct gattgttccc   1620
ctgcagtatc tgccccctgggg caaggtgctg ctcttgttca cggtcgcgga catggtgtcg   1680
tcttactggc tggcgctgac cttccaggcg aaccacgttg ttgaggaagt tcagtggccg   1740
ttgcctgacg agaacgggat catccaaaag gactgggcag ctatgcaggt cgagactacg   1800
caggattacg cacacgattc gcacctctgg accagcatca ctggcagctt gaactaccag   1860
gctgtgcacc atctgttccc caacgtgtcg cagcaccatt atcccgatat tctggccatc   1920
atcaagaaca cctgcagcga gtacaaggtt ccataccttg tcaaggatac gtttttggcaa   1980
gcatttgctt cacatttgga gcacttgcgt gttcttggac tccgtcccaa ggaagagtag   2040
gcggccgcat ttcgcaccaa atcaatgaaa gtaataatga aaagtctgaa taagaatact   2100
taggcttaga tgcctttgtt acttgtgtaa aataacttga gtcatgtacc tttggcggaa   2160
```

```
acagaataaa taaaaggtga aattccaatg ctctatgtat aagttagtaa tacttaatgt    2220
gttctacggt tgtttcaata tcatcaaact ctaattgaaa ctttagaacc acaaatctca    2280
atcttttctt aatgaaatga aaaatcttaa ttgtaccatg tttatgttaa acaccttaca    2340
attggttgga gaggaggacc aaccgatggg acaacattgg gagaaagaga ttcaatggag    2400
atttggatag gagaacaaca ttcttttca cttcaataca agatgagtgc aacactaagg     2460
atatgtatga gactttcaga agctacgaca acatagatga gtgaggtggt gattcctagc    2520
aagaaagaca ttagaggaag ccaaaatcga acaaggaaga catcaagggc aagagacagg    2580
accatccatc tcaggaaaag gagctttggg atagtccgag aagttgtaca agaaattttt    2640
tggagggtga gtgatgcatt gctggtgact ttaactcaat caaaattgag aaagaaagaa    2700
aagggagggg gctcacatgt gaatagaagg gaaacgggag aattttacag ttttgatcta    2760
atgggcatcc cagctagtgg taacatattc accatgttta accttcacgt acggatccgt    2820
cgacggcgcg cccgatcatc cggatatagt tcctcctttc agcaaaaaac ccctcaagac    2880
ccgtttagag gccccaaggg gttatgctag ttattgctca gcggtggcag cagccaactc    2940
agcttccttt cgggctttgt tagcagccgg atcgatccaa gctgtacctc actattcctt    3000
tgccctcgga cgagtgctgg ggcgtcggtt tccactatcg gcgagtactt ctacacagcc    3060
atcggtccag acgccgcgc ttctgcgggc gatttgtgta cgcccgacag tcccggctcc     3120
ggatcggacg attgcgtcgc atcgaccctg cgcccaagct gcatcatcga aattgccgtc    3180
aaccaagctc tgatagagtt ggtcaagacc aatgcggagc atatacgccc ggagccgcgg    3240
cgatcctgca agctccggat gcctccgctc gaagtagcgc gtctgctgct ccatacaagc    3300
caaccacggc ctccagaaga agatgttggc gacctcgtat tgggaatccc cgaacatcgc    3360
ctcgctccag tcaatgaccg ctgttatgcg gccattgtcc gtcaggacat tgttggagcc    3420
gaaatccgcg tgcacgaggt gccggacttc ggggcagtcc tcggcccaaa gcatcagctc    3480
atcgagagcc tgcgcgacgg acgcactgac ggtgtcgtcc atcacagttt gccagtgata    3540
cacatgggga tcagcaatcg cgcatatgaa atcacgccat gtagtgtatt gaccgattcc    3600
ttgcggtccg aatgggccga acccgctcgt ctggctaaga tcggccgcag cgatcgcatc    3660
catagcctcc gcgaccggct gcagaacagc gggcagttcg gtttcaggca ggtcttgcaa    3720
cgtgacaccc tgtgcacggc gggagatgca ataggtcagg ctctcgctga attccccaat    3780
gtcaagcact tccggaatcg ggagcgcggc cgatgcaaag tgccgataaa cataacgatc    3840
tttgtagaaa ccatcggcgc agctatttac ccgcaggaca tatccacgcc ctcctacatc    3900
gaagctgaaa gcacgagatt cttcgccctc cgagagctgc atcaggtcgg agacgctgtc    3960
gaacttttcg atcagaaact tctcgacaga cgtcgcggtg agttcaggct tttccatggg    4020
tatatctcct tcttaaagtt aaacaaaatt atttctagag ggaaaccgtt gtggtctccc    4080
tatagtgagt cgtattaatt tcgcgggatc gagatctgat caacctgcat taatgaatcg    4140
gccaacgcgc ggggagaggc ggtttgcgta ttgggcgctc ttccgcttcc tcgctcactg    4200
actcgctgcg ctcggtcgtt cggctgcggc gagcggtatc agctcactca aaggcggtaa    4260
tacggttatc cacagaatca ggggataacg caggaaagaa catgtgagca aaaggccagc    4320
aaaaggccag gaaccgtaaa aaggccgcgt tgctggcgtt tttccatagg ctccgccccc    4380
ctgacgagca tcacaaaaat cgacgctcaa gtcagaggtg gcgaaacccg acaggactat    4440
aaagatacca ggcgtttccc cctggaagct ccctcgtgcg ctctcctgtt ccgaccctgc    4500
cgcttaccgg atacctgtcc gcctttctcc cttcgggaag cgtggcgctt tctcaatgct    4560
```

```
cacgctgtag gtatctcagt tcggtgtagg tcgttcgctc caagctgggc tgtgtgcacg   4620
aaccccccgt tcagcccgac cgctgcgcct tatccggtaa ctatcgtctt gagtccaacc   4680
cggtaagaca cgacttatcg ccactggcag cagccactgg taacaggatt agcagagcga   4740
ggtatgtagg cggtgctaca gagttcttga agtggtggcc taactacggc tacactagaa   4800
ggacagtatt tggtatctgc gctctgctga agccagttac cttcggaaaa agagttggta   4860
gctcttgatc cggcaaacaa accaccgctg gtagcggtgg ttttttttgtt tgcaagcagc   4920 agattacgcg cagaaaaaaa ggatctcaag aagatccttt gatcttttct acggggtctg   4980
acgctcagtg gaacgaaaac tcacgttaag ggattttggt catgacatta acctataaaa   5040
ataggcgtat cacgaggccc tttcgtctcg cgcgtttcgg tgatgacggt gaaaacctct   5100
gacacatgca gctcccggag acggtcacag cttgtctgta gcggatgcc gggagcagac   5160 aagcccgtca gggcgcgtca gcgggtgttg gcgggtgtcg gggctggctt aactatgcgg   5220
catcagagca gattgtactg agagtgcacc atatggacat attgtcgtta gaacgcggct   5280
acaattaata cataacctta tgtatcatac acatacgatt taggtgacac tatagaacgg   5340
cgcgccaagc ttggatctcc tgca                                         5364

<210> SEQ ID NO 42
<211> LENGTH: 5252
<212> TYPE: DNA
<213> ORGANISM: Artificial Sequence
<220> FEATURE:
<223> OTHER INFORMATION: plasmid pKR457
<220> FEATURE:
<221> NAME/KEY: misc_feature
<222> LOCATION: (3872)..(3872)
<223> OTHER INFORMATION: n is a, c, g, or t

<400> SEQUENCE: 42
gtacgtgggc ggatccccg ggctgcagga attcactggc cgtcgtttta caacgtcgtg     60
actgggaaaa ccctggcgtt acccaactta atcgccttgc agcacatccc cctttcgcca    120
gctggcgtaa tagcgaagag gcccgcaccg atcgcccttc ccaacagttg cgcagcctga    180
atggcgaatg gcgcctgatg cggtattttc tccttacgca tctgtgcggt atttcacacc    240
gcatatggtg cactctcagt acaatctgct ctgatgccgc atagttaagc cagccccgac    300
acccgccaac acccgctgac gcgccctgac gggcttgtct gctcccggca tccgcttaca    360
gacaagctgt gaccgtctcc gggagctgca tgtgtcagag gttttcaccg tcatcaccga    420
aacgcgcgag acgaaagggc ctcgtgatac gcctattttt ataggttaat gtcatgataa    480
taatggtttc ttagacgtca ggtggcactt ttcgggaaa tgtgcgcgga accctatttt    540
gtttattttt ctaaatacat tcaaatatgt atccgctcat gagacaataa ccctgataaa    600
tgcttcaata atattgaaaa aggaagagta tgagtattca actttccgt gtcgccctta    660 ttccctttt tgcggcattt tgccttcctg ttttgctca cccagaaacg ctggtgaaag    720
taaaagatgc tgaagatcag ttgggtgcac gagtgggtta catcgaactg gatctcaaca    780
gcggtaagat ccttgagagt tttcgccccg aagaacgttt tccaatgatg agcacttttta   840 aagttctgct atgtggcgcg gtattatccc gtattgacgc cgggcaagag caactcggtc    900
gccgcataca ctattctcag aatgacttgg ttgagtactc accagtcaca gaaaagcatc    960
ttacggatgg catgacagta agagaattat gcagtgctgc cataaccatg agtgataaca   1020
ctgcggccaa cttacttctg acaacgatcg gaggaccgaa ggagctaacc gcttttttgc   1080
acaacatggg ggatcatgta actcgccttg atcgttggga accggagctg aatgaagcca   1140
```

-continued

```
taccaaacga cgagcgtgac accacgatgc ctgtagcaat ggcaacaacg ttgcgcaaac   1200
tattaactgg cgaactactt actctagctt cccggcaaca attaatagac tggatggagg   1260
cggataaagt tgcaggacca cttctgcgct cggcccttcc ggctggctgg tttattgctg   1320
ataaatctgg agccggtgag cgtgggtctc gcggtatcat tgcagcactg gggccagatg   1380
gtaagccctc ccgtatcgta gttatctaca cgacgggag tcaggcaact atggatgaac   1440
gaaatagaca gatcgctgag ataggtgcct cactgattaa gcattggtaa ctgtcagacc   1500
aagtttactc atatatactt tagattgatt taaaacttca tttttaattt aaaaggatct   1560
aggtgaagat cctttttgat aatctcatga ccaaaatccc ttaacgtgag ttttcgttcc   1620
actgagcgtc agacccgta gaaaagatca aggatcttc ttgagatcct ttttttctgc   1680
gcgtaatctg ctgcttgcaa acaaaaaaac caccgctacc agcggtggtt tgtttgccgg   1740
atcaagagct accaactctt tttccgaagg taactggctt cagcagagcg cagataccaa   1800
atactgtcct tctagtgtag ccgtagttag gccaccactt caagaactct gtagcaccgc   1860
ctacatacct cgctctgcta atcctgttac cagtggctgc tgccagtggc gataagtcgt   1920
gtcttaccgg gttggactca agacgatagt taccggataa ggcgcagcgg tcgggctgaa   1980
cggggggttc gtgcacacag cccagcttgg agcgaacgac ctacaccgaa ctgagatacc   2040
tacagcgtga gctatgagaa agcgccacgc ttcccgaagg gagaaaggcg gacaggtatc   2100
cggtaagcgg cagggtcgga acaggagagc gcacgaggga gcttccaggg ggaaacgcct   2160
ggtatcttta tagtcctgtc gggtttcgcc acctctgact tgagcgtcga ttttgtgat   2220 gctcgtcagg ggggcggagc ctatggaaaa acgccagcaa cgcggccttt ttacggttcc   2280
tggccttttg ctggcctttt gctcacatgt tctttcctgc gttatcccct gattctgtgg   2340
ataaccgtat taccgccttt gagtgagctg ataccgctcg ccgcagccga acgaccgagc   2400
gcagcgagtc agtgagcgag gaagcggaag agcgcccaat acgcaaaccg cctctccccg   2460
cgcgttggcc gattcattaa tgcagctggc acgacaggtt cccgactgg aaagcgggca   2520 gtgagcgcaa cgcaattaat gtgagttagc tcactcatta ggcaccccag gctttacact   2580
ttatgcttcc ggctcgtatg ttgtgtggaa ttgtgagcgg ataacaattt cacacaggaa   2640
acagctatga ccatgattac gccaagcttg catgcctgca ggtcgactcg acgtacgtcc   2700
tcgaagagaa gggttaataa cacattttt aacattttta acacaaattt tagttattta   2760
aaaatttatt aaaaaattta aaataagaag aggaactctt taaataaatc taacttacaa   2820
aatttatgat ttttaataag ttttcaccaa taaaaaatgt cataaaaata tgttaaaaag   2880
tatattatca atattctctt tatgataaat aaaagaaaa aaaaaataaa agttaagtga   2940
aaatgagatt gaagtgactt taggtgtgta taaatatatc aaccccgcca acaatttatt   3000
taatccaaat atattgaagt atattattcc atagccttta tttatttata tatttattat   3060
ataaaagctt tatttgttct aggttgttca tgaaatattt ttttggtttt atctccgttg   3120
taagaaaatc atgtgctttg tgtcgccact cactattgca gctttttcat gcattggtca   3180
gattgacggt tgattgtatt tttgttttt atggttttgt gttatgactt aagtcttcat   3240
ctctttatct cttcatcagg tttgatggtt acctaatatg gtccatgggt acatgcatgg   3300
ttaaattagg tggccaactt tgttgtgaac gatagaattt ttttatatt aagtaaacta   3360 tttttatatt atgaaataat aataaaaaaa atatttatc attattaaca aaatcatatt   3420
agttaatttg ttaactctat aataaaagaa atactgtaac attcacatta catggtaaca   3480
tctttccacc ctttcatttg ttttttgttt gatgactttt tttcttgttt aaatttattt   3540
```

```
cccttctttt aaatttggaa tacattatca tcatatataa actaaaatac taaaaacagg    3600
attacacaaa tgataaataa taacacaaat atttataaat ctagctgcaa tatatttaaa    3660
ctagctatat cgatattgta aaataaaact agctgcattg atactgataa aaaaatatca    3720
tgtgctttct ggactgatga tgcagtatac ttttgacatt gcctttattt tattttttcag   3780 aaaagctttc ttagttctgg gttcttcatt atttgtttcc catctccatt gtgaattgaa    3840
tcatttgctt cgtgtcacaa atacaattta gntaggtaca tgcattggtc agattcacgg    3900
tttattatgt catgacttaa gttcatggta gtacattacc tgccacgcat gcattatatt    3960
ggttagattt gataggcaaa tttggttgtc aacaatataa atataaataa tgtttttata    4020
ttacgaaata acagtgatca aaacaaacag ttttatcttt attaacaaga ttttgttttt    4080
gtttgatgac gttttttaat gtttacgctt tcccccttct tttgaattta gaacacttta    4140
tcatcataaa atcaaatact aaaaaaatta catatttcat aaataataac acaaatattt    4200
ttaaaaaatc tgaaataata atgaacaata ttacatatta tcacgaaaat tcattaataa    4260
aaatattata taaataaaat gtaatagtag ttatatgtag gaaaaaagta ctgcacgcat    4320
aatatataca aaaagattaa aatgaactat tataaataat aacactaaat taatggtgaa    4380
tcatatcaaa ataatgaaaa agtaaataaa atttgtaatt aacttctata tgtattacac    4440
acacaaataa taaataatag taaaaaaaat tatgataaat atttaccatc tcataagata    4500
tttaaaataa tgataaaaat atagattatt ttttatgcaa ctagctagcc aaaaagagaa    4560
cacgggtata tataaaaaga gtacctttaa attctactgt acttcctta  ttcctgacgt    4620 ttttatatca agtggacata cgtgaagatt ttaattatca gtctaaatat ttcattagca    4680
cttaatactt ttctgtttta ttcctatcct ataagtagtc ccgattctcc caacattgct    4740
tattcacaca actaactaag aaagtcttcc atagcccccc aagcggccgc gacacaagtg    4800
tgagagtact aaataaatgc tttggttgta cgaaatcatt acactaaata aaataatcaa    4860
agcttatata tgccttccgc taaggccgaa tgcaaagaaa ttggttcttt ctcgttatct    4920
tttgccactt ttactagtac gtattaatta ctacttaatc atctttgttt acggctcatt    4980
atatccggtc tagaggatcc aaggccgcga agttaaaagc aatgttgtca cttgtcgtac    5040
taacacatga tgtgatagtt tatgctagct agctataaca taagctgtct ctgagtgtgt    5100
tgtatattaa taaagatcat cactggtgaa tggtgatcgt gtacgtaccc tacttagtag    5160
gcaatggaag cacttagagt gtgctttgtg catggccttg cctctgtttt gagacttttg    5220
taatgttttc gagtttaaat ctttgccttt gc                                  5252
```

<210> SEQ ID NO 43
<211> LENGTH: 2635
<212> TYPE: DNA
<213> ORGANISM: Artificial Sequence
<220> FEATURE:
<223> OTHER INFORMATION: modified Kti-NotI-Kti3primeSalb3prime cassette
<220> FEATURE:
<221> NAME/KEY: misc_feature
<222> LOCATION: (1229)..(1229)
<223> OTHER INFORMATION: n is a, c, g, or t

<400> SEQUENCE: 43

```
ggtaccgggc ccccccctcga ggtcgcccgg gggatccgcc ctaagcttcg tacgtcctcg     60
aagagaaggg ttaataacac attttttaac attttttaaca caaattttag ttatttaaaa    120
atttattaaa aaatttaaaa taagaagagg aactctttaa ataaatctaa cttacaaaat    180
ttatgatttt taataagttt tcaccaataa aaaatgtcat aaaaatatgt taaaaagtat    240
```

-continued

```
attatcaata ttctctttat gataaataaa aagaaaaaaa aaataaaagt taagtgaaaa    300
tgagattgaa gtgactttag gtgtgtataa atatatcaac cccgccaaca atttatttaa    360
tccaaatata ttgaagtata ttattccata gcctttattt atttatatat ttattatata    420
aaagctttat ttgttctagg ttgttcatga aatattttt tggttttatc tccgttgtaa     480
gaaaatcatg tgctttgtgt cgccactcac tattgcagct ttttcatgca ttggtcagat    540
tgacggttga ttgtattttt gttttttatg gttttgtgtt atgacttaag tcttcatctc    600
tttatctctt catcaggttt gatggttacc taatatggtc catgggtaca tgcatggtta    660
aattaggtgg ccaactttgt tgtgaacgat agaattttt ttatattaag taaactattt     720
ttatattatg aaataataat aaaaaaaata ttttatcatt attaacaaaa tcatattagt    780
taatttgtta actctataat aaaagaaata ctgtaacatt cacattacat ggtaacatct    840
ttccacccct tcatttgttt tttgtttgat gactttttt cttgtttaaa tttatttccc     900
ttcttttaaa tttggaatac attatcatca tatataaact aaaatactaa aaacaggatt    960
acacaaatga taaataataa cacaaatatt tataaatcta gctgcaatat atttaaacta   1020
gctatatcga tattgtaaaa taaaactagc tgcattgata ctgataaaaa aatatcatgt   1080
gctttctgga ctgatgatgc agtatacttt tgacattgcc tttattttat ttttcagaaa   1140
agctttctta gttctgggtt cttcattatt tgtttcccat ctccattgtg aattgaatca   1200
tttgcttcgt gtcacaaata caatttagnt aggtacatgc attggtcaga ttcacggttt   1260
attatgtcat gacttaagtt catggtagta cattacctgc cacgcatgca ttatattggt   1320
tagatttgat aggcaaattt ggttgtcaac aatataaata taaataatgt ttttatatta   1380
cgaaataaca gtgatcaaaa caaacagttt tatctttatt aacaagattt tgttttgtt    1440 tgatgacgtt tttaatgtt tacgctttcc cccttctttt gaatttagaa cactttatca    1500
tcataaaatc aaatactaaa aaattacat atttcataaa taataacaca aatatttta    1560 aaaaatctga aataataatg aacaatatta catattatca cgaaaattca ttaataaaaa   1620
tattatataa ataaaatgta atagtagtta tatgtaggaa aaaagtactg cacgcataat   1680
atatacaaaa agattaaaat gaactattat aaataataac actaaattaa tggtgaatca   1740
tatcaaaata atgaaaaagt aaataaaatt tgtaattaac ttctatatgt attacacaca   1800
caaataataa ataatagtaa aaaaaattat gataaatatt taccatctca taagatattt   1860
aaaataatga taaaaatata gattattttt tatgcaacta gctagccaaa aagagaacac   1920
gggtatatat aaaagagta cctttaaatt ctactgtact tcctttattc ctgacgtttt    1980
tatatcaagt ggacatacgt gaagatttta attatcagtc taaatatttc attagcactt   2040 aatactttc tgttttattc ctatcctata agtagtcccg attctcccaa cattgcttat    2100
tcacacaact aactaagaaa gtcttccata gccccccaag cggccgcgac acaagtgtga   2160
gagtactaaa taaatgcttt ggttgtacga aatcattaca ctaaataaaa taatcaaagc   2220
ttatatatgc cttccgctaa ggccgaatgc aaagaaattg gttctttctc gttatctttt   2280 gccacttta ctagtacgta ttaattacta cttaatcatc tttgtttacg gctcattata    2340
tccggtctag aggatccaag gccgcgaagt taaaagcaat gttgtcactt gtcgtactaa   2400
cacatgatgt gatagtttat gctagctagc tataacataa gctgtctctg agtgtgttgt   2460
atattaataa agatcatcac tggtgaatgg tgatcgtgta cgtaccctac ttagtaggca   2520
atggaagcac ttagagtgtg ctttgtgcat ggccttgcct ctgttttgag acttttgtaa   2580
tgttttcgag tttaaatctt tgcctttgcg tacgtctaga ggatccccgg gtacc        2635
```

<210> SEQ ID NO 44
<211> LENGTH: 9276
<212> TYPE: DNA
<213> ORGANISM: Artificial Sequence
<220> FEATURE:
<223> OTHER INFORMATION: plasmid pKR970
<220> FEATURE:
<221> NAME/KEY: misc_feature
<222> LOCATION: (6592)..(6592)
<223> OTHER INFORMATION: n is a, c, g, or t

<400> SEQUENCE: 44

| | | | | | |
|---|---|---|---|---|---|
| gtacggatcc | gtcgacggcg | cgcccgatca | tccggatata | gttcctcctt | tcagcaaaaa | 60 |
| acccctcaag | acccgtttag | aggccccaag | gggttatgct | agttattgct | cagcggtggc | 120 |
| agcagccaac | tcagcttcct | ttcgggcttt | gttagcagcc | ggatcgatcc | aagctgtacc | 180 |
| tcactattcc | tttgccctcg | gacgagtgct | ggggcgtcgg | tttccactat | cggcgagtac | 240 |
| ttctacacag | ccatcggtcc | agacggccgc | gcttctgcgg | gcgatttgtg | tacgcccgac | 300 |
| agtcccggct | ccggatcgga | cgattgcgtc | gcatcgaccc | tgcgcccaag | ctgcatcatc | 360 |
| gaaattgccg | tcaaccaagc | tctgatagag | ttggtcaaga | ccaatgcgga | gcatatacgc | 420 |
| ccggagccgc | ggcgatcctg | caagctccgg | atgcctccgc | tcgaagtagc | gcgtctgctg | 480 |
| ctccatacaa | gccaaccacg | gcctccagaa | gaagatgttg | gcgacctcgt | attgggaatc | 540 |
| cccgaacatc | gcctcgctcc | agtcaatgac | cgctgttatg | cggccattgt | ccgtcaggac | 600 |
| attgttggag | ccgaaatccg | cgtgcacgag | gtgccggact | tcgggcagt | cctcggccca | 660 |
| aagcatcagc | tcatcgagag | cctgcgcgac | ggacgcactg | acggtgtcgt | ccatcacagt | 720 |
| ttgccagtga | tacacatggg | gatcagcaat | cgcgcatatg | aaatcacgcc | atgtagtgta | 780 |
| ttgaccgatt | ccttgcggtc | cgaatgggcc | gaacccgctc | gtctggctaa | gatcggccgc | 840 |
| agcgatcgca | tccatagcct | ccgcgaccgg | ctgcagaaca | gcgggcagtt | cggtttcagg | 900 |
| caggtcttgc | aacgtgacac | cctgtgcacg | gcggagatg | caataggtca | ggctctcgct | 960 |
| gaattcccca | atgtcaagca | cttccggaat | cgggagcgcg | gccgatgcaa | agtgccgata | 1020 |
| aacataacga | tctttgtaga | aaccatcggc | gcagctattt | acccgcagga | catatccacg | 1080 |
| ccctcctaca | tcgaagctga | aagcacgaga | ttcttcgccc | tccgagagct | gcatcaggtc | 1140 |
| ggagacgctg | tcgaactttt | cgatcagaaa | cttctcgaca | gacgtcgcgg | tgagttcagg | 1200 |
| cttttccatg | ggtatatctc | cttcttaaag | ttaaacaaaa | ttatttctag | agggaaaccg | 1260 |
| ttgtggtctc | cctatagtga | gtcgtattaa | tttcgcggga | tcgagatctg | atcaacctgc | 1320 |
| attaatgaat | cggccaacgc | gcggggagag | gcggtttgcg | tattgggcgc | tcttccgctt | 1380 |
| cctcgctcac | tgactcgctg | cgctcggtcg | ttcggctgcg | gcgagcggta | tcagctcact | 1440 |
| caaaggcggt | aatacggtta | tccacagaat | caggggataa | cgcaggaaag | aacatgtgag | 1500 |
| caaaaggcca | gcaaaaggcc | aggaaccgta | aaaaggccgc | gttgctggcg | tttttccata | 1560 |
| ggctccgccc | ccctgacgag | catcacaaaa | atcgacgctc | aagtcagagg | tggcgaaacc | 1620 |
| cgacaggact | ataaagatac | caggcgtttc | ccctggaag | ctccctcgtg | cgctctcctg | 1680 |
| ttccgaccct | gccgcttacc | ggatacctgt | ccgcctttct | cccttcggga | agcgtggcgc | 1740 |
| tttctcaatg | ctcacgctgt | aggtatctca | gttcggtgta | ggtcgttcgc | tccaagctgg | 1800 |
| gctgtgtgca | cgaaccccc | gttcagcccg | accgctgcgc | cttatccggt | aactatcgtc | 1860 |
| ttgagtccaa | cccggtaaga | cacgacttat | cgccactggc | agcagccact | ggtaacagga | 1920 |
| ttagcagagc | gaggtatgta | ggcggtgcta | cagagttctt | gaagtggtgg | cctaactacg | 1980 |

```
gctacactag aaggacagta tttggtatct gcgctctgct gaagccagtt accttcggaa   2040
aaagagttgg tagctcttga tccggcaaac aaaccaccgc tggtagcggt ggttttttg    2100 tttgcaagca gcagattacg cgcagaaaaa aaggatctca agaagatcct tgatctttt    2160 ctacggggtc tgacgctcag tggaacgaaa actcacgtta agggattttg gtcatgacat   2220
taacctataa aaataggcgt atcacgaggc cctttcgtct cgcgcgtttc ggtgatgacg   2280
gtgaaaacct ctgacacatg cagctcccgg agacggtcac agcttgtctg taagcggatg   2340
ccgggagcag acaagcccgt cagggcgcgt cagcgggtgt tggcgggtgt cggggctggc   2400
ttaactatgc ggcatcagag cagattgtac tgagagtgca ccatatggac atattgtcgt   2460
tagaacgcgg ctacaattaa tacataacct tatgtatcat acacatacga tttaggtgac   2520
actatagaac ggcgcgccaa gcttggatct cctgcaggct agcctaagta cgtactcaaa   2580
atgccaacaa ataaaaaaaa agttgcttta ataatgccaa acaaattaa taaaacactt    2640 acaacaccgg attttttta attaaaatgt gccatttagg ataaatagtt aatatttta    2700 ataattattt aaaaagccgt atctactaaa atgatttta tttggttgaa aatattaata    2760
tgtttaaatc aacacaatct atcaaaatta aactaaaaaa aaaataagtg tacgtggtta   2820
acattagtac agtaatataa gaggaaaatg agaaattaag aaattgaaag cgagtctaat   2880
ttttaaatta tgaacctgca tatataaaag gaaagaaaga atccaggaag aaaagaaatg   2940
aaaccatgca tggtcccctc gtcatcacga gtttctgcca tttgcaatag aaacactgaa   3000
acacctttct ctttgtcact taattgagat gccgaagcca cctcacacca tgaacttcat   3060
gaggtgtagc acccaaggct tccatagcca tgcatactga agaatgtctc aagctcagca   3120
ccctacttct gtgacgtgtc cctcattcac cttcctctct tccctataaa taaccacgcc   3180
tcaggttctc cgcttcacaa ctcaaacatt ctctccattg gtccttaaac actcatcagt   3240
catcaccgcg gccgcatggg aacggaccaa ggaaaaacct tcacctggga agagctggcg   3300
gcccataaca ccaaggacga cctactcttg gccatccgcg gcagggtgta cgatgtcaca   3360
aagttcttga gccgccatcc tggtggagtg gacactctcc tgctcggagc tggccgagat   3420
gttactccgg tctttgagat gtatcacgcg tttggggctg cagatgccat tatgaagaag   3480
tactatgtcg gtacactggt ctcgaatgag ctgcccatct tcccggagcc aacggtgttc   3540
cacaaaacca tcaagacgag agtcgagggc tactttacgg atcggaacat tgatcccaag   3600
aatagaccag agatctgggg acgatacgct cttatctttg gatccttgat cgcttcctac   3660
tacgcgcagc tctttgtgcc tttcgttgtc gaacgcacat ggcttcaggt ggtgtttgca   3720
atcatcatgg gatttgcgtg cgcacaagtc ggactcaacc ctcttcatga tgcgtctcac   3780
ttttcagtga cccacaaccc cactgtctgg aagattctgg gagccacgca cgactttttc   3840
aacggagcat cgtacctggt gtggatgtac caacatatgc tcggccatca ccctacacc    3900 aacattgctg gagcagatcc cgacgtgtcg acgtctgagc ccgatgttcg tcgtatcaag   3960
cccaaccaaa agtggtttgt caaccacatc aaccagcaca tgtttgttcc tttcctgtac   4020
ggactgctgg cgttcaaggt gcgcattcag gacatcaaca ttttgtactt tgtcaagacc   4080
aatgacgcta ttcgtgtcaa tcccatctcg acatggcaca ctgtgatgtt ctggggcggc   4140 aaggcttttct ttgtctggta tcgcctgatt gttcccctgc agtatctgcc cctgggcaag   4200
gtgctgctct tgttcacggt cgcggacatg gtgtcgtctt actggctggc gctgaccttc   4260
caggcgaacc acgttgttga ggaagttcag tggccgttgc ctgacgagaa cgggatcatc   4320
caaaaggact gggcagctat gcaggtcgag actacgcagg attacgcaca cgattcgcac   4380
```

```
ctctggacca gcatcactgg cagcttgaac taccaggctg tgcaccatct gttccccaac      4440
gtgtcgcagc accattatcc cgatattctg gccatcatca agaacacctg cagcgagtac      4500
aaggttccat accttgtcaa ggatacgttt tggcaagcat ttgcttcaca tttggagcac      4560
ttgcgtgttc ttggactccg tcccaaggaa gagtaggcgg ccgcatttcg caccaaatca      4620
atgaaagtaa taatgaaaag tctgaataag aatacttagg cttagatgcc tttgttactt      4680
gtgtaaaata acttgagtca tgtacctttg gcggaaacag aataaataaa aggtgaaatt      4740
ccaatgctct atgtataagt tagtaatact taatgtgttc tacggttgtt tcaatatcat      4800
caaactctaa ttgaaacttt agaaccacaa atctcaatct tttcttaatg aaatgaaaaa      4860
tcttaattgt accatgttta tgttaaacac cttacaattg gttggagagg aggaccaacc      4920
gatgggacaa cattgggaga aagagattca atggagattt ggataggaga acaacattct      4980
ttttcacttc aatacaagat gagtgcaaca ctaaggatat gtatgagact ttcagaagct      5040
acgacaacat agatgagtga ggtggtgatt cctagcaaga aagacattag aggaagccaa      5100
aatcgaacaa ggaagacatc aagggcaaga gacaggacca tccatctcag gaaaaggagc      5160
tttgggatag tccgagaagt tgtacaagaa attttttgga gggtgagtga tgcattgctg      5220
gtgactttaa ctcaatcaaa attgagaaag aaagaaaagg gaggggctc acatgtgaat      5280 agaagggaaa cgggagaatt ttacagtttt gatctaatgg gcatcccagc tagtggtaac      5340
atattcacca tgtttaacct tcacgtaccg ggcccccct cgaggtcgcc cggggatcc      5400 gccctaagct tcgtacgtcc tcgaagagaa gggttaataa cacatttttt aacattttta      5460
acacaaattt tagttattta aaatttatt aaaaaattta aataagaag aggaactctt      5520 taaataaatc taacttacaa aatttatgat ttttaataag ttttcaccaa taaaaaatgt      5580
cataaaaata tgttaaaaag tatattatca atattctctt tatgataaat aaaaagaaaa      5640
aaaaaataaa agttaagtga aaatgagatt gaagtgactt taggtgtgta taaatatatc      5700
aaccccgcca acaatttatt taatccaaat atattgaagt atattattcc atagccttta      5760
tttatttata tatttattat ataaaagctt tatttgttct aggttgttca tgaaatattt      5820
ttttggtttt atctccgttg taagaaaatc atgtgctttg tgtcgccact cactattgca      5880 gcttttttcat gcattggtca gattgacggt tgattgtatt tttgtttttt atggttttgt      5940
gttatgactt aagtcttcat ctctttatct cttcatcagg tttgatggtt acctaatatg      6000
gtccatgggt acatgcatgg ttaaattagg tggccaactt tgttgtgaac gatagaattt      6060
tttttatatt aagtaaacta ttttatatt atgaaataat aataaaaaaa atattttatc      6120
attattaaca aaatcatatt agttaatttg ttaactctat aataaaagaa atactgtaac      6180
attcacatta catggtaaca tctttccacc ctttcatttg ttttttgttt gatgactttt      6240
tttcttgttt aaatttattt cccttctttt aaatttggaa tacattatca tcatatataa      6300
actaaaatac taaaaacagg attacacaaa tgataaataa taacacaaat atttataaat      6360
ctagctgcaa tatatttaaa ctagctatat cgatattgta aaataaaact agctgcattg      6420
atactgataa aaaaatatca tgtgcttcct ggactgatga tgcagtatac ttttgacatt      6480
gcctttattt tattttcag aaaagctttc ttagttctgg gttcttcatt atttgtttcc      6540
catctccatt gtgaattgaa tcatttgctt cgtgtcacaa atacaattta gntaggtaca      6600
tgcattggtc agattcacgg tttattatgt catgacttaa gttcatggta gtacattacc      6660
tgccacgcat gcattatatt ggttagattt gataggcaaa tttggttgtc aacaatataa      6720
atataaataa tgttttttata ttacgaaata acagtgatca aaacaaacag ttttatcttt      6780
```

```
attaacaaga ttttgttttt gtttgatgac gttttttaat gtttacgctt tccccttct      6840
tttgaattta gaacacttta tcatcataaa atcaaatact aaaaaaatta catatttcat      6900
aaataataac acaaatattt ttaaaaaatc tgaataata atgaacaata ttacatatta       6960
tcacgaaaat tcattaataa aaatattata taaataaaat gtaatagtag ttatatgtag      7020
gaaaaaagta ctgcacgcat aatatataca aaaagattaa aatgaactat tataaataat      7080
aacactaaat taatggtgaa tcatatcaaa ataatgaaaa agtaaataaa atttgtaatt      7140
aacttctata tgtattacac acacaaataa taaataatag taaaaaaaat tatgataaat      7200
atttaccatc tcataagata tttaaaataa tgataaaaat atagattatt ttttatgcaa      7260
ctagctagcc aaaaagagaa cacgggtata tataaaaaga gtacctttaa attctactgt      7320
acttcctta ttcctgacgt ttttatatca agtggacata cgtgaagatt ttaattatca      7380
gtctaaatat ttcattagca cttaatactt ttctgtttta ttcctatcct ataagtagtc     7440
ccgattctcc caacattgct tattcacaca actaactaag aaagtcttcc atagcccccc     7500
aagcggccgc accatgggca agggtggaga cggcggcgcg caggcggtga gcgggaccga     7560
cgcgtctctc gctgaggtga gctccgtcga tagcaagagc gtgcacgtcg tgctctacgg     7620
caagcgcgtg gatgtcacaa agttccagaa ggcacacccg ggcgggagca aggtgttccg     7680
catcttccag gagcgcgacg cgacggagca gttcgagtct taccactcgc ccaaggccat     7740
caagatgatg gagggcatgc tcaagaagtc ggaggatgcg cccgcttccg tgcccctgcc     7800
ctcgcggtcc accatgggca cggagttcaa ggagatgatt gagcgccaca agagggctgg     7860
tctctacgac ccttgcccgt tggacgagct gttcaagctc accatcgtcc ttgcgcccat     7920
cttcgtgggc gcctatctcg tgcggagcgg cgtctcgccc ctcgcgggcg cgctctccat     7980
gggcttggc ttctacctcg acggctggct tgctcacgac tacctgcatc acgcagtctt      8040
caagggctcg gtcaacacgc tcgtcaaggc gaacaacgcc atgggatacg ccctcggctt     8100
cctccagggc tacgacgtgg cctggtggcg cgcgcgccat aacacgcacc acgtgtgcac     8160
caacgaggat ggttcggacc cggacatcaa gacggcgccc ctgctcatct acgtgcgaga     8220
gaacccgtcc attgccaagc ggctcaactt cttccagcgc tggcagcagt actactatgt     8280
gccgaccatg gccatcctcg acctctactg gcgcctggag tccatcgcgt acgtggctgt     8340
gcgcctgcct aagatgtgga tgcaggccgc cgctcttgcc gctcactacg cgctcctgtg     8400
ctgggtcttc gcagcgcatc tcaacctcat ccctctcatg atggttgcac gcggcttcgc     8460
gacgggcatc gttgtctttg caacccacta tggtgaggac atcctcgacc gcgagcacgt     8520
cgagggcatg acgctcgtcg agcagaccgc caagacctcc cgtaacatca cgggcggctg     8580
gctagtgaac gtgctcacgg gcttcatctc cctgcagacc gagcatcacc tcttccccat     8640
gatgccacc ggcaacctaa tgactatcca gcccgaggta cgcgacttct tcaagaagca      8700
tggcctcgag taccgcgagg gcaacctctt ccagtgcgtg caccagaaca tcaaggctct     8760
cgccttcgag cacctcctcc actgagcggc cgcgacacaa gtgtgagagt actaaataaa     8820
tgctttggtt gtacgaaatc attacactaa ataaaataat caaagcttat atatgccttc     8880
cgctaaggcc gaatgcaaag aaattggttc tttctcgtta tcttttgcca cttttactag     8940
tacgtattaa ttactactta atcatctttg tttacggctc attatatccg gtctagagga     9000
tccaaggccg cgaagttaaa agcaatgttg tcacttgtcg tactaacaca tgatgtgata     9060
gtttatgcta gctagctata acataagctg tctctgagtg tgttgtatat taataaagat     9120
catcactggt gaatggtgat cgtgtacgta ccctacttag taggcaatgg aagcacttag     9180
```

```
agtgtgcttt gtgcatggcc ttgcctctgt tttgagactt ttgtaatgtt ttcgagttta    9240
aatctttgcc tttgcgtacg tctagaggat ccccgg                              9276

<210> SEQ ID NO 45
<211> LENGTH: 11366
<212> TYPE: DNA
<213> ORGANISM: Artificial Sequence
<220> FEATURE:
<223> OTHER INFORMATION: plasmid pKR973
<220> FEATURE:
<221> NAME/KEY: misc_feature
<222> LOCATION: (5237)..(5237)
<223> OTHER INFORMATION: n is a, c, g, or t

<400> SEQUENCE: 45
ggagatccaa gcttggcgcg ccgttctata gtgtcaccta atcgtatgt gtatgataca      60 taaggttatg tattaattgt agccgcgttc taacgacaat atgtccatat ggtgcactct    120
cagtacaatc tgctctgatg ccgcatagtt aagccagccc cgacacccgc caacacccgc    180
tgacgcgccc tgacgggctt gtctgctccc ggcatccgct tacagacaag ctgtgaccgt    240
ctccgggagc tgcatgtgtc agaggttttc accgtcatca ccgaaacgcg cgagacgaaa    300
gggcctcgtg atacgcctat ttttataggt taatgtcatg accaaaatcc cttaacgtga    360
gttttcgttc cactgagcgt cagacccccgt agaaaagatc aaaggatctt cttgagatcc    420 ttttttttctg cgcgtaatct gctgcttgca acaaaaaaa ccaccgctac cagcggtggt    480
ttgtttgccg gatcaagagc taccaactct ttttccgaag gtaactggct tcagcagagc    540
gcagatacca aatactgtcc ttctagtgta gccgtagtta ggccaccact tcaagaactc    600
tgtagcaccg cctacatacc tcgctctgct aatcctgtta ccagtggctg ctgccagtgg    660
cgataagtcg tgtcttaccg ggttggactc aagacgatag ttaccggata aggcgcagcg    720
gtcgggctga acggggggtt cgtgcacaca gcccagcttg gagcgaacga cctacaccga    780
actgagatac ctacagcgtg agcattgaga aagcgccacg cttcccgaag ggagaaaggc    840
ggacaggtat ccggtaagcg gcagggtcgg aacaggagag cgcacgaggg agcttccagg    900
gggaaacgcc tggtatcttt atagtcctgt cgggtttcgc cacctctgac ttgagcgtcg    960 attttttgtga tgctcgtcag gggggcggag cctatggaaa aacgccagca acgcggcctt   1020
tttacggttc ctggcctttt gctggccttt tgctcacatg ttctttcctg cgttatcccc   1080
tgattctgtg gataaccgta ttaccgcctt tgagtgagct gataccgctc gccgcagccg   1140
aacgaccgag cgcagcgagt cagtgagcga ggaagcggaa gagcgcccaa tacgcaaacc   1200
gcctctcccc gcgcgttggc cgattcatta atgcaggttg atcagatctc gatcccgcga   1260
aattaatacg actcactata gggagaccac aacggtttcc ctctagaaat aattttgttt   1320
aactttaaga aggagatata cccatggaaa agcctgaact caccgcgacg tctgtcgaga   1380
agtttctgat cgaaaagttc gacagcgtct ccgacctgat gcagctctcg gagggcgaag   1440
aatctcgtgc tttcagcttc gatgtaggag ggcgtggata tgtcctgcgg gtaaatagct   1500
gcgccgatgg tttctacaaa gatcgttatg tttatcggca ctttgcatcg gccgcgctcc   1560
cgattccgga agtgcttgac attggggaat tcagcgagag cctgacctat tgcatctccc   1620
gccgtgcaca gggtgtcacg ttgcaagacc tgcctgaaac cgaactgccc gctgttctgc   1680
agccggtcgc ggaggctatg gatgcgatcg ctgcggccga tcttagccag acgagcgggt   1740
tcggcccatt cggaccgcaa ggaatcggtc aatacactac atggcgtgat ttcatatgcg   1800
cgattgctga tccccatgtg tatcactggc aaactgtgat ggacgacacc gtcagtgcgt   1860
```

```
ccgtcgcgca ggctctcgat gagctgatgc tttgggccga ggactgcccc gaagtccggc    1920
acctcgtgca cgcggatttc ggctccaaca atgtcctgac ggacaatggc cgcataacag    1980
cggtcattga ctggagcgag gcgatgttcg gggattccca atacgaggtc gccaacatct    2040
tcttctggag gccgtggttg gcttgtatgg agcagcagac gcgctacttc gagcggaggc    2100
atccggagct tgcaggatcg ccgcggctcc gggcgtatat gctccgcatt ggtcttgacc    2160
aactctatca gagcttggtt gacggcaatt tcgatgatgc agcttgggcg cagggtcgat    2220
gcgacgcaat cgtccgatcc ggagccggga ctgtcgggcg tacacaaatc gcccgcagaa    2280
gcgcggccgt ctggaccgat ggctgtgtag aagtactcgc cgatagtgga aaccgacgcc    2340
ccagcactcg tccgagggca aggaatagt gaggtacagc ttggatcgat ccggctgcta    2400
acaaagcccg aaaggaagct gagttggctg ctgccaccgc tgagcaataa ctagcataac    2460 cccttgggc ctctaaacgg gtcttgaggg gttttttgct gaaaggagga actatatccg    2520
gatgatcggg cgcgccgtcg acggatccgt acccggggat cctctagacg tacgcaaagg    2580
caaagattta aactcgaaaa cattacaaaa gtctcaaaac agaggcaagg ccatgcacaa    2640
agcacactct aagtgcttcc attgcctact aagtagggta cgtacacgat caccattcac    2700
cagtgatgat ctttattaat atacaacaca ctcagagaca gcttatgtta tagctagcta    2760
gcataaacta tcacatcatg tgttagtacg acaagtgaca acattgcttt taacttcgcg    2820
gccttggatc ctctagaccg gatataatga gccgtaaaca aagatgatta agtagtaatt    2880
aatacgtact agtaaagtg gcaaaagata acgagaaaga accaatttct ttgcattcgg    2940
ccttagcgga aggcatatat aagctttgat tattttattt agtgtaatga tttcgtacaa    3000
ccaaagcatt tatttagtac tctcacactt gtgtcgcggc cgctcagtgg aggaggtgct    3060
cgaaggcgag agccttgatg ttctggtgca cgcactggaa gaggttgccc tcgcggtact    3120
cgaggccatg cttcttgaag aagtcgcgta cctcgggctg gatagtcatt aggttgccgg    3180
tgggcatcat ggggaagagg tgatgctcgg tctgcaggga gatgaagccc gtgagcacgt    3240
tcactagcca gccgcccgtg atgttacggg aggtcttggc ggtctgctcg acgagcgtca    3300
tgccctcgac gtgctcgcgg tcgaggatgt cctcaccata gtgggttgca agacaacga    3360 tgcccgtcgc gaagccgcgt gcaaccatca tgagagggat gaggttgaga tgcgctgcga    3420
agacccagca caggagcgcg tagtgagcgg caagagcggc ggcctgcatc cacatcttag    3480
gcaggcgcac agccacgtac gcgatggact ccaggcgcca gtagaggtcg aggatggcca    3540
tggtcggcac atagtagtac tgctgccagc gctggaagaa gttgagccgc ttggcaatgg    3600
acgggttctc tcgcacgtag atgagcaggg gcgccgtctt gatgtccggg tccgaaccat    3660
cctcgttggt gcacacgtgg tgcgtgttat ggcgcgcgcg ccaccaggcc acgtcgtagc    3720
cctggaggaa gccgagggcg tatcccatgg cgttgttcgc cttgacgagc gtgttgaccg    3780
agcccttgaa gactgcgtga tgcaggtagt cgtgagcaag ccagccgtcg aggtagaagc    3840
caaagcccat ggagagcgcg cccgcgaggg gcgagacgcc gctccgcacg agataggcgc    3900
ccacgaagat gggcgcaagg acgatggtga gcttgaacag ctcgtccaac gggcaagggt    3960
cgtagagacc agccctcttg tggcgctcaa tcatctcctt gaactccgtg cccatggtgg    4020
accgcgaggg caggggcacg gaagcgggcg catcctccga cttcttgagc atgcctcca    4080 tcatcttgat ggccttgggc gagtggtaag actcgaactg ctccgtcgcg tcgcgctcct    4140
ggaagatgcg gaacaccttg ctcccgcccg ggtgtgcctt ctggaacttt gtgacatcca    4200
cgcgcttgcc gtagagcacg acgtgcacgc tcttgctatc gacggagctc acctcagcga    4260
```

```
gagacgcgtc ggtcccgctc accgcctgcg cgccgccgtc tccacccttg cccatggtgc    4320
ggccgcttgg ggggctatgg aagactttct tagttagttg tgtgaataag caatgttggg    4380
agaatcggga ctacttatag gataggaata aaacagaaaa gtattaagtg ctaatgaaat    4440
atttagactg ataattaaaa tcttcacgta tgtccacttg atataaaaac gtcaggaata    4500
aaggaagtac agtagaattt aaaggtactc ttttttatata tacccgtgtt ctcttttttgg   4560 ctagctagtt gcataaaaaa taatctatat ttttatcatt attttaaata tcttatgaga    4620
tggtaaatat ttatcataat ttttttttact attatttatt atttgtgtgt gtaatacata    4680
tagaagttaa ttacaaattt tatttactttt ttcattattt tgatatgatt caccattaat    4740
ttagtgttat tatttataat agttcatttt aatcttttttg tatatattat gcgtgcagta    4800 ctttttttcct acatataact actattcat tttatttata taatattttt attaatgaat    4860
tttcgtgata atatgtaata ttgttcatta ttatttcaga ttttttaaaa atatttgtgt    4920
tattatttat gaaatatgta attttttttag tatttgattt tatgatgata aagtgttcta    4980
aattcaaaag aagggggaaa gcgtaaacat taaaaaacgt catcaaacaa aaacaaaatc    5040
ttgttaataa agataaaact gtttgttttg atcactgtta tttcgtaata taaaaacatt    5100
atttatattt atattgttga caaccaaatt tgcctatcaa atctaaccaa tataatgcat    5160
gcgtggcagg taatgtacta ccatgaactt aagtcatgac ataataaacc gtgaatctga    5220
ccaatgcatg tacctancta aattgtattt gtgacacgaa gcaaatgatt caattcacaa    5280
tggagatggg aaacaaataa tgaagaaccc agaactaaga aagcttttct gaaaaataaa    5340
ataaaggcaa tgtcaaaagt atactgcatc atcagtccag aaagcacatg atatttttttt   5400 atcagtatca atgcagctag ttttattttta caatatcgat atagctagtt taaatatatt    5460
gcagctagat ttataaatat ttgtgttatt attttatcatt tgtgtaatcc tgttttttagt   5520 attttagttt atatatgatg ataatgtatt ccaaatttaa aagaagggaa ataaatttaa    5580
acaagaaaaa aagtcatcaa acaaaaaaca aatgaaaggg tggaaagatg ttaccatgta    5640
atgtgaatgt tacagtattt cttttattat agagttaaca aattaactaa tatgattttg    5700
ttaataatga taaaatatttt ttttttattat tattccataa tataaaaata gtttacttaa    5760
tataaaaaaa attctatcgt tcacaacaaa gttggccacc taatttaacc atgcatgtac    5820
ccatggacca tattaggtaa ccatcaaacc tgatgaagag ataaagagat gaagacttaa    5880
gtcataacac aaaaccataa aaaacaaaaa tacaatcaac cgtcaatctg accaatgcat    5940
gaaaaagctg caatagtgag tggcgacaca aagcacatga ttttcttaca acggagataa    6000
aaccaaaaaa atatttcatg aacaacctag aacaaataaa gcttttatat aataaatata    6060
taaataaata aaggctatgg aataatatac ttcaatatat ttggattaaa taaattgttg    6120
gcggggttga tatatttata cacacctaaa gtcacttcaa tctcattttc acttaactttt   6180 tattttttttt ttcttttttat ttatcataaa gagaatattg ataatatact ttttaacata    6240
tttttatgac atttttttatt ggtgaaaact tattaaaaat cataaatttt gtaagttaga    6300
tttatttaaa gagttcctct tcttatttta aattttttaa taaattttta aataactaaa    6360
atttgtgtta aaaatgttaa aaaatgtgtt attaacccctt ctcttcgagg acgtacgaag    6420
cttagggcgg atccccccggg cgacctcgag gggggggcccg gtacgtgaag gttaaacatg    6480
gtgaatatgt taccactagc tgggatgccc attagatcaa aactgtaaaa ttctcccgtt    6540
tcccttctat tcacatgtga gccccctccc ttttctttct ttctcaatttt tgattgagtt    6600 aaagtcacca gcaatgcatc actcaccctc caaaaaattt cttgtacaac ttctcggact    6660
```

```
atcccaaagc tccttttcct gagatggatg gtcctgtctc ttgcccttga tgtcttcctt    6720
gttcgatttt ggcttcctct aatgtctttc ttgctaggaa tcaccacctc actcatctat    6780
gttgtcgtag cttctgaaag tctcatacat atccttagtg ttgcactcat cttgtattga    6840
agtgaaaaag aatgttgttc tcctatccaa atctccattg aatctctttc tcccaatgtt    6900
gtcccatcgg ttggtcctcc tctccaacca attgtaaggt gtttaacata aacatggtac    6960
aattaagatt tttcatttca ttaagaaaag attgagattt gtggttctaa agtttcaatt    7020
agagtttgat gatattgaaa caaccgtaga acacattaag tattactaac ttatacatag    7080
agcattggaa tttcaccttt tatttattct gtttccgcca aaggtacatg actcaagtta    7140
ttttacacaa gtaacaaagg catctaagcc taagtattct tattcagact tttcattatt    7200
actttcattg atttggtgcg aaatgcggcc gcctactctt ccttgggacg gagtccaaga    7260
acacgcaagt gctccaaatg tgaagcaaat gcttgccaaa acgtatcctt gacaaggtat    7320
ggaaccttgt actcgctgca ggtgttcttg atgatggcca gaatatcggg ataatggtgc    7380
tgcgacacgt tggggaacag atggtgcaca gcctggtagt tcaagctgcc agtgatgctg    7440
gtccagaggt gcgaatcgtg tgcgtaatcc tgcgtagtct cgacctgcat agctgcccag    7500
tccttttgga tgatcccgtt ctcgtcaggc aacggccact gaacttcctc aacaacgtgg    7560
ttcgcctgga aggtcagcgc cagccagtaa gacgacacca tgtccgcgac cgtgaacaag    7620
agcagcacct tgcccagggg cagatactgc aggggaacaa tcaggcgata ccagacaaag    7680
aaagccttgc cgccccagaa catcacagtg tgccatgtcg agatgggatt gacacgaata    7740
gcgtcattgg tcttgacaaa gtacaaaatg ttgatgtcct gaatgcgcac cttgaacgcc    7800
agcagtccgt acaggaaagg aacaaacatg tgctggttga tgtggttgac aaaccacttt    7860
tggttgggct tgatacgacg aacatcgggc tcagacgtcg acacgtcggg atctgctcca    7920
gcaatgttgg tgtaggggtg atggccgagc atatgttggt acatccacac caggtacgat    7980
gctccgttga aaaagtcgtg cgtggctccc agaatcttcc agacagtggg gttgtgggtc    8040
actgaaaagt gagacgcatc atgaagaggg ttgagtccga cttgtgcgca cgcaaatccc    8100
atgatgattg caaacaccac ctgaagccat gtgcgttcga caacgaaagg cacaaagagc    8160
tgcgcgtagt aggaagcgat caaggatcca aagataagag cgtatcgtcc ccagatctct    8220
ggtctattct tgggatcaat gttccgatcc gtaaagtagc cctcgactct cgtcttgatg    8280
gttttgtgga acaccgttgg ctccgggaag atgggcagct cattcgagac cagtgtaccg    8340
acatagtact tcttcataat ggcatctgca gccccaaacg cgtgatacat ctcaaagacc    8400
ggagtaacat ctcggccagc tccgagcagg agagtgtcca ctccaccagg atggcggctc    8460
aagaactttg tgacatcgta cacctgccg cggatggcca agagtaggtc gtccttggtg    8520
ttatgggccg ccagctcttc ccaggtgaag gttttccctt ggtccgttcc catgcggccg    8580
cggtgatgac tgatgagtgt ttaaggacca atggagagaa tgtttgagtt gtgaagcgga    8640
gaacctgagg cgtggttatt tatagggaag agaggaaggt gaatgaggga cacgtcacag    8700
aagtagggtg ctgagcttga gacattcttc agtatgcatg gctatggaag ccttgggtgc    8760
tacacctcat gaagttcatg gtgtgaggtg gcttcggcat ctcaattaag tgacaaagag    8820
aaaggtgttt cagtgtttct attgcaaatg gcagaaactc gtgatgacga ggggaccatg    8880
catggtttca tttctttct tcctggattc tttctttcct tttatatatg caggttcata    8940
atttaaaaat tagactcgct ttcaatttct taatttctca ttttcctctt atattactgt    9000
actaatgtta accacgtaca cttatttttt ttttagttta attttgatag attgtgttga    9060
```

```
tttaaacata ttaatatttt caaccaaata aaaatcattt tagtagatac ggcttttaa   9120
ataattatta aaaatattaa ctatttatcc taaatggcac attttaatta aaaaaaatcc   9180
ggtgttgtaa gtgttttatt aatttgtttt ggcattatta aagcaacttt ttttttattt   9240
gttggcattt tgagtacgta cttaggctag cctgcaggcc aactgcgttt ggggctccag   9300
attaaacgac gccgtttcgt tcctttcgct tcacggctta acgatgtcgt ttctgtctgt   9360
gcccaaaaaa taaaggcatt tgttatttgc accagatatt tactaagtgc accctagttt   9420
gacaagtagg cgataattac aaatagatgc ggtgcaaata ataaattttg aaggaaataa   9480
ttacaaaaga acagaactta tatttacttt attttaaaaa actaaaatga aagaacaaaa   9540
aaagtaaaaa atacaaaaaa tgtgctttaa ccactttcat tatttgttac agaaagtatg   9600
attctactca aattgatctg ttgtatctgg tgctgccttg tcacactggc gatttcaatc   9660
ccctaaagat atggtgcaaa ctgcgaagtg atcaatatct gctcggttaa tttagattaa   9720
ttaataatat tcaacgtgat gtaccaaaaa aagacaattt tttgctccat tgacaaatta   9780
aacctcatca aggtaatttc caaacctata agcaaaaaaa tttcacatta attggcccgc   9840
aatcctatta gtcttattat actagagtag gaaaaaaaac aattacacaa cttgtcttat   9900
tattctctat gctaatgaat attttttccct tttgttagaa atcagtgttt cctaatttat   9960
tgagtattaa ttccactcac cgcatatatt taccgttgaa taagaaaatt ttacacataa  10020
ttcttttttaa gataaataat ttttttatac tagatcttat atgattacgt gaagccaagt  10080
gggttatact aatgatatat aatgtttgat agtaatcagt ttataaacca aatgcatgga  10140
aatgttacgt ggaagcacgt aaattaacaa gcattgaagc aaatgcagcc accgcaccaa  10200
aaccacccca cttcacttcc acgtaccata ttccatgcaa ctacaacacc ctaaaacttc  10260
aataaatgcc cccaccttca cttcacttca cccatcaata gcaagcggcc gcaccatgga  10320
ggtggtgaat gaaatagtct caattgggca ggaagtttta cccaaagttg attatgccca  10380
actctggagt gatgccagtc actgtgaggt gctttacttg tccatcgcat ttgtcatctt  10440
gaagttcact cttggccccc ttggtccaaa aggtcagtct cgtatgaagt tgttttcac   10500
caattacaac cttctcatgt ccatttattc gttgggatca ttcctctcaa tggcatatgc  10560
catgtacacc atcggtgtta tgtctgacaa ctgcgagaag gcttttgaca acaacgtctt  10620
caggatcacc acgcagttgt tctatttgag caagttcctg gagtatattg actccttcta  10680
tttgccactg atgggcaagc ctctgacctg gttgcaattc ttccatcatt tgggggcacc  10740
gatggatatg tggctgttct ataattaccg aaatgaagct gtttggattt ttgtgctgtt  10800
gaatggtttc atccactgga tcatgtacgg ttattattgg accagattga tcaagctgaa  10860
gttccccatg ccaaaatccc tgattacatc aatgcagatc attcaattca atgttggttt  10920
ctacattgtc tggaagtaca ggaacattcc ctgttatcgc caagatggga tgaggatgtt  10980
tggctggttc ttcaattact tttatgttgg cacagtcttg tgtttgttct tgaatttcta  11040
tgtgcaaacg tatatcgtca ggaagcacaa gggagccaaa aagattcagt gagcggccgc  11100
gaagttaaaa gcaatgttgt cacttgtcgt actaacacat gatgtgatag tttatgctag  11160
ctagctataa cataagctgt ctctgagtgt gttgtatatt aataaagatc atcactggtg  11220
aatggtgatc gtgtacgtac cctacttagt aggcaatgga agcacttaga gtgtgctttg  11280
tgcatggcct tgcctctgtt ttgagacttt tgtaatgttt tcgagtttaa atctttgcct  11340
ttgcgtacgt ctagagtcga cctgca                                       11366
```

<210> SEQ ID NO 46

<211> LENGTH: 7085
<212> TYPE: DNA
<213> ORGANISM: Artificial Sequence
<220> FEATURE:
<223> OTHER INFORMATION: plasmid pKR72

<400> SEQUENCE: 46

```
gtacggatcc gtcgacggcg cgcccgatca tccggatata gttcctcctt tcagcaaaaa      60
acccctcaag acccgtttag aggccccaag gggttatgct agttattgct cagcggtggc     120
agcagccaac tcagcttcct ttcgggcttt gttagcagcc ggatcgatcc aagctgtacc     180
tcactattcc tttgccctcg gacgagtgct ggggcgtcgg tttccactat cggcgagtac     240
ttctacacag ccatcggtcc agacggccgc gcttctgcgg gcgatttgtg tacgcccgac     300
agtcccggct ccggatcgga cgattgcgtc gcatcgaccc tgcgcccaag ctgcatcatc     360
gaaattgccg tcaaccaagc tctgatagag ttggtcaaga ccaatgcgga gcatatacgc     420
ccggagccgc ggcgatcctg caagctccgg atgcctccgc tcgaagtagc gcgtctgctg     480
ctccatacaa gccaaccacg gcctccagaa gaagatgttg gcgacctcgt attgggaatc     540
cccgaacatc gcctcgctcc agtcaatgac cgctgttatg cggccattgt ccgtcaggac     600
attgttggag ccgaaatccg cgtgcacgag gtgccggact cggggcagt cctcggccca      660
aagcatcagc tcatcgagag cctgcgcgac ggacgcactg acggtgtcgt ccatcacagt     720
ttgccagtga tacacatggg gatcagcaat cgcgcatatg aaatcacgcc atgtagtgta     780
ttgaccgatt ccttgcggtc cgaatgggcc gaacccgctc gtctggctaa gatcggccgc     840
agcgatcgca tccatagcct ccgcgaccgg ctgcagaaca gcgggcagtt cggtttcagg     900
caggtcttgc aacgtgacac cctgtgcacg gcgggagatg caataggtca ggctctcgct     960
gaattcccca atgtcaagca cttccggaat cgggagcgcg gccgatgcaa agtgccgata    1020
aacataacga tctttgtaga aaccatcggc gcagctattt acccgcagga catatccacg    1080
ccctcctaca tcgaagctga aagcacgaga ttcttcgccc tccgagagct gcatcaggtc    1140
ggagacgctg tcgaactttt cgatcagaaa cttctcgaca gacgtcgcgg tgagttcagg    1200
cttttccatg gtatatctcc ttcttaaag ttaaacaaaa ttatttctag agggaaaccg    1260
ttgtggtctc cctatagtga gtcgtattaa tttcgcggga tcgagatcga tccaattcca    1320
atcccacaaa aatctgagct taacagcaca gttgctcctc tcagagcaga atcgggtatt    1380
caacaccctc atatcaacta ctacgttgtg tataacggtc cacatgccgg tatatacgat    1440
gactggggtt gtacaaaggc ggcaacaaac ggcgttccg gagttgcaca caagaaattt     1500
gccactatta cagaggcaag agcagcagct gacgcgtaca caacaagtca gcaaacagac    1560
aggttgaact tcatcccca aggagaagct caactcaagc caagagctt tgctaaggcc      1620
ctaacaagcc caccaaagca aaaagcccac tggctcacgc taggaaccaa aaggcccagc    1680
agtgatccag ccccaaaaga gatctccttt gccccggaga ttacaatgga cgatttcctc    1740
tatctttacg atctaggaag gaagttcgaa ggtgaaggtg acgacactat gttcaccact    1800
gataatgaga aggttagcct cttcaatttc agaaagaatg ctgacccaca gatggttaga    1860
gaggcctacg cagcaggtct catcaagacg atctacccga gtaacaatct ccaggagatc    1920
aaataccttc ccaagaaggt taagatgca gtcaaaagat tcaggactaa ttgcatcaag    1980
aacacagaga aagacatatt tctcaagatc agaagtacta ttccagtatg gacgattcaa    2040
ggcttgcttc ataaaccaag gcaagtaata gagattggag tctctaaaaa ggtagttcct    2100
actgaatcta aggccatgca tggagtctaa gattcaaatc gaggatctaa cagaactcgc    2160
```

-continued

```
cgtgaagact ggcgaacagt tcatacagag tcttttacga ctcaatgaca agaagaaaat   2220
cttcgtcaac atggtggagc acgacactct ggtctactcc aaaaatgtca agatacagt    2280
ctcagaagac caagggcta ttgagacttt tcaacaaagg ataatttcgg gaaacctcct    2340
cggattccat tgcccagcta tctgtcactt catcgaaagg acagtagaaa aggaaggtgg   2400
ctcctacaaa tgccatcatt gcgataaagg aaaggctatc attcaagatg cctctgccga   2460
cagtggtccc aaagatggac ccccacccac gaggagcatc gtggaaaaag aagacgttcc   2520
aaccacgtct tcaaagcaag tggattgatg tgacatctcc actgacgtaa gggatgacgc   2580
acaatcccac tatccttcgc aagacccttc tctctataa ggaagttcat ttcatttgga    2640
gaggacacgc tcgagctcat ttctctatta cttcagccat aacaaaagaa ctcttttctc   2700
ttcttattaa accatgaaaa agcctgaact caccgcgacg tctgtcgaga gtttctgat    2760
cgaaaagttc gacagcgtct ccgacctgat gcagctctcg gagggcgaag aatctcgtgc   2820
tttcagcttc gatgtaggag ggcgtggata tgtcctgcgg gtaaatagct gcgccgatgg   2880
tttctacaaa gatcgttatg tttatcggca ctttgcatcg gccgcgctcc cgattccgga   2940
agtgcttgac attggggaat tcagcgagag cctgacctat tgcatctccc gccgtgcaca   3000
gggtgtcacg ttgcaagacc tgcctgaaac cgaactgccc gctgttctgc agccggtcgc   3060
ggaggccatg gatgcgatcg ctgcggccga tcttagccag acgagcgggt tcggcccatt   3120
cggaccgcaa ggaatcggtc aatacactac atggcgtgat ttcatatgcg cgattgctga   3180
tccccatgtg tatcactggc aaactgtgat ggacgacacc gtcagtgcgt ccgtcgcgca   3240
ggctctcgat gagctgatgc tttgggccga ggactgcccc gaagtccggc acctcgtgca   3300
cgcggatttc ggctccaaca atgtcctgac ggacaatggc cgcataacag cggtcattga   3360
ctggagcgag gcgatgttcg gggattccca atacgaggtc gccaacatct tcttctggag   3420
gccgtggttg gcttgtatgg agcagcagac gcgctacttc gagcggaggc atccggagct   3480
tgcaggatcg ccgcggctcc gggcgtatat gctccgcatt ggtcttgacc aactctatca   3540
gagcttggtt gacggcaatt tcgatgatgc agcttgggcg cagggtcgat gcgacgcaat   3600
cgtccgatcc ggagccggga ctgtcgggcg tacacaaatc gcccgcagaa gcgcggccgt   3660
ctggaccgat ggctgtgtag aagtactcgc cgatagtgga aaccgacgcc ccagcactcg   3720
tccgagggca aaggaatagt gaggtaccta aagaaggagt gcgtcgaagc agatcgttca   3780
aacatttggc aataaagttt cttaagattg aatcctgttg ccggtcttgc gatgattatc   3840
atataatttc tgttgaatta cgttaagcat gtaataatta acatgtaatg catgacgtta   3900
tttatgagat gggttttat gattagagtc ccgcaattat acatttaata cgcgatagaa   3960
aacaaaatat agcgcgcaaa ctaggataaa ttatcgcgcg cggtgtcatc tatgttacta   4020
gatcgatgtc gaatcgatca acctgcatta atgaatcggc caacgcgcgg ggagaggcgg   4080
tttgcgtatt gggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcaatgctca cgctgtaggt atctcagttc   4500
ggtgtaggtc gttcgctcca agctgggctg tgtgcacgaa ccccccgttc agcccgaccg   4560
```

```
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
caccgctggt agcggtggtt ttttgtttg caagcagcag attacgcgca gaaaaaagg    4860
atctcaagaa gatcctttga tcttttctac ggggtctgac gctcagtgga acgaaaactc    4920
acgttaaggg attttggtca tgacattaac ctataaaaat aggcgtatca cgaggccctt    4980
tcgtctcgcg cgtttcggtg atgacggtga aaacctctga cacatgcagc tcccggagac    5040
ggtcacagct tgtctgtaag cggatgccgg gagcagacaa gcccgtcagg gcgcgtcagc    5100
gggtgttggc gggtgtcggg gctggcttaa ctatgcggca tcagagcaga ttgtactgag    5160
agtgcaccat atggacatat tgtcgttaga acgcggctac aattaataca taaccttatg    5220
tatcatacac atacgattta ggtgacacta tagaacggcg cgccaagctt gttgaaacat    5280
ccctgaagtg tctcatttta ttttatttat tctttgctga taaaaaata aataaaaga    5340
agctaagcac acggtcaacc attgctctac tgctaaaagg gttatgtgta gtgttttact    5400
gcataaatta tgcagcaaac aagacaactc aaattaaaaa atttcctttg cttgtttttt    5460
tgttgtctct gacttgactt tcttgtggaa gttggttgta taaggattgg gacaccattg    5520
tccttcttaa tttaatttta ttctttgctg ataaaaaaa aaatttcata tagtgttaaa    5580
taataatttg ttaaataacc aaaaagtcaa atatgtttac tctcgtttaa ataattgaga    5640
ttcgtccagc aaggctaaac gattgtatag atttatgaca atatttactt ttttatagat    5700
aaatgttata ttataataaa tttatataca tatattatat gttatttatt attattttaa    5760
atccttcaat attttatcaa accaactcat aatttttttt ttatctgtaa gaagcaataa    5820
aattaaatag acccacttta aggatgatcc aacctttata cagagtaaga gagttcaaat    5880
agtacccttt catatacata tcaactaaaa tattagaaat atcatggatc aaaccttata    5940
aagacattaa ataagtggat aagtataata tataaatggg tagtatataa tatataaatg    6000
gatacaaact tctctcttta taattgttat gtctccttaa catcctaata taatacataa    6060
gtgggtaata tataatatat aaatggagac aaacttcttc cattataatt gttatgtctt    6120
cttaacactt atgtctcgtt cacaatgcta aggttagaat tgtttagaaa gtcttatagt    6180
acacatttgt ttttgtacta tttgaagcat tccataagcc gtcacgattc agatgattta    6240
taataataag aggaaattta tcatagaaca ataaggtgca tagatagagt gttaatatat    6300
cataacatcc tttgtttatt catagaagaa gtgagatgga gctcagttat tatactgtta    6360
catggtcgga tacaatattc catgctctcc atgagctctt acacctacat gcattttagt    6420
tcatacttgc ggccgcagta tatcttaaat tctttaatac ggtgtactag gatattgaac    6480
tggttcttga tgatgaaaac ctgggccgag attgcagcta tttatagtca taggtcttgt    6540
taacatgcat ggacatttgg ccacggggtg gcatgcagtt tgacgggtgt tgaaataaac    6600
aaaaatgagg tggcggaaga gaatacgagt ttgaggttgg gttagaaaca acaaatgtga    6660
gggctcatga tgggttgagt tggtgaatgt tttgggctgc tcgattgaca cctttgtgag    6720
tacgtgttgt tgtgcatggc ttttggggtc cagtttttt ttcttgacgc ggcgatcctg    6780
atcagctagt ggataagtga tgtccactgt gtgtgattgc gttttgttt gaattttatg    6840
aacttagaca ttgctatgca aaggatactc tcattgtgtt ttgtcttctt ttgttccttg    6900
gcttttctt atgatccaag agactagtca gtgttgtggc attcgagact accaagatta    6960
```

-continued

```
attatgatgg gggaaggata agtaactgat tagtacggac tgttaccaaa ttaattaata        7020
agcggcaaat gaagggcatg gatcaaaagc ttggatctcc tgcaggatct ggccggccgg        7080
atctc                                                                    7085
```

<210> SEQ ID NO 47
<211> LENGTH: 7873
<212> TYPE: DNA
<213> ORGANISM: Artificial Sequence
<220> FEATURE:
<223> OTHER INFORMATION: plasmid pKR912

<400> SEQUENCE: 47

```
ggccgcaagt atgaactaaa atgcatgtag gtgtaagagc tcatggagag catggaatat         60
tgtatccgac catgtaacag tataataact gagctccatc tcacttcttc tatgaataaa        120
caaaggatgt tatgatatat taacactcta tctatgcacc ttattgttct atgataaatt        180
tcctcttatt attataaatc atctgaatcg tgacggctta tggaatgctt caaatagtac        240
aaaaacaaat gtgtactata agactttcta aacaattcta accttagcat tgtgaacgag        300
acataagtgt taagaagaca taacaattat aatggaagaa gtttgtctcc atttatatat        360
tatatattac ccacttatgt attatattag gatgttaagg agacataaca attataaaga        420
gagaagtttg tatccattta tatattatat actacccatt tatatattat acttatccac        480
ttatttaatg tctttataag gtttgatcca tgatatttct aatattttag ttgatatgta        540
tatgaaaggg tactatttga actctcttac tctgtataaa ggttggatca tccttaaagt        600
gggtctattt aattttattg cttcttacag ataaaaaaaa aattatgagt tggtttgata        660
aaatattgaa ggatttaaaa taataataaa taacatataa tatatgtata taaatttatt        720
ataatataac atttatctat aaaaaagtaa atattgtcat aaatctatac aatcgtttag        780
ccttgctgga cgaatctcaa ttatttaaac gagagtaaac atatttgact ttttggttat        840
ttaacaaatt attatttaac actatatgaa attttttttt ttatcagcaa agaataaaat        900
taaattaaga aggacaatgg tgtcccaatc cttatacaac caacttccac aagaaagtca        960
agtcagagac aacaaaaaaa caagcaaagg aaatttttta atttgagttg tcttgtttgc       1020
tgcataattt atgcagtaaa acactacaca taaccctttt agcagtagag caatggttga       1080
ccgtgtgctt agcttctttt attttatttt tttatcagca aagaataaat aaaataaaat       1140
gagacacttc agggatgttt caacaagctt ggcgcgccgt tctatagtgt cacctaaatc       1200
gtatgtgtat gatacataag gttatgtatt aattgtagcc gcgttctaac gacaatatgt       1260
ccatatggtg cactctcagt acaatctgct ctgatgccgc atagttaagc cagccccgac       1320
acccgccaac acccgctgac gcgccctgac gggcttgtct gctcccggca tccgcttaca       1380
gacaagctgt gaccgtctcc gggagctgca tgtgtcagag gttttcaccg tcatcaccga       1440
aacgcgcgag acgaaaggc ctcgtgatac gcctattttt ataggttaat gtcatgacca       1500
aaatccctta acgtgagttt tcgttccact gagcgtcaga ccccgtagaa aagatcaaag       1560
gatcttcttg agatcctttt tttctgcgcg taatctgctg cttgcaaaca aaaaaaccac       1620
cgctaccagc ggtggtttgt ttgccggatc aagagctacc aactctttt ccgaaggtaa       1680 ctggcttcag cagagcgcag ataccaaata ctgtccttct agtgtagccg tagttaggcc       1740
accacttcaa gaactctgta gcaccgccta catacctcgc tctgctaatc ctgttaccag       1800
tggctgctgc cagtggcgat aagtcgtgtc ttaccgggtt ggactcaaga cgatagttac       1860
cggataaggc gcagcggtcg ggctgaacgg ggggttcgtg cacacagccc agcttggagc       1920
```

```
gaacgaccta caccgaactg agatacctac agcgtgagca ttgagaaagc gccacgcttc    1980
ccgaagggag aaaggcggac aggtatccgg taagcggcag ggtcggaaca ggagagcgca    2040
cgagggagct tccaggggga aacgcctggt atctttatag tcctgtcggg tttcgccacc    2100
tctgacttga gcgtcgattt ttgtgatgct cgtcaggggg gcggagccta tggaaaaacg    2160
ccagcaacgc ggcctttttta cggttcctgg ccttttgctg gccttttgct cacatgttct    2220
ttcctgcgtt atcccctgat tctgtggata accgtattac cgcctttgag tgagctgata    2280
ccgctcgccg cagccgaacg accgagcgca gcgagtcagt gagcgaggaa gcggaagagc    2340
gcccaatacg caaaccgcct ctccccgcgc gttggccgat tcattaatgc aggttgatcg    2400
attcgacatc gatctagtaa catagatgac accgcgcgcg ataatttatc ctagtttgcg    2460
cgctatattt tgttttctat cgcgtattaa atgtataatt gcgggactct aatcataaaa    2520
acccatctca taaataacgt catgcattac atgttaatta ttacatgctt aacgtaattc    2580
aacagaaatt atatgataat catcgcaaga ccggcaacag gattcaatct aagaaacttt    2640
tattgccaaa tgtttgaacg atctgcttcg acgcactcct tctttaggta cctcactatt    2700
cctttgccct cggacgagtg ctggggcgtc ggtttccact atcggcgagt acttctacac    2760
agccatcggt ccagacggcc gcgcttctgc gggcgatttg tgtacgcccg acagtcccgg    2820
ctccggatcg gacgattgcg tcgcatcgac cctgcgccca agctgcatca tcgaaattgc    2880
cgtcaaccaa gctctgatag agttggtcaa gaccaatgcg gagcatatac gcccggagcc    2940
gcggcgatcc tgcaagctcc ggatgcctcc gctcgaagta gcgcgtctgc tgctccatac    3000
aagccaacca cggcctccag aagaagatgt tggcgacctc gtattgggaa tccccgaaca    3060
tcgcctcgct ccagtcaatg accgctgtta tgcggccatt gtccgtcagg acattgttgg    3120
agccgaaatc cgcgtgcacg aggtgccgga cttcggggca gtcctcggcc caaagcatca    3180
gctcatcgag agcctgcgcg acggacgcac tgacggtgtc gtccatcaca gtttgccagt    3240
gatacacatg gggatcagca atcgcgcata tgaaatcacg ccatgtagtg tattgaccga    3300
ttccttgcgg tccgaatggg ccgaacccgc tcgtctggct aagatcggcc gcagcgatcg    3360
catccatggc ctccgcgacc ggctgcagaa cagcgggcag ttcggtttca ggcaggtctt    3420
gcaacgtgac accctgtgca cggcgggaga tgcaataggt caggctctcg ctgaattccc    3480
caatgtcaag cacttccgga atcgggagcg cggccgatgc aaagtgccga taaacataac    3540
gatctttgta gaaaccatcg gcgcagctat ttacccgcag gacatatcca cgccctccta    3600
catcgaagct gaaagcacga gattcttcgc cctccgagag ctgcatcagg tcggagacgc    3660
tgtcgaactt ttcgatcaga aacttctcga cagacgtcgc ggtgagttca ggcttttttca    3720 tggtttaata agaagagaaa agagttcttt tgttatggct gaagtaatag agaaatgagc    3780
tcgagcgtgt cctctccaaa tgaaatgaac ttccttatat agaggaaggg tcttgcgaag    3840
gatagtggga ttgtgcgtca tcccttacgt cagtggagat gtcacatcaa tccacttgct    3900
ttgaagacgt ggttggaacg tcttcttttt ccacgatgct cctcgtgggt gggggtccat    3960
ctttgggacc actgtcggca gaggcatctt gaatgatagc cttTCCttta tcgcaatgat    4020
ggcatttgta ggagccacct tccttttcta ctgtccttc gatgaagtga cagatagctg    4080
ggcaatggaa tccgaggagg tttcccgaaa ttatcctttg ttgaaaagtc tcaatagccc    4140
tttggtcttc tgagactgta tctttgacat ttttggagta gaccagagtg tcgtgctcca    4200
ccatgttgac gaagattttc ttcttgtcat tgagtcgtaa aagactctgt atgaactgtt    4260
cgccagtctt cacggcgagt tctgttagat cctcgatttg aatcttagac tccatgcatg    4320
```

```
gccttagatt cagtaggaac tacctttta gagactccaa tctctattac ttgccttggt      4380
ttatgaagca agccttgaat cgtccatact ggaatagtac ttctgatctt gagaaatatg     4440
tctttctctg tgttcttgat gcaattagtc ctgaatcttt tgactgcatc tttaaccttc     4500
ttgggaaggt atttgatctc ctggagattg ttactcgggt agatcgtctt gatgagacct     4560
gctgcgtagg cctctctaac catctgtggg tcagcattct ttctgaaatt gaagaggcta     4620
accttctcat tatcagtggt gaacatagtg tcgtcacctt caccttcgaa cttccttcct     4680
agatcgtaaa gatagaggaa atcgtccatt gtaatctccg gggcaaagga gatctctttt     4740
ggggctggat cactgctggg ccttttggtt cctagcgtga gccagtgggc ttttgctt      4800
ggtgggcttg ttagggcctt agcaaagctc ttgggcttga gttgagcttc tcctttgggg    4860
atgaagttca acctgtctgt ttgctgactt gttgtgtacg cgtcagctgc tgctcttgcc    4920
tctgtaatag tggcaaattt cttgtgtgca actccgggaa cgccgtttgt tgccgccttt    4980
gtacaacccc agtcatcgta tataccggca tgtggaccgt tatacacaac gtagtagttg    5040
atatgagggt gttgaatacc cgattctgct ctgagaggag caactgtgct gttaagctca    5100
gatttttgtg ggattggaat tggatcgatc tcgatcccgc gaaattaata cgactcacta    5160
tagggagacc acaacggttt ccctctagaa ataattttgt ttaactttaa gaaggagata    5220
tacccatgga aaagcctgaa ctcaccgcga cgtctgtcga agtttctg atcgaaaagt       5280
tcgacagcgt ctccgacctg atgcagctct cggagggcga agaatctcgt gctttcagct    5340
tcgatgtagg agggcgtgga tatgtcctgc gggtaaatag ctgcgccgat ggtttctaca    5400
aagatcgtta tgtttatcgg cactttgcat cggccgcgct cccgattccg gaagtgcttg    5460
acattgggga attcagcgag agcctgacct attgcatctc ccgccgtgca cagggtgtca    5520
cgttgcaaga cctgcctgaa accgaactgc ccgctgttct gcagccggtc gcggaggcta    5580
tggatgcgat cgctgcggcc gatcttagcc agacgagcgg gttcggccca ttcggaccgc    5640
aaggaatcgg tcaatacact acatggcgtg atttcatatg cgcgattgct gatccccatg    5700
tgtatcactg gcaaactgtg atggacgaca ccgtcagtgc gtccgtcgcg caggctctcg    5760
atgagctgat gctttgggcc gaggactgcc ccgaagtccg gcacctcgtg cacgcggatt    5820
tcggctccaa caatgtcctg acggacaatg gccgcataac agcggtcatt gactggagcg    5880
aggcgatgtt cggggattcc caatacgagg tcgccaacat cttcttctgg aggccgtggt    5940
tggcttgtat ggagcagcag acgcgctact tcgagcggag gcatccggag cttgcaggat    6000
cgccgcggct ccgggcgtat atgctccgca ttggtcttga ccaactctat cagagcttgg    6060
ttgacggcaa tttcgatgat gcagcttggg cgcagggtcg atgcgacgca atcgtccgat    6120
ccggagccgg gactgtcggg cgtacacaaa tcgcccgcag aagcgcggcc gtctggaccg    6180
atggctgtgt agaagtactc gccgatagtg gaaaccgacg ccccagcact cgtccgaggg    6240
caaaggaata gtgaggtaca gcttggatcg atccggctgc taacaaagcc cgaaaggaag    6300
ctgagttggc tgctgccacc gctgagcaat aactagcata ccccttgggg cctctaaac    6360
gggtcttgag gggttttttg ctgaaaggag gaactatatc cggatgatcg ggcgcgccgt    6420
cgacggatcc gtacgagatc cggccggcca gatcctgcag gagatccaag cttttgatcc    6480
atgcccttca tttgccgctt attaattaat tggtaacag tccgtactaa tcagttactt    6540
atccttcccc catcataatt aatcttggta gtctcgaatg ccacaacact gactagtctc    6600
ttggatcata agaaaagcc aaggaacaaa agaagacaaa acacaatgag agtatccttt      6660
gcatagcaat gtctaagttc ataaaattca aacaaaaacg caatcacaca cagtggacat    6720
```

| | |
|---|---|
| cacttatcca ctagctgatc aggatcgccg cgtcaagaaa aaaaaactgg accccaaaag | 6780 |
| ccatgcacaa caacacgtac tcacaaaggt gtcaatcgag cagcccaaaa cattcaccaa | 6840 |
| ctcaacccat catgagccct cacatttgtt gtttctaacc caacctcaaa ctcgtattct | 6900 |
| cttccgccac ctcattttg tttatttcaa cacccgtcaa actgcatgcc accccgtggc | 6960 |
| caaatgtcca tgcatgttaa caagacctat gactataaat agctgcaatc tcggcccagg | 7020 |
| ttttcatcat caagaaccag ttcaatatcc tagtacaccg tattaaagaa tttaagatat | 7080 |
| actgcggccg caccatggag gtggtgaatg aaatagtctc aattgggcag gaagttttac | 7140 |
| ccaaagttga ttatgcccaa ctctggagtg atgccagtca ctgtgaggtg ctttacttgt | 7200 |
| ccatcgcatt tgtcatcttg aagttcactc ttggcccccct tggtccaaaa ggtcagtctc | 7260 |
| gtatgaagtt tgttttcacc aattacaacc ttctcatgtc catttattcg ttgggatcat | 7320 |
| tcctctcaat ggcatatgcc atgtacacca tcggtgttat gtctgacaac tgcgagaagg | 7380 |
| cttttgacaa caacgtcttc aggatcacca cgcagttgtt ctatttgagc aagttcctgg | 7440 |
| agtatattga ctccttctat ttgccactga tgggcaagcc tctgacctgg ttgcaattct | 7500 |
| tccatcattt gggggcaccg atggatatgt ggctgttcta taattaccga aatgaagctg | 7560 |
| tttggatttt tgtgctgttg aatggtttca tccactggat catgtacggt tattattgga | 7620 |
| ccagattgat caagctgaag ttccccatgc caaaatccct gattcatca atgcagatca | 7680 |
| ttcaattcaa tgttggtttc tacattgtct ggaagtacag gaacattccc tgttatcgcc | 7740 |
| aagatgggat gaggatgttt ggctggttct tcaattactt ttatgttggc acagtcttgt | 7800 |
| gtttgttctt gaattctat gtgcaaacgt atatcgtcag gaagcacaag ggagccaaaa | 7860 |
| agattcagtg agc | 7873 |

<210> SEQ ID NO 48
<211> LENGTH: 9892
<212> TYPE: DNA
<213> ORGANISM: Artificial Sequence
<220> FEATURE:
<223> OTHER INFORMATION: plasmid pKR886r

<400> SEQUENCE: 48

| | |
|---|---|
| ggtcgactcg acgtacgtct agaggatccg tcgacggcgc gcccgatcat ccggatatag | 60 |
| ttcctccttt cagcaaaaaa ccccctcaaga cccgtttaga ggccccaagg ggttatgcta | 120 |
| gttattgctc agcggtggca gcagccaact cagcttcctt tcgggctttg ttagcagccg | 180 |
| gatcgatcca agctgtacct cactattcct ttgccctcgg acgagtgctg gggcgtcggt | 240 |
| ttccactatc ggcgagtact tctacacagc catcggtcca gacggccgcg cttctgcggg | 300 |
| cgatttgtgt acgcccgaca gtcccggctc cggatcggac gattgcgtcg catcgaccct | 360 |
| gcgcccaagc tgcatcatcg aaattgccgt caaccaagct ctgatagagt tggtcaagac | 420 |
| caatgcggag catatacgcc cggagccgcg gcgatcctgc aagctccgga tgcctccgct | 480 |
| cgaagtagcg cgtctgctgc tccatacaag ccaaccacgg cctccagaag aagatgttgg | 540 |
| cgacctcgta ttgggaatcc ccgaacatcg cctcgctcca gtcaatgacc gctgttatgc | 600 |
| ggccattgtc cgtcaggaca ttgttggagc cgaaatccgc gtgcacgagg tgccggactt | 660 |
| cggggcagtc ctcggcccaa agcatcagct catcgagagc ctgcgcgacg gacgcactga | 720 |
| cggtgtcgtc catcacagtt tgccagtgat acacatgggg atcagcaatc gcgcatatga | 780 |
| aatcacgcca tgtagtgtat tgaccgattc cttgcggtcc gaatgggccg aacccgctcg | 840 |
| tctggctaag atcggccgca gcgatcgcat ccatagcctc cgcgaccggc tgcagaacag | 900 |

```
cgggcagttc ggtttcaggc aggtcttgca acgtgacacc ctgtgcacgg cgggagatgc      960
aataggtcag gctctcgctg aattccccaa tgtcaagcac ttccggaatc gggagcgcgg     1020
ccgatgcaaa gtgccgataa acataacgat ctttgtagaa accatcggcg cagctattta     1080
cccgcaggac atatccacgc cctcctacat cgaagctgaa agcacgagat tcttcgccct     1140
ccgagagctg catcaggtcg gagacgctgt cgaacttttc gatcagaaac ttctcgacag     1200
acgtcgcggt gagttcaggc ttttccatgg gtatatctcc ttcttaaagt taaacaaaat     1260
tatttctaga gggaaaccgt tgtggtctcc ctatagtgag tcgtattaat ttcgcgggat     1320
cgagatctga tcaacctgca ttaatgaatc ggccaacgcg cggggagagg cggtttgcgt     1380
attgggcgct cttccgcttc ctcgctcact gactcgctgc gctcggtcgt tcggctgcgg     1440
cgagcggtat cagctcactc aaaggcggta atacggttat ccacagaatc agggga taac     1500 gcaggaaaga acatgtgagc aaaaggccag caaaaggcca ggaaccgtaa aaaggccgcg     1560 ttgctgcgt ttttccatag gctccgcccc cctgacgagc atcacaaaaa tcgacgctca     1620
agtcagaggt ggcgaaaccc gacaggacta taaagatacc aggcgtttcc ccctggaagc     1680
tccctcgtgc gctctcctgt tccgaccctg ccgcttaccg gatacctgtc cgcctttctc     1740
ccttcgggaa gcgtggcgct ttctcaatgc tcacgctgta ggtatctcag ttcggtgtag     1800
gtcgttcgct ccaagctggg ctgtgtgcac gaaccccccg ttcagcccga ccgctgcgcc     1860
ttatccggta actatcgtct tgagtccaac ccggtaagac acgacttatc gccactggca     1920
gcagccactg gtaacaggat tagcagagcg aggtatgtag gcggtgctac agagttcttg     1980
aagtggtggc ctaactacgg ctacactaga aggacagtat ttggtatctg cgctctgctg     2040
aagccagtta ccttcggaaa aagagttggt agctcttgat ccggcaaaca aaccaccgct     2100
ggtagcggtg gttttttgt ttgcaagcag cagattacgc gcagaaaaaa aggatctcaa     2160
gaagatcctt tgatctttc tacggggtct gacgctcagt ggaacgaaaa ctcacgttaa     2220
gggattttgg tcatgacatt aacctataaa aataggcgta tcacgaggcc ctttcgtctc     2280
gcgcgtttcg gtgatgacgg tgaaaacctc tgacacatgc agctcccgga cggtcaca     2340 gcttgtctgt aagcggatgc cgggagcaga caagcccgtc agggcgcgtc agcgggtgtt     2400
ggcgggtgtc ggggctggct taactatgcg gcatcagagc agattgtact gagagtgcac     2460
catatggaca tattgtcgtt agaacgcggc tacaattaat acataacctt atgtatcata     2520
cacatacgat ttaggtgaca ctatagaacg gcgcgccaag ctgggtctag aactagaaac     2580
gtgatgccac ttgttattga agtcgattac agcatctatt ctgttttact atttataact     2640
ttgccatttc tgacttttga aaactatctc tggatttcgg tatcgctttg tgaagatcga     2700
gcaaaagaga cgttttgtgg acgcaatggt ccaaatccgt tctacatgaa caaattggtc     2760
acaatttcca ctaaaagtaa ataaatggca agttaaaaaa ggaatatgca ttttactgat     2820
tgcctaggtg agctccaaga gaagttgaat ctacacgtct accaaccgct aaaaaaagaa     2880
aaacattgat atgtaacctg attccattag cttttgactt cttcaacaga ttctctactt     2940
agatttctaa cagaaatatt attactagca catcattttc agtctcacta cagcaaaaaa     3000
tccaacggca aatacagac aacaggagat atcagactac agagatagat agatgctact     3060
gcatgtagta agttaaataa aaggaaaata aaatgtcttg ctaccaaaac tactacagac     3120
tatgatgctc accacaggcc aaatcctgca actaggacag cattatctta tatatattgt     3180
acaaaacaag catcaaggaa catttggtct aggcaatcag tacctcgttc taccatcacc     3240
ctcagttatc acatccttga aggatccatt actgggaatc atcggcaaca catgctcctg     3300
```

```
atggggcaca atgacatcaa gaaggtaggg gccaggggtg tccaacattc tctgaattgc    3360
cgctctaagc tcttccttct tcgtcactcg cgctgccggt atcccacaag catcagcaaa    3420
cttgagcatg tttgggaata tctcgctctc gctagacgga tctccaagat aggtgtgagc    3480
tctattggac ttgtagaacc tatcctccaa ctgaaccacc atacccaaat gctgattgtt    3540
caacaacaat atcttaactg ggagattctc cactcttata gtggccaact cctgaacatt    3600
catgatgaaa ctaccatccc catcaatgtc aaccacaaca gccccagggt tagcaacagc    3660
agcaccaata gccgcaggca atccaaaacc catggctcca agacccccctg aggtcaacca    3720
ctgcctcggt ctcttgtact tgtaaaactg cgcagcccac atttgatgct gcccaacccc    3780
agtactaaca atagcatctc cattagtcaa ctcatcaaga acctcgatag catgctgcgg    3840
agaaatcgcg tcctggaatg tcttgtaacc caatggaaac ttgtgtttct gcacattaat    3900
ctcttctctc caacctccaa gatcaaactt accctccact cctttctcct ccaaaatcat    3960
attaattccc ttcaaggcca acttcaaatc cgcgcaaacc gacacgtgcg cctgcttgtt    4020
cttcccaatc tcggcagaat caatatcaat gtgaacaatc ttagccctac tagcaaaagc    4080
ctcaagcttc ccagtaacac ggtcatcaaa ccttacccca aaggcaagca acaaatcact    4140
attgtcaaca gcatagttag cataaacagt accatgcata cccagcatct gaagggaata    4200
ttcatcacca ataggaaaag ttccaagacc cattaaagtg ctagcaacgg gaataccagt    4260
gagttcaaca aagcgcctca attcagcact ggaattcaaa ctgccaccgc cgacgtagag    4320
aacgggcttt tgggcctcca tgatgagtct gacaatgtgt tccaattggg cctcggcggg    4380
gggcctgggc agcctggcga ggtaaccggg gaggttaacg ggctcgtccc aattaggcac    4440
ggcgagttgc tgctgaacgt ctttgggaat gtcgatgagg accggaccgg gcggccgga    4500
ggtggcgacg aagaaagcct cggcgacgac gcggggggatg tcgtcgacgt cgaggatgag    4560
gtagttgtgc ttcgtgatgg atctgctcac ctccacgatc gggtttctt ggaaggcgtc    4620
ggtgccgatc atccggcggg cgacctggcc ggtgatggcg acgactggga cgctgtccat    4680
taaagcgtcg gcgaggccgc tcacgaggtt ggtggcgccg gggccggagg tggcaatgca    4740
gacgccgggg aggccggagg aacgcgcgta gccttcggcg gcgaagacgc cgccctgctc    4800
gtggcgcggg agcacgttgc ggatggcggc ggagcgcgtg agcgcctggt ggatctccat    4860
cgacgcaccg ccggggtacg cgaacaccgt cgtcacgccc tgcctctcca gcgcctccac    4920
aaggatgtcc gcgcccttgc gaggttcgcc ggaggcgaac cgtgacacga agggctccgt    4980
ggtcggcgct tccttggtga agggcgccgc cgtgggggt ttggagatgg aacatttgat    5040
tttgagagcg tggttgggtt tggtgagggt ttgatgagag agagggaggg tggatctagt    5100
aatgcgtttg gggaaggtgg ggtgtgaaga ggaagaagag aatcgggtgg ttctggaagc    5160
ggtggccgcc attgtgttgt gtggcatggt tatacttcaa aaactgcaca acaagcctag    5220
agttagtacc taaacagtaa atttacaaca gagagcaaag acacatgcaa aaatttcagc    5280
cataaaaaaa gttataatag aatttaaagc aaaagtttca ttttttaaac atatatacaa    5340
acaaactgga tttgaaggaa gggattaatt cccctgctca agtttgaat tcctattgtg    5400
acctatactc gaataaaatt gaagcctaag gaatgtatga gaaacaagaa aacaaaacaa    5460
aactacagac aaaacaagtac aattacaaaa ttcgctaaaa ttctgtaatc accaaacccc    5520
atctcagtca gcacaaggcc caaggtttat tttgaaataa aaaaaagtg attttatttc    5580
tcataagcta aagaaagaa aggcaattat gaaatgattt cgactagatc tgaaagtcca    5640
acgcgtattc cgcagatatt aaagaaagag tagagtttca catggatcct agatggaccc    5700
```

```
agttgaggaa aaagcaaggc aaagcaaacc agaagtgcaa gatccgaaat tgaaccacgg    5760
aatctaggat ttggtagagg gagaagaaaa gtacctgag aggtagaaga gaagagaaga     5820
gcagagagat atatgaacga gtgtgtcttg gtctcaactc tgaagcgata cgagtttaga    5880
ggggagcatt gagttccaat ttatagggaa accgggtggc aggggtgagt taatgacgga    5940
aaagccccta agtaacgaga ttggattgtg ggttagattc aaccgtttgc atccgcggct    6000
tagattgggg aagtcagagt gaatctcaac cgttgactga gttgaaaatt gaatgtagca    6060
accaattgag ccaaccccag cctttgccct ttgattttga tttgtttgtt gcatactttt    6120
tatttgtctt ctggttctga ctctctttct ctcgtttcaa tgccaggttg cctactccca    6180
caccactcac aagaagattc tactgttagt attaaatatt ttttaatgta ttaaatgatg    6240
aatgcttttg taaacagaac aagactatgt ctaataagtg tcttgcaaca ttttttaaga    6300
aattaaaaaa aatatattta ttatcaaaat caaatgtatg aaaaatcatg aataatataa    6360
ttttatacat ttttttaaaa aatcttttaa tttcttaatt aatatcttaa aaataatgat    6420
taatatttaa cccaaaataa ttagtatgat tggtaaggaa gatatccatg ttatgtttgg    6480
atgtgagttt gatctagagc aaagcttact agagtcgacc tgcagccgg gggatccgcc     6540 cacgtacggt accatctgct aatattttaa atcacatgca agagaggagg catggttcca    6600
ttttctacct tcacattatt tgagaaaaac gaacttgttc tgtgttttat ttttgccctt    6660
cacattagta caacgtggaa gactcatggt tacacagaat catacataag tacaatgctt    6720
gtccctaaga aaacaagcac tcgttgtatt gaacctttac ggctcatgcg gccgcgaatt    6780
cactagtgat tgaattcgcg gccgcttagt ccgacttggc cttggcggcc gcggccgact    6840
ctttgagcgt gaagatctgc gccgtctcgg gcacagcgcc gtagttgaca aagaggtgcg    6900
cggtcttgaa gaaggccgtg atgatgggct cgtcgttcct gcgcacgagg tgcgggtacg    6960
cggccgcaaa gtgcttggtg gcttcgttga gcttgtagtg cggaatgatc gggaacaagt    7020
ggtggacctg gtgcgtgcca atgtggtggc tcaggttgtc cacgaacgcg ccgtacgagc    7080
ggtcgacgct cgagaggttg cccttgacgt acgtccactc cgagtcgccg taccacggcg    7140
tcgcttcgtc gttgtggtgc aagaaggtcg taatgacgag gaacgaagca agacaaaga    7200 gcggcgcata gtagtagagg cccatgacgg caaagccgag cgagtatgtg aggtacgcgt    7260
acgcggcgaa gaaggcggcc cagacgccga gcgacgat gacggccgac gcgcggcgaa     7320
ggaggagcgg gtcccacggg tcaaagtggc tcatcgtgcg cggggcatac ccgaccttca    7380
agtagacaaa ccacgcaccg ccgagcgtgt agacccattg gcgcacgtcc tggaggtcct    7440
tgaccgaccg gtgcgggtaa agatctcgt ccttatcaat gttgcccgtg ttcttgtggt     7500
ggtggcggtg cgtcacgcgc cagctctcga acggcgtcaa aatcgcagag tgcatgatgc    7560
agccgatgat aaagttgacg ctgtggtagc gcgagaaggc cgagtggccg cagtcgtggc    7620
cgaccgtgaa gaagccccag aagatgacgc cctgcacgta gatgtaggtg gcgcaaacga    7680
gcgcgtggag cagaacgtta tcggcaatga acggcgtcga gcgcgccgcg tagagcagcg    7740
ccgccgaggc cgacgcgttg aagatcgcgc gggccgtgta gtagagcgag aggccgaggt    7800
tcgactcaaa gcacgcgttc gggatcgagt gcttgagctc cgtgagcgtc gggaactcga    7860
ccttcgtctt atcctcagtc atgcggccgc tgaagtattg cttcttagtt aacctttcct    7920
ttctctctca gctatgtgaa ttcatttttgc tttcgtcaca atttatatag tgaaattgga    7980
tctttggagt taacgccttc acaggattat cgtgttagaa caatgctttt tcatgttcta    8040
attagtagta cattacaaat gtgcactcta ttcaataagc atcttttggc acgttaataa    8100
```

```
atcatgtgaa aaaaaaatac tactatttca aagaaagtgt tgtaaaaaga aacggaaaga    8160
gagctggctt cagttgttga gacttgtttg ctagtaaaaa tggtgtgaag agtgattcat    8220
ggtgaggtgg tttttcgtcc ctttctgttt gcatgaaaaa caaatggcaa gagatgacgt    8280
aggattcctt cccttaacga ttatctgttt ttaatttcaa atatacatat aggaatttat    8340
gaattactaa ggttgtaaaa tatgctggtc atttatttat ggctaaaata tttttttttc    8400
tcgtaaatat aaaaatattt aaaatttatt tttatcatat tttttatcct tataaaatta    8460
tgtgtacaac ctatataaaa aaatatcata tttaatattg attatatgtt taatcaatat    8520
aaaaaatcat tatcatatat ttagatttat tcgaatatac atctaaacaa aaaataacat    8580
attttaattt tatgaagaaa aaaaaatatt ttatcctta tttatttaag attaattaat    8640
agttatgtat tgtggaaaga cttttacaca tgcaatagat atactgaatc aattagatgc    8700
caatgctgag ttgaaaatca cttgaggagg ggaggagact tgccaatgct tttcagtttc    8760
atttaaatga tttagtggag gagatagagt agtgataaag gcatgcccca attttggagt    8820
gtatatatga gtgaaataa gagagggata gagagaaaaa ataaagagag taaaaataat    8880
taatgtgaaa tgatatgata aaaaaataaa gaaagagata aagagaaaaa tgaaatgaga    8940
gatagatgaa atagagagta gatacatgtt tgtttaggtt ttttttagga aataacacat    9000
ttttttctca tcacttatta ctcactgtca atttcctctc tttcaatcat aatgatatga    9060
tttgtttaac aaaaatgtga aaaacatat aaagtaaaat attttataa attgataaat    9120
aaaaatttac aaaatttatt tcttattaaa ttgaatagaa aatgaaagaa agaaaaagaa    9180
aaagtatata taaaatgata tagctttaaa aagaataaat ttttcatatc agtctttttt    9240
taataattta gaaatattta agtatatagc aaaaatataa tgtactttac atatgcataa    9300
ataataattt gaaatagaa ctaatagaat agagaaaaaa gtaatataat aattaactat    9360
atgaaaattt agaagggaca atatttttaa ttaagaatat aaacaatatt tcttttcatg    9420
taatgaggga cggatgtacg gggccagtgt tggagtcaaa gccaaaatag tcacgggaa    9480
attaatgcac tgcatgacta ttcgaaaaaa ttcactagcc ttacttagat gttagattaa    9540
tagctagggg gtgcagataa ttttgaaagg catgaaaaac attaatttgt acattgcaag    9600
cttttgatga caagctttgc aattgttcac actaccttat gccatttata aatagagtga    9660
ttggcatatg aaggaaatca tgagagtcga agcgaaaaac aaagcttgag agtgtaggaa    9720
aaatacagtt tttttggtaa aaatacagta tttgaatagg agcgaaaaat atcctttcaa    9780
aatgatcctt ttctttttt ttttttttct tgttgttctt ggtcagttat tcaaaggaaa    9840
agggattgaa ataaaaactt gcatgtggga tcgtacgtcg agtcgacctg ca            9892
```

<210> SEQ ID NO 49
<211> LENGTH: 6021
<212> TYPE: DNA
<213> ORGANISM: Artificial Sequence
<220> FEATURE:
<223> OTHER INFORMATION: plasmid pKR271

<400> SEQUENCE: 49

```
ggccgcgaat tcaatcacta gtgaattcgc ggccgcatga gccgtaaagg ttcaatacaa      60
cgagtgcttg ttttcttagg gacaagcatt gtacttatgt atgattctgt gtaaccatga     120
gtcttccacg ttgtactaat gtgaagggca aaaataaaac acagaacaag ttcgttttc     180
tcaaataatg tgaaggtaga aaatggaacc atgcctcctc tcttgcatgt gatttaaaat     240
attagcagat ggtaccgtac gtgggcggat ccccgggct gcaggaattc actggccgtc     300
```

```
gttttacaac gtcgtgactg ggaaaaccct ggcgttaccc aacttaatcg ccttgcagca    360 catcccctt tcgccagctg gcgtaatagc gaagaggccc gcaccgatcg cccttcccaa    420
cagttgcgca gcctgaatgg cgaatggcgc ctgatgcggt attttctcct tacgcatctg    480
tgcggtattt cacaccgcat atggtgcact ctcagtacaa tctgctctga tgccgcatag    540
ttaagccagc cccgacaccc gccaacaccc gctgacgcgc cctgacgggc ttgtctgctc    600
ccggcatccg cttacagaca agctgtgacc gtctccggga gctgcatgtg tcagaggttt    660
tcaccgtcat caccgaaacg cgcgagacga agggcctcg tgatacgcct attttttatag    720 gttaatgtca tgataataat ggtttcttag acgtcaggtg gcacttttcg gggaaatgtg    780
cgcggaaccc ctatttgttt attttttctaa atacattcaa atatgtatcc gctcatgaga    840
caataaccct gataaatgct tcaataatat tgaaaaagga agagtatgag tattcaacat    900
ttccgtgtcg cccttattcc cttttttgcg gcattttgcc ttcctgtttt tgctcaccca    960
gaaacgctgg tgaaagtaaa agatgctgaa gatcagttgg gtgcacgagt gggttacatc   1020
gaactggatc tcaacagcgg taagatcctt gagagttttc gccccgaaga acgttttcca   1080
atgatgagca ctttttaaagt tctgctatgt ggcgcggtat tatcccgtat tgacgccggg   1140
caagagcaac tcggtcgccg catacactat tctcagaatg acttggttga gtactcacca   1200
gtcacagaaa agcatcttac ggatggcatg acagtaagag aattatgcag tgctgccata   1260
accatgagtg ataacactgc ggccaactta cttctgacaa cgatcggagg accgaaggag   1320
ctaaccgctt ttttgcacaa catgggggat catgtaactc gccttgatcg ttgggaaccg   1380
gagctgaatg aagccatacc aaacgacgag cgtgacacca cgatgcctgt agcaatggca   1440
acaacgttgc gcaaactatt aactggcgaa ctacttactc tagcttcccg gcaacaatta   1500
atagactgga tggaggcgga taaagttgca ggaccacttc tgcgctcggc ccttccggct   1560
ggctggttta ttgctgataa atctggagcc ggtgagcgtg ggtctcgcgg tatcattgca   1620
gcactggggc cagatggtaa gccctcccgt atcgtagtta tctacacgac ggggagtcag   1680
gcaactatgg atgaacgaaa tagacagatc gctgagatag gtgcctcact gattaagcat   1740
tggtaactgt cagaccaagt ttactcatat atactttaga ttgatttaaa acttcattt    1800 taatttaaaa ggatctaggt gaagatcctt tttgataatc tcatgaccaa aatcccttaa   1860
cgtgagtttt cgttccactg agcgtcagac cccgtagaaa agatcaaagg atcttcttga   1920 gatcctttt ttctgcgcgt aatctgctgc ttgcaaacaa aaaaaccacc gctaccagcg   1980
gtggtttgtt tgccggatca agagctacca actctttttc cgaaggtaac tggcttcagc   2040
agagcgcaga taccaaatac tgtccttcta gtgtagccgt agttaggcca ccacttcaag   2100
aactctgtag caccgcctac atacctcgct ctgctaatcc tgttaccagt ggctgctgcc   2160
agtggcgata gtcgtgtct taccgggttg gactcaagac gatagttacc ggataaggcg   2220
cagcggtcgg gctgaacggg gggttcgtgc acacagccca gcttggagcg aacgacctac   2280
accgaactga gatacctaca gcgtgagcta tgagaaagcg ccacgcttcc gaagggaga   2340 aaggcggaca ggtatccggt aagcggcagg gtcggaacag gagagcgcac gagggagctt   2400
ccagggggaa acgcctggta tctttatagt cctgtcgggt ttcgccacct ctgacttgag   2460
cgtcgatttt tgtgatgctc gtcagggggg cggagcctat ggaaaaacgc cagcaacgcg   2520
gcctttttac ggttcctggc cttttgctgg ccttttgctc acatgttctt tcctgcgtta   2580
tcccctgatt ctgtggataa ccgtattacc gcctttgagt gagctgatac cgctcgccgc   2640
agccgaacga ccgagcgcag cgagtcagtg agcgaggaag cggaagagcg cccaatacgc   2700
```

```
aaaccgcctc tccccgcgcg ttggccgatt cattaatgca gctggcacga caggtttccc    2760
gactggaaag cgggcagtga gcgcaacgca attaatgtga gttagctcac tcattaggca    2820
ccccaggctt tacactttat gcttccggct cgtatgttgt gtggaattgt gagcggataa    2880
caatttcaca caggaaacag ctatgaccat gattacgcca agcttgcatg cctgcaggtc    2940
gactcgacgt acgatcccac atgcaagttt ttatttcaat ccctttcct ttgaataact    3000 gaccaagaac aacaagaaaa aaaaaaaaaa agaaaaggat cattttgaaa ggatatttt    3060 cgctcctatt caaatactgt attttacca aaaaactgt attttccta cactctcaag    3120 ctttgttttt cgcttcgact ctcatgattt ccttcatatg ccaatcactc tatttataaa    3180
tggcataagg tagtgtgaac aattgcaaag cttgtcatca aaagcttgca atgtacaaat    3240
taatgttttt catgcctttc aaaattatct gcaccccta gctattaatc taacatctaa    3300
gtaaggctag tgaattttt cgaatagtca tgcagtgcat taatttcccc gtgactattt    3360
tggctttgac tccaacactg gccccgtaca tccgtccctc attacatgaa aagaaatatt    3420
gtttatattc ttaattaaaa atattgtccc ttctaaattt tcatatagtt aattattata    3480
ttactttttt ctctattcta ttagttctat tttcaaatta ttatttatgc atatgtaaag    3540
tacattatat ttttgctata tacttaaata tttctaaatt attaaaaaaa gactgatatg    3600
aaaaatttat tcttttaaa gctatatcat tttatatata cttttttcttt tcttttcttt    3660 cattttctat tcaatttaat aagaaataaa ttttgtaaat tttatttat caatttataa    3720 aaatatttta ctttatatgt ttttttcacat ttttgttaaa caaatcatat cattatgatt    3780
gaaagagagg aaattgacag tgagtaataa gtgatgagaa aaaatgtgt tatttcctaa    3840 aaaaaaccta aacaaacatg tatctactct ctatttcatc tatctctcat ttcatttttc    3900
tctttatctc tttctttatt ttttatcat atcatttcac attaattatt tttactctct    3960 ttatttttc tctctatccc tctcttattt ccactcatat atacactcca aaattgggc    4020 atgcctttat cactactcta tctcctccac taaatcattt aaatgaaact gaaaagcatt    4080
ggcaagtctc ctcccctcct caagtgattt ccaactcagc attggcatct aattgattca    4140
gtatatctat tgcatgtgta aaagtctttc cacaatacat aactattaat taatcttaaa    4200
taaataaagg ataaaatatt ttttttttct cataaaatta aaatatgtta ttttttgttt    4260
agatgtatat tcgaataaat ctaaatatat gataatgatt tttatattg attaaacata    4320 taatcaatat taaatatgat atttttttat ataggttgta cacataattt tataaggata    4380
aaaaatatga taaaaataaa ttttaaatat tttatattt acgagaaaaa aaaatatttt    4440
agccataaat aaatgaccag catatttac aaccttagta attcataaat tcctatatgt    4500
atatttgaaa ttaaaacag ataatcgtta agggaaggaa tcctacgtca tctcttgcca    4560
tttgtttttc atgcaaacag aaagggacga aaaccacct caccatgaat cactcttcac    4620 accatttta ctagcaaaca agtctcaaca actgaagcca gctctctttc cgtttctttt    4680
tacaacactt tctttgaaat agtagtattt ttttttcaca tgatttatta acgtgccaaa    4740
agatgcttat tgaatagagt gcacatttgt aatgtactac taattagaac atgaaaaagc    4800
attgttctaa cacgataatc ctgtgaaggc gttaactcca aagatccaat ttcactatat    4860
aaattgtgac gaaagcaaaa tgaattcaca tagctgagag agaaaggaaa ggttaactaa    4920
gaagcaatac ttcagcggcc gcatgactga ggataagacg aaggtcgagt tcccgacgct    4980
cacggagctc aagcactcga tcccgaacgc gtgctttgag tcgaacctcg gcctctcgct    5040
ctactacacg gcccgcgcga tcttcaacgc gtcggcctcg gcggcgctgc tctacgcggc    5100
```

-continued

| | |
|---|---|
| gcgctcgacg ccgttcattg ccgataacgt tctgctccac gcgctcgttt gcgccaccta | 5160 |
| catctacgtg cagggcgtca tcttctgggg cttcttcacg gtcggccacg actgcggcca | 5220 |
| ctcggccttc tcgcgctacc acagcgtcaa ctttatcatc ggctgcatca tgcactctgc | 5280 |
| gattttgacg ccgttcgaga gctggcgcgt gacgcaccgc caccaccaca agaacacggg | 5340 |
| caacattgat aaggacgaga tcttttaccc gcaccggtcg gtcaaggacc tccaggacgt | 5400 |
| gcgccaatgg gtctacacgc tcggcggtgc gtggtttgtc tacttgaagg tcgggtatgc | 5460 |
| ccgcgcacg atgagccact ttgacccgtg ggacccgctc ctccttcgcc gcgcgtcggc | 5520 |
| cgtcatcgtg tcgctcggcg tctgggccgc cttcttcgcc gcgtacgcgt acctcacata | 5580 |
| ctcgctcggc tttgccgtca tgggcctcta ctactatgcg ccgctctttg tctttgcttc | 5640 |
| gttcctcgtc attacgacct tcttgcacca caacgacgaa gcgacgccgt ggtacgcgcga | 5700 |
| ctcggagtgg acgtacgtca agggcaacct ctcgagcgtc gaccgctcgt acggcgcgtt | 5760 |
| cgtggacaac ctgagccacc acattggcac gcaccaggtc caccacttgt tcccgatcat | 5820 |
| tccgcactac aagctcaacg aagccaccaa gcactttgcg gccgcgtacc cgcacctcgt | 5880 |
| gcgcaggaac gacgagccca tcatcacggc cttcttcaag accgcgcacc tctttgtcaa | 5940 |
| ctacggcgct gtgcccgaga cggcgcagat cttcacgctc aaagagtcgg ccgcggccgc | 6000 |
| caaggccaag tcggactaag c | 6021 |

<210> SEQ ID NO 50
<211> LENGTH: 6524
<212> TYPE: DNA
<213> ORGANISM: Artificial Sequence
<220> FEATURE:
<223> OTHER INFORMATION: plasmid pKR226

<400> SEQUENCE: 50

| | |
|---|---|
| gtacgtctag aggatccgtc gacggcgcgc ccgatcatcc ggatatagtt cctcctttca | 60 |
| gcaaaaaacc cctcaagacc cgtttagagg ccccaagggg ttatgctagt tattgctcag | 120 |
| cggtggcagc agccaactca gcttcctttc gggctttgtt agcagccgga tcgatccaag | 180 |
| ctgtacctca ctattccttt gccctcggac gagtgctggg gcgtcggttt ccactatcgg | 240 |
| cgagtacttc tacacagcca tcggtccaga cggccgcgct tctgcgggcg atttgtgtac | 300 |
| gcccgacagt cccggctccg gatcggacga ttgcgtcgca tcgaccctgc gcccaagctg | 360 |
| catcatcgaa attgccgtca accaagctct gatagagttg gtcaagacca atgcggagca | 420 |
| tatacgcccg gagccgcggc gatcctgcaa gctccggatg cctccgctcg aagtagcgcg | 480 |
| tctgctgctc catacaagcc aaccacggcc tccagaagaa gatgttggcg acctcgtatt | 540 |
| gggaatcccc gaacatcgcc tcgctccagt caatgaccgc tgttatgcgg ccattgtccg | 600 |
| tcaggacatt gttggagccg aaatccgcgt gcacgaggtg ccggacttcg ggcagtcct | 660 |
| cggcccaaag catcagctca tcgagagcct gcgcgacgga cgcactgacg gtgtcgtcca | 720 |
| tcacagtttg ccagtgatac acatggggat cagcaatcgc gcatatgaaa tcacgccatg | 780 |
| tagtgtattg accgattcct tgcggtccga atgggccgaa cccgctcgtc tggctaagat | 840 |
| cggccgcagc gatcgcatcc atagcctccg cgaccggctg cagaacagcg gcagttcgg | 900 |
| tttcaggcag gtcttgcaac gtgacaccct gtgcacggcg ggagatgcaa taggtcaggc | 960 |
| tctcgctgaa ttccccaatg tcaagcactt ccggaatcgg agcgcggcc gatgcaaagt | 1020 |
| gccgataaac ataacgatct ttgtagaaac catcggcgca gctatttacc cgcaggacat | 1080 |
| atccacgccc tcctacatcg aagctgaaag cacgagattc ttcgccctcc gagagctgca | 1140 |

```
tcaggtcgga gacgctgtcg aacttttcga tcagaaactt ctcgacagac gtcgcggtga   1200
gttcaggctt ttccatgggt atatctcctt cttaaagtta aacaaaatta tttctagagg   1260
gaaaccgttg tggtctccct atagtgagtc gtattaattt cgcgggatcg agatctgatc   1320
aacctgcatt aatgaatcgg ccaacgcgcg gggagaggcg gtttgcgtat tgggcgctct   1380
tccgcttcct cgctcactga ctcgctgcgc tcggtcgttc ggctgcggcg agcggtatca   1440
gctcactcaa aggcggtaat acggttatcc acagaatcag gggataacgc aggaaagaac   1500
atgtgagcaa aaggccagca aaaggccagg aaccgtaaaa aggccgcgtt gctggcgttt   1560
ttccataggc tccgcccccc tgacgagcat cacaaaaatc gacgctcaag tcagaggtgg   1620
cgaaacccga caggactata aagataccag gcgtttcccc ctggaagctc cctcgtgcgc   1680
tctcctgttc cgaccctgcc gcttaccgga tacctgtccg cctttctccc ttcgggaagc   1740
gtggcgcttt ctcaatgctc acgctgtagg tatctcagtt cggtgtaggt cgttcgctcc   1800
aagctgggct gtgtgcacga accccccgtt cagcccgacc gctgcgcctt atccggtaac   1860
tatcgtcttg agtccaaccc ggtaagacac gacttatcgc cactggcagc agccactggt   1920
aacaggatta gcagagcgag gtatgtaggc ggtgctacag agttcttgaa gtggtggcct   1980
aactacggct acactagaag gacagtattt ggtatctgcg ctctgctgaa gccagttacc   2040
ttcggaaaaa gagttggtag ctcttgatcc ggcaaacaaa ccaccgctgg tagcggtggt   2100
ttttttgttt gcaagcagca gattacgcgc agaaaaaaag gatctcaaga agatcctttg   2160
atcttttcta cggggtctga cgctcagtgg aacgaaaact cacgttaagg gattttggtc   2220
atgacattaa cctataaaaa taggcgtatc acgaggccct ttcgtctcgc gcgtttcggt   2280
gatgacggtg aaaacctctg acacatgcag ctcccggaga cggtcacagc ttgtctgtaa   2340
gcggatgccg ggagcagaca agcccgtcag gcgcgtcag cgggtgttgg cgggtgtcgg    2400
ggctggctta actatgcggc atcagagcag attgtactga gagtgcacca tatggacata   2460
ttgtcgttag aacgcggcta caattaatac ataaccttat gtatcataca catacgattt   2520
aggtgacact atagaacggc gcgccaagct gggtctagaa ctagaaacgt gatgccactt   2580
gttattgaag tcgattacag catctattct gttttactat ttataacttt gccatttctg   2640
acttttgaaa actatctctg gatttcggta tcgctttgtg aagatcgagc aaaagagacg   2700
ttttgtggac gcaatggtcc aaatccgttc tacatgaaca aattggtcac aatttccact   2760
aaaagtaaat aaatggcaag ttaaaaaagg aatatgcatt ttactgattg cctaggtgag   2820
ctccaagaga agttgaatct acacgtctac caaccgctaa aaaagaaaa acattgtatt    2880
gtaacctgat tccattagct tttgacttct tcaacagatt ctctacttag atttctaaca   2940
gaaatattat tactagcaca tcattttcag tctcactaca gcaaaaaatc caacggcaca   3000
atacagacaa caggagatat cagactacag agatagatag atgctactgc atgtagtaag   3060
ttaaataaaa ggaaaataaa atgtcttgct accaaaacta ctacgactaa tgatgctcac   3120
cacaggccaa atcctgcaac taggacagca ttatcttata tatattgtac aaaacaagca   3180
tcaaggaaca tttggtctag gcaatcagta cctcgttcta ccatcaccct cagttatcac   3240
atccttgaag gatccattac tgggaatcat cggcaacaca tgctcctgat ggggcacaat   3300
gacatcaaga aggtaggggc caggggtgtc caacattctc tgaattgccg ctctaagctc   3360
ttccttcttc gtcactcgcg ctgccggtat cccacaagca tcagcaaact tgagcatgtt   3420
tgggaatatc tcgctctcgc tagacggatc tccaagatag gtgtgagctc tattggactt   3480
gtagaaccta tcctccaact gaaccaccat acccaaatgc tgattgttca acaacaatat   3540
```

```
cttaactggg agattctcca ctcttatagt ggccaactcc tgaacattca tgatgaaact   3600
accatcccca tcaatgtcaa ccacaacagc cccagggtta gcaacagcag caccaatagc   3660
cgcaggcaat ccaaaaccca tggctccaag acccccctgag gtcaaccact gcctcggtct   3720
cttgtacttg taaaactgcg cagcccacat ttgatgctgc ccaaccccag tactaacaat   3780
agcatctcca ttagtcaact catcaagaac ctcgatagca tgctgcggag aaatcgcgtc   3840
ctggaatgtc ttgtaaccca atggaaactt gtgtttctgc acattaatct cttctctcca   3900
acctccaaga tcaaacttac cctccactcc tttctcctcc aaaatcatat taattcccct   3960
caaggccaac ttcaaatccg cgcaaaccga cacgtgcgcc tgcttgttct tcccaatctc   4020
ggcagaatca atatcaatgt gaacaatctt agccctacta gcaaaagcct caagcttccc   4080
agtaacacgg tcatcaaacc ttaccccaaa ggcaagcaac aaatcactat tgtcaacagc   4140
atagttagca taaacagtac catgcatacc cagcatctga agggaatatt catcaccaat   4200
aggaaaagtt ccaagaccca ttaaagtgct agcaacggga ataccagtga gttcaacaaa   4260
gcgcctcaat tcagcactgg aattcaaact gccaccgccg acgtagagaa cgggcttttg   4320
ggcctccatg atgagtctga caatgtgttc caattgggcc tcggcggggg gcctgggcag   4380
cctggcgagg taaccgggga ggttaacggg ctcgtcccaa ttaggcacgg cgagttgctg   4440
ctgaacgtct ttgggaatgt cgatgaggac cggaccgggg cggccggagg tggcgacgaa   4500
gaaagcctcg gcgacgacgc gggggatgtc gtcgacgtcg aggatgaggt agttgtgctt   4560
cgtgatggat ctgctcacct ccacgatcgg ggtttcttgg aaggcgtcgg tgccgatcat   4620
ccggcgggcg acctggccgg tgatggcgac gactgggacg ctgtccatta aagcgtcggc   4680
gaggccgctc acgaggttgg tggcgccggg gccggaggtg gcaatgcaga cgccggggag   4740
gccggaggaa cgcgcgtagc cttcggcggc gaagacgccg ccctgctcgt ggcgcgggag   4800
cacgttgcgg atggcggcgg agcgcgtgag cgcctggtgg atctccatcg acgcaccgcc   4860
ggggtacgcg aacaccgtcg tcacgccctg cctctccagc gcctccacaa ggatgtccgc   4920
gcccttgcga ggttcgccgg aggcgaaccg tgacacgaag gctccgtgg tcggcgcttc    4980
cttggtgaag ggcgccgccg tgggggggttt ggagatggaa catttgattt tgagagcgtg   5040
gttgggtttg gtgagggttt gatgagagag agggagggtg gatctagtaa tgcgtttggg   5100
gaaggtgggg tgtgaagagg aagaagagaa tcgggtggtt ctggaagcgg tggccgccat   5160
tgtgttgtgt ggcatggtta tacttcaaaa actgcacaac aagcctagag ttagtaccta   5220
aacagtaaat ttacaacaga gagcaaagac acatgcaaaa atttcagcca taaaaaaagt   5280
tataatagaa tttaaagcaa aagtttcatt ttttaaacat atatacaaac aaactggatt   5340
tgaaggaagg gattaattcc cctgctcaaa gtttgaattc ctattgtgac ctatactcga   5400
ataaaattga agcctaagga atgtatgaga acaagaaaa caaaacaaaa ctacagacaa    5460
acaagtacaa ttcaaaaatt cgctaaaatt ctgtaatcac caaacccccat ctcagtcagc   5520
acaaggccca aggtttattt tgaaataaaa aaaagtgat tttatttctc ataagctaaa    5580
agaaagaaag gcaattatga aatgatttcg actagatctg aaagtccaac gcgtattccg   5640
cagatattaa agaaagagta gagtttcaca tggatcctag atggacccag ttgaggaaaa   5700
agcaaggcaa agcaaaccag aagtgcaaga tccgaaattg aaccacggaa tctaggatt    5760
ggtagaggga gaagaaaagt accttgagag gtagaagaga agagaagagc agagagatat   5820
atgaacgagt gtgtcttggt ctcaactctg aagcgatacg agtttagagg ggagcattga   5880
gttccaattt atagggaaac cgggtggcag gggtgagtta atgacggaaa agcccctaag   5940
```

```
taacgagatt ggattgtggg ttagattcaa ccgtttgcat ccgcggctta gattggggaa    6000
gtcagagtga atctcaaccg ttgactgagt tgaaaattga atgtagcaac caattgagcc    6060
aaccccagcc tttgcccttt gattttgatt tgtttgttgc atacttttta tttgtcttct    6120
ggttctgact ctctttctct cgtttcaatg ccaggttgcc tactcccaca ccactcacaa    6180
gaagattcta ctgttagtat taaatatttt ttaatgtatt aaatgatgaa tgcttttgta    6240
aacagaacaa gactatgtct aataagtgtc ttgcaacatt ttttaagaaa ttaaaaaaaa    6300
tatatttatt atcaaaatca aatgtatgaa aaatcatgaa taatataatt ttatacatttt    6360 tttttaaaaaa tcttttaatt tcttaattaa tatcttaaaa ataatgatta atatttaacc    6420
caaaataatt agtatgattg gtaaggaaga tatccatgtt atgtttggat gtgagtttga    6480
tctagagcaa agcttactag agtcgacctg caggtcgact cgac                    6524
```

```
<210> SEQ ID NO 51
<211> LENGTH: 32
<212> TYPE: DNA
<213> ORGANISM: Artificial Sequence
<220> FEATURE:
<223> OTHER INFORMATION: Con-1 primer

<400> SEQUENCE: 51
aatctagacc tgcaggatcc atgcccttca tt                                    32

<210> SEQ ID NO 52
<211> LENGTH: 33
<212> TYPE: DNA
<213> ORGANISM: Artificial Sequence
<220> FEATURE:
<223> OTHER INFORMATION: Con-2 primer

<400> SEQUENCE: 52
tttctagacc tgcaggttga acatccctg aag                                    33

<210> SEQ ID NO 53
<211> LENGTH: 4480
<212> TYPE: DNA
<213> ORGANISM: Artificial Sequence
<220> FEATURE:
<223> OTHER INFORMATION: plasmid pKR179

<400> SEQUENCE: 53
ctagacctgc aggatccatg cccttcattt gccgcttatt aattaatttg gtaacagtcc     60
gtactaatca gttacttatc cttcccccat cataattaat cttggtagtc tcgaatgcca    120
caacactgac tagtctcttg gatcataaga aaagccaag gaacaaaaga agacaaaaca     180
caatgagagt atcctttgca tagcaatgtc taagttcata aaattcaaac aaaaacgcaa    240
tcacacacag tggacatcac ttatccacta gctgatcagg atcgccgcgt caagaaaaaa    300
aaactggacc ccaaaagcca tgcacaacaa cacgtactca caaggtgtc aatcgagcag      360 cccaaaacat tcaccaactc aacccatcat gagccctcac atttgttgtt ctaacccaa     420 cctcaaaactc gtattctctt ccgccacctc attttttgttt atttcaacac ccgtcaaact   480
gcatgccacc ccgtggccaa atgtccatgc atgttaacaa gacctatgac tataaatagc    540
tgcaatctcg gccaggtttt tcatcatcaa gaaccagttc aatatcctag tacaccgtat    600
taaagaattt aagatatact gcggccgcaa gtatgaacta aaatgcatgt aggtgtaaga    660
gctcatggag agcatggaat attgtatccg accatgtaac agtataataa ctgagctcca    720
tctcacttct tctatgaata aacaaaggat gttatgatat attaacactc tatctatgca    780
```

-continued

```
ccttattgtt ctatgataaa tttcctctta ttattataaa tcatctgaat cgtgacggct      840
tatggaatgc ttcaaatagt acaaaaacaa atgtgtacta taagactttc taaacaattc      900
taaccttagc attgtgaacg agacataagt gttaagaaga cataacaatt ataatggaag      960
aagtttgtct ccatttatat attatatatt acccacttat gtattatatt aggatgttaa     1020
ggagacataa caattataaa gagagaagtt tgtatccatt tatatattat atactaccca     1080
tttatatatt atacttatcc acttatttaa tgtcttt ata aggtttgatc catgatattt     1140
ctaatatttt agttgatatg tatatgaaag ggtactattt gaactctctt actctgtata     1200
aaggttggat catccttaaa gtgggtctat ttaattttat tgcttcttac agataaaaaa     1260
aaaattatga gttggtttga taaaatattg aaggatttaa aataataata ataacatat      1320 aatatatgta tataaattta ttataatata acatttatct ataaaaaagt aaatattgtc     1380
ataaatctat acaatcgttt agccttgctg gacgaatctc aattatttaa acgagagtaa     1440
acatatttga ctttttggtt atttaacaaa ttattattta acactatatg aaatttttt      1500 ttttatcagc aaagaataaa attaaattaa gaaggacaat ggtgtcccaa tccttataca     1560
accaacttcc acaagaaagt caagtcagag acaacaaaaa aacaagcaaa ggaaattttt     1620
taatttgagt tgtcttgttt gctgcataat ttatgcagta aaacactaca cataacccctt    1680 ttagcagtag agcaatggtt gaccgtgtgc ttagcttctt ttattttatt tttttatcag     1740
caaagaataa ataaaataaa atgagacact tcagggatgt ttcaacctgc aggtctagag     1800 gatcccggg taccgagctc gaattcactg gccgtcgttt tacaacgtcg tgactgggaa      1860
aaccctggcg ttacccaact taatcgcctt gcagcacatc cccctttcgc cagctggcgt     1920
aatagcgaag aggcccgcac cgatcgccct tcccaacagt tgcgcagcct gaatggcgaa     1980
tggcgcctga tgcggtattt tctccttacg catctgtgcg gtatttcaca ccgcatatgg     2040
tgcactctca gtacaatctg ctctgatgcc gcatagttaa gccagccccg acacccgcca     2100
acacccgctg acgcgccctg acgggcttgt ctgctcccgg catccgctta cagacaagct     2160
gtgaccgtct ccgggagctg catgtgtcag aggttttcac cgtcatcacc gaaacgcgcg     2220
agacgaaagg gcctcgtgat acgcctattt ttataggtta atgtcatgat aataatggtt     2280
tcttagacgt caggtggcac ttttcgggga atgtgcgcg gaaccccctat ttgtttattt     2340 ttctaaatac attcaaatat gtatccgctc atgagacaat aaccctgata atgcttcaa      2400 taatattgaa aaaggaagag tatgagtatt caacatttcc gtgtcgccct tattccctt      2460 tttgcggcat tttgccttcc tgtttttgct cacccagaaa cgctggtgaa agtaaaagat     2520
gctgaagatc agttgggtgc acgagtgggt tacatcgaac tggatctcaa cagcggtaag     2580
atccttgaga gttttcgccc cgaagaacgt tttccaatga tgagcacttt taaagttctg     2640
ctatgtggcg cggtattatc ccgtattgac gccgggcaag agcaactcgg tcgccgcata     2700
cactattctc agaatgactt ggttgagtac tcaccagtca cagaaaagca tcttacggat     2760
ggcatgacag taagagaatt atgcagtgct gccataacca tgagtgataa cactgcggcc     2820
aacttacttc tgacaacgat cggaggaccg aaggagctaa ccgcttttt gcacaacatg     2880 ggggatcatg taactcgcct tgatcgttgg gaaccggagc tgaatgaagc cataccaaac     2940
gacgagcgtg acaccacgat gcctgtagca atggcaacaa cgttgcgcaa actattaact     3000
ggcgaactac ttactctagc ttcccggcaa caattaatag actggatgga ggcggataaa     3060
gttgcaggac cacttctgcg ctcggccctt ccggctggct ggtttattgc tgataaatct     3120
ggagccggtg agcgtgggtc tcgcggtatc attgcagcac tggggccaga tggtaagccc     3180
```

-continued

| | | | | |
|---|---|---|---|---|
| tcccgtatcg | tagttatcta | cacgacgggg | agtcaggcaa | ctatggatga acgaaataga | 3240 |
| cagatcgctg | agataggtgc | ctcactgatt | aagcattggt | aactgtcaga ccaagtttac | 3300 |
| tcatatatac | tttagattga | tttaaaactt | catttttaat | ttaaaaggat ctaggtgaag | 3360 |
| atccttttttg | ataatctcat | gaccaaaatc | ccttaacgtg | agttttcgtt ccactgagcg | 3420 |
| tcagacccccg | tagaaaagat | caaaggatct | tcttgagatc | ctttttttct gcgcgtaatc | 3480 |
| tgctgcttgc | aaacaaaaaa | accaccgcta | ccagcggtgg | tttgtttgcc ggatcaagag | 3540 |
| ctaccaactc | ttttttccgaa | ggtaactggc | ttcagcagag | cgcagatacc aaatactgtc | 3600 |
| cttctagtgt | agccgtagtt | aggccaccac | ttcaagaact | ctgtagcacc gcctacatac | 3660 |
| ctcgctctgc | taatcctgtt | accagtggct | gctgccagtg | gcgataagtc gtgtcttacc | 3720 |
| gggttggact | caagacgata | gttaccggat | aaggcgcagc | ggtcgggctg aacggggggt | 3780 |
| tcgtgcacac | agcccagctt | ggagcgaacg | acctacaccg | aactgagata cctacagcgt | 3840 |
| gagctatgag | aaagcgccac | gcttcccgaa | gggagaaagg | cggacaggta tccggtaagc | 3900 |
| ggcagggtcg | gaacaggaga | gcgcacgagg | gagcttccag | ggggaaacgc ctggtatctt | 3960 |
| tatagtcctg | tcgggtttcg | ccacctctga | cttgagcgtc | gatttttgtg atgctcgtca | 4020 |
| ggggggcgga | gcctatggaa | aaacgccagc | aacgcggcct | ttttacggtt cctggccttt | 4080 |
| tgctggcctt | ttgctcacat | gttctttcct | gcgttatccc | ctgattctgt ggataaccgt | 4140 |
| attaccgcct | ttgagtgagc | tgataccgct | cgccgcagcc | gaacgaccga gcgcagcgag | 4200 |
| tcagtgagcg | aggaagcgga | agagcgccca | atacgcaaac | cgcctctccc cgcgcgttgg | 4260 |
| ccgattcatt | aatgcagctg | gcacgacagg | tttcccgact | ggaaagcggg cagtgagcgc | 4320 |
| aacgcaatta | atgtgagtta | gctcactcat | taggcacccc | aggctttaca ctttatgctt | 4380 |
| ccggctcgta | tgttgtgtgg | aattgtgagc | ggataacaat | ttcacacagg aaacagctat | 4440 |
| gaccatgatt | acgccaagct | tgcatgcctg | caggtcgact | | 4480 |

<210> SEQ ID NO 54
<211> LENGTH: 9088
<212> TYPE: DNA
<213> ORGANISM: Artificial Sequence
<220> FEATURE:
<223> OTHER INFORMATION: plasmid pKR578
<220> FEATURE:
<221> NAME/KEY: misc_feature
<222> LOCATION: (6951)..(6951)
<223> OTHER INFORMATION: n is a, c, g, or t

<400> SEQUENCE: 54

| | | | | |
|---|---|---|---|---|
| ggccgcgaca | caagtgtgag | agtactaaat | aaatgctttg | gttgtacgaa atcattacac | 60 |
| taaataaaat | aatcaaagct | tatatatgcc | ttccgctaag | gccgaatgca agaaaattgg | 120 |
| ttctttctcg | ttatcttttg | ccacttttac | tagtacgtat | taattactac ttaatcatct | 180 |
| ttgtttacgg | ctcattatat | ccggtctaga | ggatccaagg | ccgcgaagtt aaaagcaatg | 240 |
| ttgtcacttg | tcgtactaac | acatgatgtg | atagtttatg | ctagctagct ataacataag | 300 |
| ctgtctctga | gtgtgttgta | tattaataaa | gatcatcact | ggtgaatggt gatcgtgtac | 360 |
| gtaccctact | tagtaggcaa | tggaagcact | tagagtgtgc | tttgtgcatg gccttgcctc | 420 |
| tgttttgaga | cttttgtaat | gttttcgagt | ttaaatcttt | gcctttgcgt acggatccgt | 480 |
| cgacggcgcg | cccgatcatc | cggatatagt | tcctcctttc | agcaaaaaac ccctcaagac | 540 |
| ccgtttagag | gccccaaggg | gttatgctag | ttattgctca | gcggtggcag cagccaactc | 600 |
| agcttccttt | cgggctttgt | tagcagccgg | atcgatccaa | gctgtacctc actattcctt | 660 |

-continued

```
tgccctcgga cgagtgctgg ggcgtcggtt tccactatcg gcgagtactt ctacacagcc    720
atcggtccag acggccgcgc ttctgcgggc gatttgtgta cgcccgacag tcccggctcc    780
ggatcggacg attgcgtcgc atcgaccctg cgcccaagct gcatcatcga aattgccgtc    840
aaccaagctc tgatagagtt ggtcaagacc aatgcggagc atatacgccc ggagccgcgg    900
cgatcctgca agctccggat gcctccgctc gaagtagcgc gtctgctgct ccatacaagc    960
caaccacggc ctccagaaga agatgttggc gacctcgtat tgggaatccc cgaacatcgc   1020
ctcgctccag tcaatgaccg ctgttatgcg gccattgtcc gtcaggacat tgttggagcc   1080
gaaatccgcg tgcacgaggt gccggacttc ggggcagtcc tcggcccaaa gcatcagctc   1140
atcgagagcc tgcgcgacgg acgcactgac ggtgtcgtcc atcacagttt gccagtgata   1200
cacatgggga tcagcaatcg cgcatatgaa atcacgccat gtagtgtatt gaccgattcc   1260
ttgcggtccg aatgggccga acccgctcgt ctggctaaga tcggccgcag cgatcgcatc   1320
catagcctcc gcgaccggct gcagaacagc gggcagttcg gtttcaggca ggtcttgcaa   1380
cgtgacaccc tgtgcacggc gggagatgca ataggtcagg ctctcgctga attccccaat   1440
gtcaagcact tccggaatcg ggagcgcggc cgatgcaaag tgccgataaa cataacgatc   1500
tttgtagaaa ccatcggcgc agctatttac ccgcaggaca tatccacgcc ctcctacatc   1560
gaagctgaaa gcacgagatt cttcgccctc cgagagctgc atcaggtcgg agacgctgtc   1620
gaacttttcg atcagaaact tctcgacaga cgtcgcggtg agttcaggct tttccatggg   1680
tatatctcct tcttaaagtt aaacaaaatt atttctagag ggaaaccgtt gtggtctccc   1740
tatagtgagt cgtattaatt tcgcgggatc gagatcgatc caattccaat cccacaaaaa   1800
tctgagctta acagcacagt tgctcctctc agagcagaat cgggtattca cacccctcat   1860
atcaactact acgttgtgta taacggtcca catgccggta tatacgatga ctggggttgt   1920
acaaaggcgg caacaaacgg cgttcccgga gttgcacaca agaaatttgc cactattaca   1980
gaggcaagag cagcagctga cgcgtacaca acaagtcagc aaacagacag gttgaacttc   2040
atccccaaag gagaagctca actcaagccc aagagctttg ctaaggccct aacaagccca   2100
ccaaagcaaa agcccactg gctcacgcta ggaaccaaaa ggcccagcag tgatccagcc   2160
ccaaaagaga tctcctttgc cccggagatt acaatggacg atttcctcta tctttacgat   2220
ctaggaagga agttcgaagg tgaaggtgac gacactatgt tcaccactga taatgagaag   2280
gttagcctct tcaatttcag aaagaatgct gacccacaga tggttagaga ggcctacgca   2340
gcaggtctca tcaagacgat ctacccgagt aacaatctcc aggagatcaa ataccttccc   2400
aagaaggtta agatgcagt caaaagattc aggactaatt gcatcaagaa cacagagaaa   2460
gacatatttc tcaagatcag aagtactatt ccagtatgga cgattcaagg cttgcttcat   2520
aaaccaaggc aagtaataga gattggagtc tctaaaaagg tagttcctac tgaatctaag   2580
gccatgcatg gagtctaaga ttcaaatcga ggatctaaca gaactcgccg tgaagactgg   2640
cgaacagttc atacagagtc ttttacgact caatgacaag aagaaaatct tcgtcaacat   2700
ggtggagcac gacactctgg tctactccaa aaatgtcaaa gatacagtct cagaagacca   2760
aagggctatt gagacttttc aacaaggat aatttcggga aacctcctcg gattccattg   2820
cccagctatc tgtcacttca tcgaaaggac agtagaaaag gaaggtggct cctacaaatg   2880
ccatcattgc gataaaggaa aggctatcat tcaagatgcc tctgccgaca gtggtcccaa   2940
agatggaccc ccacccacga ggagcatcgt ggaaaaagaa gacgttccaa ccacgtcttc   3000
aaagcaagtg gattgatgtg acatctccac tgacgtaagg gatgacgcac aatcccacta   3060
```

```
tccttcgcaa gacccttcct ctatataagg aagttcattt catttggaga ggacacgctc   3120
gagctcattt ctctattact tcagccataa caaaagaact cttttctctt cttattaaac   3180
catgaaaaag cctgaactca ccgcgacgtc tgtcgagaag tttctgatcg aaaagttcga   3240
cagcgtctcc gacctgatgc agctctcgga gggcgaagaa tctcgtgctt tcagcttcga   3300
tgtaggaggg cgtggatatg tcctgcgggt aaatagctgc gccgatggtt tctacaaaga   3360
tcgttatgtt tatcggcact ttgcatcggc cgcgctcccg attccggaag tgcttgacat   3420
tggggaattc agcgagagcc tgacctattg catctcccgc cgtgcacagg gtgtcacgtt   3480
gcaagacctg cctgaaaccg aactgcccgc tgttctgcag ccggtcgcgg aggccatgga   3540
tgcgatcgct gcggccgatc ttagccagac gagcgggttc ggcccattcg gaccgcaagg   3600
aatcggtcaa tacactacat ggcgtgattt catatgcgcg attgctgatc ccatgtgta   3660
tcactggcaa actgtgatgg acgacaccgt cagtgcgtcc gtcgcgcagg ctctcgatga   3720
gctgatgctt tgggccgagg actgccccga agtccggcac ctcgtgcacg cggatttcgg   3780
ctccaacaat gtcctgacgg acaatggccg cataacagcg gtcattgact ggagcgaggc   3840
gatgttcggg gattcccaat acgaggtcgc caacatcttc ttctggaggc cgtggttggc   3900
ttgtatggag cagcagacgc gctacttcga gcggaggcat ccggagcttg caggatcgcc   3960
gcggctccgg gcgtatatgc tccgcattgg tcttgaccaa ctctatcaga gcttggttga   4020
cggcaatttc gatgatgcag cttgggcgca gggtcgatgc gacgcaatcg tccgatccgg   4080
agccgggact gtcgggcgta cacaaatcgc ccgcagaagc gcggccgtct ggaccgatgg   4140
ctgtgtagaa gtactcgccg atagtggaaa ccgacgcccc agcactcgtc cgagggcaaa   4200
ggaatagtga ggtacctaaa gaaggagtgc gtcgaagcag atcgttcaaa catttggcaa   4260
taaagtttct taagattgaa tcctgttgcc ggtcttgcga tgattatcat ataatttctg   4320
ttgaattacg ttaagcatgt aataattaac atgtaatgca tgacgttatt tatgagatgg   4380
gtttttatga ttagagtccc gcaattatac atttaatacg cgatagaaaa caaaatatag   4440
cgcgcaaact aggataaaatt atcgcgcgcg gtgtcatcta tgttactaga tcgatgtcga   4500
atcgatcaac ctgcattaat gaatcggcca acgcgcgggg agaggcggtt tgcgtattgg   4560
gcgctcttcc gcttcctcgc tcactgactc gctgcgctcg tcgttcggc tgcggcgagc   4620
ggtatcagct cactcaaagg cggtaatacg gttatccaca gaatcagggg ataacgcagg   4680
aaagaacatg tgagcaaaag gccagcaaaa ggccaggaac cgtaaaaagg ccgcgttgct   4740
ggcgtttttc cataggctcc gcccccctga cgagcatcac aaaaatcgac gctcaagtca   4800
gaggtggcga aacccgacag gactataaag ataccaggcg tttccccctg gaagctccct   4860
cgtgcgctct cctgttccga ccctgccgct taccggatac ctgtccgcct ttctcccttc   4920
gggaagcgtg gcgctttctc aatgctcacg ctgtaggtat ctcagttcgg tgtaggtcgt   4980
tcgctccaag ctgggctgtg tgcacgaacc ccccgttcag cccgaccgct gcgccttatc   5040
cggtaactat cgtcttgagt ccaacccggt aagacacgac ttatcgccac tggcagcagc   5100
cactggtaac aggattagca gagcgaggta tgtaggcggt gctacagagt tcttgaagtg   5160
gtggcctaac tacggctaca ctagaaggac agtatttggt atctgcgctc tgctgaagcc   5220
agttaccttc ggaaaaagag ttggtagctc ttgatccggc aaacaaacca ccgctggtag   5280
cggtggtttt tttgtttgca agcagcagat tacgcgcaga aaaaaaggat ctcaagaaga   5340
tccttttgatc ttttctacgg ggtctgacgc tcagtggaac gaaaactcac gttaagggat   5400
tttggtcatg acattaacct ataaaaatag gcgtatcacg aggccctttc gtctcgcgcg   5460
```

```
tttcggtgat gacggtgaaa acctctgaca catgcagctc ccggagacgg tcacagcttg   5520
tctgtaagcg gatgccggga gcagacaagc ccgtcagggc gcgtcagcgg gtgttggcgg   5580 gtgtcgggc tggcttaact atgcggcatc agagcagatt gtactgagag tgcaccatat    5640
ggacatattg tcgttagaac gcggctacaa ttaatacata accttatgta tcatacacat   5700
acgatttagg tgacactata gaacggcgcg ccaagcttgg atctcctgca ggatctggcc   5760
ggccggatct cgtacgtcct cgaagagaag ggttaataac acatttttta acatttttaa   5820 cacaatttt agttatttaa aaatttatta aaaatttaa aataagaaga ggaactcttt     5880
aaataaatct aacttacaaa atttatgatt tttaataagt tttcaccaat aaaaaatgtc   5940
ataaaaatat gttaaaaagt atattatcaa tattctcttt atgataaata aaagaaaaa    6000 aaaaataaaa gttaagtgaa aatgagattg aagtgacttt aggtgtgtat aaatatatca   6060
accccgccaa caatttattt aatccaaata tattgaagta tattattcca tagcctttat   6120
ttatttatat atttattata taaaagcttt atttgttcta ggttgttcat gaaatatttt   6180 tttggttta tctccgttgt aagaaaatca tgtgctttgt gtcgccactc actattgcag    6240
ctttttcatg cattggtcag attgacggtt gattgtattt ttgttttta tggttttgtg    6300 ttatgactta agtcttcatc tctttatctc ttcatcaggt ttgatggtta cctaatatgg   6360
tccatgggta catgcatggt taaattaggt ggccaacttt gttgtgaacg atagaatttt   6420
ttttatatta agtaaactat ttttatatta tgaaataata ataaaaaaa tattttatca    6480 ttattaacaa aatcatatta gttaatttgt taactctata ataaagaaa tactgtaaca    6540 ttcacattac atggtaacat ctttccaccc tttcatttgt tttttgtttg atgacttttt   6600
ttcttgttta aatttatttc ccttcttta aatttggaat acattatcat catatataaa    6660
ctaaaatact aaaacagga ttacacaaat gataaataat aacacaaata tttataaatc    6720
tagctgcaat atatttaaac tagctatatc gatattgtaa aataaaacta gctgcattga   6780
tactgataaa aaaatatcat gtgctttctg gactgatgat gcagtatact tttgacattg   6840 ccttttatttt attttttcaga aaagcttttct tagttctggg ttcttcatta tttgtttccc 6900
atctccattg tgaattgaat catttgcttc gtgtcacaaa tacaatttag ntaggtacat   6960
gcattggtca gattcacggt ttattatgtc atgacttaag ttcatggtag tacattacct   7020
gccacgcatg cattatattg gttagatttg ataggcaaat ttggttgtca acaatataaa   7080
tataaataat gttttatat tacgaaataa cagtgatcaa acaaacagt tttatcttta     7140 ttaacaagat tttgttttg tttgatgacg tttttaatg tttacgcttt ccccttctt      7200 ttgaatttag aacactttat catcataaaa tcaaatacta aaaaattac atatttcata    7260 aataataaca caaatatttt taaaaatct gaaataataa tgaacaatat tacatattat    7320
cacgaaaatt cattaataaa aatattatat aaataaaatg taatagtagt tatatgtagg   7380
aaaaaagtac tgcacgcata atatatacaa aaagattaaa atgaactatt ataaataata   7440
acactaaatt aatggtgaat catatcaaaa taatgaaaaa gtaaataaaa tttgtaatta   7500
acttctatat gtattacaca cacaataat aaataatagt aaaaaaaatt atgataaata   7560
tttaccatct cataagatat ttaaaataat gataaaaata tagattattt tttatgcaac   7620
tagctagcca aaaagagaac acgggtatat ataaaaagag tacctttaaa ttctactgta   7680
cttcctttat tcctgacgtt tttatatcaa gtggacatac gtgaagattt taattatcag   7740
tctaaatatt tcattagcac ttaatacttt tctgttttat tcctatccta taagtagtcc   7800
cgattctccc aacattgctt attcacacaa ctaactaaga aagtcttcca tagcccccca   7860
```

| | |
|---|---|
| agcggccgca caatggcgac tcgacagcga actgccacca ctgttgtggt cgaggacctt | 7920 |
| cccaaggtca ctcttgaggc caagtctgaa cctgtgttcc ccgatatcaa gaccatcaag | 7980 |
| gatgccattc ccgcgcactg cttccagccc tcgctcgtca cctcattcta ctacgtcttc | 8040 |
| cgcgattttg ccatggtctc tgccctcgtc tgggctgctc tcacctacat ccccagcatc | 8100 |
| cccgaccaga ccctccgcgt cgcagcttgg atggtctacg gcttcgtcca gggtctgttc | 8160 |
| tgcaccggtg tctggattct cggccatgag tgcggccacg tgctttctc tctccacgga | 8220 |
| aaggtcaaca atgtgaccgg ctggttcctc cactcgttcc tcctcgtccc ctacttcagc | 8280 |
| tggaagtact ctcaccaccg ccaccaccgc ttcaccggcc acatggatct cgacatggct | 8340 |
| ttcgtcccca agactgagcc caagccctcc aagtcgctca tgattgctgg cattgacgtc | 8400 |
| gccgagcttg ttgaggacac ccccgctgct cagatggtca agctcatctt ccaccagctt | 8460 |
| ttcggatggc aggcgtacct cttcttcaac gctagctctg gcaagggcag caagcagtgg | 8520 |
| gagcccaaga ctggcctctc caagtggttc cgagtcagtc acttcgagcc taccagcgct | 8580 |
| gtcttccgcc caacgaggc catcttcatc ctcatctccg atatcggtct tgctctaatg | 8640 |
| ggaactgctc tgtactttgc ttccaagcaa gttggtgttt cgaccattct cttcctctac | 8700 |
| cttgttccct acctgtgggt tcaccactgg ctcgttgcca ttacctacct ccaccaccac | 8760 |
| cacaccgagc tccctcacta caccgctgag ggctggacct acgtcaaggg agctctcgcc | 8820 |
| actgtcgacc gtgagtttgg cttcatcgga aagcacctct tccacggtat cattgagaag | 8880 |
| cacgttgttc accatctctt cccctaagatc cccttctaca aggctgacga ggccaccgag | 8940 |
| gccatcaagc ccgtcattgg cgaccactac tgccacgacg accgaagctt cctgggccag | 9000 |
| ctgtggacca tcttcggcac gctcaagtac gtcgagcacg accctgcccg acccggtgcc | 9060 |
| atgcgatgga acaaggacta ggctaggc | 9088 |

<210> SEQ ID NO 55
<211> LENGTH: 5705
<212> TYPE: DNA
<213> ORGANISM: Artificial Sequence
<220> FEATURE:
<223> OTHER INFORMATION: plasmid pKR582

<400> SEQUENCE: 55

| | |
|---|---|
| ggccgcacaa tggcgactcg acagcgaact gccaccactg ttgtggtcga ggacttccc | 60 |
| aaggtcactc ttgaggccaa gtctgaacct gtgttccccg atatcaagac catcaaggat | 120 |
| gccattcccg cgcactgctt ccagccctcg ctcgtcacct cattctacta cgtcttccgc | 180 |
| gattttgcca tggtctctgc cctcgtctgg gctgctctca cctacatccc cagcatcccc | 240 |
| gaccagaccc tccgcgtcgc agcttggatg gtctacggct tcgtccaggg tctgttctgc | 300 |
| accggtgtct ggattctcgg ccatgagtgc ggccacggtg ctttctctct ccacggaaag | 360 |
| gtcaacaatg tgaccggctg gttcctccac tcgttcctcc tcgtccccta cttcagctgg | 420 |
| aagtactctc accaccgcca ccaccgcttc accggccaca tggatctcga catggctttc | 480 |
| gtccccaaga ctgagcccaa gccctccaag tcgctcatga ttgctggcat tgacgtcgcc | 540 |
| gagcttgttg aggacacccc cgctgctcag atggtcaagc tcatcttcca ccagcttttc | 600 |
| ggatggcagg cgtacctctt cttcaacgct agctctggca agggcagcaa gcagtgggag | 660 |
| cccaagactg gcctctccaa gtggttccga gtcagtcact tcgagcctac cagcgctgtc | 720 |
| ttccgcccca acgaggccat cttcatcctc atccgata tcggtcttgc tctaatggga | 780 |
| actgctctgt actttgcttc caagcaagtt ggtgtttcga ccattctctt cctctacctt | 840 |

```
gttccctacc tgtgggttca ccactggctc gttgccatta cctacctcca ccaccaccac    900
accgagctcc ctcactacac cgctgagggc tggacctacg tcaagggagc tctcgccact    960
gtcgaccgtg agtttggctt catcggaaag cacctcttcc acggtatcat tgagaagcac   1020
gttgttcacc atctcttccc taagatcccc ttctacaagg ctgacgaggc caccgaggcc   1080
atcaagcccg tcattggcga ccactactgc cacgacgacc gaagcttcct gggccagctg   1140
tggaccatct tcggcacgct caagtacgtc gagcacgacc ctgcccgacc cggtgccatg   1200
cgatggaaca aggactaggc taggcggccg caagtatgaa ctaaaatgca tgtaggtgta   1260
agagctcatg gagagcatgg aatattgtat ccgaccatgt aacagtataa taactgagct   1320
ccatctcact tcttctatga ataaacaaag gatgttatga tatattaaca ctctatctat   1380
gcaccttatt gttctatgat aaatttcctc ttattattat aaatcatctg aatcgtgacg   1440
gcttatggaa tgcttcaaat agtacaaaaa caaatgtgta ctataagact ttctaaacaa   1500
ttctaacctt agcattgtga acgagacata agtgttaaga agacataaca attataatgg   1560
aagaagtttg tctccattta tatattatat attaccccact tatgtattat attaggatgt   1620
taaggagaca taacaattat aaagagagaa gtttgtatcc atttatatat tatatactac   1680
ccatttatat attatactta tccacttatt taatgtcttt ataaggtttg atccatgata   1740
tttctaatat tttagttgat atgtatatga aagggtacta tttgaactct cttactctgt   1800
ataaggttg gatcatcctt aaagtgggtc tatttaattt tattgcttct tacagataaa   1860
aaaaaaatta tgagttggtt tgataaaata ttgaaggatt taaaataata ataaataaca   1920
tataatatat gtatataaat ttattataat ataacattta tctataaaaa agtaaatatt   1980
gtcataaatc tatacaatcg tttagccttg ctggacgaat ctcaattatt taaacgagag   2040
taaacatatt tgactttttg gttatttaac aaattattat ttaacactat atgaaatttt   2100
tttttttatc agcaaagaat aaaattaaat taagaaggac aatggtgtcc caatccttat   2160
acaaccaact tccacaagaa agtcaagtca gagacaacaa aaaaacaagc aaaggaaatt   2220
ttttaatttg agttgtcttg tttgctgcat aatttatgca gtaaaacact acacataacc   2280
cttttagcag tagagcaatg gttgaccgtg tgcttagctt ctttttatttt attttttat   2340
cagcaaagaa taaataaaat aaaatgagac acttcaggga tgtttcaacc tgcaggtcta   2400
gaggatcccc gggtaccgag ctcgaattca ctggccgtcg ttttacaacg tcgtgactgg   2460
gaaaaccctg gcgttaccca acttaatcgc cttgcagcac atccccctt cgccagctgg   2520
cgtaatagcg aagaggcccg caccgatcgc ccttcccaac agttgcgcag cctgaatggc   2580
gaatggcgcc tgatgcggta ttttctcctt acgcatctgt gcggtatttc acaccgcata   2640
tggtgcactc tcagtacaat ctgctctgat gccgcatagt taagccagcc ccgacacccg   2700
ccaacacccg ctgacgcgcc ctgacgggct tgtctgctcc cggcatccgc ttacagacaa   2760
gctgtgaccg tctccgggag ctgcatgtgt cagaggtttt caccgtcatc accgaaacgc   2820
gcgagacgaa agggcctcgt gatacgccta tttttatagg ttaatgtcat gataataatg   2880
gtttcttaga cgtcaggtgg cacttttcgg ggaaatgtgc gcggaacccc tatttgttta   2940
tttttctaaa tacattcaaa tatgtatccg ctcatgagac aataaccctg ataaatgctt   3000
caataatatt gaaaaggaa gagtatgagt attcaacatt tccgtgtcgc ccttattccc   3060
ttttttgcgg cattttgcct tcctgttttt gctcacccag aaacgctggt gaaagtaaaa   3120
gatgctgaag atcagttggg tgcacgagtg ggttacatcg aactggatct caacagcggt   3180
aagatccttg agagttttcg ccccgaagaa cgttttccaa tgatgagcac ttttaaagtt   3240
```

```
ctgctatgtg gcgcggtatt atcccgtatt gacgccgggc aagagcaact cggtcgccgc    3300
atacactatt ctcagaatga cttggttgag tactcaccag tcacagaaaa gcatcttacg    3360
gatggcatga cagtaagaga attatgcagt gctgccataa ccatgagtga taacactgcg    3420
gccaacttac ttctgacaac gatcggagga ccgaaggagc taaccgcttt tttgcacaac    3480 atggggatc atgtaactcg ccttgatcgt tgggaaccgg agctgaatga agccatacca     3540
aacgacgagc gtgacaccac gatgcctgta gcaatggcaa caacgttgcg caaactatta    3600
actggcgaac tacttactct agcttcccgg caacaattaa tagactggat ggaggcggat    3660
aaagttgcag gaccacttct gcgctcggcc cttccggctg gctggtttat tgctgataaa    3720
tctggagccg gtgagcgtgg gtctcgcggt atcattgcag cactggggcc agatggtaag    3780
ccctcccgta tcgtagttat ctacacgacg gggagtcagg caactatgga tgaacgaaat    3840
agacagatcg ctgagatagg tgcctcactg attaagcatt ggtaactgtc agaccaagtt    3900
tactcatata ctttagat tgatttaaaa cttcattttt aatttaaaag gatctaggtg      3960
aagatccttt ttgataatct catgaccaaa atcccttaac gtgagttttc gttccactga    4020
gcgtcagacc ccgtagaaaa gatcaaagga tcttcttgag atcctttttt tctgcgcgta    4080
atctgctgct tgcaaacaaa aaaaccaccg ctaccagcgg tggtttgttt gccggatcaa    4140
gagctaccaa ctctttttcc gaaggtaact ggcttcagca gagcgcagat accaaatact    4200
gtccttctag tgtagccgta gttaggccac cacttcaaga actctgtagc accgcctaca    4260
tacctcgctc tgctaatcct gttaccagtg gctgctgcca gtggcgataa gtcgtgtctt    4320
accgggttgg actcaagacg atagttaccg gataaggcgc agcggtcggg ctgaacgggg    4380
ggttcgtgca cacagcccag cttggagcga acgacctaca ccgaactgag atacctacag    4440
cgtgagctat gagaaagcgc cacgcttccc gaagggagaa aggcggacag gtatccggta    4500
agcggcaggg tcggaacagg agagcgcacg agggagcttc caggggggaaa cgcctggtat    4560 ctttatagtc ctgtcgggtt cgccacctc tgacttgagc gtcgattttt gtgatgctcg     4620 tcagggggc ggagcctatg gaaaaacgcc agcaacgcgg ccttttttacg gttcctggcc     4680 ttttgctggc cttttgctca catgttcttt cctgcgttat cccctgattc tgtggataac    4740
cgtattaccg cctttgagtg agctgatacc gctcgccgca gccgaacgac cgagcgcagc    4800
gagtcagtga gcgaggaagc ggaagagcgc ccaatacgca aaccgcctct ccccgcgcgt    4860
tggccgattc attaatgcag ctggcacgac aggtttcccg actggaaagc gggcagtgag    4920
cgcaacgcaa ttaatgtgag ttagctcact cattaggcac cccaggcttt acactttatg    4980
cttccggctc gtatgttgtg tggaattgtg agcggataac aatttcacac aggaaacagc    5040
tatgaccatg attacgccaa gcttgcatgc ctgcaggtcg actctagacc tgcaggatcc    5100
atgcccttca tttgccgctt attaattaat ttggtaacag tccgtactaa tcagttactt    5160
atccttcccc catcataatt aatcttggta gtctcgaatg ccacaacact gactagtctc    5220
ttggatcata agaaaagcc aaggaacaaa agaagacaaa acacaatgag agtatccttt     5280
gcatagcaat gtctaagttc ataaaattca acaaaaacg caatcacaca cagtggacat     5340
cacttatcca ctagctgatc aggatcgccg cgtcaagaaa aaaaactgg accccaaaag     5400 ccatgcacaa caacacgtac tcacaaaggt gtcaatcgag cagcccaaaa cattcaccaa    5460
ctcaacccat catgagccct cacatttgtt gtttctaacc caacctcaaa ctcgtattct    5520
cttccgccac ctcattttg tttatttcaa caccgtcaa actgcatgcc accccgtggc      5580
caaatgtcca tgcatgttaa caagacctat gactataaat agctgcaatc tcggcccagg    5640
```

-continued

| | |
|---|---|
| ttttcatcat caagaaccag ttcaatatcc tagtacaccg tattaaagaa tttaagatat | 5700 |
| actgc | 5705 |

<210> SEQ ID NO 56
<211> LENGTH: 12897
<212> TYPE: DNA
<213> ORGANISM: Artificial Sequence
<220> FEATURE:
<223> OTHER INFORMATION: plasmid pKR983

<400> SEQUENCE: 56

| | |
|---|---|
| ggtcgactcg acgtacgtct agaggatccg tcgacggcgc gcccgatcat ccggatatag | 60 |
| ttcctccttt cagcaaaaaa cccctcaaga cccgtttaga ggccccaagg ggttatgcta | 120 |
| gttattgctc agcggtggca gcagccaact cagcttcctt tcgggctttg ttagcagccg | 180 |
| gatcgatcca agctgtacct cactattcct ttgccctcgg acgagtgctg ggcgtcggt | 240 |
| ttccactatc ggcgagtact tctacacagc catcggtcca gacggccgcg cttctgcggg | 300 |
| cgatttgtgt acgcccgaca gtcccggctc cggatcggac gattgcgtcg catcgaccct | 360 |
| gcgcccaagc tgcatcatcg aaattgccgt caaccaagct ctgatagagt tggtcaagac | 420 |
| caatgcggag catatacgcc cggagccgcg gcgatcctgc aagctccgga tgcctccgct | 480 |
| cgaagtagcg cgtctgctgc tccatacaag ccaaccacgg cctccagaag aagatgttgg | 540 |
| cgacctcgta ttgggaatcc ccgaacatcg cctcgctcca gtcaatgacc gctgttatgc | 600 |
| ggccattgtc cgtcaggaca ttgttggagc cgaaatccgc gtgcacgagg tgccggactt | 660 |
| cggggcagtc ctcggcccaa agcatcagct catcgagagc ctgcgcgacg gacgcactga | 720 |
| cggtgtcgtc catcacagtt tgccagtgat acacatgggg atcagcaatc gcgcatatga | 780 |
| aatcacgcca tgtagtgtat tgaccgattc cttgcggtcc gaatgggccg aacccgctcg | 840 |
| tctggctaag atcggccgca gcgatcgcat ccatagcctc cgcgaccggc tgcagaacag | 900 |
| cgggcagttc ggtttcaggc aggtcttgca acgtgacacc ctgtgcacgg cgggagatgc | 960 |
| aataggtcag gctctcgctg aattccccaa tgtcaagcac ttccggaatc gggagcgcgg | 1020 |
| ccgatgcaaa gtgccgataa acataacgat cttttgtagaa accatcggcg cagctattta | 1080 |
| cccgcaggac atatccacgc cctcctacat cgaagctgaa agcacgagat tcttcgccct | 1140 |
| ccgagagctg catcaggtcg gagacgctgt cgaacttttc gatcagaaac ttctcgacag | 1200 |
| acgtcgcggt gagttcaggc ttttccatgg gtatatctcc ttcttaaagt taaacaaaat | 1260 |
| tatttctaga gggaaaccgt tgtggtctcc ctatagtgag tcgtattaat ttcgcgggat | 1320 |
| cgagatctga tcaacctgca ttaatgaatc ggccaacgcg cggggagagg cggtttgcgt | 1380 |
| attgggcgct cttccgcttc ctcgctcact gactcgctgc gctcggtcgt tcggctgcgg | 1440 |
| cgagcggtat cagctcactc aaaggcggta atacggttat ccacagaatc aggggataac | 1500 |
| gcaggaaaga acatgtgagc aaaaggccag caaaaggcca ggaaccgtaa aaaggccgcg | 1560 |
| ttgctggcgt ttttccatag gctccgcccc cctgacgagc atcacaaaaa tcgacgctca | 1620 |
| agtcagaggt ggcgaaaccc gacaggacta taaagatacc aggcgtttcc ccctggaagc | 1680 |
| tccctcgtgc gctctcctgt tccgaccctg ccgcttaccg gatacctgtc cgcctttctc | 1740 |
| ccttcgggaa gcgtggcgct ttctcaatgc tcacgctgta ggtatctcag ttcggtgtag | 1800 |
| gtcgttcgct ccaagctggg ctgtgtgcac gaaccccccg ttcagcccga ccgctgcgcc | 1860 |
| ttatccggta actatcgtct tgagtccaac ccggtaagac acgacttatc gccactggca | 1920 |
| gcagccactg gtaacaggat tagcagagcg aggtatgtag gcggtgctac agagttcttg | 1980 |

```
aagtggtggc ctaactacgg ctacactaga aggacagtat ttggtatctg cgctctgctg    2040
aagccagtta ccttcggaaa aagagttggt agctcttgat ccggcaaaca aaccaccgct    2100
ggtagcggtg gttttttttgt ttgcaagcag cagattacgc gcagaaaaaa aggatctcaa    2160
gaagatcctt tgatcttttc tacggggtct gacgctcagt ggaacgaaaa ctcacgttaa    2220
gggattttgg tcatgacatt aacctataaa aataggcgta tcacgaggcc ctttcgtctc    2280
gcgcgtttcg gtgatgacgg tgaaaacctc tgacacatgc agctcccgga gacggtcaca    2340
gcttgtctgt aagcggatgc cgggagcaga caagcccgtc agggcgcgtc agcgggtgtt    2400
ggcgggtgtc ggggctggct taactatgcg gcatcagagc agattgtact gagagtgcac    2460
catatggaca tattgtcgtt agaacgcggc tacaattaat acataacctt atgtatcata    2520
cacatacgat ttaggtgaca ctatagaacg gcgcgccaag ctgggtctag aactagaaac    2580
gtgatgccac ttgttattga agtcgattac agcatctatt ctgttttact atttataact    2640
ttgccatttc tgacttttga aaactatctc tggatttcgg tatcgctttg tgaagatcga    2700
gcaaaagaga cgttttgtgg acgcaatggt ccaaatccgt tctacatgaa caaattggtc    2760
acaatttcca ctaaaagtaa ataaatggca agttaaaaaa ggaatatgca ttttactgat    2820
tgcctaggtg agctccaaga gaagttgaat ctacacgtct accaaccgct aaaaaaagaa    2880
aaacattgat atgtaacctg attccattag cttttgactt cttcaacaga ttctctactt    2940
agatttctaa cagaaatatt attactagca catcattttc agtctcacta cagcaaaaaa    3000
tccaacggca caatacagac aacaggagat atcagactac agagatagat agatgctact    3060
gcatgtagta agttaaataa aaggaaaata aaatgtcttg ctaccaaaac tactacagac    3120
tatgatgctc accacaggcc aaatcctgca actaggacag cattatctta tatatattgt    3180
acaaaacaag catcaaggaa catttggtct aggcaatcag tacctcgttc taccatcacc    3240
ctcagttatc acatccttga aggatccatt actgggaatc atcggcaaca catgctcctg    3300
atggggcaca atgacatcaa gaaggtaggg gccaggggtg tccaacattc tctgaattgc    3360
cgctctaagc tcttccttct tcgtcactcg cgctgccggt atcccacaag catcagcaaa    3420
cttgagcatg tttgggaata tctcgctctc gctagacgga tctccaagat aggtgtgagc    3480
tctattggac ttgtagaacc tatcctccaa ctgaaccacc ataccaaat gctgattgtt    3540 caacaacaat atcttaactg ggagattctc cactcttata gtggccaact cctgaacatt    3600
catgatgaaa ctaccatccc catcaatgtc aaccacaaca gccccagggt tagcaacagc    3660
agcaccaata gccgcaggca atccaaaacc catggctcca agacccctg aggtcaacca    3720 ctgcctcggt ctcttgtact tgtaaaactg cgcagcccac atttgatgct gcccaacccc    3780
agtactaaca atagcatctc cattagtcaa ctcatcaaga acctcgatag catgctgcgg    3840
agaaatcgcg tcctggaatg tcttgtaacc caatggaaac ttgtgtttct gcacattaat    3900
ctcttctctc caacctccaa gatcaaactt accctccact cctttctcct ccaaaatcat    3960
attaattccc ttcaaggcca acttcaaatc cgcgcaaacc gacacgtgcg cctgcttgtt    4020
cttcccaatc tcggcagaat caatatcaat gtgaacaatc ttagccctac tagcaaaagc    4080
ctcaagcttc ccagtaacac ggtcatcaaa ccttacccca aaggcaagca acaaatcact    4140
attgtcaaca gcatagttag cataaacagt accatgcata cccagcatct gaagggaata    4200
ttcatcacca ataggaaaag ttccaagacc cattaaagtg ctagcaacgg gaataccagt    4260
gagttcaaca aagcgcctca attcagcact ggaattcaaa ctgccaccgc cgacgtagag    4320
aacgggcttt tgggcctcca tgatgagtct gacaatgtgt tccaattggg cctcggcggg    4380
```

```
gggcctgggc agcctggcga ggtaaccggg gaggttaacg ggctcgtccc aattaggcac    4440
ggcgagttgc tgctgaacgt ctttgggaat gtcgatgagg accggaccgg ggcggccgga    4500
ggtggcgacg aagaaagcct cggcgacgac gcggggatg tcgtcgacgt cgaggatgag     4560
gtagttgtgc ttcgtgatgg atctgctcac ctccacgatc ggggtttctt ggaaggcgtc    4620
ggtgccgatc atccggcggg cgacctggcc ggtgatggcg acgactggga cgctgtccat    4680
taaagcgtcg gcgaggccgc tcacgaggtt ggtggcgccg gggccggagg tggcaatgca    4740
gacgccgggg aggccggagg aacgcgcgta gccttcggcg gcgaagacgc cgccctgctc    4800
gtggcgcggg agcacgttgc ggatggcggc ggagcgcgtg agcgcctggt ggatctccat    4860
cgacgcaccg ccgggtacg cgaacaccgt cgtcacgccc tgcctctcca gcgcctccac     4920
aaggatgtcc gcgcccttgc gaggttcgcc ggaggcgaac cgtgacacga agggctccgt    4980
ggtcggcgct tccttggtga agggcgccgc cgtgggggt ttggagatgg aacatttgat     5040
tttgagagcg tggttgggtt tggtgagggt tgatgagag agaggggagg tggatctagt      5100
aatgcgtttg gggaaggtgg ggtgtgaaga ggaagaagag aatcgggtgg ttctggaagc    5160 ggtgccgcc attgtgttgt gtggcatggt tatacttcaa aaactgcaca acaagcctag      5220
agttagtacc taaacagtaa atttacaaca gagagcaaag acacatgcaa aaatttcagc    5280
cataaaaaaa gttataatag aatttaaagc aaaagtttca tttttttaaac atatatacaa    5340 acaaactgga tttgaaggaa gggattaatt cccctgctca aagtttgaat tcctattgtg     5400
acctatactc gaataaaatt gaagcctaag gaatgtatga gaaacaagaa aacaaaacaa    5460
aactacagac aaacaagtac aattacaaaa ttcgctaaaa ttctgtaatc accaaacccc    5520
atctcagtca gcacaaggcc caaggtttat tttgaaataa aaaaaagtg atttatttc       5580 tcataagcta aagaaagaa aggcaattat gaaatgattt cgactagatc tgaaagtcca      5640
acgcgtattc cgcagatatt aaagaaagag tagagtttca catggatcct agatggaccc    5700
agttgaggaa aaagcaaggc aaagcaaacc agaagtgcaa gatccgaaat tgaaccacgg    5760
aatctaggat ttggtagagg gagaagaaaa gtaccttgag aggtagaaga gaagagaaga    5820
gcagagagat atatgaacga gtgtgtcttg gtctcaactc tgaagcgata cgagtttaga    5880
ggggagcatt gagttccaat ttataggaa accgggtggc aggggtgagt taatgacgga     5940
aaagccccta agtaacgaga ttggattgtg ggttagattc aaccgtttgc atccgcggct    6000
tagattgggg aagtcagagt gaatctcaac cgttgactga gttgaaaatt gaatgtagca    6060
accaattgag ccaaccccag cctttgccct ttgattttga tttgtttgtt gcatactttt     6120
tatttgtctt ctggttctga ctctctttct ctcgtttcaa tgccaggttg cctactccca    6180
caccactcac aagaagattc tactgttagt attaaatatt ttttaatgta ttaaatgatg    6240
aatgcttttg taaacagaac aagactatgt ctaataagtg tcttgcaaca ttttttaaga    6300
aattaaaaaa aatatattta ttatcaaaat caaatgtatg aaaaatcatg aataatataa    6360
ttttatacat ttttttaaaa aatcttttaa tttcttaatt aatatcttaa aaataatgat    6420 taatattaa cccaaaataa ttagtatgat tggtaaggaa gatatccatg ttatgtttgg      6480
atgtgagttt gatctagagc aaagcttact agagtcgacc tgcagcccgg gggatccgcc    6540
cacgtacggt accatctgct aatattttaa atcacatgca agagaggagg catgttcca     6600 ttttctacct tcacattatt tgagaaaaac gaacttgttc tgtgttttat ttttgccctt    6660
cacattagta caacgtggaa gactcatggt tacacagaat catacataag tacaatgctt    6720
gtccctaaga aaacaagcac tcgttgtatt gaacctttac ggctcatgcg gccgcgaatt    6780
```

```
cactagtgat tgaattcgcg gccgcttagt ccgacttggc cttggcggcc gcggccgact    6840
cttttgagcgt gaagatctgc gccgtctcgg gcacagcgcc gtagttgaca aagaggtgcg   6900
cggtcttgaa gaaggccgtg atgatgggct cgtcgttcct gcgcacgagg tgcgggtacg   6960
cggccgcaaa gtgcttggtg gcttcgttga gcttgtagtg cggaatgatc gggaacaagt   7020
ggtggacctg gtgcgtgcca atgtggtggc tcaggttgtc cacgaacgcg ccgtacgagc   7080
ggtcgacgct cgagaggttg cccttgacgt acgtccactc cgagtcgccg taccacggcg   7140
tcgcttcgtc gttgtggtgc aagaaggtcg taatgacgag gaacgaagca agacaaaga    7200
gcggcgcata gtagtagagg cccatgacgg caaagccgag cgagtatgtg aggtacgcgt   7260
acgcggcgaa gaaggcggcc cagacgccga gcgacacgat gacggccgac gcgcggcgaa   7320
ggaggagcgg gtcccacggg tcaaagtggc tcatcgtgcg cggggcatac ccgaccttca   7380
agtagacaaa ccacgcaccg ccgagcgtgt agacccattg gcgcacgtcc tggaggtcct   7440
tgaccgaccg gtgcgggtaa aagatctcgt cctatcaat gttgcccgtg ttcttgtggt    7500
ggtggcggtg cgtcacgcgc cagctctcga acggcgtcaa aatcgcagag tgcatgatgc   7560
agccgatgat aaagttgacg ctgtggtagc gcgagaaggc cgagtggccg cagtcgtggc   7620
cgaccgtgaa gaagccccag aagatgacgc cctgcacgta gatgtaggtg gcgcaaacga   7680
gcgcgtggag cagaacgtta tcggcaatga acggcgtcga gcgcgccgcg tagagcagcg   7740
ccgccgaggc cgacgcgttg aagatcgcgc gggccgtgta gtagagcgag aggccgaggt   7800
tcgactcaaa gcacgcgttc gggatcgagt gcttgagctc cgtgagcgtc gggaactcga   7860
ccttcgtctt atcctcagtc atgcggccgc tgaagtattg cttcttagtt aacctttcct   7920
ttctctctca gctatgtgaa ttcattttgc tttcgtcaca atttatatag tgaaattgga   7980
tctttggagt taacgccttc acaggattat cgtgttagaa caatgctttt tcatgttcta   8040
attagtagta cattacaaat gtgcactcta ttcaataagc atcttttggc acgttaataa   8100
atcatgtgaa aaaaaatac tactatttca aagaaagtgt tgtaaaaaga aacgaaaga     8160
gagctggctt cagttgttga gacttgtttg ctagtaaaaa tggtgtgaag agtgattcat   8220
ggtgaggtgg ttttttcgtcc ctttctgttt gcatgaaaaa caaatggcaa gagatgacgt  8280
aggattcctt cccttaacga ttatctgttt ttaatttcaa atatacatat aggaatttat   8340
gaattactaa ggttgtaaaa tatgctggtc atttatttat ggctaaaata ttttttttc    8400
tcgtaaatat aaaaatattt aaaatttatt tttatcatat tttttatcct tataaaatta   8460
tgtgtacaac ctatataaaa aaatatcata tttaatattg attatatgtt taatcaatat   8520
aaaaaatcat tatcatatat ttagatttat tcgaatatac atctaaacaa aaaataacat   8580
attttaatttt tatgaagaaa aaaaaatatt ttatccttta tttatttaag attaattaat  8640
agttatgtat tgtggaaaga cttttacaca tgcaatagat atactgaatc aattagatgc   8700
caatgctgag ttgaaaatca cttgaggagg ggaggagact tgccaatgct tttcagtttc   8760
atttaaatga tttagtggag gagatagagt agtgataaag gcatgcccca attttggagt   8820
gtatatatga gtgaaataa gagagggata gagagaaaaa ataagagag taaaaataat    8880
taatgtgaaa tgatatgata aaaaaataaa gaaagagata agagaaaaa tgaaatgaga    8940
gatagatgaa atagagagta gatacatgtt tgtttaggtt ttttttagga aataacacat   9000
ttttttctca tcacttatta ctcactgtca atttcctctc tttcaatcat aatgatatga   9060
tttgtttaac aaaaatgtga aaaaacatat aaagtaaaat attttttataa attgataaat   9120
aaaaatttac aaaattttatt tcttattaaa ttgaatagaa aatgaaagaa aagaaaagaa   9180
```

```
aaagtatata taaaatgata tagctttaaa aagaataaat ttttcatatc agtcttttt     9240 taataattta gaaatattta agtatatagc aaaaatataa tgtactttac atatgcataa    9300
ataataattt gaaaatagaa ctaatagaat agagaaaaaa gtaatataat aattaactat    9360
atgaaaattt agaagggaca atattttttaa ttaagaatat aaacaatatt tcttttcatg   9420
taatgaggga cggatgtacg gggccagtgt tggagtcaaa gccaaaatag tcacggggaa    9480
attaatgcac tgcatgacta ttcgaaaaaa ttcactagcc ttacttagat gttagattaa    9540
tagctagggg gtgcagataa ttttgaaagg catgaaaaac attaatttgt acattgcaag    9600
cttttgatga caagctttgc aattgttcac actaccttat gccatttata aatagagtga    9660
ttggcatatg aaggaaatca tgagagtcga agcgaaaaac aaagcttgag agtgtaggaa    9720
aaatacagtt ttttggtaa aaatacagta tttgaatagg agcgaaaaat atcctttcaa     9780
aatgatcctt ttcttttttt ttttttttct tgttgttctt ggtcagttat tcaaaggaaa   9840
agggattgaa ataaaaactt gcatgtggga tcgtacgtcg agtcgacctg caggatccat    9900
gcccttcatt tgccgcttat taattaattt ggtaacagtc cgtactaatc agttacttat    9960 ccttcccca tcataattaa tcttggtagt ctcgaatgcc acaacactga ctagtctctt    10020
ggatcataag aaaagccaa ggaacaaaag aagacaaaac acaatgagag tatcctttgc    10080
atagcaatgt ctaagttcat aaaattcaaa caaaaacgca atcacacaca gtggacatca    10140
cttatccact agctgatcag gatcgccgcg tcaagaaaaa aaaactggac cccaaaagcc    10200
atgcacaaca acacgtactc acaaggtgt caatcgagca gcccaaaaca ttcaccaact    10260
caacccatca tgagccctca catttgttgt ttctaaccca acctcaaact cgtattctct    10320
tccgccacct cattttttgtt tatttcaaca cccgtcaaac tgcatgccac cccgtggcca   10380
aatgtccatg catgttaaca agacctatga ctataaatag ctgcaatctc ggcccaggtt   10440
ttcatcatca agaaccagtt caatatccta gtacaccgta ttaaagaatt taagatatac    10500
tgcggccgca caatggcgac tcgacagcga actgccacca ctgttgtggt cgaggacctt   10560
cccaaggtca ctcttgaggc caagtctgaa cctgtgttcc ccgatatcaa gaccatcaag    10620
gatgccattc ccgcgcactg cttccagccc tcgctcgtca cctcattcta ctacgtcttc   10680
cgcgattttg ccatggtctc tgccctcgtc tgggctgctc tcacctacat ccccagcatc   10740
cccgaccaga ccctccgcgt cgcagcttgg atggtctacg gcttcgtcca gggtctgttc    10800
tgcaccggtg tctggattct cggccatgag tgcggccacg gtgctttctc tctccacgga   10860
aaggtcaaca atgtgaccgg ctggttcctc cactcgttcc tcctcgtccc ctacttcagc    10920
tggaagtact ctcaccaccg ccaccaccgc ttcaccggcc acatggatct cgacatggct   10980
ttcgtcccca agactgagcc caagccctcc aagtcgctca tgattgctgg cattgacgtc    11040
gccgagcttg ttgaggacac ccccgctgct cagatggtca agctcatctt ccaccagctt   11100
ttcggatggc aggcgtacct cttcttcaac gctagctctg gcaagggcag caagcagtgg    11160
gagcccaaga ctggcctctc caagtggttc cgagtcagtc acttcgagcc taccagcgct   11220
gtcttccgcc ccaacgaggc catcttcatc ctcatctccg atatcggtct tgctctaatg    11280
ggaactgctc tgtactttgc ttccaagcaa gttggtgttt cgaccattct cttcctctac    11340
cttgttccct acctgtgggt tcaccactgg ctcgttgcca ttacctacct ccaccaccac    11400
cacaccgagc tccctcacta caccgctgag ggctggacct acgtcaaggg agctctcgcc    11460
actgtcgacc gtgagtttgg cttcatcgga aagcacctct tccacggtat cattgagaag    11520
cacgttgttc accatctctt cctaagatc cccttctaca aggctgacga ggccaccgag    11580
```

```
gccatcaagc cgtcattgg cgaccactac tgccacgacg accgaagctt cctgggccag    11640
ctgtggacca tcttcggcac gctcaagtac gtcgagcacg accctgcccg acccggtgcc    11700
atgcgatgga acaaggacta ggctaggcgg ccgcaagtat gaactaaaat gcatgtaggt    11760
gtaagagctc atggagagca tggaatattg tatccgacca tgtaacagta taataactga    11820
gctccatctc acttcttcta tgaataaaca aggatgtta tgatatatta acactctatc    11880
tatgcacctt attgttctat gataaatttc ctcttattat tataaatcat ctgaatcgtg    11940
acggcttatg gaatgcttca aatagtacaa aaacaaatgt gtactataag actttctaaa    12000
caattctaac cttagcattg tgaacgagac ataagtgtta agaagacata acaattataa    12060
tggaagaagt ttgtctccat ttatatatta tatattaccc acttatgtat tatattagga    12120
tgttaaggag acataacaat tataaagaga gaagtttgta tccatttata tattatatac    12180
tacccattta tatattatac ttatccactt atttaatgtc tttataaggt ttgatccatg    12240
atatttctaa tattttagtt gatatgtata tgaaagggta ctatttgaac tctcttactc    12300
tgtataaagg ttggatcatc cttaaagtgg gtctatttaa ttttattgct tcttacagat    12360
aaaaaaaaaa ttatgagttg gtttgataaa atattgaagg atttaaaata ataaaaata    12420 acatataata tatgtatata aatttattat aatataacat ttatctataa aaaagtaaat    12480
attgtcataa atctatacaa tcgtttagcc ttgctggacg aatctcaatt atttaaacga    12540
gagtaaacat atttgacttt ttggttattt aacaaattat tatttaacac tatatgaaat    12600
tttttttttt atcagcaaag aataaaatta aattaagaag gacaatggtg tcccaatcct    12660
tatacaacca acttccacaa gaaagtcaag tcagagacaa caaaaaaaca agcaaaggaa    12720
attttttaat ttgagttgtc ttgtttgctg cataattat gcagtaaaac actacacata    12780
acccttttag cagtagagca atggttgacc gtgtgcttag cttcttttat tttattttt    12840 tatcagcaaa gaataaataa aataaaatga gacacttcag ggatgtttca acctgca    12897
```

<210> SEQ ID NO 57
<211> LENGTH: 1272
<212> TYPE: DNA
<213> ORGANISM: Artificial Sequence
<220> FEATURE:
<223> OTHER INFORMATION: synthetic delta-8 desaturase (codon-optimized
      for Yarrowia lipolytica)

<400> SEQUENCE: 57

```
atgggcaagg gtggagacgg tggagcacag gctgtgtctg gcaccgatgc ctccctcgct     60
gaggtctcct ctgtggacag caagtccgtc cacgtggttc tgtacggcaa gcgagtggat    120
gtcaccaagt tccagaaggc tcaccctgga ggttcgaagg tgttccgaat ctttcaggag    180
cgagacgcca cagaacagtt cgagtcctac cactctccca aggccatcaa gatgatggaa    240
ggtatgctca aaaagtcgga ggatgctccc gcttccgtgc ctcttccctc tcgatccact    300
atgggcaccg agttcaagga gatgatcgaa cgacacaaga gagccggtct ctacgaccct    360
tgtcccttgg acgagctgtt caagctcacc attgtccttg ctcctatctt tgtgggagcc    420
tatctcgttc gatccggtgt ctctcctctt gctggagccc tgtcgatggg cttcggattc    480
tacctcgacg gctggcttgc tcacgactac ctgcatcacg cagtgttcaa gggctccgtc    540
aacacactcg tcaaggccaa caacgctatg ggatacgcct gggcttcct ccagggttac    600 gacgttgctt ggtggcgagc cagacacaac actcatcacg tgtgcaccaa cgaggacggc    660
tccgatcccg acatcaagac ggctcctctg ctcatttacg tgcgagagaa tcctccatt    720 gccaagcggc tcaacttctt tcagcgatgg caacagtact actatgttcc tactatggcc    780
```

```
attctggatc tctactggcg actggagtct atcgcatacg tcgctgtgcg actgcccaag     840
atgtggatgc aggctgccgc tcttgccgct cactacgcac tcctgtgttg ggtcttcgct     900
gcccatctca acctgattcc tctcatgatg gttgcacgag gtttcgcgac cggaatcgtg     960
gtctttgcca cccactatgg cgaggacatt ctcgaccgag agcacgtcga aggcatgact    1020
ctggtcgagc agaccgccaa gacctcccga aacatcactg gtggatggct tgtcaacgtg    1080
ctcaccggct tcatttctct gcagaccgag catcatctgt ttcccatgat gcctactgga    1140
aacctcatga ccattcaacc cgaggttcga gacttttttca aaaagcacgg tctcgagtac    1200
cgagaaggaa acctgtttca gtgcgtgcat cagaacatca aggctctcgc cttcgagcac    1260
ctgcttcact aa                                                         1272
```

<210> SEQ ID NO 58
<211> LENGTH: 3992
<212> TYPE: DNA
<213> ORGANISM: Artificial Sequence
<220> FEATURE:
<223> OTHER INFORMATION: plasmid pPiD8S

<400> SEQUENCE: 58

```
tcgcgcgttt cggtgatgac ggtgaaaacc tctgacacat gcagctcccg gagacggtca      60
cagcttgtct gtaagcggat gccgggagca gacaagcccg tcaggcgcgc tcagcgggtg     120
ttggcgggtg tcgggctggc ttaactatgc ggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acctcgcgaa     420
tgcatctaga tccatgggca agggtggaga cggtggagca caggctgtgt ctggcaccga     480
tgcctccctc gctgaggtct cctctgtgga cagcaagtcc gtccacgtgg ttctgtacgg     540
caagcgagtg gatgtcacca gttccagaa ggctcaccct ggaggttcga aggtgttccg      600
aatctttcag gagcgagacg ccacagaaca gttcgagtcc taccactctc caaggccat      660 caagatgatg gaaggtatgc tcaaaaagtc ggaggatgct cccgcttccg tgcctcttcc     720
ctctcgatcc actatgggca ccgagttcaa ggagatgatc gaacgacaca agagagccgg     780
tctctacgac ccttgtccct tggacgagct gttcaagctc accattgtcc ttgctcctat     840 cttttgtggga gcctatctcg ttcgatccgg tgtctctcct cttgctggag ccctgtcgat     900
gggcttcgga ttctacctcg acggctggct tgctcacgac tacctgcatc acgcagtgtt     960
caagggctcc gtcaacacac tcgtcaaggc caacaacgct atgggatacg ccttgggctt    1020
cctccagggt tacgacgttg cttggtggcg agccagacac aacactcatc acgtgtgcac    1080
caacgaggac ggctccgatc ccgacatcaa gacggctcct ctgctcattt acgtgcgaga    1140
gaatccctcc attgccaagc ggctcaactt ctttcagcga tggcaacagt actactatgt    1200
tcctactatg ccattctgg atctctactg gcgactggag tctatcgcat acgtcgctgt    1260
gcgactgccc aagatgtgga tgcaggctgc cgctcttgcc gctcactacg cactcctgtg    1320
ttgggtcttc gctgcccatc tcaacctgat tcctctcatg atggttgcac gaggtttcgc    1380
gaccggaatc gtggtctttg ccacccacta tggcgaggac attctcgacc gagagcacgt    1440
cgaaggcatg actctggtcg agcagaccgc caagacctcc cgaaacatca ctggtggatg    1500
gcttgtcaac gtgctcaccg gcttcatttc tctgcagacc gagcatcatc tgtttcccat    1560
```

```
gatgcctact ggaaacctca tgaccattca acccgaggtt cgagactttt tcaaaaagca    1620
cggtctcgag taccgagaag gaaacctgtt tcagtgcgtg catcagaaca tcaaggctct    1680
cgccttcgag cacctgcttc actaagcggc cgcatcggat cccgggcccg tcgactgcag    1740
aggcctgcat gcaagcttgg cgtaatcatg gtcatagctg tttcctgtgt gaaattgtta    1800
tccgctcaca attccacaca acatacgagc cggaagcata aagtgtaaag cctggggtgc    1860
ctaatgagtg agctaactca cattaattgc gttgcgctca ctgcccgctt tccagtcggg    1920
aaacctgtcg tgccagctgc attaatgaat cggccaacgc gcgggagag gcggtttgcg    1980 tattgggcgc tcttccgctt cctcgctcac tgactcgctg cgctcggtcg ttcggctgcg    2040
gcgagcggta tcagctcact caaaggcggt aatacggtta tccacagaat caggggataa    2100
cgcaggaaag aacatgtgag caaaaggcca gcaaaaggcc aggaaccgta aaaaggccgc    2160
gttgctggcg tttttccata ggctccgccc ccctgacgag catcacaaaa atcgacgctc    2220
aagtcagagg tggcgaaacc cgacaggact ataaagatac caggcgtttc ccctggaag   2280 ctccctcgtg cgctctcctg ttccgaccct gccgcttacc ggatacctgt ccgcctttct    2340
cccttcggga agcgtggcgc tttctcatag ctcacgctgt aggtatctca gttcggtgta    2400
ggtcgttcgc tccaagctgg gctgtgtgca cgaaccccc gttcagcccg accgctgcgc    2460
cttatccggt aactatcgtc ttgagtccaa cccggtaaga cacgacttat cgccactggc    2520
agcagccact ggtaacagga ttagcagagc gaggtatgta ggcggtgcta cagagttctt    2580
gaagtggtgg cctaactacg gctacactag aagaacagta tttggtatct gcgctctgct    2640
gaagccagtt accttcggaa aaagagttgg tagctcttga tccggcaaac aaaccaccgc    2700
tggtagcggt ggtttttttg tttgcaagca gcagattacg cgcagaaaaa aaggatctca    2760
agaagatcct ttgatctttt ctacggggtc tgacgctcag tggaacgaaa actcacgtta    2820
agggattttg gtcatgagat tatcaaaaag gatcttcacc tagatccttt taaattaaaa    2880
atgaagtttt aaatcaatct aaagtatata tgagtaaact tggtctgaca gttaccaatg    2940
cttaatcagt gaggcaccta tctcagcgat ctgtctattt cgttcatcca tagttgcctg    3000
actccccgtc gtgtagataa ctacgatacg ggagggctta ccatctggcc ccagtgctgc    3060
aatgataccg cgagacccac gctcaccggc tccagattta tcagcaataa accagccagc    3120
cggaagggcc gagcgcagaa gtggtcctgc aactttatcc gcctccatcc agtctattaa    3180
ttgttgccgg gaagctagag taagtagttc gccagttaat agtttgcgca acgttgttgc    3240
cattgctaca ggcatcgtgg tgtcacgctc gtcgtttggt atggcttcat tcagctccgg    3300
ttcccaacga tcaaggcgag ttacatgatc ccccatgttg tgcaaaaaag cggttagctc    3360
cttcggtcct ccgatcgttg tcagaagtaa gttggccgca gtgttatcac tcatggttat    3420
ggcagcactg cataattctc ttactgtcat gccatccgta agatgctttt ctgtgactgg    3480
tgagtactca accaagtcat tctgagaata gtgtatgcgg cgaccgagtt gctcttgccc    3540
ggcgtcaata cgggataata ccgcgccaca tagcagaact ttaaaagtgc tcatcattgg    3600
aaaacgttct tcggggcgaa aactctcaag gatcttaccg ctgttgagat ccagttcgat    3660
gtaacccact cgtgcaccca actgatcttc agcatctttt actttcacca gcgtttctgg    3720
gtgagcaaaa acaggaaggc aaaatgccgc aaaaaaggga ataagggcga cacggaaatg    3780
ttgaatactc atactcttcc ttttcaata ttattgaagc atttatcagg gttattgtct    3840
catgagcgga tacatatttg aatgtattta gaaaaataaa caataggggg ttccgcgcac    3900
atttccccga aaagtgccac ctgacgtcta agaaaccatt attatcatga cattaaccta    3960
```

```
taaaaatagg cgtatcacga ggcccttccg tc                                  3992

<210> SEQ ID NO 59
<211> LENGTH: 792
<212> TYPE: DNA
<213> ORGANISM: Isochrysis galbana

<400> SEQUENCE: 59
atggccctcg caaacgacgc gggagagcgc atctgggcgg ctgtgaccga cccggaaatc      60
ctcattggca ccttctcgta cttgctactc aaaccgctgc tccgcaattc cgggctggtg     120
gatgagaaga agggcgcata caggacgtcc atgatctggt acaacgttct gctggcgctc     180
ttctctgcgc tgagcttcta cgtgacggcg accgccctcg gctgggacta tggtacgggc     240
gcgtggctgc gcaggcaaac cggcgacaca ccgcagccgc tcttccagtg cccgtccccg     300
gtttgggact cgaagctctt cacatggacc gccaaggcat tctattactc caagtacgtg     360
gagtacctcg cacggcctg gctggtgctc aagggcaaga gggtctcctt ctccaggcc      420 ttccaccact ttggcgcgcc gtgggatgtg tacctcggca ttcggctgca acgagggc       480 gtatggatct tcatgttttt caactcgttc attcacacca tcatgtacac ctactacggc     540
ctcaccgccg ccgggtataa gttcaaggcc aagccgctca tcaccgcgat gcagatctgc     600
cagttcgtgg gcggcttcct gttggtctgg gactacatca acgtccctg cttcaactcg      660 gacaaaggga agttgttcag ctgggctttc aactatgcat acgtcggctc ggtcttcttg     720
ctcttctgcc actttttcta ccaggacaac ttggcaacga agaaatcggc caaggcgggc     780
aagcagctct ag                                                        792

<210> SEQ ID NO 60
<211> LENGTH: 757
<212> TYPE: DNA
<213> ORGANISM: Euglena gracilis
<220> FEATURE:
<221> NAME/KEY: misc_feature
<222> LOCATION: (677)..(677)
<223> OTHER INFORMATION: n is a, c, g, or t

<400> SEQUENCE: 60
ttttttttcg aacacttaat ggaggtggtg aatgaaatag tctcaattgg gcaggaagtt      60
ttacccaaag ttgattatgc ccaactctgg agtgatgcca gtcactgtga ggtgctttac     120
ttgtccatcg catttgtcat cttgaagttc actcttggcc cccttggtcc aaaaggtcag     180
tctcgtatga agtttgtttt caccaattac aaccttctca tgtccattta ttcgtttggga     240 tcattcctct caatggcata tgccatgtac accatcggtg ttatgtctga caactgcgag     300
aaggcttttg acaacaacgt cttcaggatc accacgcagt tgttctattt gagcaagttc     360
ctggagtata ttgactcctt ctatttgcca ctgatgggca agcctctgac ctggttgcaa     420
ttcttccatc atttggggc accgatggat atgtggctgt tctataatta ccgaaatgaa     480
gctgtttgga ttttgtgct gttgaatggt ttcatccact ggatcatgta cggttattat     540
tggaccagat tgatcaagct gaagttcccc atgccaaaat ccctgattac atcaatgcag     600
atcattcaat tcaatgttgg ttctacatt gtctggaagt acaggaacat tccctgttat     660
cgccaagatg ggatgangat gtttggctgg ttcttcaatt actttatgt tggcacagtc     720 ttgtgtttgt tcttgaattt ctatgtgcaa acgtata                             757

<210> SEQ ID NO 61
<211> LENGTH: 774
```

<212> TYPE: DNA
<213> ORGANISM: Euglena gracilis
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (218)..(220)
<223> OTHER INFORMATION: n is a, c, g, or t
<220> FEATURE:
<221> NAME/KEY: misc_feature
<222> LOCATION: (707)..(709)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t

<400> SEQUENCE: 61

```
tcaggatcac cacgcagttg ttctatttga gcangttcct ggagtatatt gactccttct      60
atttgccant gatgggcaag cntctgacct ggttgcaatt cttccatcat tnggggcac     120
cgatggatat gtggctgttc tataattacc gaaatgaagc tgtttggatt tttgtgctgt    180
tgaatggttt catccactgg atcatgtacg gttattannn gaccagattg atcaagctga    240
agttccccat gccaaaatcc ctgattacat caatgcagat cattcaattc aatgttggtt    300
tctacattgt ctggaagtac aggaacattc cctgttatcg ccaagatggg atgaggatgt    360
ttggctggtt cttcaattac ttttatgttg gcacagtctt gtgtttgttc ttgaatttct    420
atgtgcaaac gtatatcgtc aggaagcaca agggagccaa aaagattcag tgatatttcc    480
tcctctgcgg tggcctcttt tgacctcccc ttgacaccta taatgtggag gtgtcgggct    540
ctctccgtct caccagcact tgactctgca ggtgctcact tttattttt  acccatcttt    600
gcttgttgac cattcacctc tcccacttcc acatagtcca ttctaactgt tgcagactgc    660
ggtccatttt ttccagagct cccaatgacc atacgcgaca ccttgtnnnc ncccagccca    720
ttgtgcacaa ttcatagtgg catcgttttg ccttgatacg tgtgcatcca gcgg          774
```

<210> SEQ ID NO 62
<211> LENGTH: 1201
<212> TYPE: DNA
<213> ORGANISM: Euglena gracilis
<220> FEATURE:
<221> NAME/KEY: misc_feature
<222> LOCATION: (1134)..(1136)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t

<400> SEQUENCE: 62

```
gacatggcaa ctatgatttt attttgactg atagtgacct gttcgttgca acaaattgat      60
gagcaatgct tttttataat gccaactttg tacaaaaaag ttggattttt ttcgaacac     120
ttaatggagg tggtgaatga aatagtctca attgggcagg aagttttacc caaagttgat    180
```

```
tatgcccaac tctggagtga tgccagtcac tgtgaggtgc tttacttgtc catcgcattt       240
gtcatcttga agttcactct ggccccctt ggtccaaaag gtcagtctcg tatgaagttt        300
gttttcacca attacaacct tctcatgtcc atttattcgt tgggatcatt cctctcaatg       360
gcatatgcca tgtacaccat cggtgttatg tctgacaact gcgagaaggc ttttgacaac       420
aacgtcttca ggatcaccac gcagttgttc tatttgagca agttcctgga gtatattgac       480
tccttctatt tgccactgat gggcaagcct ctgacctggt tgcaattctt ccatcatttg       540
ggggcaccga tggatatgtg gctgttctat aattaccgaa atgaagctgt ttggattttt       600
gtgctgttga atggtttcat ccactggatc atgtacggtt attattggac cagattgatc       660
aagctgaagt tccccatgcc aaaatccctg attacatcaa tgcagatcat tcaattcaat       720
gttggtttct acattgtctg gaagtacagg aacattccct gttatcgcca agatgggatg       780
aggatgtttg gctggttctt caattacttt tatgttggca cagtcttgtg tttgttcttg       840
aatttctatg tgcaaacgta tatcgtcagg aagcacaagg gagccaaaaa gattcagtga       900
tatttcctcc tctgcggtgg cctctttga cctcccctg acacctataa tgtggaggtg         960
tcgggctctc tccgtctcac cagcacttga ctctgcaggt gctcactttt atttttacc      1020 catctttgct tgttgaccat tcacctctcc cacttccaca tagtccattc taactgttgc      1080
agactgcggt ccattttttc cagagctccc aatgaccata cgcgacacct tgtnnncncc      1140
cagcccattg tgcacaattc atagtggcat cgttttgcct tgatacgtgt gcatccagcg      1200
g                                                                     1201
```

<210> SEQ ID NO 63
<211> LENGTH: 18
<212> TYPE: DNA
<213> ORGANISM: Artificial Sequence
<220> FEATURE:
<223> OTHER INFORMATION: M13F universal primer

<400> SEQUENCE: 63

```
tgtaaaacga cggccagt                                                      18
```

<210> SEQ ID NO 64
<211> LENGTH: 258
<212> TYPE: PRT
<213> ORGANISM: Euglena gracilis

<400> SEQUENCE: 64

```
Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125
```

```
Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 65
<211> LENGTH: 263
<212> TYPE: PRT
<213> ORGANISM: Isochrysis galbana

<400> SEQUENCE: 65

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240
```

```
Leu Phe Cys His Phe Phe Tyr Gln Asp Asn Leu Ala Thr Lys Lys Ser
            245                 250                 255

Ala Lys Ala Gly Lys Gln Leu
        260
```

<210> SEQ ID NO 66
<211> LENGTH: 777
<212> TYPE: DNA
<213> ORGANISM: Artificial Sequence
<220> FEATURE:
<223> OTHER INFORMATION: synthetic (codon-optimized) delta-9 elongase
    derived from Isochrysis galbana codon-optimized for expression in
    Yarrowia lipolytica

<400> SEQUENCE: 66

```
atggaggtcg tgaacgaaat cgtctccatt ggccaggagg ttcttcccaa ggtcgactat      60
gctcagctct ggtctgatgc ctcgcactgc gaggtgctgt acctctccat cgccttcgtc     120
atcctgaagt tcaccttgg tcctctcgga cccaagggtc agtctcgaat gaagtttgtg      180
ttcaccaact acaacctgct catgtccatc tactcgctgg gctccttcct ctctatggcc     240
tacgccatgt acaccattgg tgtcatgtcc gacaactgcg agaaggcttt cgacaacaat     300
gtcttccgaa tcaccactca gctgttctac ctcagcaagt ccctcgagta cattgactcc     360
ttctatctgc ccctcatggg caagcctctg acctggttgc agttcttca ccatctcgga     420
gctcctatgg acatgtggct gttctacaac taccgaaacg aagccgtttg gatctttgtg     480
ctgctcaacg gcttcattca ctggatcatg tacggctact attggacccg actgatcaag     540
ctcaagttcc ctatgcccaa gtccctgatt acttctatgc agatcattca gttcaacgtt     600
ggcttctaca tcgtctggaa gtaccggaac attcccgct accgacaaga tggaatgaga     660
atgtttggct ggttttcaa ctacttctac gttggtactg tcctgtgtct gttcctcaac     720
ttctacgtgc agacctacat cgtccgaaag cacaagggag ccaaaaagat tcagtga       777
```

<210> SEQ ID NO 67
<211> LENGTH: 3497
<212> TYPE: DNA
<213> ORGANISM: Artificial Sequence
<220> FEATURE:
<223> OTHER INFORMATION: plasmid pEgD9ES

<400> SEQUENCE: 67

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acctcgcgaa     420
tgcatctaga tccatggagg tcgtgaacga aatcgtctcc attggccagg aggttcttcc     480
caaggtcgac tatgctcagc tctggtctga tgcctcgcac tgcgaggtgc tgtacctctc     540
catcgccttc gtcatcctga gttcaccct tggtcctctc ggacccaagg gtcagtctcg     600
aatgaagttt gtgttcacca actacaacct gctcatgtcc atctactcgc tgggctcctt     660
cctctctatg gcctacgcca tgtacaccat tggtgtcatg tccgacaact gcgagaaggc     720
tttcgacaac aatgtcttcc gaatcaccac tcagctgttc tacctcagca gttcctcga     780
```

-continued

```
gtacattgac tccttctatc tgcccctcat gggcaagcct ctgacctggt tgcagttctt    840
tcaccatctc ggagctccta tggacatgtg gctgttctac aactaccgaa acgaagccgt    900
ttggatcttt gtgctgctca acggcttcat tcactggatc atgtacggct actattggac    960
ccgactgatc aagctcaagt tcccctatgcc caagtccctg attacttcta tgcagatcat   1020
tcagttcaac gttggcttct acatcgtctg gaagtaccgg aacattccct gctaccgaca   1080
agatggaatg agaatgtttg gctggttttt caactacttc tacgttggta ctgtcctgtg   1140
tctgttcctc aacttctacg tgcagaccta catcgtccga aagcacaagg gagccaaaaa   1200
gattcagtga gcggccgcat cggatcccgg gcccgtcgac tgcagaggcc tgcatgcaag   1260
cttggcgtaa tcatggtcat agctgttttcc tgtgtgaaat tgttatccgc tcacaattcc   1320
acacaacata cgagccggaa gcataaagtg taaagcctgg ggtgcctaat gagtgagcta   1380
actcacatta attgcgttgc gctcactgcc cgctttccag tcgggaaacc tgtcgtgcca   1440
gctgcattaa tgaatcggcc aacgcgcggg gagaggcggt ttgcgtattg ggcgctcttc   1500
cgcttcctcg ctcactgact cgctgcgctc ggtcgttcgg ctgcggcgag cggtatcagc   1560
tcactcaaag gcggtaatac ggttatccac agaatcaggg gataacgcag gaaagaacat   1620
gtgagcaaaa ggccagcaaa aggccaggaa ccgtaaaaag gccgcgttgc tggcgttttt   1680
ccataggctc cgcccccctg acgagcatca caaaaatcga cgctcaagtc agaggtggcg   1740
aaacccgaca ggactataaa gataccaggc gtttccccct ggaagctccc tcgtgcgctc   1800
tcctgttccg accctgccgc ttaccggata cctgtccgcc tttctccctt cgggaagcgt   1860
ggcgctttct catagctcac gctgtaggta tctcagttcg gtgtaggtcg ttcgctccaa   1920
gctgggctgt gtgcacgaac cccccgttca gcccgaccgc tgcgccttat ccggtaacta   1980
tcgtcttgag tccaacccgg taagacacga cttatcgcca ctggcagcag ccactggtaa   2040
caggattagc agagcgaggt atgtaggcgg tgctacagag ttcttgaagt ggtggcctaa   2100
ctacggctac actagaagaa cagtatttgg tatctgcgct ctgctgaagc cagttacctt   2160
cggaaaaaga gttggtagct cttgatccgg caaacaaacc accgctggta gcggtggttt   2220
ttttgtttgc aagcagcaga ttacgcgcag aaaaaaagga tctcaagaag atcctttgat   2280
cttttctacg gggtctgacg ctcagtggaa cgaaaactca cgttaaggga ttttggtcat   2340
gagattatca aaaaggatct tcacctagat ccttttaaat taaaaatgaa gttttaaatc   2400
aatctaaagt atatatgagt aaacttggtc tgacagttac caatgcttaa tcagtgaggc   2460
acctatctca gcgatctgtc tatttcgttc atccatagtt gcctgactcc ccgtcgtgta   2520
gataactacg atacgggagg gcttaccatc tggccccagt gctgcaatga taccgcgaga   2580
cccacgctca ccggctccag atttatcagc aataaaccag ccagccggaa gggccgagcg   2640
cagaagtggt cctgcaactt tatccgcctc catccagtct attaattgtt gccgggaagc   2700
tagagtaagt agttcgccag ttaatagttt gcgcaacgtt gttgccattg ctacaggcat   2760
cgtggtgtca cgctcgtcgt ttggtatggc ttcattcagc tccggttccc aacgatcaag   2820
gcgagttaca tgatccccca tgttgtgcaa aaaagcggtt agctccttcg gtcctccgat   2880
cgttgtcaga agtaagttgg ccgcagtgtt atcactcatg gttatggcag cactgcataa   2940
ttctcttact gtcatgccat ccgtaagatg cttttctgtg actggtgagt actcaaccaa   3000
gtcattctga gaatagtgta tgcggcgacc gagttgctct tgcccggcgt caatacggga   3060
taataccgcg ccacatagca gaactttaaa agtgctcatc attggaaaac gttcttcggg   3120
gcgaaaactc tcaaggatct taccgctgtt gagatccagt tcgatgtaac ccactcgtgc   3180
```

-continued

| | |
|---|---|
| acccaactga tcttcagcat cttttacttt caccagcgtt tctgggtgag caaaaacagg | 3240 |
| aaggcaaaat gccgcaaaaa agggaataag ggcgacacgg aaatgttgaa tactcatact | 3300 |
| cttccttttt caatattatt gaagcattta tcagggttat tgtctcatga gcggatacat | 3360 |
| atttgaatgt atttagaaaa ataaacaaat aggggttccg cgcacatttc cccgaaaagt | 3420 |
| gccacctgac gtctaagaaa ccattattat catgacatta acctataaaa ataggcgtat | 3480 |
| cacgaggccc tttcgtc | 3497 |

<210> SEQ ID NO 68
<211> LENGTH: 9472
<212> TYPE: DNA
<213> ORGANISM: Artificial Sequence
<220> FEATURE:
<223> OTHER INFORMATION: plasmid pDMW263

<400> SEQUENCE: 68

| | |
|---|---|
| catggcatgg atggtacgtc ctgtagaaac cccaacccgt gaaatcaaaa aactcgacgg | 60 |
| cctgtgggca ttcagtctgg atcgcgaaaa ctgtggaatt gatcagcgtt ggtgggaaag | 120 |
| cgcgttacaa gaaagccggg caattgctgt gccaggcagt tttaacgatc agttcgccga | 180 |
| tgcagatatt cgtaattatg cgggcaacgt ctggtatcag cgcgaagtct ttataccgaa | 240 |
| aggttgggca ggccagcgta tcgtgctgcg tttcgatgcg gtcactcatt acggcaaagt | 300 |
| gtgggtcaat aatcaggaag tgatggagca tcagggcggc tatacgccat ttgaagccga | 360 |
| tgtcacgccg tatgttattg ccgggaaaag tgtacgtatc accgtttgtg tgaacaacga | 420 |
| actgaactgg cagactatcc cgccgggaat ggtgattacc gacgaaaacg gcaagaaaaa | 480 |
| gcagtcttac ttccatgatt tctttaacta tgccgggatc catcgcagcg taatgctcta | 540 |
| caccacgccg aacacctggg tggacgatat caccgtggtg acgcatgtcg cgcaagactg | 600 |
| taaccacgcg tctgttgact ggcaggtggt ggccaatggt gatgtcagcg ttgaactgcg | 660 |
| tgatgcggat caacaggtgg ttgcaactgg acaaggcact agcgggactt gcaagtggt | 720 |
| gaatccgcac ctctggcaac cgggtgaagg ttatctctat gaactgtgcg tcacagccaa | 780 |
| aagccagaca gagtgtgata tctacccgct tcgcgtcggc atccggtcag tggcagtgaa | 840 |
| gggcgaacag ttcctgatta accacaaacc gttctacttt actggctttg gtcgtcatga | 900 |
| agatgcggac ttacgtggca aaggattcga taacgtgctg atggtgcacg accacgcatt | 960 |
| aatggactgg attggggcca actcctaccg tacctcgcat taccctttacg ctgaagagat | 1020 |
| gctcgactgg gcagatgaac atggcatcgt ggtgattgat gaaactgctg ctgtcggctt | 1080 |
| taacctctct ttaggcattg gtttcgaagc gggcaacaag ccgaaagaac tgtacagcga | 1140 |
| agaggcagtc aacggggaaa ctcagcaagc gcacttacag gcgattaaag agctgatagc | 1200 |
| gcgtgacaaa aaccacccaa gcgtggtgat gtggagtatt gccaacgaac cggatacccg | 1260 |
| tccgcaagtg cacgggaata tttcgccact ggcggaagca acgcgtaaac tcgacccgac | 1320 |
| gcgtccgatc acctgcgtca atgtaatgtt ctgcgacgct cacaccgata ccatcagcga | 1380 |
| tctctttgat gtgctgtgcc tgaaccgtta ttacggatgg tatgtccaaa gcggcgattt | 1440 |
| ggaaacggca gagaaggtac tggaaaaaga acttctggcc tggcaggaga actgcatca | 1500 |
| gccgattatc atcaccgaat acggcgtgga tacgttagcc gggctgcact caatgtacac | 1560 |
| cgacatgtgg agtgaagagt atcagtgtgc atggctggat atgtatcacc gcgtctttga | 1620 |
| tcgcgtcagc gccgtcgtcg gtgaacaggt atggaatttc gccgattttg cgacctcgca | 1680 |
| aggcatattg cgcgttggcg gtaacaagaa agggatcttc actcgcgacc gcaaaccgaa | 1740 |

-continued

```
gtcggcggct tttctgctgc aaaaacgctg gactggcatg aacttcggtg aaaaaccgca    1800
gcagggaggc aaacaatgat taattaacta gagcggccgc caccgcggcc cgagattccg    1860
gcctcttcgg ccgccaagcg acccgggtgg acgtctagag gtacctagca attaacagat    1920
agtttgccgg tgataattct cttaacctcc cacactcctt tgacataacg atttatgtaa    1980
cgaaactgaa atttgaccag atattgtgtc cgcggtggag ctccagcttt tgttcccttt    2040
agtgagggtt aatttcgagc ttggcgtaat catggtcata gctgtttcct gtgtgaaatt    2100
gttatccgct cacaattcca cacaacatac gagccggaag cataaagtgt aaagcctggg    2160
gtgcctaatg agtgagctaa ctcacattaa ttgcgttgcg ctcactgccc gctttccagt    2220
cgggaaacct gtcgtgccag ctgcattaat gaatcggcca acgcgcgggg agaggcggtt    2280
tgcgtattgg cgctcttcc  gcttcctcgc tcactgactc gctgcgctcg gtcgttcggc     2340
tgcggcgagc ggtatcagct cactcaaagg cggtaatacg ttatccaca gaatcagggg     2400 ataacgcaga aagaacatg tgagcaaaag gccagcaaaa ggccaggaac cgtaaaaagg     2460
ccgcgttgct ggcgtttttc cataggctcc gccccctga cgagcatcac aaaaatcgac     2520
gctcaagtca gaggtggcga aacccgacag gactataaag ataccaggcg tttccccctg    2580
gaagctccct cgtgcgctct cctgttccga ccctgccgct taccggatac ctgtccgcct    2640
ttctcccttc gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccgt  aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaggat     3060 ctcaagaaga tccttt gatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
```

```
gtctcatgag cggatacata tttgaatgta tttagaaaaa taaacaaata ggggttccgc   4200
gcacatttcc ccgaaaagtg ccacctgacg cgccctgtag cggcgcatta agcgcggcgg   4260
gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc   4380
gggggctccc tttagggttc cgatttagtg ctttacggca cctcgacccc aaaaaacttg   4440
attagggtga tggttcacgt agtgggccat cgccctgata cacggttttt cgccctttga   4500
cgttggagtc cacgttcttt aatagtggac tcttgttcca aactggaaca cactcaacc    4560
ctatctcggt ctattctttt gatttataag ggattttgcc gatttcggcc tattggttaa   4620
aaaatgagct gatttaacaa aaatttaacg cgaattttaa caaaatatta acgcttacaa   4680
tttccattcg ccattcaggc tgcgcaactg ttgggaaggg cgatcggtgc gggcctcttc   4740
gctattacgc cagctggcga aggggggatg tgctgcaagg cgattaagtt gggtaacgcc   4800
agggttttcc cagtcacgac gttgtaaaac gacggccagt gaattgtaat acgactcact   4860
atagggcgaa ttgggtaccg ggccccccct cgaggtcgat ggtgtcgata agcttgatat   4920
cgaattcatg tcacacaaac cgatcttcgc ctcaaggaaa cctaattcta catccgagag   4980
actgccgaga tccagtctac actgattaat tttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaaggggtc   5160
atctcgcatt gtttaataat aaacagactc catctaccgc ctccaaatga tgttctcaaa   5220
atatattgta tgaacttatt tttattactt agtattatta gacaacttac ttgctttatg   5280
aaaaacactt cctatttagg aaacaattta taatggcagt tcgttcattt aacaatttat   5340
gtagaataaa tgttataaat gcgtatggga atcttaaat atggatagca taaatgatat    5400
ctgcattgcc taattcgaaa tcaacagcaa cgaaaaaaat cccttgtaca acataaatag   5460
tcatcgagaa atatcaacta tcaaagaaca gctattcaca cgttactatt gagattatta   5520
ttggacgaga atcacacact caactgtctt tctctcttct agaaatacag gtacaagtat   5580
gtactattct cattgttcat acttctagtc atttcatccc acatattcct tggatttctc   5640
tccaatgaat gacattctat cttgcaaatt caacaattat aataagatat accaaagtag   5700
cggtatagtg gcaatcaaaa agcttctctg gtgtgcttct cgtatttatt tttattctaa   5760
tgatccatta aaggtatata tttatttctt gttatataat cctttgtttt attacatggg   5820
ctggatacat aaaggtattt tgatttaatt ttttgcttaa attcaatccc cctcgttca    5880
gtgtcaactg taatggtagg aaattaccat acttttgaag aagcaaaaaa aatgaaagaa   5940
aaaaaaaatc gtatttccag gttagacgtt ccgcagaatc tagaatgcgg tatgcggtac   6000
attgttcttc gaacgtaaaa gttgcgctcc ctgagatatt gtacatttt gctttacaa     6060
gtacaagtac atcgtacaac tatgtactac tgttgatgca tccacaacag tttgttttgt   6120
ttttttttgt ttttttttt tctaatgatt cattaccgct atgtatacct acttgtactt    6180
gtagtaagcc gggttattgg cgttcaatta atcatagact tatgaatctg cacggtgtgc   6240
gctgcgagtt acttttagct tatgcatgct acttgggtgt aatattggga tctgttcgga   6300
aatcaacgga tgctcaaccg atttcgacag taataatttg aatcgaatcg agcctaaaa    6360
tgaacccgag tatatctcat aaaattctcg gtgagaggtc tgtgactgtc agtacaaggt   6420
gccttcatta tgccctcaac cttaccatac ctcactgaat gtagtgtacc tctaaaaatg   6480
aaatacagtg ccaaaagcca aggcactgag ctcgtctaac ggacttgata tacaaccaat   6540
```

```
taaaacaaat gaaagaaat acagttcttt gtatcatttg taacaattac cctgtacaaa    6600
ctaaggtatt gaaatcccac aatattccca aagtccaccc cttttccaaat tgtcatgcct   6660 acaactcata taccaagcac taacctacca acaccacta aaaccccaca aaatatatct    6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacgcagc ctcaacagcg tcaccggcgg gcttcatgtt aagagagaac    7260
ttgagcatca tggcggcaga cagaatggtg gcaatggggt tgaccttctg cttgccgaga    7320 tcggggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctgggggaat    7560
tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga agtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggct ggcaaacgct cttgtatata tacgcacttt tgcccgtgct atgtggaaga    8340
ctaaacctcc gaagattgtg actcaggtag tgcggtatcg gctagggacc caaaccttgt    8400
cgatgccgat agcgctatcg aacgtacccc agccggccgg gagtatgtcg gaggggacat    8460
acgagatcgt caagggtttg tggccaactg gtaaataaat gatgtcgacg tttaaacagt    8520
gtacgcagat ctactataga ggaacattta aattgccccg gagaagacgg ccaggccgcc    8580
tagatgacaa attcaacaac tcacagctga ctttctgcca ttgccactag ggggggcct    8640 ttttatatgg ccaagccaag ctctccacgt cggttgggct gcacccaaca ataaatgggt    8700
agggttgcac caacaaaggg atgggatggg ggtagaaga tacgaggata acggggctca    8760
atggcacaaa taagaacgaa tactgccatt aagactcgtg atccagcgac tgacaccatt    8820
gcatcatcta agggcctcaa aactacctcg gaactgctgc gctgatctgg acaccacaga    8880
ggttccgagc actttaggtt gcaccaaatg tcccaccagg tgcaggcaga aaacgctgga    8940
```

```
acagcgtgta cagtttgtct taacaaaaag tgagggcgct gaggtcgagc agggtggtgt    9000
gacttgttat agcctttaga gctgcgaaag cgcgtatgga tttggctcat caggccagat    9060
tgagggtctg tggacacatg tcatgttagt gtacttcaat cgcccctgg atatagcccc     9120 gacaataggc cgtggcctca ttttttgcc ttccgcacat ttccattgct cgatacccac     9180
accttgcttc tcctgcactt gccaacctta atactggttt acattgacca acatcttaca    9240
agcggggggc ttgtctaggg tatatataaa cagtggctct cccaatcggt tgccagtctc    9300
ttttttcctt tctttcccca cagattcgaa atctaaacta cacatcacag aattccgagc    9360
cgtgagtatc cacgcaaaga tcagtgtcga gacgacgcgt tttgtgtaat gacacaatcc    9420
gaaagtcgct agcaacacac actctctaca caaactaacc cagctctggt ac            9472
```

<210> SEQ ID NO 69
<211> LENGTH: 8165
<212> TYPE: DNA
<213> ORGANISM: Artificial Sequence
<220> FEATURE:
<223> OTHER INFORMATION: plasmid pZUF17

<400> SEQUENCE: 69

```
gtacgagccg gaagcataaa gtgtaaagcc tggggtgcct aatgagtgag ctaactcaca      60
ttaattgcgt tgcgctcact gcccgctttc cagtcgggaa acctgtcgtg ccagctgcat     120
taatgaatcg gccaacgcgc ggggagaggc ggtttgcgta ttgggcgctc ttccgcttcc     180
tcgctcactg actcgctgcg ctcggtcgtt cggctgcggc gagcggtatc agctcactca     240
aaggcggtaa tacggttatc cacagaatca ggggataacg caggaaagaa catgtgagca     300
aaaggccagc aaaaggccag gaaccgtaaa aaggccgcgt tgctggcgtt tttccatagg     360
ctccgccccc ctgacgagca tcacaaaaat cgacgctcaa gtcagaggtg gcgaaacccg     420
acaggactat aaagatacca ggcgtttccc cctggaagct ccctcgtgcg ctctcctgtt     480
ccgaccctgc cgcttaccgg atacctgtcc gcctttctcc cttcgggaag cgtggcgctt     540
tctcatagct cacgctgtag gtatctcagt tcggtgtagg tcgttcgctc caagctgggc     600
tgtgtgcacg aaccccccgt tcagcccgac cgctgcgcct tatccggtaa ctatcgtctt     660
gagtccaacc cggtaagaca cgacttatcg ccactggcag cagccactgg taacaggatt     720
agcagagcga ggtatgtagg cggtgctaca gagttcttga agtggtggcc taactacggc     780
tacactagaa ggacagtatt tggtatctgc gctctgctga agccagttac cttcggaaaa     840
agagttggta gctcttgatc cggcaaacaa accaccgctg gtagcggtgg ttttttgtt     900 tgcaagcagc agattacgcg cagaaaaaaa ggatctcaag aagatccttt gatcttttct     960
acggggtctg acgctcagtg gaacgaaaac tcacgttaag ggattttggt catgagatta    1020
tcaaaaagga tcttcaccta gatccttta aattaaaaat gaagttttaa atcaatctaa    1080
agtatatatg agtaaacttg gtctgacagt taccaatgct taatcagtga ggcacctatc    1140
tcagcgatct gtctatttcg ttcatccata gttgcctgac tccccgtcgt gtagataact    1200
acgatacggg agggcttacc atctggcccc agtgctgcaa tgataccgcg agacccacgc    1260
tcaccggctc cagatttatc agcaataaac cagccagccg aagggccga gcgcagaagt    1320 ggtcctgcaa ctttatccgc ctccatccag tctattaatt gttgccggga agctagagta    1380
agtagttcgc cagttaatag tttgcgcaac gttgttgcca ttgctacagg catcgtggtg    1440
tcacgctcgt cgtttggtat ggcttcattc agctccggtt cccaacgatc aaggcgagtt    1500
acatgatccc ccatgttgtg caaaaaagcg gttagctcct tcggtcctcc gatcgttgtc    1560
```

-continued

```
agaagtaagt tggccgcagt gttatcactc atggttatgg cagcactgca taattctctt    1620
actgtcatgc catccgtaag atgctttttct gtgactggtg agtactcaac caagtcattc   1680
tgagaatagt gtatgcggcg accgagttgc tcttgcccgg cgtcaatacg ggataatacc    1740
gcgccacata gcagaacttt aaaagtgctc atcattggaa aacgttcttc ggggcgaaaa    1800
ctctcaagga tcttaccgct gttgagatcc agttcgatgt aacccactcg tgcacccaac    1860
tgatcttcag catcttttac tttcaccagc gtttctgggt gagcaaaaac aggaaggcaa    1920
aatgccgcaa aaagggaat aagggcgaca cggaaatgtt gaatactcat actcttcctt    1980
tttcaatatt attgaagcat ttatcagggt tattgtctca tgagcggata catatttgaa    2040
tgtatttaga aaaataaaca ataggggtt ccgcgcacat ttccccgaaa agtgccacct    2100
gacgcgccct gtagcggcgc attaagcgcg cggtgtgg tggttacgcg cagcgtgacc      2160
gctacacttg ccagcgccct agcgcccgct cctttcgctt tcttccttc ctttctcgcc    2220
acgttcgccg gctttccccg tcaagctcta atcgggggc tccctttagg gttccgattt     2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt    2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat    2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tattttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatccttttt gtttattaca tgggctggat acataaaggt attttgattt    3720
aattttttgc ttaaattcaa tcccccctcg ttcagtgtca actgtaatgg taggaaatta   3780
ccatactttt gaagaagcaa aaaaaatgaa agaaaaaaaa aatcgtatttt ccaggttaga   3840
cgttccgcag aatctagaat gcggtatgcg gtacattgtt cttcgaacgt aaaagttgcg   3900
ctcccctgaga tattgtacat ttttgctttt acaagtacaa gtacatcgta caactatgta    3960
```

```
ctactgttga tgcatccaca acagtttgtt ttgttttttt ttgttttttt ttttctaat    4020
gattcattac cgctatgtat acctacttgt acttgtagta agccgggtta ttggcgttca    4080
attaatcata gacttatgaa tctgcacggt gtgcgctgcg agttactttt agcttatgca    4140
tgctacttgg gtgtaatatt gggatctgtt cggaaatcaa cggatgctca atcgatttcg    4200
acagtaatta attaagtcat acacaagtca gctttcttcg agcctcatat aagtataagt    4260
agttcaacgt attagcactg tacccagcat ctccgtatcg agaaacacaa caacatgccc    4320
cattggacag atcatgcgga tacacaggtt gtgcagtatc atacatactc gatcagacag    4380
gtcgtctgac catcatacaa gctgaacaag cgctccatac ttgcacgctc tctatataca    4440
cagttaaatt acatatccat agtctaacct ctaacagtta atcttctggt aagcctccca    4500
gccagccttc tggtatcgct tggcctcctc aataggatct cggttctggc cgtacagacc    4560
tcggccgaca attatgatat ccgttccggt agacatgaca tcctcaacag ttcggtactg    4620
ctgtccgaga gcgtctccct tgtcgtcaag acccacccccg ggggtcagaa taagccagtc    4680
ctcagagtcg cccttaggtc ggttctgggc aatgaagcca accacaaact cggggtcgga    4740
tcgggcaagc tcaatggtct gcttggagta ctcgccagtg ccagagagc ccttgcaaga    4800
cagctcggcc agcatgagca gacctctggc cagcttctcg ttgggagagg ggactaggaa    4860
ctccttgtac tgggagttct cgtagtcaga gacgtcctcc ttcttctgtt cagagacagt    4920
ttcctcggca ccagctcgca ggccagcaat gattccggtt ccgggtacac cgtgggcgtt    4980
ggtgatatcg gaccactcgg cgattcggtg acaccggtac tggtgcttga cagtgttgcc    5040
aatatctgcg aactttctgt cctcgaacag gaagaaaccg tgcttaagag caagttcctt    5100
gaggggggagc acagtgccgg cgtaggtgaa gtcgtcaatg atgtcgatat gggttttgat    5160
catgcacaca taaggtccga ccttatcggc aagctcaatg agctccttgg tggtggtaac    5220
atccagagaa gcacacaggt tggttttctt ggctgccacg agcttgagca ctcgagcggc    5280
aaaggcggac ttgtggacgt tagctcgagc ttcgtaggag ggcattttgg tggtgaagag    5340
gagactgaaa taaatttagt ctgcagaact ttttatcgga accttatctg ggcagtgaa    5400
gtatatgtta tggtaatagt tacgagttag ttgaacttat agatagactg gactatacgg    5460
ctatcggtcc aaattagaaa gaacgtcaat ggctctctgg gcgtcgcctt tgccgacaaa    5520
aatgtgatca tgatgaaagc cagcaatgac gttgcagctg atattgttgt cggccaaccg    5580
cgccgaaaac gcagctgtca gacccacagc ctccaacgaa gaatgtatcg tcaaagtgat    5640
ccaagcacac tcatagttgg agtcgtactc caaaggcggc aatgacgagt cagcagata    5700
ctcgtcgact caggcgacga cggaattcct gcagcccatc tgcagaattc aggagagacc    5760
gggttggcgg cgtatttgtg tcccaaaaaa cagccccaat tgccccggag aagacggcca    5820
ggccgcctag atgacaaatt caacaactca cagctgactt tctgccattg ccactagggg    5880
ggggccttttt tatatggcca agccaagctc tccacgtcgg ttgggctgca cccaacaata    5940
aatgggtagg gttgcaccaa caaagggatg ggatggggggg tagaagatac gaggataacg    6000
gggctcaatg gcacaaataa gaacgaatac tgccattaag actcgtgatc cagcgactga    6060
caccattgca tcatctaagg gcctcaaaac tacctcggaa ctgctgcgct gatctggaca    6120
ccacagaggt tccgagcact ttaggttgca ccaaatgtcc caccaggtgc aggcagaaaa    6180
cgctggaaca gcgtgtacag tttgtcttaa caaaaagtga gggcgctgag gtcgagcagg    6240
gtggtgtgac ttgttatagc ctttagagct gcgaaagcgc gtatgatttt ggctcatcag    6300
gccagattga gggtctgtgg acacatgtca tgttagtgta cttcaatcgc ccctggata    6360
```

```
tagccccgac aataggccgt ggcctcattt ttttgccttc cgcacatttc cattgctcgg    6420
tacccacacc ttgcttctcc tgcacttgcc aaccttaata ctggtttaca ttgaccaaca    6480
tcttacaagc gggggggcttg tctagggtat atataaacag tggctctccc aatcggttgc   6540
cagtctcttt tttcctttct ttccccacag attcgaaatc taaactacac atcacacaat   6600
gcctgttact gacgtcctta agcgaaagtc cggtgtcatc gtcggcgacg atgtccgagc   6660
cgtgagtatc cacgacaaga tcagtgtcga gacgacgcgt tttgtgtaat gacacaatcc   6720
gaaagtcgct agcaacacac actctctaca caaactaacc cagctctcca tggctgagga   6780
taagaccaag gtcgagttcc ctaccctgac tgagctgaag cactctatcc ctaacgcttg   6840
ctttgagtcc aacctcggac tctcgctcta ctacactgcc cgagcgatct tcaacgcatc   6900
tgcctctgct gctctgctct acgctgcccg atctactccc ttcattgccg ataacgttct   6960
gctccacgct ctggtttgcg ccacctacat ctacgtgcag ggtgtcatct tctggggttt   7020
ctttaccgtc ggtcacgact gtggtcactc tgccttctcc cgataccact ccgtcaactt   7080
catcattggc tgcatcatgc actctgccat tctgactccc ttcgagtcct ggcgagtgac   7140
ccaccgacac catcacaaga acactggcaa cattgataag gacgagatct tctaccctca   7200
tcggtccgtc aaggacctcc aggacgtgcg acaatgggtc tacaccctcg gaggtgcttg   7260
gtttgtctac ctgaaggtcg atatgctcc tcgaaccatg tcccactttg accctggga    7320
ccctctcctg cttcgacgag cctccgctgt catcgtgtcc ctcggagtct gggctgcctt   7380
cttcgctgcc tacgcctacc tcacatactc gctcggcttt gccgtcatgg gcctctacta   7440
ctatgctcct ctctttgtct ttgcttcgtt cctcgtcatt actaccttct tgcatcacaa   7500
cgacgaagct actccctggt acggtgactc ggagtggacc tacgtcaagg gcaacctgag   7560
ctccgtcgac cgatcgtacg gagctttcgt ggacaacctg tctcaccaca ttggcaccca   7620
ccaggtccat cacttgttcc ctatcattcc ccactacaag ctcaacgaag ccaccaagca   7680
cttttgctgcc gcttaccctc acctcgtgag acgtaacgac gagcccatca ttactgcctt   7740
cttcaagacc gctcacctct ttgtcaacta cggagctgtg cccgagactg ctcagatttt   7800
caccctcaaa gagtctgccg ctgcagccaa ggccaagagc gactaagcgg ccgcaagtgt   7860
ggatggggaa gtgagtgccc ggttctgtgt gcacaattgg caatccaaga tggatggatt   7920
caacacaggg atatagcgag ctacgtggtg gtgcgaggat atagcaacgg atatttatgt   7980
ttgacacttg agaatgtacg atacaagcac tgtccaagta caatactaaa catactgtac   8040
atactcatac tcgtacccgg gcaacggttt cacttgagtg cagtggctag tgctcttact   8100
cgtacagtgt gcaatactgc gtatcatagt ctttgatgta tatcgtattc attcatgtta   8160
gttgc                                                               8165
```

<210> SEQ ID NO 70  
<211> LENGTH: 7769  
<212> TYPE: DNA  
<213> ORGANISM: Artificial Sequence  
<220> FEATURE:  
<223> OTHER INFORMATION: plasmid pZUFmEgD9ES
<400> SEQUENCE: 70

```
ggccgcaagt gtggatgggg aagtgagtgc ccggttctgt gtgcacaatt ggcaatccaa     60
gatggatgga ttcaacacag ggatatagcg agctacgtgg tggtgcgagg atatagcaac    120
ggatatttat gtttgacact tgagaatgta cgatacaagc actgtccaag tacaatacta    180
aacatactgt acatactcat actcgtaccc ggcaacggtt tcacttgagt gcagtggct    240
```

-continued

```
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg ggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttcctttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgcctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca gctctaaat cggggggctcc   2580
ctttagggtt ccgatttagt gctttacggc acctcgaccc caaaaaactt gattagggtg   2640
```

```
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaatgagc    2820 tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaaggggat gtgctgcaag gcgattaagt tgggtaacgc cagggttttc    3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaagggt catctcgcat    3360 tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tcctttttgtt tattacatgg gctggataca   4020
taaaggtatt ttgatttaat ttttttgctta aattcaatcc ccctcgttc agtgtcaact    4080 gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg ttttttttg    4320 ttttttttt  ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
```

```
acaaactcgg ggtcggatcg ggcaagctca atggtctgct tggagtactc gccagtggcc    5100
agagagccct tgcaagacag ctcggccagc atgagcagac tctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcttttt tatatggcca agccaagctc    6180
tccacgtcgg ttgggctgca cccaacaata aatgggtagg gttgcaccaa caaagggatg    6240
ggatgggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc ggggggcttg tctagggtat    6780
atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggaggtcg tgaacgaaat cgtctccatt    7020
ggccaggagg ttcttcccaa ggtcgactat gctcagctct ggtctgatgc ctcgcactgc    7080
gaggtgctgt acctctccat cgccttcgtc atcctgaagt tcacccttgg tcctctcgga    7140
cccaagggtc agtctcgaat gaagtttgtg ttcaccaact acaacctgct catgtccatc    7200
tactcgctgg gctccttcct ctctatggcc tacgccatgt acaccattgg tgtcatgtcc    7260
gacaactgcg agaaggcttt cgacaacaat gtcttccgaa tcaccactca gctgttctac    7320
ctcagcaagt tcctcgagta cattgactcc ttctatctgc ccctcatggg caagcctctg    7380
acctggttgc agttctttca ccatctcgga gctcctatgg acatgtggct gttctacaac    7440
```

```
taccgaaacg aagccgtttg gatctttgtg ctgctcaacg gcttcattca ctggatcatg    7500
tacggctact attggacccg actgatcaag ctcaagttcc ctatgcccaa gtccctgatt    7560
acttctatgc agatcattca gttcaacgtt ggcttctaca tcgtctggaa gtaccggaac    7620
attccctgct accgacaaga tggaatgaga atgtttggct ggttttttcaa ctacttctac    7680 gttggtactg tcctgtgtct gttcctcaac ttctacgtgc agacctacat cgtccgaaag    7740
cacaagggag ccaaaaagat tcagtgagc                                      7769
```

```
<210> SEQ ID NO 71
<211> LENGTH: 10206
<212> TYPE: DNA
<213> ORGANISM: Artificial Sequence
<220> FEATURE:
<223> OTHER INFORMATION: plasmid pZUFmE9SP8S

<400> SEQUENCE: 71
```

```
taagtcatac acaagtcagc tttcttcgag cctcatataa gtataagtag ttcaacgtat      60
tagcactgta cccagcatct ccgtatcgag aaacacaaca acatgcccca ttggacagat     120
catgcggata cacaggttgt gcagtatcat acatactcga tcagacaggt cgtctgacca     180
tcatacaagc tgaacaagcg ctccatactt gcacgctctc tatatacaca gttaaattac     240
atatccatag tctaacctct aacagttaat cttctggtaa gcctcccagc cagccttctg     300
gtatcgcttg gcctcctcaa taggatctcg gttctggccg tacagacctc ggccgacaat     360
tatgatatcc gttccggtag acatgacatc ctcaacagtt cggtactgct gtccgagagc     420
gtctcccttg tcgtcaagac ccaccccggg ggtcagaata agccagtcct cagagtcgcc     480
cttaggtcgg ttctgggcaa tgaagccaac cacaaactcg ggtcggatc gggcaagctc      540 aatggtctgc ttggagtact cgccagtggc cagagagccc ttgcaagaca gctcggccag     600
catgagcaga cctctggcca gcttctcgtt gggagagggg actaggaact ccttgtactg     660
ggagttctcg tagtcagaga cgtcctcctt cttctgttca gagacagttt cctcggcacc     720
agctcgcagg ccagcaatga ttccggttcc gggtacaccg tgggcgttgg tgatatcgga     780
ccactcggcg attcggtgac accggtactg gtgcttgaca gtgttgccaa tatctgcgaa     840
ctttctgtcc tcgaacagga agaaaccgtg cttaagagca agttccttga ggggagcac       900 agtgccggcg taggtgaagt cgtcaatgat gtcgatatgg gttttgatca tgcacacata     960
aggtccgacc ttatcggcaa gctcaatgag ctccttggtg gtggtaacat ccagagaagc    1020
acacaggttg gttttcttgg ctgccacgag cttgagcact cgagcggcaa aggcggactt    1080
gtggacgtta gctcgagctt cgtaggaggg catttggtg gtgaagagga gactgaaata    1140
aatttagtct gcagaacttt ttatcggaac cttatctggg gcagtgaagt atatgttatg    1200
gtaatagtta cgagttagtt gaacttatag atagactgga ctatacggct atcggtccaa    1260
attagaaaga acgtcaatgg ctctctgggc gtcgcctttg ccgacaaaaa tgtgatcatg    1320
atgaaagcca gcaatgacgt tgcagctgat attgttgtcg gccaaccgcg ccgaaaacgc    1380
agctgtcaga cccacagcct ccaacgaaga atgtatcgtc aaagtgatcc aagcacactc    1440
atagttggag tcgtactcca aaggcggcaa tgacgagtca gacagatact cgtcgacgtt    1500
taaacagtgt acgcagatct actatagagg aacatttaaa ttgccccgga gaagacggcc    1560
aggccgccta gatgacaaat tcaacaactc acagctgact ttctgccatt gccactaggg    1620
gggggccttt ttatatggcc aagccaagct ctccacgtcg gttgggctgc acccaacaat    1680
aaatgggtag ggttgcacca acaaagggat gggatggggg gtagaagata cgaggataac    1740
```

```
gggctcaat ggcacaaata agaacgaata ctgccattaa gactcgtgat ccagcgactg    1800
acaccattgc atcatctaag ggcctcaaaa ctacctcgga actgctgcgc tgatctggac    1860
accacagagg ttccgagcac tttaggttgc accaaatgtc ccaccaggtg caggcagaaa    1920
acgctggaac agcgtgtaca gtttgtctta acaaaaagtg agggcgctga ggtcgagcag    1980
ggtggtgtga cttgttatag cctttagagc tgcgaaagcg cgtatggatt tggctcatca    2040
ggccagattg agggtctgtg gacacatgtc atgttagtgt acttcaatcg ccccctggat    2100
atagccccga caataggccg tggcctcatt tttttgcctt ccgcacattt ccattgctcg    2160
atacccacac cttgcttctc ctgcacttgc aaccttaat actggtttac attgaccaac    2220
atcttacaag cgggggctt gtctagggta tatataaaca gtggctctcc caatcggttg    2280
ccagtctctt ttttcctttc ttcccccaca gattcgaaat ctaaactaca catcacagaa    2340
ttccgagccg tgagtatcca cgacaagatc agtgtcgaga cgacgcgttt tgtgtaatga    2400
cacaatccga aagtcgctag caacacacac tctctacaca aactaaccca gctctggtac    2460
catggaggtc gtgaacgaaa tcgtctccat tggccaggag gttcttccca aggtcgacta    2520
tgctcagctc tggtctgatg cctcgcactg cgaggtgctg tacctctcca tcgccttcgt    2580
catcctgaag ttcacccttg gtcctctcgg acccaagggt cagtctcgaa tgaagtttgt    2640
gttcaccaac tacaacctgc tcatgtccat ctactcgctg gctccttcc tctctatggc    2700 ctacgccatg tacaccattg gtgtcatgtc cgacaactgc gagaaggctt tcgacaacaa    2760
tgtcttccga atcaccactc agctgttcta cctcagcaag ttcctcgagt acattgactc    2820
cttctatctg cccctcatgg gcaagcctct gacctggttg cagttctttc accatctcgg    2880
agctcctatg gacatgtggc tgttctacaa ctaccgaaac gaagccgttt ggatctttgt    2940
gctgctcaac ggcttcattc actggatcat gtacggctac tattggaccc gactgatcaa    3000
gctcaagttc cctatgccca gtccctgat tacttctatg cagatcattc agttcaacgt    3060
tggcttctac atcgtctgga gtaccggaa cattccctgc taccgacaag atggaatgag    3120
aatgtttggc tggtttttca actacttcta cgttggtact gtcctgtgtc tgttcctcaa    3180
cttctacgtg cagacctaca tcgtccgaaa gcacaaggga gccaaaaaga ttcagtgagc    3240
ggccgcaagt gtggatgggg aagtgagtgc ccggttctgt gtgcacaatt ggcaatccaa    3300
gatggatgga ttcaacacag ggatatagcg agctacgtgg tggtgcgagg atatagcaac    3360
ggatatttat gtttgacact tgagaatgta cgatacaagc actgtccaag tacaatacta    3420
aacatactgt acatactcat actcgtaccc gggcaacggt ttcacttgag tgcagtggct    3480
agtgctctta ctcgtacagt gtgcaatact gcgtatcata gtctttgatg tatatcgtat    3540
tcattcatgt tagttgcgta cgagccgaaa gcataaagtg taaagcctgg ggtgcctaat    3600
gagtgagcta actcacatta attgcgttgc gctcactgcc cgctttccag tcgggaaacc    3660
tgtcgtgcca gctgcattaa tgaatcggcc aacgcgcggg gagaggcggt ttgcgtattg    3720
ggcgctcttc cgcttcctcg ctcactgact cgctgcgctc ggtcgttcgg ctgcggcgag    3780
cggtatcagc tcactcaaag gcggtaatac ggttatccac agaatcaggg gataacgcag    3840
gaaagaacat gtgagcaaaa ggccagcaaa aggccaggaa ccgtaaaaag gccgcgttgc    3900
tggcgttttt ccataggctc cgcccccctg acgagcatca caaaaatcga cgctcaagtc    3960
agaggtggcg aaacccgaca ggactataaa gataccaggc gtttccccct ggaagctccc    4020
tcgtgcgctc tcctgttccg accctgccgc ttaccggata cctgtccgcc tttctccctt    4080
cgggaagcgt ggcgctttct catagctcac gctgtaggta tctcagttcg gtgtaggtcg    4140
```

```
ttcgctccaa gctgggctgt gtgcacgaac ccccgttca gcccgaccgc tgcgccttat    4200
ccggtaacta tcgtcttgag tccaacccgg taagacacga cttatcgcca ctggcagcag    4260
ccactggtaa caggattagc agagcgaggt atgtaggcgg tgctacagag ttcttgaagt    4320
ggtggcctaa ctacggctac actagaagga cagtatttgg tatctgcgct ctgctgaagc    4380
cagttacctt cggaaaaaga gttggtagct cttgatccgg caaacaaacc accgctggta    4440
gcggtggttt ttttgtttgc aagcagcaga ttacgcgcag aaaaaaagga tctcaagaag    4500
atcctttgat cttttctacg gggtctgacg ctcagtggaa cgaaaactca cgttaaggga    4560
ttttggtcat gagattatca aaaggatct tcacctagat ccttttaaat taaaaatgaa    4620
gttttaaatc aatctaaagt atatatgagt aaacttggtc tgacagttac caatgcttaa    4680
tcagtgaggc acctatctca gcgatctgtc tatttcgttc atccatagtt gcctgactcc    4740
ccgtcgtgta gataactacg atacgggagg gcttaccatc tggccccagt gctgcaatga    4800
taccgcgaga cccacgctca ccggctccag atttatcagc aataaaccag ccagccggaa    4860
gggccgagcg cagaagtggt cctgcaactt tatccgcctc catccagtct attaattgtt    4920
gccgggaagc tagagtaagt agttcgccag ttaatagttt gcgcaacgtt gttgccattg    4980
ctacaggcat cgtggtgtca cgctcgtcgt ttggtatggc ttcattcagc tccggttccc    5040
aacgatcaag gcgagttaca tgatccccca tgttgtgcaa aaaagcggtt agctccttcg    5100
gtcctccgat cgttgtcaga agtaagttgg ccgcagtgtt atcactcatg gttatggcag    5160
cactgcataa ttctcttact gtcatgccat ccgtaagatg cttttctgtg actggtgagt    5220
actcaaccaa gtcattctga gaatagtgta tgcggcgacc gagttgctct tgcccggcgt    5280
caatacggga taataccgcg ccacatagca gaactttaaa agtgctcatc attggaaaac    5340
gttcttcggg gcgaaaactc tcaaggatct taccgctgtt gagatccagt tcgatgtaac    5400
ccactcgtgc acccaactga tcttcagcat cttttacttt caccagcgtt tctgggtgag    5460
caaaaacagg aaggcaaaat gccgcaaaaa agggaataag ggcgacacgg aaatgttgaa    5520
tactcatact cttcctttt caatattatt gaagcattta tcagggttat tgtctcatga    5580
gcggatacat atttgaatgt atttagaaaa ataaacaaat aggggttccg cgcacatttc    5640
cccgaaaagt gccacctgac gcgcctgta gcggcgcatt aagcgcggcg ggtgtggtgg    5700
ttacgcgcag cgtgaccgct acacttgcca gcgccctagc gcccgctcct ttcgctttct    5760
tcccttcctt tctcgccacg ttcgccggct ttccccgtca gctctaaat cggggggctcc    5820 ctttagggtt ccgatttagt gctttacggc acctcgaccc caaaaaactt gattagggtg    5880
atggttcacg tagtgggcca tcgccctgat agacggtttt tcgccctttg acgttggagt    5940
ccacgttctt taatagtgga ctcttgttcc aaactggaac aacactcaac cctatctcgg    6000
tctattcttt tgatttataa gggattttgc cgatttcggc ctattggtta aaaaatgagc    6060
tgatttaaca aaaatttaac gcgaatttta acaaaatatt aacgcttaca atttccattc    6120
gccattcagg ctgcgcaact gttgggaagg gcgatcggtg cgggcctctt cgctattacg    6180
ccagctggcg aaagggggat gtgctgcaag gcgattaagt tgggtaacgc cagggttttc    6240
ccagtcacga cgttgtaaaa cgacggccag tgaattgtaa tacgactcac tatagggcga    6300
attgggtacc gggccccccc tcgaggtcga tggtgtcgat aagcttgata tcgaattcat    6360
gtcacacaaa ccgatcttcg cctcaaggaa acctaattct acatccgaga gactgccgag    6420
atccagtcta cactgattaa ttttcggggcc aataatttaa aaaatcgtg ttatataata    6480 ttatatgtat tatatatata catcatgatg atactgacag tcatgtccca ttgctaaata    6540
```

```
gacagactcc atctgccgcc tccaactgat gttctcaata tttaaggggt catctcgcat    6600
tgtttaataa taaacagact ccatctaccg cctccaaatg atgttctcaa aatatattgt    6660
atgaacttat ttttattact tagtattatt agacaactta cttgctttat gaaaaacact    6720
tcctatttag gaaacaattt ataatggcag ttcgttcatt taacaattta tgtagaataa    6780
atgttataaa tgcgtatggg aaatcttaaa tatggatagc ataaatgata tctgcattgc    6840
ctaattcgaa atcaacagca acgaaaaaaa tcccttgtac aacataaata gtcatcgaga    6900
aatatcaact atcaaagaac agctattcac acgttactat tgagattatt attggacgag    6960
aatcacacac tcaactgtct ttctctcttc tagaaataca ggtacaagta tgtactattc    7020
tcattgttca tacttctagt catttcatcc cacatattcc ttggatttct ctccaatgaa    7080
tgacattcta tcttgcaaat tcaacaatta taataagata taccaaagta gcggtatagt    7140
ggcaatcaaa aagcttctct ggtgtgcttc tcgtatttat ttttattcta atgatccatt    7200
aaaggtatat atttatttct tgttatataa tccttttgtt tattacatgg gctggataca    7260
taaaggtatt ttgatttaat ttttgcttta aattcaatcc ccctcgttc agtgtcaact    7320 gtaatggtag gaaattacca tactttgaa gaagcaaaaa aaatgaaaga aaaaaaaat    7380 cgtatttcca ggttagacgt tccgcagaat ctagaatgcg gtatgcggta cattgttctt    7440
cgaacgtaaa agttgcgctc cctgagatat tgtacatttt tgcttttaca agtacaagta    7500
catcgtacaa ctatgtacta ctgttgatgc atccacaaca gtttgttttg tttttttttg    7560
tttttttttt ttctaatgat tcattaccgc tatgtatacc tacttgtact tgtagtaagc    7620
cgggttattg gcgttcaatt aatcatagac ttatgaatct gcacggtgtg cgctgcgagt    7680
tacttttagc ttatgcatgc tacttgggtg taatattggg atctgttcgg aaatcaacgg    7740
atgctcaatc gatggttaat gctgctgtgt gctgtgtgtg tgtgttgttt ggcgctcatt    7800
gttgcgttat gcagcgtaca ccacaatatt ggaagcttat tagcctttct attttttcgt    7860
ttgcaaggct taacaacatt gctgtggaga gggatgggga tatggaggcc gctggaggga    7920
gtcggagagg cgttttggag cggcttggcc tggcgcccag ctcgcgaaac gcacctagga    7980 cccttttggca cgccgaaatg tgccactttt cagtctagta acgccttacc tacgtcattc    8040
catgcgtgca tgtttgcgcc ttttttccct tgcccttgat cgccacacag tacagtgcac    8100
tgtacagtgg aggttttggg ggggtcttag atgggagcta aaagcggcct agcggtacac    8160
tagtgggatt gtatggagtg gcatggagcc taggtggagc ctgacaggac gcacgaccgg    8220
ctagcccgtg acagacgatg ggtggctcct gttgtccacc gcgtacaaat gtttgggcca    8280
aagtcttgtc agccttgctt gcgaacctaa ttcccaattt tgtcacttcg cacccccatt    8340
gatcgagccc taaccctgc ccatcaggca atccaattaa gctcgcattg tctgccttgt    8400
ttagtttggc tcctgcccgt ttcggcgtcc acttgcacaa acacaaacaa gcattatata    8460
taaggctcgt ctctccctcc caaccacact cacttttttg cccgtcttcc cttgctaaca    8520
caaaagtcaa gaacacaaac aaccacccca accccttac acacaagaca tatctacagc    8580
aatggccatg gcaagggtg gagacggtgg agcacaggct gtgtctggca ccgatgcctc    8640
cctcgctgag gtctcctctg tggacagcaa gtccgtccac gtggttctgt acggcaagcg    8700
agtggatgtc accaagttcc agaaggctca ccctggaggt tcgaaggtgt tccgaatctt    8760
tcaggagcga gacgccacag aacagttcga gtcctaccac tctcccaagg ccatcaagat    8820
gatggaaggt atgctcaaaa agtcggagga tgctcccgct tccgtgcctc ttccctctcg    8880
atccactatg ggcaccgagt tcaaggagat gatcgaacga cacaagagag ccggtctcta    8940
```

```
cgacccttgt cccttggacg agctgttcaa gctcaccatt gtccttgctc ctatctttgt    9000
gggagcctat ctcgttcgat ccggtgtctc tcctcttgct ggagccctgt cgatgggctt    9060
cggattctac ctcgacggct ggcttgctca cgactacctg catcacgcag tgttcaaggg    9120
ctccgtcaac acactcgtca aggccaacaa cgctatggga tacgccttgg gcttcctcca    9180
gggttacgac gttgcttggt ggcgagccag acacaacact catcacgtgt gcaccaacga    9240
ggacggctcc gatcccgaca tcaagacggc tcctctgctc atttacgtgc gagagaatcc    9300
ctccattgcc aagcggctca acttctttca gcgatggcaa cagtactact atgttcctac    9360
tatggccatt ctggatctct actggcgact ggagtctatc gcatacgtcg ctgtgcgact    9420
gcccaagatg tggatgcagg ctgccgctct tgccgctcac tacgcactcc tgtgttgggt    9480
cttcgctgcc catctcaacc tgattcctct catgatggtt gcacgaggtt cgcgaccgg    9540 aatcgtggtc tttgccaccc actatggcga ggacattctc gaccgagagc acgtcgaagg    9600
catgactctg gtcgagcaga ccgccaagac ctcccgaaac atcactggtg gatggcttgt    9660
caacgtgctc accggcttca tttctctgca gaccgagcat catctgtttc ccatgatgcc    9720
tactggaaac ctcatgacca ttcaacccga ggttcgagac tttttcaaaa agcacggtct    9780
cgagtaccga gaaggaaacc tgtttcagtg cgtgcatcag aacatcaagg ctctcgcctt    9840
cgagcacctg cttcactaag cggccgcatt gatgattgga acacacaca tgggttatat    9900 ctaggtgaga gttagttgga cagttatata ttaaatcagc tatgccaacg gtaacttcat    9960
tcatgtcaac gaggaaccag tgactgcaag taatatagaa tttgaccacc ttgccattct   10020
cttgcactcc tttactatat ctcatttatt tcttatatac aaatcacttc ttcttcccag   10080
catcgagctc ggaaacctca tgagcaataa catcgtggat ctcgtcaata gagggctttt   10140
tggactcctt gctgttggcc accttgtcct tgctgtctgg ctcattctgt ttcaacgcct   10200
tttaat                                                              10206
```

<210> SEQ ID NO 72
<211> LENGTH: 6871
<212> TYPE: DNA
<213> ORGANISM: Artificial Sequence
<220> FEATURE:
<223> OTHER INFORMATION: plasmid pEXPGUS1-C

<400> SEQUENCE: 72

```
aattcgtcct tgaggactcg agtgacagtc tttcgccaaa gtcgagagga ggccagcacg      60
ttggccttgt caagagacca cacgggaaga gggggggttgt gctgaagggc caggaaggcg    120
gccattcggg caattcgctc aacctcagga acggagtagg tctcggtgtc ggaagcgacg    180
ccagatccgt catcctcctt tcgctctcca aagtagatac ctccgacgag ctctcggaca    240
atgatgaagt cggtgccctc aacgtttcgg atgggggaga gatcggcgag cttgggcgac    300
agcagctggc agggtcgcag gttggcgtac aggttcaggt cctttcgcag cttgaggaga    360
ccctgctcgg gtcgcacgtc ggttcgtccg tcgggagtgg tccatacggt gttggcagcg    420
cctccgacag caccgagcat aatagagtca gcctttcggc agatgtcgag agtagcgtcg    480
gtgatgggct cgccctcctt ctcaatggca gctcctccaa tgagtcggtc ctcaaacaca    540
aactcggtgc cggaggcctc agcaacagac ttgagcacct tgacggcctc ggcaatcacc    600
tcggggccac agaagtcgcc gccgagaaga acaatcttct tggagtcagt cttggtcttc    660
ttagtttcgg gttccattgt ggatgtgtgt ggttgtatgt gtgatgtggt gtgtggagtg    720
aaaatctgtg gctggcaaac gctcttgtat atatacgcac ttttgcccgt gctatgtgga    780
```

-continued

```
agactaaacc tccgaagatt gtgactcagg tagtgcggta tcggctaggg acccaaacct      840
tgtcgatgcc gatagcgcta tcgaacgtac cccagccggc cgggagtatg tcggagggga      900
catacgagat cgtcaagggt ttgtggccaa ctggtaaata aatgatgtcg agggagtttg      960
gcgcccgttt tttcgagccc cacacgtttc ggtgagtatg agcggcggca gattcgagcg     1020
tttccggttt ccgcggctgg acgagagccc atgatggggg ctcccaccac cagcaatcag     1080
ggccctgatt acacacccac ctgtaatgtc atgctgttca tcgatggtta atgctgctgt     1140
gtgctgtgtg tgtgtgttgt ttggcgctca ttgttgcgtt atgcagcgta caccacaata     1200
ttggaagctt attagccttt ctattttttc gtttgcaagg cttaacaaca ttgctgtgga     1260
gagggatggg gatatggagg ccgctggagg gagtcggaga ggcgttttgg agcggcttgg     1320
cctggcgccc agctcgcgaa acgcacctag gacccttttgg cacgccgaaa tgtgccactt     1380
ttcagtctag taacgcctta cctacgtcat tccatgcgtg catgtttgcg cctttttttcc    1440
cttgcccttg atcgccacac agtacagtgc actgtacagt ggaggttttg gggggggtctt    1500
agatgggagc taaaagcggc ctagcggtac actagtggga ttgtatggag tggcatggag     1560
cctaggtgga gcctgacagg acgcacgacc ggctagcccg tgacagacga tgggtggctc     1620
ctgttgtcca ccgcgtacaa atgtttgggc caaagtcttg tcagccttgc ttgcgaacct     1680
aattcccaat tttgtcactt cgcaccccca ttgatcgagc cctaacccct gcccatcagg     1740
caatccaatt aagctcgcat tgtctgcctt gtttagtttg gctcctgccc gtttcggcgt     1800
ccacttgcac aaaacaaaac aagcattata tataaggctc gtctctccct cccaaccaca     1860
ctcacttttt tgcccgtctt cccttgctaa cacaaaagtc aagaacacaa acaaccaccc     1920
caacccccctt acacacaaga catatctaca gcaatggcca tggtacgtcc tgtagaaacc     1980
ccaacccgtg aaatcaaaaa actcgacggc ctgtgggcat tcagtctgga tcgcgaaaac     2040
tgtggaattg atcagcgttg gtgggaaagc gcgttacaag aaagccgggc aattgctgtg     2100
ccaggcagtt ttaacgatca gttcgccgat gcagatattc gtaattatgc gggcaacgtc     2160
tggtatcagc gcgaagtctt tataccgaaa ggttgggcag gccagcgtat cgtgctgcgt     2220
ttcgatgcgg tcactcatta cggcaaagtg tgggtcaata atcaggaagt gatggagcat     2280
cagggcggct atacgccatt tgaagccgat gtcacgccgt atgttattgc cgggaaaagt     2340
gtacgtatca ccgtttgtgt gaacaacgaa ctgaactggc agactatccc gccgggaatg     2400
gtgattaccg acgaaaacgg caagaaaaag cagtcttact tccatgattt ctttaactat     2460
gccgggatcc atcgcagcgt aatgctctac accacgccga cacctgggt ggacgatatc       2520
accgtggtga cgcatgtcgc gcaagactgt aaccacgcgt ctgttgactg caggtggtg      2580
gccaatggtg atgtcagcgt tgaactgcgt gatgcggatc aacaggtggt tgcaactgga     2640
caaggcacta gcgggacttt gcaagtggtg aatccgcacc tctggcaacc gggtgaaggt     2700
tatctctatg aactgcgcgt cacagccaaa agccagacag agtgtgatat ctacccgctt     2760
cgcgtcggca tccggtcagt ggcagtgaag gcgaacagt tcctgattaa ccacaaaccg       2820
ttctacttta ctggctttgg tcgtcatgaa gatgcggact acgtggcaa aggattcgat       2880
aacgtgctga tggtgcacga ccacgcatta atggactgga ttggggccaa ctcctaccgt     2940
acctcgcatt acccttacgc tgaagagatg ctcgactggg cagatgaaca tggcatcgtg     3000
gtgattgatg aaactgctgc tgtcggcttt aacctctctt taggcattgg tttcgaagcg     3060
ggcaacaagc cgaaagaact gtacagcgaa gaggcagtca acggggaaac tcagcaagcg     3120
cacttacagg cgattaaaga gctgatagcg cgtgacaaaa accacccaag cgtggtgatg     3180
```

```
tggagtattg ccaacgaacc ggatacccgt ccgcaagtgc acgggaatat ttcgccactg   3240
gcggaagcaa cgcgtaaact cgacccgacg cgtccgatca cctgcgtcaa tgtaatgttc   3300
tgcgacgctc acaccgatac catcagcgat ctctttgatg tgctgtgcct gaaccgttat   3360 tacgatggt atgtccaaag cggcgatttg gaaacggcag agaaggtact ggaaaaagaa    3420
cttctggcct ggcaggagaa actgcatcag ccgattatca tcaccgaata cggcgtggat   3480
acgttagccg ggctgcactc aatgtacacc gacatgtgga gtgaagagta tcagtgtgca   3540
tggctggata tgtatcaccg cgtctttgat cgcgtcagcg ccgtcgtcgg tgaacaggta   3600
tggaatttcg ccgattttgc gacctcgcaa ggcatattgc gcgttggcgg taacaagaaa   3660
gggatcttca ctcgcgaccg caaaccgaag tcggcggctt ttctgctgca aaaacgctgg   3720
actggcatga acttcggtga aaaaccgcag caggaggca aacaatgatt aattaactag    3780
agcggccgcc accgcggccc gagattccgg cctcttcggc cgccaagcga cccgggtgga   3840
cgtctagagg tacctagcaa ttaacagata gtttgccggt gataattctc ttaacctccc   3900
acactccttt gacataacga tttatgtaac gaaactgaaa tttgaccaga tattgtgtcc   3960
gcggtggagc tccagctttt gttcccttta gtgagggtta atttcgagct tggcgtaatc   4020
atggtcatag ctgtttcctg tgtgaaattg ttatccgctc acaattccac acaacatacg   4080
agccggaagc ataaagtgta aagcctgggg tgcctaatga gtgagctaac tcacattaat   4140
tgcgttgcgc tcactgcccg ctttccagtc gggaaacctg tcgtgccagc tgcattaatg   4200
aatcggccaa cgcgcgggga gaggcggttt gcgtattggg cgctcttccg cttcctcgct   4260
cactgactcg ctgcgctcgg tcgttcggct gcggcgagcg gtatcagctc actcaaaggc   4320
ggtaatacgg ttatccacag aatcagggga taacgcagga agaacatgt gagcaaaagg    4380 ccagcaaaag gccaggaacc gtaaaaaggc cgcgttgctg gcgttttcc ataggctccg    4440 cccccctgac gagcatcaca aaaatcgacg ctcaagtcag aggtggcgaa acccgacagg   4500
actataaaga taccaggcgt ttccccctgg aagctccctc gtgcgctctc ctgttccgac   4560
cctgccgctt accggatacc tgtccgcctt tctcccttcg ggaagcgtgg cgctttctca   4620
tagctcacgc tgtaggtatc tcagttcggt gtaggtcgtt cgctccaagc tgggctgtgt   4680
gcacgaaccc cccgttcagc ccgaccgctg cgccttatcc ggtaactatc gtcttgagtc   4740
caacccggta agacacgact tatcgccact ggcagcagcc actggtaaca ggattagcag   4800
agcgaggtat gtaggcggtg ctacagagtt cttgaagtgg tggcctaact acggctacac   4860
tagaaggaca gtatttggta tctgcgctct gctgaagcca gttaccttcg gaaaaagagt   4920
tggtagctct tgatccggca aacaaaccac cgctggtagc ggtggttttt tgtttgcaa    4980 gcagcagatt acgcgcagaa aaaaaggatc tcaagaagat cctttgatct tttctacggg   5040
gtctgacgct cagtggaacg aaaactcacg ttaagggatt ttggtcatga gattatcaaa   5100
aaggatcttc acctagatcc ttttaaatta aaaatgaagt tttaaatcaa tctaaagtat   5160
atatgagtaa acttggtctg acagttacca atgcttaatc agtgaggcac ctatctcagc   5220
gatctgtcta tttcgttcat ccatagttgc ctgactcccc gtcgtgtaga taactacgat   5280
acgggagggc ttaccatctg gccccagtgc tgcaatgata ccgcgagacc cacgctcacc   5340
ggctccagat ttatcagcaa taaaccagcc agcggaagg gccgagcgca gaagtggtcc    5400
tgcaacttta tccgcctcca tccagtctat taattgttgc cgggaagcta gagtaagtag   5460
ttcgccagtt aatagtttgc gcaacgttgt tgccattgct acaggcatcg tggtgtcacg   5520
ctcgtcgttt ggtatggctt cattcagctc cggttcccaa cgatcaaggc gagttacatg   5580
```

```
atcccccatg ttgtgcaaaa aagcggttag ctccttcggt cctccgatcg ttgtcagaag    5640
taagttggcc gcagtgttat cactcatggt tatggcagca ctgcataatt ctcttactgt    5700
catgccatcc gtaagatgct tttctgtgac tggtgagtac tcaaccaagt cattctgaga    5760
atagtgtatg cggcgaccga gttgctcttg cccggcgtca atacgggata ataccgcgcc    5820
acatagcaga actttaaaag tgctcatcat tggaaaacgt tcttcggggc gaaaactctc    5880
aaggatctta ccgctgttga gatccagttc gatgtaaccc actcgtgcac ccaactgatc    5940
ttcagcatct tttactttca ccagcgtttc tgggtgagca aaaacaggaa ggcaaaatgc    6000
cgcaaaaaag ggaataaggg cgacacggaa atgttgaata ctcatactct tcctttttca    6060
atattattga agcatttatc agggttattg tctcatgagc ggatacatat ttgaatgtat    6120
ttagaaaaat aaacaaatag gggttccgcg cacatttccc cgaaaagtgc cacctgacgc    6180
gccctgtagc ggcgcattaa gcgcggcggg tgtggtggtt acgcgcagcg tgaccgctac    6240
acttgccagc gccctagcgc ccgctccttt cgctttcttc ccttcctttc tcgccacgtt    6300
cgccggcttt ccccgtcaag ctctaaatcg ggggctccct ttagggttcc gatttagtgc    6360
tttacggcac ctcgacccca aaaaacttga ttagggtgat ggttcacgta gtgggccatc    6420
gccctgatag acggtttttc gccctttgac gttggagtcc acgttcttta atagtggact    6480
cttgttccaa actggaacaa cactcaaccc tatctcggtc tattcttttg atttataagg    6540
gattttgccg atttcggcct attggttaaa aaatgagctg atttaacaaa aatttaacgc    6600
gaattttaac aaaatattaa cgcttacaat ttccattcgc cattcaggct gcgcaactgt    6660
tgggaagggc gatcggtgcg ggcctcttcg ctattacgcc agctggcgaa agggggatgt    6720
gctgcaaggc gattaagttg ggtaacgcca gggttttccc agtcacgacg ttgtaaaacg    6780
acggccagtg aattgtaata cgactcacta tagggcgaat gggtaccgg gcccccctc     6840 gaggtcgatg gtgtcgataa gcttgatatc g                                   6871
```

<210> SEQ ID NO 73
<211> LENGTH: 5460
<212> TYPE: DNA
<213> ORGANISM: Artificial Sequence
<220> FEATURE:
<223> OTHER INFORMATION: plasmid pZGD5T-CP

<400> SEQUENCE: 73

```
ggccgcattg atgattggaa acacacacat gggttatatc taggtgagag ttagttggac      60
agttatatat taaatcagct atgccaacgg taacttcatt catgtcaacg aggaaccagt     120
gactgcaagt aatatagaat ttgaccacct tgccattctc ttgcactcct ttactatatc     180
tcatttattt cttatataca aatcacttct tcttcccagc atcgagctcg aaacctcat     240 gagcaataac atcgtggatc tcgtcaatag agggcttttt ggactccttg ctgttggcca     300
ccttgtcctt gctgtctggc tcattctgtt tcaacgcctt ttaattaatc gagcttggcg     360
taatcatggt catagctgtt tcctgtgtga aattgttatc cgctcacaat tccacacaac     420
atacgagccg gaagcataaa gtgtaaagcc tggggtgcct aatgagtgag ctaactcaca     480
ttaattgcgt tgcgctcact gcccgctttc cagtcgggaa acctgtcgtg ccagctgcat     540
taatgaatcg gccaacgcgc ggggagaggc ggtttgcgta ttgggcgctc ttccgcttcc     600
tcgctcactg actcgctgcg ctcggtcgtt cggctgcggc gagcggtatc agctcactca     660
aaggcggtaa tacggttatc cacagaatca ggggataacg caggaaagaa catgtgagca     720
aaaggccagc aaaaggccag gaaccgtaaa aaggccgcgt tgctggcgtt tttccatagg     780
```

```
ctccgccccc ctgacgagca tcacaaaaat cgacgctcaa gtcagaggtg gcgaaacccg    840
acaggactat aaagatacca ggcgtttccc cctggaagct ccctcgtgcg ctctcctgtt    900
ccgaccctgc cgcttaccgg atacctgtcc gcctttctcc cttcgggaag cgtggcgctt    960
tctcatagct cacgctgtag gtatctcagt tcggtgtagg tcgttcgctc caagctgggc   1020
tgtgtgcacg aaccccccgt tcagcccgac cgctgcgcct tatccggtaa ctatcgtctt   1080
gagtccaacc cggtaagaca cgacttatcg ccactggcag cagccactgg taacaggatt   1140
agcagagcga ggtatgtagg cggtgctaca gagttcttga agtggtggcc taactacggc   1200
tacactagaa ggacagtatt tggtatctgc gctctgctga agccagttac cttcggaaaa   1260
agagttggta gctcttgatc cggcaaacaa accaccgctg gtagcggtgg ttttttttgtt   1320 tgcaagcagc agattacgcg cagaaaaaaa ggatctcaag aagatccttt gatcttttct   1380
acggggtctg acgctcagtg gaacgaaaac tcacgttaag ggattttggt catgagatta   1440
tcaaaaagga tcttcaccta gatcctttta aattaaaaat gaagttttaa atcaatctaa   1500
agtatatatg agtaaacttg gtctgacagt taccaatgct taatcagtga ggcacctatc   1560
tcagcgatct gtctatttcg ttcatccata gttgcctgac tccccgtcgt gtagataact   1620
acgatacggg agggcttacc atctggcccc agtgctgcaa tgataccgcg agacccacgc   1680
tcaccggctc cagatttatc agcaataaac cagccagccg aagggccgag cgcagaagt   1740 ggtcctgcaa ctttatccgc ctccatccag tctattaatt gttgccggga agctagagta   1800
agtagttcgc cagttaatag tttgcgcaac gttgttgcca ttgctacagg catcgtggtg   1860
tcacgctcgt cgtttggtat ggcttcattc agctccggtt cccaacgatc aaggcgagtt   1920
acatgatccc ccatgttgtg caaaaaagcg gttagctcct tcggtcctcc gatcgttgtc   1980
agaagtaagt tggccgcagt gttatcactc atggttatgg cagcactgca taattctctt   2040
actgtcatgc catccgtaag atgcttttct gtgactggtg agtactcaac caagtcattc   2100
tgagaatagt gtatgcggcg accgagttgc tcttgcccgg cgtcaatacg ggataatacc   2160
gcgccacata gcagaacttt aaaagtgctc atcattggaa aacgttcttc ggggcgaaaa   2220
ctctcaagga tcttaccgct gttgagatcc agttcgatgt aacccactcg tgcacccaac   2280
tgatcttcag catcttttac tttcaccagc gtttctgggt gagcaaaaac aggaaggcaa   2340
aatgccgcaa aaaagggaat aagggcgaca cggaaatgtt gaatactcat actcttcctt   2400
tttcaatatt attgaagcat ttatcagggt tattgtctca tgagcggata catatttgaa   2460
tgtatttaga aaaataaaca ataggggtt ccgcgcacat ttccccgaaa agtgccacct   2520
gacgcgccct gtagcggcgc attaagcgcg gcgggtgtgg tggttacgcg cagcgtgacc   2580
gctacacttg ccagcgccct agcgcccgct cctttcgctt tcttcccttc ctttctcgcc   2640
acgttcgccg gctttccccg tcaagctcta aatcggggc tccctttagg gttccgattt   2700
agtgctttac ggcacctcga cccaaaaaaa cttgattagg gtgatggttc acgtagtggg   2760
ccatcgccct gatagacggt ttttcgccct ttgacgttgg agtccacgtt ctttaatagt   2820
ggactcttgt tccaaactgg aacaacactc aaccctatct cggtctattc ttttgattta   2880
taagggattt tgccgatttc ggcctattgg ttaaaaaatg agctgattta acaaaaattt   2940
aacgcgaatt ttaacaaaat attaacgctt acaatttcca ttcgccattc aggctgcgca   3000
actgttggga agggcgatcg gtgcgggcct cttcgctatt acgccagctg gcgaaagggg   3060
gatgtgctgc aaggcgatta agttgggtaa cgccagggtt ttcccagtca cgacgttgta   3120
aaacgacggc cagtgaattg taatacgact cactataggg cgaattgggt accgggcccc   3180
```

-continued

```
ccctcgaggt cgacggtatc gatggaagcc ggtagaaccg ggctgcttgt gcttggagat    3240
ggaagccggt agaaccgggc tgcttggggg gatttggggc cgctgggctc caaagagggg    3300
taggcatttc gttggggtta cgtaattgcg gcatttgggt cctgcgcgca tgtcccattg    3360
gtcagaatta gtccggatag gagacttatc agccaatcac agcgccggat ccacctgtag    3420
gttgggttgg gtgggagcac ccctccacag agtagagtca aacagcagca gcaacatgat    3480
agttgggggt gtgcgtgtta aaggaaaaaa aagaagcttg ggttatattc ccgctctatt    3540
tagaggttgc gggatagacg ccgacggagg gcaatggcgc tatggaacct tgcggatatc    3600
catacgccgc ggcggactgc gtccgaacca gctccagcag cgtttttttcc gggccattga    3660 gccgactgcg accccgccaa cgtgtcttgg cccacgcact catgtcatgt tggtgtttggg   3720 aggccacttt ttaagtagca caaggcacct agctcgcagc aaggtgtccg aaccaaagaa    3780
gcggctgcag tggtgcaaac ggggcggaaa cggcgggaaa aagccacggg ggcacgaatt    3840
gaggcacgcc ctcgaatttg agacgagtca cggccccatt cgcccgcgca atggctcgcc    3900
aacgcccggt cttttgcacc acatcaggtt accccaagcc aaacctttgt gttaaaaagc    3960
ttaacatatt ataccgaacg taggtttggg cgggcttgct ccgtctgtcc aaggcaacat    4020
ttatataagg gtctgcatcg ccggctcaat tgaatctttt ttcttcttct cttctctata    4080
ttcattcttg aattaaacac acatcaacca tgggaacgga ccaaggaaaa accttcacct    4140
gggaagagct ggcggcccat aacaccaagg acgacctact cttggccatc cgcggcaggg    4200
tgtacgatgt cacaaagttc ttgagccgcc atcctggtgg agtggacact ctcctgctcg    4260
gagctggccg agatgttact ccggtctttg agatgtatca cgcgtttggg gctgcagatg    4320
ccattatgaa gaagtactat gtcggtacac tggtctcgaa tgagctgccc atcttcccgg    4380
agccaacggt gttccacaaa accatcaaga cgagagtcga gggctacttt acggatcgga    4440
acattgatcc caagaataga ccagagatct ggggacgata cgctcttatc tttggatcct    4500
tgatcgcttc ctactacgcg cagctctttg tgcctttcgt tgtcgaacgc acatggcttc    4560
aggtggtgtt tgcaatcatc atgggatttg cgtgcgcaca agtcggactc aaccctcttc    4620
atgatgcgtc tcacttttca gtgacccaca accccactgt ctggaagatt ctgggagcca    4680
cgcacgactt tttcaacgga gcatcgtacc tggtgtggat gtaccaacat atgctcggcc    4740
atcaccccta caccaacatt gctggagcag atcccgacgt gtcgacgtct gagcccgatg    4800
ttcgtcgtat caagcccaac caaaagtggt tgtcaaccca catcaaccag cacatgtttg    4860
ttcctttcct gtacgactg ctggcgttca aggtgcgcat tcaggacatc aacatttttgt    4920 actttgtcaa gaccaatgac gctattcgtg tcaatcccat ctcgacatgg cacactgtga    4980
tgttctgggg cggcaaggct ttcttttgtct ggtatcgcct gattgttccc ctgcagtatc    5040
tgcccctggg caaggtgctg ctcttgttca cggtcgcgga catggtgtcg tcttactggc    5100
tggcgctgac cttccaggcg aaccacgttg ttgaggaagt tcagtggccg ttgcctgacg    5160
agaacgggat catccaaaag gactgggcag ctatgcaggt cgagactacg caggattacg    5220
cacacgattc gcacctctgg accagcatca ctggcagctt gaactaccag gctgtgcacc    5280
atctgttccc caacgtgtcg cagcaccatt atcccgatat tctggccatc atcaagaaca    5340
cctgcagcga gtacaaggtt ccatacccttg tcaaggatac gtttttggcaa gcatttgctt    5400 cacatttgga gcacttgcgt gttcttggac tccgtcccaa ggaagagtag gcagctaagc    5460
```

<210> SEQ ID NO 74
<211> LENGTH: 8630
<212> TYPE: DNA

<213> ORGANISM: Artificial Sequence
<220> FEATURE:
<223> OTHER INFORMATION: plasmid pYZDE2-S

<400> SEQUENCE: 74

```
ggtggagctc cagcttttgt tccctttagt gagggttaat ttcgagcttg gcgtaatcat      60
ggtcatagct gtttcctgtg tgaaattgtt atccgctcac aattccacac aacgtacgag     120
ccggaagcat aaagtgtaaa gcctggggtg cctaatgagt gagctaactc acattaattg     180
cgttgcgctc actgcccgct ttccagtcgg gaaacctgtc gtgccagctg cattaatgaa     240
tcggccaacg cgcggggaga ggcggtttgc gtattgggcg ctcttccgct tcctcgctca     300
ctgactcgct gcgctcggtc gttcggctgc ggcgagcggt atcagctcac tcaaaggcgg     360
taatacggtt atccacagaa tcaggggata acgcaggaaa gaacatgtga gcaaaaggcc     420
agcaaaaggc caggaaccgt aaaaaggccg cgttgctggc gtttttccat aggctccgcc     480
cccctgacga gcatcacaaa aatcgacgct caagtcagag gtggcgaaac ccgacaggac     540
tataaagata ccaggcgttt ccccctggaa gctccctcgt gcgctctcct gttccgaccc     600
tgccgcttac cggatacctg tccgcctttc tcccttcggg aagcgtggcg ctttctcata     660
gctcacgctg taggtatctc agttcggtgt aggtcgttcg ctccaagctg ggctgtgtgc     720
acgaaccccc cgttcagccc gaccgctgcg ccttatccgg taactatcgt cttgagtcca     780
acccggtaag acacgactta tcgccactgg cagcagccac tggtaacagg attagcagag     840
cgaggtatgt aggcggtgct acagagttct tgaagtggtg gcctaactac ggctacacta     900
gaaggacagt atttggtatc tgcgctctgc tgaagccagt taccttcgga aaaagagttg     960
gtagctcttg atccggcaaa caaaccaccg ctggtagcgg tggttttttt gtttgcaagc    1020
agcagattac gcgcagaaaa aaggatctc aagaagatcc tttgatcttt tctacggggt    1080
ctgacgctca gtggaacgaa aactcacgtt aagggatttt ggtcatgaga ttatcaaaaa    1140
ggatcttcac ctagatcctt ttaaattaaa aatgaagttt taaatcaatc taaagtatat    1200
atgagtaaac ttggtctgac agttaccaat gcttaatcag tgaggcacct atctcagcga    1260
tctgtctatt tcgttcatcc atagttgcct gactccccgt cgtgtagata actacgatac    1320
gggagggctt accatctggc cccagtgctg caatgatacc gcgagaccca cgctcaccgg    1380
ctccagattt atcagcaata aaccagccag ccggaagggc cgagcgcaga agtggtcctg    1440
caactttatc cgcctccatc cagtctatta attgttgccg ggaagctaga gtaagtagtt    1500
cgccagttaa tagtttgcgc aacgttgttg ccattgctac aggcatcgtg gtgtcacgct    1560
cgtcgtttgg tatggcttca ttcagctccg gttcccaacg atcaaggcga gttacatgat    1620
cccccatgtt gtgcaaaaaa gcggttagct ccttcggtcc tccgatcgtt gtcagaagta    1680
agttggccgc agtgttatca ctcatggtta tggcagcact gcataattct cttactgtca    1740
tgccatccgt aagatgcttt tctgtgactg gtgagtactc aaccaagtca ttctgagaat    1800
agtgtatgcg gcgaccgagt tgctcttgcc cggcgtcaat acgggataat accgcgccac    1860
atagcagaac tttaaaagtg ctcatcattg gaaaacgttc ttcggggcga aaactctcaa    1920
ggatcttacc gctgttgaga tccagttcga tgtaacccac tcgtgcaccc aactgatctt    1980
cagcatcttt tactttcacc agcgtttctg ggtgagcaaa aacaggaagg caaaatgccg    2040
caaaaaaggg aataagggcg acacggaaat gttgaatact catactcttc cttttttcaat    2100
attattgaag catttatcag ggttattgtc tcatgagcgg atacatattt gaatgtattt    2160
agaaaaataa acaaataggg gttccgcgca catttccccg aaaagtgcca cctgacgcgc    2220
```

```
cctgtagcgg cgcattaagc gcggcgggtg tggtggttac gcgcagcgtg accgctacac    2280
ttgccagcgc cctagcgccc gctcctttcg ctttcttccc ttcctttctc gccacgttcg    2340
ccggctttcc ccgtcaagct ctaaatcggg gctcccttt  agggttccga tttagtgctt    2400
tacggcacct cgaccccaaa aaacttgatt agggtgatgg ttcacgtagt gggccatcgc    2460
cctgatagac ggttttcgc cctttgacgt tggagtccac gttctttaat agtggactct     2520
tgttccaaac tggaacaaca ctcaaccta tctcggtcta ttcttttgat ttataaggga     2580
ttttgccgat ttcggcctat tggttaaaaa atgagctgat ttaacaaaaa tttaacgcga    2640
attttaacaa atattaacg cttacaattt ccattcgcca ttcaggctgc gcaactgttg     2700
ggaagggcga tcggtgcggg cctcttcgct attacgccag ctggcgaaag ggggatgtgc    2760
tgcaaggcga ttaagttggg taacgccagg gttttcccag tcacgacgtt gtaaaacgac    2820
ggccagtgaa ttgtaatacg actcactata gggcgaattg ggtaccgggc cccccctcga    2880
ggtcgatggt gtcgataagc ttgatatcga attcatgtca cacaaaccga tcttcgcctc    2940
aaggaaacct aattctacat ccgagagact gccgagatcc agtctacact gattaatttt    3000
cgggccaata atttaaaaaa atcgtgttat ataatattat atgtattata tatatacatc    3060
atgatgatac tgacagtcat gtcccattgc taaatagaca gactccatct gccgcctcca    3120
actgatgttc tcaatattta aggggtcatc tcgcattgtt taataataaa cagactccat    3180
ctaccgcctc caaatgatgt tctcaaaata tattgtatga acttattttt attacttagt    3240
attattagac aacttacttg ctttatgaaa aacacttcct attaggaaa caatttataa     3300
tggcagttcg ttcatttaac aatttatgta gaataaatgt tataaatgcg tatgggaaat    3360
cttaaatatg gatagcataa atgatatctg cattgcctaa ttcgaaatca acagcaacga    3420
aaaaaatccc ttgtacaaca taaatagtca tcgagaaata tcaactatca aagaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt attattttt  attctaatga tccattaaag gtatatattt atttcttgtt    3780
atataatcct tttgtttatt acatgggctg gatacataaa ggtattttga tttaattttt    3840
tgcttaaatt caatcccccc tcgttcagtg tcaactgtaa tggtaggaaa ttaccatact    3900
tttgaagaag caaaaaaat gaaagaaaaa aaaaatcgta tttccaggtt agacgttccg     3960
cagaatctag aatgcggtat gcggtacatt gttcttcgaa cgtaaaagtt gcgctccctg    4020
agatattgta cattttgct  tttacaagta caagtcacatc gtacaactat gtactactgt    4080
tgatgcatcc acaacagttt gttttgtttt ttttgtttt  tttttttct aatgattcat     4140
taccgctatg tatacctact tgtacttgta gtaagccggg ttattggcgt tcaattaatc    4200
atagacttat gaatctgcac ggtgtgcgct gcgagttact tttagcttat gcatgctact    4260
tgggtgtaat attgggatct gttcggaaat caacggatgc tcaaccgatt tcgacagtaa    4320
taatttgaat cgaatcggag cctaaaatga acccgagtat atctcataaa attctcggtg    4380
agaggtctgt gactgtcagt acaaggtgcc ttcattatgc cctcaacctt accatacctc    4440
actgaatgta gtgtacctct aaaaatgaaa tacagtgcca aaagccaagg cactgagctc    4500
gtctaacgga cttgatatac aaccaattaa aacaaatgaa aagaaataca gttctttgta    4560
tcatttgtaa caattaccct gtacaaacta aggtattgaa atcccacaat attcccaaag    4620
```

```
tccacccctt tccaaattgt catgcctaca actcatatac caagcactaa cctaccaaac    4680
accactaaaa ccccacaaaa tatatcttac cgaatataca gtaacaagct accaccacac    4740
tcgttgggtg cagtcgccag cttaaagata tctatccaca tcagccacaa ctcccttcct    4800
ttaataaacc gactacaccc ttggctattg aggttatgag tgaatatact gtagacaaga    4860
cactttcaag aagactgttt ccaaaacgta ccactgtcct ccactacaaa cacacccaat    4920
ctgcttcttc tagtcaaggt tgctacaccg gtaaattata aatcatcatt tcattagcag    4980
ggcagggccc tttttataga gtcttataca ctagcggacc ctgccggtag accaacccgc    5040
aggcgcgtca gtttgctcct tccatcaatg cgtcgtagaa acgacttact ccttcttgag    5100
cagctccttg accttgttgg caacaagtct ccgacctcgg aggtggagga agagcctccg    5160
atatcggcgg tagtgatacc agcctcgacg gactccttga cggcagcctc aacagcgtca    5220
ccggcgggct tcatgttaag agagaacttg agcatcatgg cggcagacag aatggtggca    5280
atggggttga ccttctgctt gccgagatcg ggggcagatc cgtgacaggg ctcgtacaga    5340
ccgaacgcct cgttggtgtc gggcagagaa gccagagagg cggagggcag cagacccaga    5400
gaaccgggga tgacggaggc ctcgtcggag atgatatcgc caaacatgtt ggtggtgatg    5460
atgataccat tcatcttgga gggctgcttg atgaggatca tggcggccga gtcgatcagc    5520
tggtggttga gctcgagctg ggggaattcg tccttgagga ctcgagtgac agtctttcgc    5580
caaagtcgag aggaggccag cacgttggcc ttgtcaagag accacacggg aagaggggggg   5640 ttgtgctgaa gggccaggaa ggcggccatt cgggcaattc gctcaacctc aggaacggag    5700
taggtctcgg tgtcggaagc gacgccagat ccgtcatcct cctttcgctc tccaaagtag    5760
atacctccga cgagctctcg gacaatgatg aagtcggtgc cctcaacgtt tcggatgggg    5820
gagagatcgg cgagcttggg cgacagcagc tggcagggtc gcaggttggc gtacaggttc    5880
aggtcctttc gcagcttgag gagacccgtc tcgggtcgca cgtcggttcg tccgtcggga    5940
gtggtccata cggtgttggc agcgcctccg acagcaccga gcataataga gtcagccttt    6000
cggcagatgt cgagagtagc gtcggtgatg ggctcgccct ccttctcaat ggcagctcct    6060
ccaatgagtc ggtcctcaaa cacaaactcg gtgccggagg cctcagcaac agacttgagc    6120
accttgacgg cctcggcaat cacctcgggg ccacagaagt cgccgccgag aagaacaatc    6180
ttcttggagt cagtcttggt cttcttagtt tcgggttcca ttgtggatgt gtgtggttgt    6240
atgtgtgatg tggtgtgtgg agtgaaaatc tgtggctggc aaacgctctt gtatatatac    6300 gcactttttgc ccgtgctatg tggaagacta aacctccgaa gattgtgact caggtagtgc    6360
ggtatcggct agggacccaa accttgtcga tgccgatagc gctatcgaac gtaccccagc    6420 cggccggag tatgtcggag gggacatacg agatcgtcaa gggtttgtgg ccaactggta    6480
aatttaaatg atgtcgacgc agtaggatgt cctgcacggg tcttttttgtg gggtgtggag    6540 aaaggggtgc ttgagatgg aagccggtag aaccgggctg cttgtgcttg gagatggaag    6600
ccggtagaac cgggctgctt gggggggattt ggggccgctg ggctccaaag aggggtaggc    6660
atttcgttgg ggttacgtaa ttgcggcatt tgggtcctgc gcgcatgtcc cattggtcag    6720
aattagtccg gataggagac ttatcagcca atcacagcgc cggatccacc tgtaggttgg    6780
gttgggtggg agcacccctc cacagagtag agtcaaacag cagcagcaac atgatagttg    6840
ggggtgtgcg tgttaaagga aaaaaagaa gcttgggtta tattcccgct ctatttagag    6900
gttgcgggat agacgccgac ggagggcaat ggcgccatgg aaccttgcgg atatcgatac    6960
gccgcggcgg actgcgtccg aaccagctcc agcagcgttt tttccgggcc attgagccga    7020
```

| | |
|---|---|
| ctgcgacccc gccaacgtgt cttggcccac gcactcatgt catgttggtg ttgggaggcc | 7080 |
| acttttaag tagcacaagg cacctagctc gcagcaagg gtccgaacca agaagcggc | 7140 |
| tgcagtggtg caaacggggc ggaaacggcg ggaaaagcc acgggggcac gaattgaggc | 7200 |
| acgccctcga atttgagacg agtcacggcc ccattcgccc gcgcaatggc tcgccaacgc | 7260 |
| ccggtctttt gcaccacatc aggttacccc aagccaaacc tttgtgttaa aaagcttaac | 7320 |
| atattatacc gaacgtaggt ttgggcgggc ttgctccgtc tgtccaaggc aacatttata | 7380 |
| taagggtctg catcgccggc tcaattgaat cttttttctt cttctcttct ctatattcat | 7440 |
| tcttgaatta aacacacatc aatccatggc aaacagcagc gtgtgggatg atgtggtggg | 7500 |
| ccgcgtggag accggcgtgg accagtggat ggatggcgcc aagccgtacg cactcaccga | 7560 |
| tgggctcccg atgatggacg tgtccaccat gctggcattc gaggtgggat acatggccat | 7620 |
| gctgctcttc ggcatcccga tcatgaagca gatggagaag cctttttgagc tcaagaccat | 7680 |
| caagctcttg cacaacttgt ttctcttcgg acttttccttg tacatgtgcg tggagaccat | 7740 |
| ccgccaggct atcctcggag gctacaaagt gtttggaaac gacatggaga agggcaacga | 7800 |
| gtctcatgct cagggcatgt ctcgcatcgt gtacgtgttc tacgtgtcca aggcatacga | 7860 |
| gttcttggat accgccatca tgatcctttg caagaagttc aaccaggttt ccttcttgca | 7920 |
| tgtgtaccac catgccactc attttttgcca tctggtgggc tatccgccaa gtacgctcca | 7980 |
| ggaggtgatg cgtacttttt cagtgatcct caactctttc gtgcacaccg tcatgtacgg | 8040 |
| catactactt cttctcctcc caagggttcg ggttcgtgaa gccaatcaag ccgtacatca | 8100 |
| ccacccttca gatgacccag ttcatggcaa tgcttgtgca gtccttgtac gactacctct | 8160 |
| tcccatgcga ctaccacag gctcttgtgc agctccttgg agtgtacatg atcaccttgc | 8220 |
| ttgccctctt cggcaacttt tttgtgcaga gctatcttaa aaagccaaaa aagagcaaga | 8280 |
| ccaactaaaa ctgcctgcat gatatgccgc tcgccggcgt tcgaattgac tcagaaagcg | 8340 |
| agttaaggcg acacgcaaac tctatatttt ttcaaacgtg ttgccgtcac tcattcgcca | 8400 |
| tctgtttact acgtgtctgt tcaatgagca tgttcttgaa tctaaagaat ctcgaatgtt | 8460 |
| ttttaaaaaa agaattcgat atcaagctta cgcgtcgacc cgggtggacg tctagaggta | 8520 |
| cctagcaatt aacagatagt ttgccggtga taattctctt aacctcccac actcctttga | 8580 |
| cataacgatt tatgtaacga aactgaaatt tgaccagata ttgtgtccgc | 8630 |

<210> SEQ ID NO 75
<211> LENGTH: 6473
<212> TYPE: DNA
<213> ORGANISM: Artificial Sequence
<220> FEATURE:
<223> OTHER INFORMATION: plasmid pY5-22

<400> SEQUENCE: 75

| | |
|---|---|
| ggtggagctc cagcttttgt tccctttagt gagggttaat ttcgagcttg gcgtaatcat | 60 |
| ggtcatagct gtttcctgtg tgaaattgtt atccgctcac aattccacac aacgtacgag | 120 |
| ccggaagcat aaagtgtaaa gcctggggtg cctaatgagt gagctaactc acattaattg | 180 |
| cgttgcgctc actgcccgct ttccagtcgg gaaacctgtc gtgccagctg cattaatgaa | 240 |
| tcggccaacg cgcggggaga ggcggtttgc gtattgggcg ctcttccgct tcctcgctca | 300 |
| ctgactcgct gcgctcggtc gttcggctgc ggcgagcggt atcagctcac tcaaaggcgg | 360 |
| taatacggtt atccacagaa tcaggggata acgcaggaaa gaacatgtga gcaaaaggcc | 420 |
| agcaaaaggc caggaaccgt aaaaaggccg cgttgctggc gttttccat aggctccgcc | 480 |

-continued

```
cccctgacga gcatcacaaa aatcgacgct caagtcagag gtggcgaaac ccgacaggac    540
tataaagata ccaggcgttt ccccctggaa gctcccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg ggctgtgtgc    720
acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg gcctaactac ggctacacta    900
gaaggacagt atttggtatc tgcgctctgc tgaagccagt taccttcgga aaaagagttg    960
gtagctcttg atccggcaaa caaaccaccg ctggtagcgg tggttttttt gtttgcaagc   1020
agcagattac gcgcagaaaa aaaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt taaatcaatc taaagtatat   1200
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga gtggtcctg   1440 caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc cttttttcaat   2100 attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggtttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc cccccctcga   2880
```

```
ggtcgatggt gtcgataagc ttgatatcga attcatgtca cacaaaccga tcttcgcctc    2940
aaggaaacct aattctacat ccgagagact gccgagatcc agtctacact gattaatttt    3000
cgggccaata atttaaaaaa atcgtgttat ataatattat atgtattata tatatacatc    3060
atgatgatac tgacagtcat gtcccattgc taaatagaca gactccatct gccgcctcca    3120
actgatgttc tcaatattta aggggtcatc tcgcattgtt taataataaa cagactccat    3180
ctaccgcctc caaatgatgt tctcaaaata tattgtatga acttattttt attacttagt    3240
attattagac aacttacttg ctttatgaaa aacacttcct atttaggaaa caatttataa    3300
tggcagttcg ttcatttaac aatttatgta gaataaatgt tataaatgcg tatgggaaat    3360
cttaaatatg gatagcataa atgatatctg cattgcctaa ttcgaaatca acagcaacga    3420
aaaaaatccc ttgtacaaca taaatagtca tcgagaaata tcaactatca aagaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt atttatttt attctaatga tccattaaag gtatatattt atttcttgtt    3780
atataatcct tttgtttatt acatgggctg gatacataaa ggtattttga tttaattttt    3840
tgcttaaatt caatcccccc tcgttcagtg tcaactgtaa tggtaggaaa ttaccatact    3900
tttgaagaag caaaaaaaat gaaagaaaaa aaaaatcgta tttccaggtt agacgttccg    3960
cagaatctag aatgcggtat gcggtacatt gttcttcgaa cgtaaaagtt gcgctccctg    4020
agatattgta cattttgct tttacaagta caagtacatc gtacaactat gtactactgt    4080
tgatgcatcc acaacagttt gttttgtttt ttttttgtttt ttttttttct aatgattcat    4140
taccgctatg tatacctact tgtacttgta gtaagccggg ttattggcgt tcaattaatc    4200
atagacttat gaatctgcac ggtgtgcgct gcgagttact tttagcttat gcatgctact    4260
tgggtgtaat attgggatct gttcggaaat caacggatgc tcaaccgatt tcgacagtaa    4320
ttaattaagt catacacaag tcagcttcct tcgagcctca tataagtata agtagttcaa    4380
cgtattagca ctgtacccag catctccgta tcgagaaaca caacaacatg ccccattgga    4440
cagatcatgc ggatacacag gttgtgcagt atcatacata ctcgatcaga caggtcgtct    4500
gaccatcata caagctgaac aagcgctcca tacttgcacg ctctctatat acacagttaa    4560
attacatatc catagtctaa cctctaacag ttaatcttct ggtaagcctc ccagccagcc    4620
ttctggtatc gcttggcctc ctcaataggg tctcggttct ggccgtacag acctcggccg    4680
acaattatga tatccgttcc ggtagacatg acatcctcaa cagttcggta ctgctgtccg    4740
agagcgtctc ccttgtcgtc aagacccacc ccgggggtca gaataagcca gtcctcagag    4800
tcgcccttag gtcggttctg ggcaatgaag ccaaccacaa actcgggggtc ggatcgggca    4860 agctcaatgg tctgcttgga gtactcgcca gtggccagag agcccttgca agacagctcg    4920
gccagcatga gcagacctct ggccagcttc tcgttgggag aggggactag gaactccttg    4980
tactgggagt tctcgtagtc agagacgtcc tccttcttct gttcagagac agtttcctcg    5040
gcaccagctc gcaggccagc aatgattccg gttccgggta caccgtgggc gttggtgata    5100
tcggaccact cggcgattcg gtgacaccgg tactggtgct tgacagtgtt gccaatatct    5160
gcgaactttc tgtcctcgaa caggaagaaa ccgtgcttaa gagcaagttc cttgaggggg    5220
agcacagtgc cggcgtaggt gaagtcgtca atgatgtcga tatgggtttt gatcatgcac    5280
```

-continued

```
acataaggtc cgaccttatc ggcaagctca atgagctcct tggtggtggt aacatccaga      5340
gaagcacaca ggttggtttt cttggctgcc acgagcttga gcactcgagc ggcaaaggcg      5400
gacttgtgga cgttagctcg agcttcgtag gagggcattt tggtggtgaa gaggagactg      5460
aaataaattt agtctgcaga acttttatc ggaaccttat ctggggcagt gaagtatatg       5520
ttatggtaat agttacgagt tagttgaact tatagataga ctggactata cggctatcgg      5580
tccaaattag aaagaacgtc aatggctctc tgggcgtcgc cttgtccgac aaaatgtga      5640 tcatgatgaa agccagcaat gacgttgcag ctgatattgt tgtcggccaa ccgcgccgaa      5700
aacgcagctg tcagacccac agcctccaac gaagaatgta tcgtcaaagt gatccaagca      5760
cactcatagt tggagtcgta ctccaaaggc ggcaatgacg agtcagacag atactcgtcg      5820
actcaggcga cgacggaatt cctgcagccc atctgcagaa ttcaggagag accgggttgg      5880
cggcgtattt gtgtcccaaa aaacagcccc aattgcccca attgacccca aattgaccca      5940
gtagcgggcc caaccccggc gagagccccc ttcaccccac atatcaaacc tcccccggtt      6000
cccacacttg ccgttaaggg cgtagggtac tgcagtctgg aatctacgct tgttcagact      6060
ttgtactagt ttctttgtct ggccatccgg gtaacccatg ccggacgcaa aatagactac      6120
tgaaaatttt tttgctttgt ggttgggact ttagccaagg gtataaaaga ccaccgtccc      6180
cgaattacct ttcctcttct tttctctctc tccttgtcaa ctcacacccg aaatcgttaa      6240
gcatttcctt ctgagtataa gaatcattca ccatggatcc actagttcta gagcggccgc      6300
caccgcggcc cgagattccg gcctcttcgg ccgccaagcg acccgggtgg acgtctagag      6360
gtacctagca attaacagat agtttgccgg tgataattct cttaacctcc cacactccctt     6420 tgacataacg atttatgtaa cgaaactgaa atttgaccag atattgtgtc cgc             6473
```

<210> SEQ ID NO 76
<211> LENGTH: 427
<212> TYPE: PRT
<213> ORGANISM: Pavlova salina

<400> SEQUENCE: 76

```
Met Gly Arg Gly Gly Asp Ser Ser Gly Gln Ala His Pro Ala Ala Glu
1               5                   10                  15

Leu Ala Val Pro Ser Asp Arg Ala Glu Val Ser Asn Ala Asp Ser Lys
            20                  25                  30

Ala Leu His Ile Val Leu Tyr Gly Lys Arg Val Asp Val Thr Lys Phe
        35                  40                  45

Gln Arg Thr His Pro Gly Gly Ser Lys Val Phe Arg Ile Phe Gln Asp
    50                  55                  60

Arg Asp Ala Thr Glu Gln Phe Glu Ser Tyr His Ser Lys Arg Ala Ile
65                  70                  75                  80

Lys Met Met Glu Gly Met Leu Lys Lys Ser Glu Asp Ala Pro Ala Asp
                85                  90                  95

Thr Pro Leu Pro Ser Gln Ser Pro Met Gly Lys Asp Phe Lys Ala Met
            100                 105                 110

Ile Glu Arg His Val Ala Ala Gly Tyr Tyr Asp Pro Cys Pro Leu Asp
        115                 120                 125

Glu Leu Phe Lys Leu Ser Leu Val Leu Leu Pro Thr Phe Ala Gly Met
    130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
                165                 170                 175
```

His His Ser Val Phe Lys Gly Ser Val Ala Arg Thr Val Gly Trp Asn
              180                 185                 190

Asn Ala Ala Gly Tyr Phe Leu Gly Phe Val Gln Gly Tyr Ala Val Glu
              195                 200                 205

Trp Trp Arg Ala Arg His Asn Thr His His Val Cys Thr Asn Glu Asp
210                 215                 220

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
              245                 250                 255

Gln Tyr Tyr Tyr Val Pro Val Met Ala Ile Leu Asp Leu Tyr Trp Arg
              260                 265                 270

Leu Glu Ser Ile Ala Tyr Val Ala Met Arg Leu Pro Lys Met Leu Pro
              275                 280                 285

Gln Ala Leu Ala Leu Val Ala His Tyr Ala Ile Val Ala Trp Val Phe
              290                 295                 300

Ala Gly Asn Tyr His Leu Leu Pro Leu Val Thr Val Leu Arg Gly Phe
305                 310                 315                 320

Gly Thr Gly Ile Thr Val Phe Ala Thr His Tyr Gly Glu Asp Ile Leu
              325                 330                 335

Asp Ala Asp Gln Val Arg His Met Thr Leu Val Glu Gly Thr Ala Leu
              340                 345                 350

Thr Ser Arg Asn Ile Ser Gly Gly Trp Leu Val Asn Val Leu Thr Gly
              355                 360                 365

Phe Ile Ser Leu Gln Thr Glu His His Leu Phe Pro Met Met Pro Thr
370                 375                 380

Gly Asn Leu Met Thr Ile Gln Pro Glu Val Arg Ala Phe Phe Lys Lys
385                 390                 395                 400

His Gly Leu Glu Tyr Arg Glu Gly Asn Leu Ile Glu Cys Val Arg Gln
              405                 410                 415

Asn Ile Arg Ala Leu Ala Phe Glu His Leu Leu
              420                 425

<210> SEQ ID NO 77
<211> LENGTH: 421
<212> TYPE: PRT
<213> ORGANISM: Euglena gracilis

<400> SEQUENCE: 77

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
              20                  25                  30

Ile Glu Asn Tyr Gln Gly Arg Asp Ala Thr Asp Ala Phe Met Val Met
              35                  40                  45

His Ser Gln Glu Ala Phe Asp Lys Leu Lys Arg Met Pro Lys Ile Asn
              50                  55                  60

Pro Ser Ser Glu Leu Pro Pro Gln Ala Val Asn Glu Ala Gln Glu
65                  70                  75                  80

Asp Phe Arg Lys Leu Arg Glu Glu Leu Ile Ala Thr Gly Met Phe Asp
              85                  90                  95

Ala Ser Pro Leu Trp Tyr Ser Tyr Lys Ile Ser Thr Thr Leu Gly Leu
              100                 105                 110

Gly Val Leu Gly Tyr Phe Leu Met Val Gln Tyr Gln Met Tyr Phe Ile
              115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
    210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Met Pro Ser Ile
        275                 280                 285

Leu Thr Ser Leu Leu Val Phe Phe Val Ser Glu Leu Val Gly Gly Phe
    290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
    370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420

<210> SEQ ID NO 78
<211> LENGTH: 8953
<212> TYPE: DNA
<213> ORGANISM: Artificial Sequence
<220> FEATURE:
<223> OTHER INFORMATION: plasmid pY5-30

<400> SEQUENCE: 78
ggtggagctc cagcttttgt tccctttagt gagggttaat ttcgagcttg gcgtaatcat      60
ggtcatagct gtttcctgtg tgaaattgtt atccgctcac aattccacac aacatacgag     120
ccggaagcat aaagtgtaaa gcctggggtg cctaatgagt gagctaactc acattaattg     180
cgttgcgctc actgcccgct ttccagtcgg gaaacctgtc gtgccagctg cattaatgaa     240
tcggccaacg cgcggggaga ggcggtttgc gtattgggcg ctcttccgct tcctcgctca     300
ctgactcgct gcgctcggtc gttcggctgc ggcgagcggt atcagctcac tcaaaggcgg     360

-continued

```
taatacggtt atccacagaa tcaggggata acgcaggaaa gaacatgtga gcaaaaggcc    420
agcaaaaggc caggaaccgt aaaaaggccg cgttgctggc gtttttccat aggctccgcc    480
cccctgacga gcatcacaaa aatcgacgct caagtcagag gtggcgaaac ccgacaggac    540
tataaagata ccaggcgttt ccccctggaa gctccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg gctgtgtgc    720 acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg gcctaactac ggctacacta    900
gaaggacagt atttggtatc tgcgctctgc tgaagccagt taccttcgga aaaagagttg    960
gtagctcttg atccggcaaa caaaccaccg ctggtagcgg tggttttttt gtttgcaagc   1020
agcagattac gcgcagaaaa aaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt taaatcaatc taaagtatat   1200
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc cttttttcaat  2100 attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
```

-continued

```
tgcaaggcga ttaagttggg taacgccagg gttttcccag tcacgacgtt gtaaaacgac    2820
ggccagtgaa ttgtaatacg actcactata gggcgaattg ggtaccgggc cccccctcga    2880
ggtcgatggt gtcgataagc ttgatatcga attcatgtca cacaaaccga tcttcgcctc    2940
aaggaaacct aattctacat ccgagagact gccgagatcc agtctacact gattaatttt    3000
cgggccaata atttaaaaaa atcgtgttat ataatattat atgtattata tatatacatc    3060
atgatgatac tgacagtcat gtcccattgc taaatagaca gactccatct gccgcctcca    3120
actgatgttc tcaatattta aggggtcatc tcgcattgtt taataataaa cagactccat    3180
ctaccgcctc caaatgatgt tctcaaaata tattgtatga acttattttt attacttagt    3240
attattagac aacttacttg ctttatgaaa aacacttcct atttaggaaa caatttataa    3300
tggcagttcg ttcatttaac aatttatgta gaataaatgt tataaatgcg tatgggaaat    3360
cttaaatatg gatagcataa atgatatctg cattgcctaa ttcgaaatca acagcaacga    3420
aaaaaatccc ttgtacaaca taaatagtca tcgagaaata tcaactatca aagaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt atttattttt attctaatga tccattaaag gtatatattt atttcttgtt    3780
atataatcct tttgtttatt acatgggctg gatacataaa ggtatttga tttaattttt    3840 tgcttaaatt caatcccccc tcgttcagtg tcaactgtaa tggtaggaaa ttaccatact    3900
tttgaagaag caaaaaaaat gaaagaaaaa aaaaatcgta tttccaggtt agacgttccg    3960
cagaatctag aatgcggtat gcggtacatt gttcttcgaa cgtaaaagtt gcgctccctg    4020
agatattgta catttttgct tttacaagta caagtacatc gtacaactat gtactactgt    4080
tgatgcatcc acaacagttt gttttgtttt ttttgtgttt ttttttttct aatgattcat    4140
taccgctatg tatacctact tgtacttgta gtaagccggg ttattggcgt tcaattaatc    4200
atagacttat gaatctgcac ggtgtgcgct gcgagttact tttagcttat gcatgctact    4260
tgggtgtaat attgggatct gttcggaaat caacggatgc tcaaccgatt tcgacagtaa    4320
taatttgaat cgaatcggag cctaaaatga acccgagtat atctcataaa attctcggtg    4380
agaggtctgt gactgtcagt acaaggtgcc ttcattatgc cctcaacctt accataccct    4440
actgaatgta gtgtacctct aaaaatgaaa tacagtgcca aaagccaagg cactgagctc    4500
gtctaacgga cttgatatac aaccaattaa acaaatgaa aagaaataca gttctttgta    4560
tcatttgtaa caattaccct gtacaaacta aggtattgaa atcccacaat attcccaaag    4620
tccacccctt tccaaattgt catgcctaca actcatatac caagcactaa cctaccaaac    4680
accactaaaa ccccacaaaa tatatcttac cgaatataca gtaacaagct accaccacac    4740
tcgttgggtg cagtcgccag cttaaagata tctatccaca tcagccacaa ctcccttcct    4800
ttaataaacc gactacaccc ttggctattg aggttatgag tgaatatact gtagacaaga    4860
cactttcaag aagactgttt ccaaaacgta ccactgtcct ccactacaaa cacacccaat    4920
ctgcttcttc tagtcaaggt tgctacaccg gtaaattata aatcatcatt tcattagcag    4980
ggcagggccc ttttttataga gtcttataca ctagcggacc ctgccggtag accaacccgc    5040
aggcgcgtca gtttgctcct tccatcaatg cgtcgtagaa acgacttact ccttcttgag    5100
cagctccttg accttgttgg caacaagtct ccgacctcgg aggtggagga agagcctccg    5160
```

```
atatcggcgg tagtgatacc agcctcgacg gactccttga cggcagcctc aacagcgtca   5220
ccggcgggct tcatgttaag agagaacttg agcatcatgg cggcagacag aatggtggca   5280
atggggttga ccttctgctt gccgagatcg ggggcagatc cgtgacaggg ctcgtacaga   5340
ccgaacgcct cgttggtgtc gggcagagaa gccagagagg cggagggcag cagacccaga   5400
gaaccgggga tgacggaggc ctcgtcggag atgatatcgc caaacatgtt ggtggtgatg   5460
atgataccat tcatcttgga gggctgcttg atgaggatca tggcggccga gtcgatcagc   5520
tggtggttga gctcgagctg ggggaattcg tccttgagga ctcgagtgac agtctttcgc   5580
caaagtcgag aggaggccag cacgttggcc ttgtcaagag accacacggg aagaggggga   5640
ttgtgctgaa gggccaggaa ggcggccatt cgggcaattc gctcaacctc aggaacggag   5700
taggtctcgg tgtcggaagc gacgccagat ccgtcatcct cctttcgctc tccaaagtag   5760
atacctccga cgagctctcg gacaatgatg aagtcggtgc cctcaacgtt tcggatgggg   5820
gagagatcgg cgagcttggg cgacagcagc tggcagggtc gcaggttggc gtacaggttc   5880
aggtcctttc gcagcttgag gagaccctgc tcgggtcgca cgtcggttcg tccgtcggga   5940
gtggtccata cggtgttggc agcgcctccg acagcaccga gcataataga gtcagccttt   6000
cggcagatgt cgagagtagc gtcggtgatg ggctcgccct ccttctcaat ggcagctcct   6060
ccaatgagtc ggtcctcaaa cacaaactcg gtgccgagg cctcagcaac agacttgagc   6120
accttgacgg cctcggcaat cacctcgggg ccacagaagt cgccgccgag aagaacaatc   6180
ttcttggagt cagtcttggt cttcttagtt tcgggttcca ttgtggatgt gtgtggttgt   6240
atgtgtgatg tggtgtgtgg agtgaaaatc tgtggctggc aaacgctctt gtatatatac   6300
gcacttttgc ccgtgctatg tggaagacta aacctccgaa gattgtgact caggtagtgc   6360
ggtatcggct agggacccaa accttgtcga tgccgatagc gctatcgaac gtaccccagc   6420
cggccgggag tatgtcggag gggacatacg agatcgtcaa gggtttgtgg ccaactggta   6480
aataaatgat gtcgactcag gcgacgacgg aattcctgca gcccatctgc agaattcagg   6540
agagaccggg ttggcggcgt atttgtgtcc caaaaaacag cccaattgc cccaattgac   6600 cccaaattga cccagtagcg ggcccaaccc cggcgagagc cccttcacc ccacatatca   6660 aacctccccc ggttcccaca cttgccgtta agggcgtagg gtactgcagt ctggaatcta   6720
cgcttgttca gactttgtac tagtttcttt gtctggccat ccgggtaacc catgccggac   6780
gcaaaataga ctactgaaaa tttttttgct ttgtggttgg gactttagcc aagggtataa   6840
aagaccaccg tccccgaatt acctttcctc ttctttctc tctctccttg tcaactcaca   6900
cccgaaatcg ttaagcattt ccttctgagt ataagaatca ttcaccatgg atggtacgtc   6960
ctgtagaaac cccaacccgt gaaatcaaaa aactcgacgg cctgtgggca ttcagtctgg   7020
atcgcgaaaa ctgtggaatt gatcagcgtt ggtgggaaag cgcgttacaa gaaagccggg   7080
caattgctgt gccaggcagt tttaacgatc agttcgccga tgcagatatt cgtaattatg   7140
cgggcaacgt ctggtatcag cgcgaagtct ttataccgaa aggttgggca ggccagcgta   7200
tcgtgctgcg tttcgatgcg gtcactcatt acggcaaagt gtgggtcaat aatcaggaag   7260
tgatggagca tcagggcggc tatacgccat ttgaagccga tgtcacgccg tatgttattg   7320
ccgggaaaag tgtacgtatc accgtttgtg tgaacaacga actgaactgg cagactatcc   7380
cgccgggaat ggtgattacc gacgaaaacg gcaagaaaaa gcagtcttac ttccatgatt   7440
tctttaacta tgccgggatc catcgcagcg taatgctcta caccacgccg aacacctggg   7500
tggacgatat caccgtggtg acgcatgtcg cgcaagactg taaccacgcg tctgttgact   7560
```

```
ggcaggtggt ggccaatggt gatgtcagcg ttgaactgcg tgatgcggat caacaggtgg    7620
ttgcaactgg acaaggcact agcgggactt tgcaagtggt gaatccgcac ctctggcaac    7680
cgggtgaagg ttatctctat gaactgtgcg tcacagccaa aagccagaca gagtgtgata    7740
tctacccgct tcgcgtcggc atccggtcag tggcagtgaa gggcgaacag ttcctgatta    7800
accacaaacc gttctacttt actggctttg gtcgtcatga agatgcggac ttacgtggca    7860
aaggattcga taacgtgctg atggtgcacg accacgcatt aatggactgg attggggcca    7920
actcctaccg tacctcgcat taccttacg ctgaagagat gctcgactgg gcagatgaac     7980
atggcatcgt ggtgattgat gaaactgctg ctgtcggctt taacctctct ttaggcattg    8040
gtttcgaagc gggcaacaag ccgaaagaac tgtacagcga agaggcagtc aacggggaaa    8100
ctcagcaagc gcacttacag gcgattaaag agctgatagc gcgtgacaaa aaccacccaa    8160
gcgtggtgat gtggagtatt gccaacgaac cggatacccg tccgcaagtg cacgggaata    8220
tttcgccact ggcggaagca acgcgtaaac tcgacccgac gcgtccgatc acctgcgtca    8280
atgtaatgtt ctgcgacgct cacaccgata ccatcagcga tctctttgat gtgctgtgcc    8340
tgaaccgtta ttacggatgg tatgtccaaa gcggcgattt ggaaacggca gagaaggtac    8400
tggaaaaaga acttctggcc tggcaggaga aactgcatca gccgattatc atcaccgaat    8460
acggcgtgga tacgttagcc gggctgcact caatgtacac cgacatgtgg agtgaagagt    8520
atcagtgtgc atggctggat atgtatcacc gcgtctttga tcgcgtcagc gccgtcgtcg    8580
gtgaacaggt atggaatttc gccgattttg cgacctcgca aggcatattg cgcgttggcg    8640
gtaacaagaa agggatcttc actcgcgacc gcaaaccgaa gtcggcggct tttctgctgc    8700
aaaaacgctg gactggcatg aacttcggtg aaaaaccgca gcagggaggc aaacaatgat    8760
taattaacta gagcggccgc caccgcggcc cgagattccg gcctcttcgg ccgccaagcg    8820
acccgggtgg acgtctagag gtacctagca attaacagat agtttgccgg tgataattct    8880
cttaacctcc cacactcctt tgacataacg atttatgtaa cgaaactgaa atttgaccag    8940
atattgtgtc cgc                                                       8953
```